(12) United States Patent
Oxford et al.

(10) Patent No.: US 7,803,841 B2
(45) Date of Patent: Sep. 28, 2010

(54) EP₂ RECEPTOR AGONISTS

(75) Inventors: Alexander William Oxford, Royston (GB); Richard Jon Davis, Royston (GB); Robert Alexander Coleman, Royston (GB); Kenneth Lyle Clark, Royston (GB); David Edward Clark, Harlow (GB); Neil Victor Harris, Harlow (GB); Garry Fenton, Harlow (GB); George Hynd, Harlow (GB); Keith Alfred James Stuttle, Harlow (GB); Jonathan Mark Sutton, Harlow (GB); Mark Richard Ashton, Abingdon (GB); Edward Andrew Boyd, Abingdon (GB); Shirley Ann Brunton, Abingdon (GB)

(73) Assignee: Asterand UK Limited, Royston, Hertfordshire (GB)

(*) Notice: Subject to any disclaimer, the term of this patent is extended or adjusted under 35 U.S.C. 154(b) by 0 days.

(21) Appl. No.: 12/346,516

(22) Filed: Dec. 30, 2008

(65) Prior Publication Data
US 2009/0298899 A1 Dec. 3, 2009

Related U.S. Application Data

(62) Division of application No. 11/950,613, filed on Dec. 5, 2007, which is a division of application No. 11/055,724, filed on Feb. 11, 2005, now Pat. No. 7,326,732.

(60) Provisional application No. 60/543,538, filed on Feb. 12, 2004, provisional application No. 60/626,940, filed on Nov. 12, 2004.

(51) Int. Cl.
*A61K 31/166* (2006.01)
*C07C 233/65* (2006.01)

(52) U.S. Cl. .................. 514/617; 564/184; 564/185

(58) Field of Classification Search ................ None
See application file for complete search history.

(56) References Cited

U.S. PATENT DOCUMENTS

| 5,576,347 | A | 11/1996 | Sredni et al. |
| 5,939,332 | A | 8/1999 | Lee et al. |
| 6,562,868 | B1 | 5/2003 | Stjernschantz et al. |
| 7,326,732 | B2 | 2/2008 | Oxford et al. |
| 2005/0209336 | A1 | 9/2005 | Borman et al. |
| 2005/0256170 | A1 | 11/2005 | Oxford et al. |
| 2008/0119526 | A1 | 5/2008 | Oxford et al. |

FOREIGN PATENT DOCUMENTS

| EP | 0 496 378 | 7/1992 |
| GB | 2 293 101 | 3/1996 |
| WO | WO 98/27976 | 7/1998 |
| WO | WO 98/34916 | 8/1998 |
| WO | WO/00/27823 | 5/2000 |
| WO | WO/00/31084 | 6/2000 |
| WO | WO/00/40248 | 7/2000 |
| WO | WO/01/46140 | 6/2001 |
| WO | WO/01/85167 | 11/2001 |
| WO | WO/02/24647 | 3/2002 |
| WO | WO/03/032972 | 4/2003 |
| WO | WO 03/032972 | * 4/2003 |
| WO | WO/03/037433 | 5/2003 |
| WO | WO/03/040126 | 5/2003 |
| WO | WO/03/045371 | 6/2003 |
| WO | WO 03/070691 | * 8/2003 |
| WO | WO/2004/012656 | 2/2004 |
| WO | WO/2005/061449 | 7/2005 |

OTHER PUBLICATIONS

Morissette et al. Advanced Drug Delivery Reviews 2004, 56, 275-300.*
Patani, George A. Bioisosterism: A rational Approach in Drug Design. Chem. Rev. 96 (1996) 3147-3176.*
Vippagunta, Sudha R. "Crystalline Solids." Advanced Drug Delivery Reviews 48(2001): 3-26.*
Morissette et al., Advanced Drug Delivery Reviews, 2004, 56, pp. 275-300.
Vippagunta, Sudha R., "Crystalline Solids.", Advanced Drug Delivery Reviews 2001, 48, pp. 3-26.
Patani, George A., Bioisosterism: A Rational Approach in Drug Design, Chem. Rev. 96, 1996, 3147-3176.
McMurry, John, Fourth Edition McMurry Organic Chemistry. Brooks/Cole Publishing Company, 1996.
Berge et al., Journal of Pharmaceutical Sciences, 1977, vol. 66, No. 1, pp. 1-19.
Griffiths et al., Current Drug Targets—Inflammation & Allergy, 2004, vol. 3, pp. 157-161.
Lebwohl, The Lancet, 2003, vol. 361, pp. 1197-1204.
Nataraj et al., The Journal of Clinical Investigation, 2001, vol. 108, No. 8., pp. 1229-1235.
Salim et al., Current Opinion in Investigational Drugs, 2001, 2(11): pp. 1546-1548.
Tilley et al., Am. J. Physiol. Lung Cell Mol. Physiol., 2003, 284: pp. 599-606.
Chemical Abstract Accession No. 2003:3915608, Otava Stock Chemicals Catalogue, 26. Oct. 2003, compound with CAS Registry No. 620542-88-3.
Chemical Abstract Accession No. 2003:3848742, Akos Samples Catalogue, Sep. 2, 2004, compound with CAS Registry No. 618413-90-4.
Chemical Abstract Accession No. 2003:3849399, Akos Samples Catalogue, Sep. 2, 2004, compound with CAS Registry No. 618404-52-7.
Chemical Abstract Accession No. 2003:3849331, Akos Samples Catalogue, Sep. 2, 2004, compound with CAS Registry No. 618401-55-1.
Uesato et al., Bio Organic & Medicinal Chemistry Letters, 2002, vol. 12., pp. 1347-1349.

* cited by examiner

*Primary Examiner*—Golam M. M. Shameem
*Assistant Examiner*—Alicia L Fierro
(74) *Attorney, Agent, or Firm*—Honigman Miller Schwartz and Cohn LLP; Cynthia M. Bott

(57) ABSTRACT

The disclosure provides EP₂ receptor agonist compounds and methods for using the compounds for treating conditions which can be alleviated by agonism of an EP₂ receptor.

13 Claims, No Drawings

EP₂ RECEPTOR AGONISTS

CROSS REFERENCE TO RELATED APPLICATIONS

This application is a divisional of application Ser. No. 11/950,613, filed Dec. 5, 2007, which application is a divisional of application Ser. No. 11/055,724, filed Feb. 11, 2005, now U.S. Pat. No. 7,326,732, which claims benefit of U.S. Provisional Application Nos. 60/543,538, filed Feb. 12, 2004, and 60/626,940, filed Nov. 12, 2004; the entire contents of each which are hereby incorporated by reference in this application.

This invention relates to $EP_2$ receptor agonists, pharmaceutical compositions comprising such compounds, and the use of such compounds and compositions to treat various diseases.

BACKGROUND TO THE INVENTION

Prostanoids comprise prostaglandins (PGs) and thromboxanes (Txs) and their receptors fall into five different classes (DP, EP, FP, IP and TP) based on their sensitivity to the five naturally occurring prostanoids, $PGD_2$, $PGE_2$, $PGF_{2\alpha}$, $PGI_2$ and $TxA_2$, respectively (Coleman, R. A., Prostanoid Receptors.

*IUPHAR compendium of receptor characterisation and classification, 2$^{nd}$ edition*, 338-353, ISBN 0-9533510-3-3, 2000). EP receptors (for which the endogenous ligand is PGE2) have been subdivided into four types termed $EP_1$, $EP_2$, $EP_3$ and $EP_4$. These four types of EP receptors have been cloned and are distinct at both a molecular and pharmacological level (Coleman, R. A., 2000)

$EP_2$ agonists have been shown to be effective in the treatment of a number of conditions, including (but not limited to) dysmenorrhoea (WO 03/037433), pre-term labour (GB 2 293 101), glaucoma (WO 03/040126), ocular hypertension (WO 03/040126), immune disorders (Nataraj, C., et al., *J. Clin. Invest.*, 108, 1229-1235 (2001)), osteoporosis (WO 98/27976, WO 01/46140), asthma (Tilley, et al., *Am. J. Physiol. Lung Cell Mol. Physiol.*, 284, L599-606 (2003)), allergy, bone disease (WO 02/24647), fracture repair (WO 98/27976, WO 02/24647), male sexual dysfunction (WO 00/40248), female sexual dysfunction (U.S. Pat. No. 6,562, 868), periodontal disease (WO 00/31084), gastric ulcer (U.S. Pat. No. 5,576,347) and renal disease (WO 98/34916).

In co-pending applications GB 0329620.9, filed 22 Dec. 2003 and a corresponding US provisional application filed 24 Dec. 2003, which are hereby incorporated by reference, it has been shown that $EP_2$ agonists inhibit lymphocyte activation and the release of pro-inflammatory cytokines from alveolar macrophages. In addition, $EP_2$ activation inhibits monocyte and neutrophil activation. Thus, $EP_2$ agonists should prove useful in the treatment of inflammatory and immune disorders such as psoriasis, dermatitis, rheumatoid arthritis, multiple sclerosis, scleroderma, transplant rejection, allergy, systemic lupus erythematosus, vasculitis, type 1 diabetes mellitus, and inflammatory lung diseases such as chronic obstructive pulmonary disease, asthma, acute respiratory distress syndrome and cystic fibrosis.

In addition, $EP_2$ agonists can also be used in the treatment of fibrosis, including, but not limited to idiopathic pulmonary fibrosis, scleroderma and systemic sclerosis, post-operative fibrosis following trabulectomy, liver repair and regeneration following cirrhosis, hepatitis, toxicity, cancer or renal fibrosis. $EP_2$ agonists can also be used in the prevention of fibroblast to myofibroblast conversion to treat asthma and other fibrotic lung diseases. $EP_2$ agonists may also be used to maintain ductus arteriosus patency in infants with congenital heart disease.

Compounds which combine $EP_2$ receptor agonist and $EP_4$ receptor antagonist properties may prove useful in the treatment of several diseases including myometrial disorders, bone diseases including osteoporosis and osteoarthritis, allergic and immune disorders such as psoriasis, transplant rejection, and asthma, inflammatory diseases such as rheumatoid arthritis, chronic obstructive pulmonary disease and acute respiratory disease syndrome, and fibrotic lung diseases.

SUMMARY OF THE INVENTION

A first aspect of the present invention provides a compound of formula (I):

(I)

or a salt, solvate and chemically protected form thereof, wherein:

$R^5$ is an optionally substituted $C_{5-20}$ aryl or $C_{4-20}$ alkyl group;
A is selected from the group consisting of:

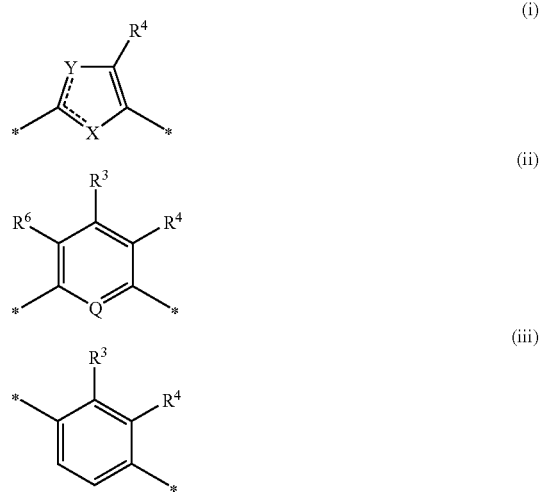

wherein X and Y are selected from the group consisting of:
O and $CR^3$; S and $CR^3$; NH and $CR^3$; NH and N; O and N; S and N; N and S; and N and O, and where the dotted lines indicate a double bond in the appropriate location, and where Q is either N or CH;

$R^3$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;

$R^4$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;

$R^6$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;

D is selected from:

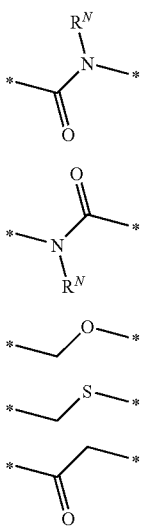

(i)

(ii)

(iii)

(iv)

(v)

B is selected from the group consisting of:

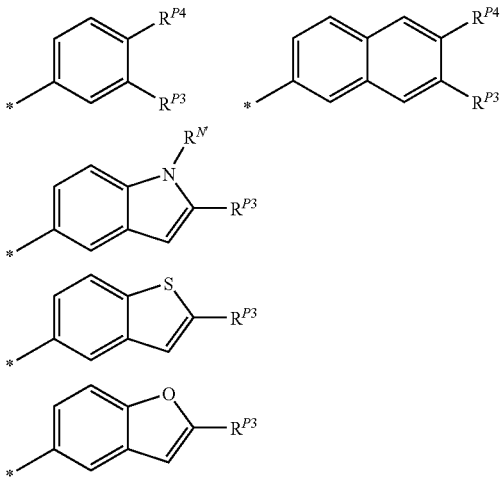

where $R^N$ is selected from H and $C_{1-4}$ alkyl;

where one of $R^{P3}$ and $R^{P4}$ is —$C_m$ alkylene-$R^2$ and the other of $R^{P3}$ and $R^{P4}$ is H, m and n can be 0 or 1, and m+n=1 or 2;

and additionally when $R^{P3}$ is —$C_m$ alkylene-$R^2$, m can also be 2 or 3, and m+n=1, 2, 3 or 4, and when $R^2$ is tetrazol-5-yl, m+n may be 0; or where one of $R^{P3}$ and $R^{P4}$ is —O—$CH_2$—$R^2$, and the other of $R^{P3}$ and $R^{P4}$ is H, n is 0;

$R^N$ is H or optionally substituted $C_{1-4}$ alkyl;

$R^2$ is either:

(i) —$CO_2H$ (carboxy)

(ii) —$CONH_2$;

(iii) —$CH_2$—OH (methoxy); or (iv) tetrazol-5-yl.

Therefore, A may be one of the following groups:

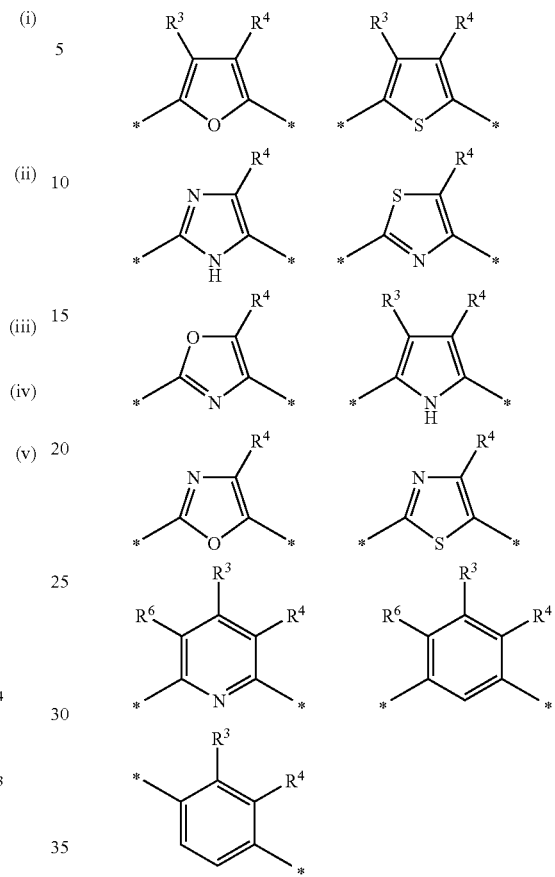

A second aspect of the present invention provides a compound of formula (I) or a pharmaceutically acceptable salt thereof for use in a method of therapy.

A third aspect of the present invention provides a pharmaceutical composition comprising a compound of formula (I) as defined in the first aspect or a pharmaceutically acceptable salt thereof together with a pharmaceutically acceptable carrier or diluent.

A fourth aspect of the present invention provides the use of a compound of formula (I) or a pharmaceutically acceptable salt thereof in the preparation of a medicament for the treatment of a condition alleviated by agonism of an $EP_2$ receptor.

A fifth aspect of the present invention provides a method of treating a condition which can be alleviated by agonism of an $EP_2$ receptor, which method comprises administering to a patient in need of treatment an effective amount of a compound of formula (I), or a pharmaceutically acceptable salt thereof.

In the fourth and fifth aspects of the invention, the agonism of the $EP_2$ receptor may be selective, or may be accompanied by antagonism of the $EP_4$ receptor.

Conditions which can be alleviated by agonism of an $EP_2$ receptor are discussed above, and particularly include dysmenorrhoea, pre-term labour, glaucoma, ocular hypertension, immune disorders, inflammatory disorders, osteoporosis, asthma, chronic obstructive pulmonary disease, allergy, bone disease, fracture repair, male sexual dysfunction, female sexual dysfunction, infertility, periodontal disease, gastric ulcer, renal disease and psoriasis.

Conditions which can be alleviated by combined agonism of $EP_2$ receptors and antagonism of $EP_4$ receptors are discussed above, and particularly include myometrial disorders, bone diseases including osteoporosis and osteoarthritis, allergic and immune disorders such as psoriasis, transplant rejection, and asthma, inflammatory diseases such as rheumatoid arthritis, chronic obstructive pulmonary disease and acute respiratory disease syndrome, and fibrotic lung diseases.

EP receptor agonists are known to be able to inhibit T-cell activation and the release of pro-inflammatory cytokines, although the EP receptor involved in mediating these effects in human T-cells has not been previously defined. Some of the present inventors have discovered that $EP_2$ agonists inhibit human T-cell activation (proliferation) and inhibit the release of multiple pro-inflammatory cytokines including interleukin 2 (IL-2) tumour necrosis factor ($TNF_\alpha$) and interferon gamma (IFNγ), as described in co-pending US and International applications entitled "$EP_2$ Agonists" filed 22 Dec. 2004 in the name of Borman, R. A. et al., (PCT/GB2004/005421), which are herein incorporated by reference. This profile of activity strongly suggests that $EP_2$ receptor agonists will be useful in treating immune and inflammatory disorders, including but not limited to psoriasis, psoriatic arthritis, dermatitis, rheumatoid arthritis, transplant rejection, inflammatory bowel disease, systemic lupus erythematosus, Graves' disease, scleroderma, multiple sclerosis, Type I diabetes, and transplant rejection, and in particular psoriasis (Griffiths, C., *Current Drugs Targets—Inflammation & Allergy*, 3, 157-161, (2004); Lebwohl, M., *Lancet*, 361, 1197-1204 (2003); Salim, A. & Emerson, R., *Curr. Opin. Investig. Drugs*, 2(11), 1546-8 (2001)). Therefore, a further condition which can be alleviated by agonism of an $EP_2$ receptor is psoriasis.

Furthermore, some of the present inventors have also shown that $EP_2$ receptor agonists inhibit the release of the pro-inflammatory cytokine, $TNF_\alpha$ from human monocytes and alveolar macrophages, as described in co-pending US and International applications entitled "$EP_2$ Agonists" filed 22 Dec. 2004 in the name of Borman, R. A. et al., (PCT/GB2004/005421), which are herein incorporated by reference. This profile of activity adds further evidence to the view that that $EP_2$ receptor agonists will be useful in treating immune and inflammatory disorders and in particular, inflammatory lung diseases (including, but not limited to: asthma, chronic obstructive pulmonary disease, acute respiratory distress syndrome, pulmonary fibrosis and cystic fibrosis).

Furthermore, aspects of the present invention relate to the use of $EP_2$ agonists to treat conditions ameliorated by the inhibition of IL-2 $TNF_\alpha$ and/or IFNγ production and the use of an $EP_2$ agonist in the preparation of a medicament for the treatment of a condition alleviated by inhibition of IL-2 production.

The present invention also provides methods of stimulating $EP_2$ receptors and/or inhibiting the production of IL-2, $TNF_\alpha$ and/or IFNγ, in vitro or in vivo, comprising contacting a cell with an effective amount of a compound of the first aspect of the present invention.

Compounds of the present invention can be assayed to determine whether they act as antagonists of an $EP_4$ receptor. Suitable assay methods are described in example 6 below.

The present invention also provides methods of agonising $EP_2$, and possible antagonizing $EP_4$ receptors, in vitro or in vivo, comprising contacting a cell with an effective amount of a compound of formula (I).

In some embodiments, the compounds described above which function as $EP_2$ agonists may be selective as against modulation of one or more of the other three EP receptors, i.e. $EP_1$, $EP_3$ and $EP_4$. This selectivity allows for targeting of the effect of the compounds of the invention, with possible benefits in the treatment of certain conditions.

DEFINITIONS

Monodentate Groups (i.e Groups with One Point of Covalent Attachment)

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated. Thus, the term "alkyl" includes the sub-classes alkenyl, alkynyl, cycloalkyl, cycloalkenyl, cylcoalkynyl, etc., discussed below.

In the context of alkyl groups, the prefixes (e.g. $C_{1-4}$, $C_{1-7}$, $C_{1-20}$, $C_{2-7}$, $C_{3-7}$) denote the number of carbon atoms, or range of number of carbon atoms. For example, the term "$C_{1-4}$ alkyl" as used herein, pertains to an alkyl group having from 1 to 4 carbon atoms. Examples of groups of alkyl groups include $C_{1-4}$ alkyl ("lower alkyl"), $C_{1-7}$ alkyl and $C_{4-20}$ alkyl. Note that the first prefix may vary according to other limitations; for example, for unsaturated alkyl groups, the first prefix must be at least 2; for cyclic alkyl groups, the first prefix must be at least 3; etc.

Examples of saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl" as used herein, pertains to an alkyl group having one or more carbon-carbon double bonds. Examples of alkenyl groups include $C_{2-4}$ alkenyl, $C_{2-7}$ alkenyl and $C_{2-20}$ alkenyl. Examples of alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

Alkynyl: The term "alkynyl" as used herein, pertains to an alkyl group having one or more carbon-carbon triple bonds. Examples of groups of alkynyl groups include $C_{2-4}$ alkynyl, $C_{2-7}$ alkynyl and $C_{2-20}$ alkynyl. Examples of alkynyl groups include, but are not limited to, ethynyl (ethinyl, —C≡CH) and 2-propynyl (propargyl, —$CH_2$—C≡CH).

Cycloalkyl: The term "cycloalkyl" as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated, which moiety has from 3 to 7 carbon atoms (unless otherwise specified), including from 3 to 7 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-7}$ cycloalkyl.

Examples of cycloalkyl groups include, but are not limited to, those derived from:

saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$) dimethylcyclohexane ($C_8$), menthane ($C_{10}$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$) dimethylcyclohexene ($C_8$);

saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds: camphene ($C_{10}$), limonene ($C_{10}$), pinene ($C_{10}$).

Heterocyclyl: The term "heterocyclyl" as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl" as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Aryl: The term "aryl" as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms. Examples of groups of aryl groups include $C_{3-20}$ aryl, $C_{5-20}$ aryl, $C_{5-15}$ aryl, $C_{5-12}$ aryl, $C_{5-10}$ aryl, $C_{5-7}$ aryl, $C_{5-6}$ aryl, $C_5$ aryl, and $C_6$ aryl.

The ring atoms may be all carbon atoms, as in "carboaryl groups". Examples of carboaryl groups include $C_{3-20}$ carboaryl, $C_{5-20}$ carboaryl, $C_{5-15}$ carboaryl, $C_{5-12}$ carboaryl, $C_{5-10}$ carboaryl, $C_{5-7}$ carboaryl, $C_{5-6}$ carboaryl, $C_5$ carboaryl, and $C_6$ carboaryl.

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of heteroaryl groups include $C_{3-20}$ heteroaryl, $C_{5-20}$ heteroaryl, $C_{5-15}$ heteroaryl, $C_{5-12}$ heteroaryl, $C_{5-10}$ heteroaryl, $C_{5-7}$ heteroaryl, $C_{5-6}$ heteroaryl, $C_5$ heteroaryl, and $C_6$ heteroaryl.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$), pyrazine (1,4-diazine) ($C_6$);

$N_3$: triazole ($C_5$), triazine ($C_6$); and, $N_4$: tetrazole ($C_5$).

Examples of heteroaryl groups which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

If a heteroaryl or heterocyclyl group contains a nitrogen ring atom, this ring atom, where possible, may be in a oxidised state, as an N-oxide.

The above groups, whether alone or part of another substituent, may themselves optionally be substituted with one or more groups selected from themselves, the additional monodentate substituents listed below and alkoxylene.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)O$CH_3$, —C(=O)O$CH_2CH_3$, —C(=O)OC($CH_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)$CH_3$ (acetoxy), —OC(=O)$CH_2CH_3$, —OC(=O)C($CH_3$)$_3$, —OC(=O)Ph, and —OC(=O)$CH_2$Ph.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)$NHCH_3$, —C(=O)N($CH_3$)$_2$, —C(=O)NH$CH_2CH_3$, and —C(=O)N($CH_2CH_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamino: —$NR^1$C(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl:

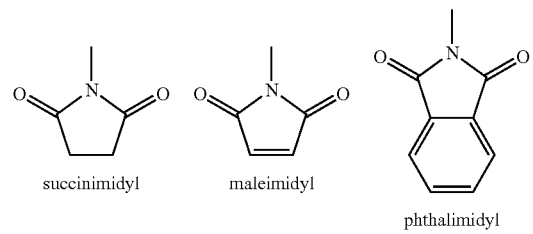

succinimidyl    maleimidyl    phthalimidyl

Thioamido (thiocarbamyl): —C(=S)$NR^1R^2$, wherein $R^1$ and $R^2$ are independently amino substituents, as defined for amino groups. Examples of thioamido groups include, but are not limited to, —C(=S)$NH_2$, —C(=S)$NHCH_3$, —C(=S)N($CH_3$)$_2$, and —C(=S)NH$CH_2CH_3$.

Ureido: —N($R^1$)CON$R^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCON$H_2$, —NHCONHMe, —NHCONHEt, —NHCONMe$_2$, —NHCONEt$_2$, —NMeCON$H_2$, —NMeCONHMe, —NMeCONHEt, —NMeCONMe$_2$, and —NMeCONEt$_2$.

Guanidino: —NH—C(=NH)$NH_2$.

Tetrazolyl: a five membered aromatic ring having four nitrogen atoms and one carbon atom,

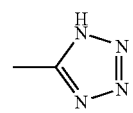

Amino: —$NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—$NH_2$), secondary (—$NHR^1$), or tertiary (—$NHR^1R^2$), and in cationic form, may be quaternary (—$^+NR^1R^2R^3$). Examples of amino groups include, but are not limited to, —$NH_2$, —$NHCH_3$, —NHC($CH_3$)$_2$, —N($CH_3$)$_2$, —N($CH_2CH_3$)$_2$, and —NHPh. Examples of cyclic amino groups include, but are not limited to, aziridino, azetidino, pyrrolidino, piperidino, piperazino, morpholino, and thiomorpholino.

Amidine (amidino): —C(=NR)$NR_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Cyano (nitrile, carbonitrile): —CN.
Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$ C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.
Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide) —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$ C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

As already mentioned, the above described groups may be substituted, and particular examples include, but are not limited to, $C_{3-20}$ aryl-$C_{1-7}$ alkyl groups, which include benzyl (phenylmethyl, PhCH$_2$—), benzhydryl (Ph$_2$CH—), trityl (triphenylmethyl, Ph$_3$C—), phenethyl (phenylethyl, Ph-CH$_2$CH$_2$—), styryl (Ph-CH=CH—) and cinnamyl (Ph-CH=CH—CH$_2$—).

Bidentate Groups (i.e. Groups with Two Points of Covalent Attachment; Linking Groups)

Alkylene: The term "$C_{1-3}$ alkylene", as used herein, pertains to a bidentate moiety obtained by removing two hydrogen atoms from each of two different carbon atoms, of a linear hydrocarbon compound having from 1 to 3 carbon atoms, which may be saturated or unsaturated. Thus, the term "alkylene" includes the sub-classes alkenylene and alkynylene.

In this context, the prefix $C_{1-3}$ denotes the number of carbon atoms, or range of number of carbon atoms.

Examples of saturated $C_{1-3}$ alkylene groups include —CH$_2$-(methylene), —CH$_2$CH$_2$— (ethylene) and —CH$_2$CH$_2$CH$_2$— (propylene).

Examples of unsaturated $C_{1-3}$ alkylene groups (which may be termed "$C_{2-3}$ alkenylene" or "$C_{2-3}$ alkynylene", as appropriate) include —CH=CH— (vinylene), —CH=CH—CH$_2$—, —CH$_2$—CH=CH—, —C≡C—, —C≡C—CH$_2$— and —CH$_2$—C≡C—.

The $C_{1-3}$ alkylene group may be substituted by any monodentate substituent described above.

Alkoxylene: The term "alkoxylene," as used herein, pertains to a bidentate group of formula —O(CH$_2$)$_n$O—, where n is 1 or 2.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates and Protected Forms

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

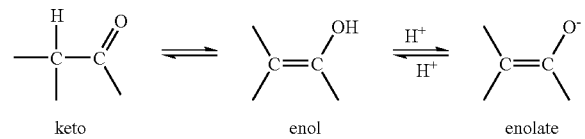

keto    enol    enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g. pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting", "blocking", or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: an acetamide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount", as used herein, pertains to that amount of an active compound, or a material, composition or dosage form comprising an active compound, which is effective for producing some desired therapeutic effect, commensurate with a reasonable benefit/risk ratio, when administered in accordance with a desired treatment regimen. Suitable dose ranges will typically be in the range of from 0.01 to 20 mg/kg/day, preferably from 0.1 to 10 mg/kg/day.

Compositions and Their Administration

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier.

Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, 20th edition, pub. Lippincott, Williams & Wilkins, 2000. The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues. Formulations suitable for vaginal administration may be presented as pessaries, tampons, creams, gels, pastes, foams or spray formulations containing in addition to the active compound, such carriers as are known in the art to be appropriate.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

General Synthesis Methods

Compounds where R$^2$ is tetrazol-5-yl may be synthesised from compounds of formula 4:

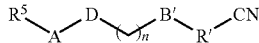

Formula 4 wherein B' represents the aromatic moiety in B, R' represents the C$_m$ alkylene group in B, and R' is on the appropriate position on the aromatic moiety, by treatment with sodium azide, trimethyltin azide or trimethylsilyl azide.

Compounds of formula 4, where D is —C(=O)—N (R$^N$)—, may be synthesised by coupling compounds of Formula 5 and Formula 6a, wherein the groups B' and R' are as defined above.

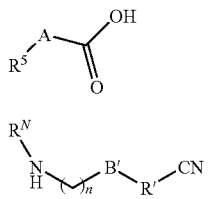

Formula 5

Formula 6a

Such a coupling step may be carried out using a coupling agent or agents, for example, O-(7-azabenzotriazol-1-yl)-N,N,N',N'-tetramethyluronium hexafluorophosphate, TBTU and DIPEA, or EDC and HOAt.

Compounds of formula 4, where D is —N(R$^N$)—C (=O)—, may be synthesised by coupling compounds of Formula 5' and Formula 6a', wherein the groups B' and R' are as defined above.

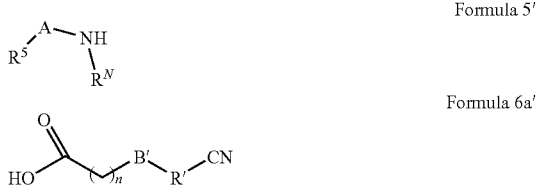

Formula 5'

Formula 6a'

Such a coupling step may be carried out using a coupling agent or agents, as described above.

Compounds where R$^2$ is carboxy, may be synthesised from compounds of formula 7:

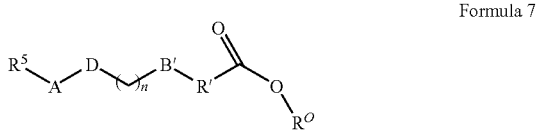

Formula 7 wherein B' and R' are as defined above, by a hydrolysis reaction, for example, using sodium hydroxide.

Compounds of formula 7, where D is —C(=O)—N (R$^N$)—, can be synthesised by coupling compounds of formula 5 and 6b, wherein B' and R' are as defined above:

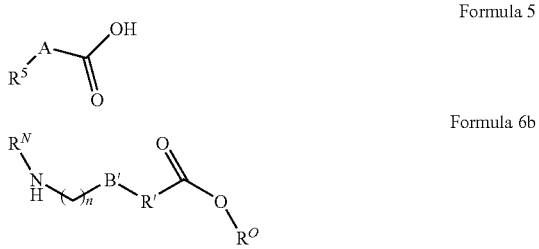

Formula 5

Formula 6b

Such a coupling step may be carried out as described above, by using a coupling agent or agents, for example, O-(7-azabenzotriazol-1-yl)-N,N,N',N'-tetramethyluronium hexafluorophosphate, TBTU and DIPEA, or EDC and HOAt.

Compounds of formula 7, where D is —N(R$^N$)—C (=O)—, may be synthesised by coupling compounds of Formula 5' and Formula 6b', wherein the groups B' and R' are as defined above.

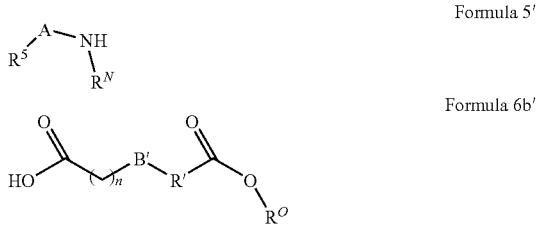

Formula 5'

Formula 6b'

Such a coupling step may be carried out using a coupling agent or agents, as described above.

Compounds of formula 5, where R$^5$ is an aryl group, may be synthesised from compounds of formula 8:

Formula 8

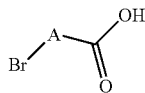

by a Suzuki coupling of a compound of formula 9a (or equivalent ester of formula 9b):

Formula 9a

Formula 9b

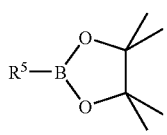

The Suzuki coupling may be achieved using, for example, [1,1'-bis(diphenylphosphino)ferrocene]dichloropalladium (II) as the palladium catalyst. Alternatively, the coupling may be achieved using $CsCO_3$, with $Pd(PPh_3)_4$ as the palladium catalyst. In this reaction, the carboxy group may be protected.

Compounds of Formula 8, where A is:

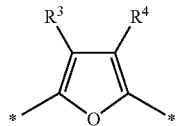

may be synthesised from compounds of formula 10:

Formula 10

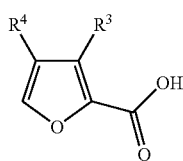

by treating the compound of formula 10 with a brominating agent, such as pyridinium tribromide. This method can be readily adapted for other A groups.

Compounds of formula 7 where $R^5$ is an optionally substituted $C_{5-7}$ aryl group may be prepared from compounds of formula 7 where $R^5$ is bromine by a Suzuki coupling with compounds of formula 9a or 9b.

Compounds of formula 5, where $R^5$ is an alkyl group, and where A is:

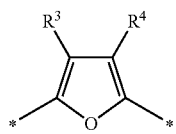

may be synthesized from compounds of formula 11:

Formula 11

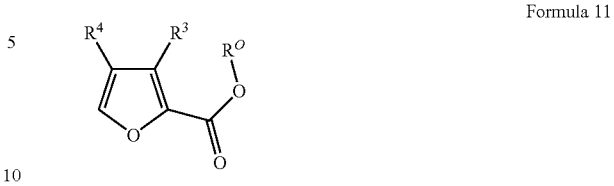

by reaction with $R^5$—Br, in the presence of $AlCl_3$, in an organic solvent, such as ortho-dichlorobenzene, followed by deprotection of the acid group. This method can be reacily adapted for other A groups.

Compounds of formula 7, where D is —$CH_2$—O— or —$CH_2$—S—, may be prepared by coupling compounds of formula 5" and 6b", wherein B' and R' are as defined above:

Formula 5"

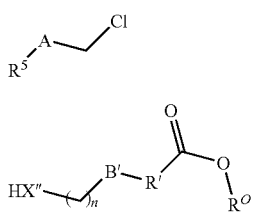

Formula 6b"

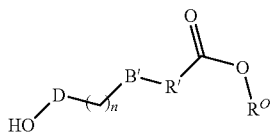

where X" is O or S, using NaH in an organic solvent, such as DMF and heptane or THF. Alternatively the coupling may take place before the addition of the $R'CO_2R^O$ group.

A key step in the synthesis of compounds of formula 7, where D is —C(=O)—$CH_2$—, is the coupling of the remainder of the molecule to $R^5$-A. This can be achieved by coupling a compound of formula 12:

Formula 12

or precursor thereof to $R^5$-A by a suitable method. For example, when A is:

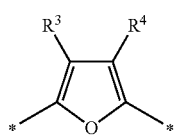

the coupling may take place in an organic solvent in the presence of $P_2O_5$.

Preferences

The following preferences may be combined with one another, and may be different for each aspect of the present invention.

$R^5$ may be a $C_{5-7}$ aryl group, such as furan-2-yl and phenyl. $R^5$ is preferably a $C_6$ aryl group, and is more preferably phenyl. $R^5$ may be substituted, and preferred substituents include $C_{1-7}$ alkoxy groups, more preferably $C_{1-4}$ alkoxy groups, e.g. —OMe, —OCF$_3$, —OEt, —OCHF$_2$, with —OCHF$_2$ being the most preferred.

When $R^5$ is phenyl, preferable substituents include: $C_{1-4}$ alkyl (e.g. methyl, —CF$_3$, isopropyl); $C_{1-4}$ alkoxy (e.g. methoxy, —OCF$_3$), including substituted $C_{1-4}$ alkoxy (e.g. benzyloxy); $C_{5-6}$ aryl (e.g. phenyl); halo (e.g. Cl, F, di-Cl); acyl (e.g. —COMe); amino (e.g. —NH$_2$, —NMe$_2$); alkoxylene (e.g. —O—CH$_2$—O—). In some embodiments, $C_{1-4}$ alkyl (e.g. methyl, —CF$_3$, isopropyl); $C_{1-4}$ alkoxy (e.g. methoxy, —OCF$_3$); halo (e.g. Cl, F, di-Cl); acyl (e.g. —COMe); and alkoxylene (e.g. —O—CH$_2$—O—) are preferred.

The substituents may be any position of the phenyl ring, e.g. 2-, 3- and 4-, and when there are two substituents (e.g. di-chloro), these may be, for example, at: 2-,3-; 2-,4-; 3-,5- or 3-,4-.

$R^5$ may preferably be furan-2-yl.

$R^5$ may preferably be a $C_{9-10}$ aryl group, e.g. napthyl (more preferably napth-1-yl) and indolyl (more preferably indol-4-yl).

When $R^5$ is a $C_{4-20}$ alkyl group, it may be a $C_{4-10}$ alkyl group, and preferably a branched $C_{4-10}$ alkyl group, e.g. t-butyl, —CH$_2$—CH(CH$_3$)$_2$ or a cyclic alkyl group, such as cyclohexyl or adamantyl. Of these the cyclic groups are more preferred, with adamantyl being the most preferred.

When A is a five membered ring:
(i) $R^3$ (if present) is preferably selected from H and optionally substituted $C_{1-4}$ alkyl (in particular, methyl) and is most preferably H; and
(ii) $R^4$ is preferably selected from H and optionally substituted $C_{1-4}$ alkyl (in particular, methyl) and is most preferably H.

When A is a six-membered ring, it is preferred that either:
(i) $R^3$, $R^4$ and $R^6$ (if present) are H; or
(ii) one of $R^3$, $R^4$ and $R^6$ (if present) are Cl or F.

One preferred option when A is:

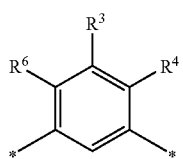

is for $R^4$ to be F.

A is preferably selected from:

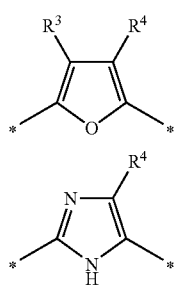

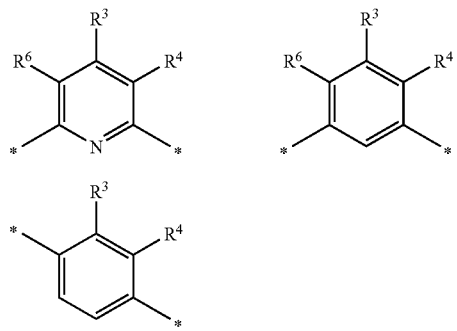

and is more preferably selected from:

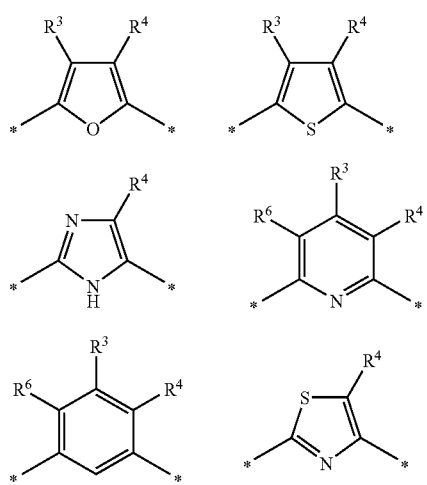

A is most preferably selected from:

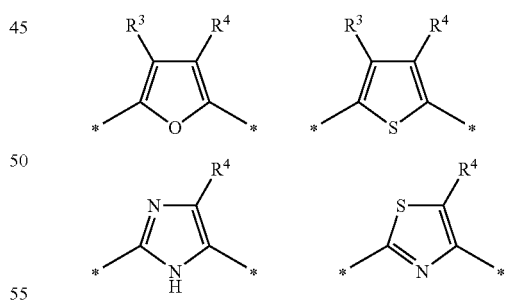

The most preferred option for A is:

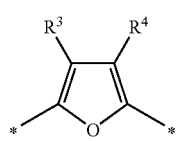

D is preferably selected from:

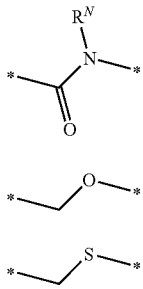

(i)

(ii)

(iii)

and is more preferably:

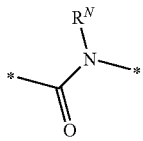

$R^N$ is preferably H or methyl, and is more preferably H.
B is preferably:

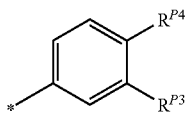 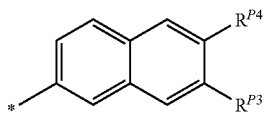

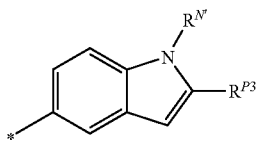

and more preferably:

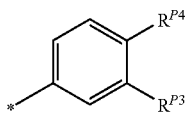

$R^2$ is preferably carboxy or tetrazoly-5-yl, with carboxy being most preferred.

When $R^{P4}$ is H, $R^{P3}$ is preferably —CH=CH—$R^2$.

In some embodiments, m and n can only be 0 or 1, and m+n can only be 1 or 2. In these embodiments, preferably n+m=1, and more preferably n is 0 and m is 1.

In other embodiments, it is preferred that n is 0, and one of $R^{P3}$ and $R^{P4}$ (preferably $R^{P3}$) is —O—CH$_2$—$R^2$, wherein $R^2$ is preferably carboxy or tetrazol-5-yl, more preferably carboxy.

In some embodiments, the compound is of formula (Ia):

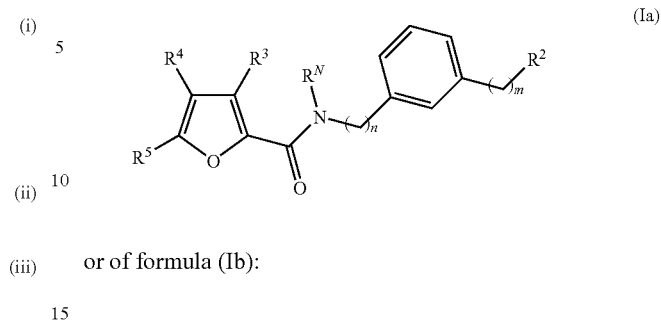

(Ia)

or of formula (Ib):

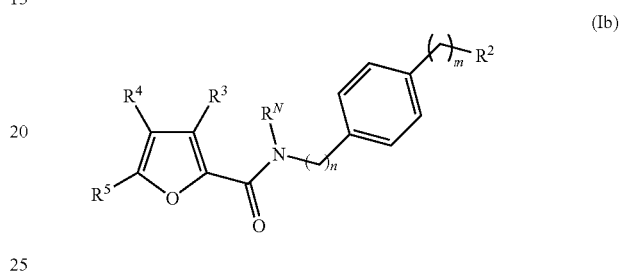

(Ib)

Particularly preferred compounds of the present invention include:
{4-[(5-Phenyl-furan-2-carbonyl)-amino]-phenyl}-acetic acid (2);
4-{[(5-Phenyl-furan-2-carbonyl)-amino]-methyl}-benzoic acid (4);
4-{[(5-Phenyl-furan-2-carbonyl)-amino]-methyl}-benzoic acid (10);
(3-[(5-(4-Methoxy-phenyl)-furan-2-carbonyl)-amino]-phenyl)-acetic acid (12);
(3-[(5-(4-Dimethylamino-phenyl)-furan-2-carbonyl)-amino]-phenyl)-acetic acid (14); and
3-{4-[(5-Phenyl-furan-2-carbonyl)-amino]-phenyl}-propionic acid (16).

Further particularly preferred compounds of the invention include:
(3-{[5-(2-Methoxy-phenyl)-furan-2-carbonyl]-amino}-phenyl)-acetic acid (17);
(3-{[5-(3-Methoxy-phenyl)-furan-2-carbonyl]-amino}-phenyl)-acetic acid (18);
(3-{[5-(3-Acetyl-phenyl)-furan-2-carbonyl]-amino}-phenyl)-acetic acid (19);
(3-{[5-(4-Acetyl-phenyl)-furan-2-carbonyl]-amino}-phenyl)-acetic acid (20);
(3-{[5-(3-Methyl-phenyl)-furan-2-carbonyl]-amino}-phenyl)-acetic acid (21);
(3-{[5-(4-Methyl-phenyl)-furan-2-carbonyl]-amino}-phenyl)-acetic acid (22);
(3-{[5-(2-Trifluoromethyl-phenyl)-furan-2-carbonyl]-amino}-phenyl)-acetic acid (23);
(3-{[5-(3-Trifluoromethyl-phenyl)-furan-2-carbonyl]-amino}-phenyl)-acetic acid (24);
(3-{[5-(2,4-Dichloro-phenyl)-furan-2-carbonyl]-amino}-phenyl)-acetic acid (25);
(3-{[5-(3,5-Dichloro-phenyl)-furan-2-carbonyl]-amino}-phenyl)-acetic acid (26);
(3-{[5-(3,4-Dichloro-phenyl)-furan-2-carbonyl]-amino}-phenyl)-acetic acid (27);
(3-{[5-(2-Methyl-phenyl)-furan-2-carbonyl]-amino}-phenyl)-acetic acid (28);
(3-{[5-(4-Methoxy-phenyl)-furan-2-carbonyl]-amino}-phenyl)-acetic acid (29);

(3-{[5-(2-Chloro-phenyl)-furan-2-carbonyl]-amino}-phenyl)-acetic acid (30);
{3-[(5-Naphthalen-1-yl-furan-2-carbonyl)-amino]-phenyl}-acetic acid (31);
(3-{[5-(3-Trifluoromethoxy-phenyl)-furan-2-carbonyl]-amino}-phenyl)-acetic acid (32);
(3-{[5-(4-Trifluoromethoxy-phenyl)-furan-2-carbonyl]-amino}-phenyl)-acetic acid (33);
(3-{[5-(3-Isopropyl-phenyl)-furan-2-carbonyl]-amino}-phenyl)-acetic acid (34);
(3-{[5-(4-Isopropyl-phenyl)-furan-2-carbonyl]-amino}-phenyl)-acetic acid (35);
{3-[(5-Benzo[1,3]dioxol-5-yl-furan-2-carbonyl)-amino]-phenyl}-acetic acid (36);
(3-{[5-(2,3-Dichloro-phenyl)-furan-2-carbonyl]-amino}-phenyl)-acetic acid (37);
{3-[([2,2']Bifuranyl-5-carbonyl)-amino]-phenyl}-acetic acid (38);
(3-{[5-(3-Chloro-phenyl)-furan-2-carbonyl]-amino}-phenyl)-acetic acid (39);
(3-{[5-(4-Chloro-phenyl)-furan-2-carbonyl]-amino}-phenyl)-acetic acid (40);
3-{[5-(1H-Indol-5-yl)-furan-2-carbonyl]-amino}-phenyl)-acetic acid (41);
(3-{[5-(4-Fluoro-phenyl)-furan-2-carbonyl]-amino}-phenyl)-acetic acid (42);
{3-[(5-Phenyl-thiophene-2-carbonyl)-amino]-phenyl}-acetic acid (43);
{3-[(4-Chloro-biphenyl-3-carbonyl)-amino]-phenyl}-acetic acid (44);
{3-[(6-Phenyl-pyridine-2-carbonyl)-amino]-phenyl}-acetic acid (45);
{3-[(6-Fluoro-biphenyl-3-carbonyl)-amino]-phenyl}-acetic acid (46);
{3-[(3-Methyl-biphenyl-4-carbonyl)-amino]-phenyl}-acetic acid (47);
{3-[(3-Chloro-biphenyl-4-carbonyl)-amino]-phenyl}-acetic acid (48)
{3-[(Biphenyl-3-carbonyl)-amino]-phenyl}-acetic acid (49);
{3-[(4-Methyl-5-phenyl-thiophene-2-carbonyl)-amino]-phenyl}-acetic acid (50);
{3-[(4-Fluoro-biphenyl-3-carbonyl)-amino]-phenyl}-acetic acid (51);
({3-[(5-Fluoro-biphenyl-3-carbonyl)-amino]-phenyl}-acetic acid (52);
{3-[(2-Phenyl-1H-imidazole-5-carbonyl)-amino]-phenyl}-acetic acid (53);
{3-[(2-Phenyl-thiazole-4-carbonyl)-amino]-phenyl}-acetic acid (54);
3-{[(5-Phenyl-furan-2-carbonyl)-amino]-methyl}-benzoic acid (57);
5-[(5-Phenyl-furan-2-carbonyl)-amino]-1H-indole-2-carboxylic acid (59);
3-{3-[(5-Phenyl-furan-2-carbonyl)-amino]-phenyl}-acrylic acid (61);
3-{3-[(5-Phenyl-furan-2-carbonyl)-amino]-phenyl}-propionic acid (62);
6-[(5-Phenyl-furan-2-carbonyl)-amino]-naphthalene-2-carboxylic acid (63);
(3-{[5-(3-Chloro-phenyl)-furan-2-carbonyl]-amino}-phenoxy)-acetic acid (66);
(3-{[5-(3,5-Dichloro-phenyl)-furan-2-carbonyl]-amino}-phenoxy)-acetic acid (68);
3-(3-{[5-(3-Chloro-phenyl)-furan-2-carbonyl]-amino}-phenyl)-acrylic acid (69);
3-(3-{[5-(3,5-Dichloro-phenyl)-furan-2-carbonyl]-amino}-phenyl)-acrylic acid (70);
3-(3-{[5-(4-Fluoro-phenyl)-furan-2-carbonyl]-amino}-phenyl)-acrylic acid (71);
5-{[5-(3-Chloro-phenyl)-furan-2-carbonyl]-amino}-1H-indole-2-carboxylic acid (72);
5-Phenyl-furan-2-carboxylic acid (3-carbamoylmethyl-phenyl)-amide (73);
Phenyl-furan-2-carboxylic acid [3-(2-hydroxy-ethyl)-phenyl]-amide (74); and
5-Phenyl-furan-2-carboxylic acid [3-(1H-tetrazol-5-ylmethyl)-phenyl]-amide (75).
Further particularly preferred compounds of the invention include:
5-Phenyl-furan-2-carboxylic acid [3-(1H-tetrazol-5-yl)-phenyl]-amide (177);
5-(3-Chloro-phenyl)-furan-2-carboxylic acid [3-(1H-tetrazol-5-ylmethyl)-phenyl]-amide (81);
5-(3,5-Dichloro-phenyl)-furan-2-carboxylic acid [3-(1H-tetrazol-5-ylmethyl)-phenyl]-amide (82);
5-(4-Fluoro-phenyl)-furan-2-carboxylic acid [3-(1H-tetrazol-5-ylmethyl)-phenyl]-amide (85);
5-(3-Fluoro-phenyl)-furan-2-carboxylic acid [3-(1H-tetrazol-5-ylmethyl)-phenyl]-amide (86);
5-(4-Chloro-phenyl)-furan-2-carboxylic acid [3-(1H-tetrazol-5-ylmethyl)-phenyl]-amide (87);
5-Phenyl-furan-2-carboxylic acid {3-[2-(1H-tetrazol-5-yl)-vinyl]-phenyl}-amide (89);
5-(3-Chloro-phenyl)-furan-2-carboxylic acid {3-[2-(1H-tetrazol-5-yl)-vinyl]-phenyl}-amide (90);
6-Phenyl-pyridine-2-carboxylic acid [3-(1H-tetrazol-5-ylmethyl)-phenyl]-amide (92);
6-(4-Fluoro-phenyl)-pyridine-2-carboxylic acid [3-(1H-tetrazol-5ylmethyl)-phenyl]-amide (93);
6-(3-Fluoro-phenyl)-pyridine-2-carboxylic acid [3-(1H-tetrazol-5ylmethyl)-phenyl]-amide (94);
6-(4-Chloro-phenyl)-pyridine-2-carboxylic acid [3-(1H-tetrazol-5ylmethyl)-phenyl]-amide (95);
5-[(5-Phenyl-furan-2-carbonyl)-amino]-benzofuran-2-carboxylic acid (96);
5-[(5-Phenyl-furan-2-carbonyl)-amino]-benzo[b]thiophene-2-carboxylic acid (97);
2-{3-[(5-Phenyl-furan-2-carbonyl)-amino]-benzylidene}-butyric acid (98);
3-(3-{[5-(3-Fluoro-phenyl)-furan-2-carbonyl]-amino}-phenyl)-acrylic acid (100);
3-{3-[(5-Benzo[1,3]dioxol-5-yl-furan-2-carbonyl)-amino]-phenyl}-acrylic acid (101);
3-(3-{[5-(3,5-Bis-trifluoromethyl-phenyl)-furan-2-carbonyl]-amino}phenyl)-acrylic acid (102);
3-{3-[(5-Biphenyl-3-yl-furan-2-carbonyl)-amino]-phenyl}-acrylic acid (103);
3-(3-{[5-(3-Benzyloxy-phenyl)-furan-2-carbonyl]-amino}-phenyl)-acrylic acid (104);
3-(3-{[5-(2-Fluoro-biphenyl-4-yl)-furan-2-carbonyl]-amino}-phenyl)-acrylic acid (105);
3-{3-[(4-Fluoro-biphenyl-3-carbonyl)-amino]-phenyl}-acrylic acid (107);
3-{3-[(4,3'-Difluoro-biphenyl-3-carbonyl)-amino]-phenyl}-acrylic acid (108);
3-(3-{[6-(3-Fluoro-phenyl)-pyridine-2-carbonyl]-amino}-phenyl)-acrylic acid (110);
3-[(4,3'-Difluoro-biphenyl-3-carbonyl)-amino]-phenyl}-acetic acid (111);
3-{3-[(4,4'-Difluoro-biphenyl-3-carbonyl)-amino]-phenyl}-acrylic acid (112);
(3-{[6-(3-Fluoro-phenyl)-pyridine-2-carbonyl]-amino}-phenyl)-acetic acid (113);

3-{3-[(2-Phenyl-thiazole-4-carbonyl)-amino]-phenyl}-acrylic acid (115);
3-(3-{[2-(3-Fluoro-phenyl)-thiazole-4-carbonyl]-amino}-phenyl)-acrylic acid (116);
[3-(Biphenyl-3-ylcarbamoyl)-phenyl]-acetic acid (117);
1-Methyl-5-[(5-phenyl-furan-2-carbonyl)-amino]-1H-indole-2-carboxylic acid (118);
3-{3-[2-Oxo-2-(5-phenyl-furan-2-yl)-ethyl]-phenyl}-acrylic acid (120);
3-[3-(2-Phenyl-thiazol-4-ylmethoxy)-phenyl]-acrylic acid (121);
3-[3-(2-Phenyl-thiazol-4-ylmethylsulfanyl)-phenyl]-acrylic acid (122);
3-{3-[(5-Adamantan-1-yl-furan-2-carbonyl)-amino]-phenyl}-acrylic acid (123);
3-(3-{[5-(3-Chloro-phenyl)-furan-2-carbonyl]-amino}-phenyl)-propionic acid (125);
3-(3-{[5-(3,5-Dichloro-phenyl)-furan-2-carbonyl]-amino}-phenyl)-propionic acid (126);
(3-{[5-(3,5-Difluoro-phenyl)-furan-2-carbonyl]-amino}-phenyl)-acetic acid (127);
(3-{[5-(3-fluoro-phenyl)-furan-2-carbonyl]-amino}-phenyl)-acetic acid (128);
(3-{[6-(3-Chloro-phenyl)-pyridine-2-carbonyl]-amino}-phenyl)-acetic acid (129);
(3-{[6-(3,5-Dichloro-phenyl)-pyridine-2-carbonyl]-amino}-phenyl)-acetic acid (130);
3-(3-{[6-(3,5-Dichloro-phenyl)-pyridine-2-carbonyl]-amino}-phenyl)-acrylic acid (132);
(3-{[6-(3,5-Dichloro-phenyl)-pyridine-2-carbonyl]-amino}-phenoxy)-acetic acid (133);
3-(3-{[6-(3,5-Dichloro-phenyl)-pyridine-2-carbonyl]-amino}-phenyl)-propionic acid (134);
5-{[6-(3,5-Dichloro-phenyl)-pyridine-2-carbonyl]-amino}-1H-indole-2-carboxylic acid (135);
3-(3-{[6-(3-Chloro-phenyl)-pyridine-2-carbonyl]-amino}-phenyl)-acrylic acid (137);
(3-{[6-(3-Chloro-phenyl)-pyridine-2-carbonyl]-amino}-phenoxy)-acetic acid (138);
{3-[(3'-Chloro-4-fluoro-biphenyl-3-carbonyl)-amino]-phenoxy}-acetic acid (140);
3-{3-[(3'-Chloro-4-fluoro-biphenyl-3-carbonyl)-amino]-phenyl}-acrylic acid (142);
{3-[(3',5'-Dichloro-4-fluoro-biphenyl-3-carbonyl)-amino]-phenoxy}-acetic acid (143);
3-{3-[(3',5'-Dichloro-4-fluoro-biphenyl-3-carbonyl)-amino]-phenyl}-acrylic acid (144);
3-(3-{[5-(4-Chloro-phenyl)-furan-2-carbonyl]-amino}-phenyl)-acrylic acid (146);
3-(3-{[5-(4-Chloro-phenyl)-furan-2-carbonyl]-amino}-phenyl)-propionic acid (147);
3-(3-{[5-(4-Fluoro-phenyl)-furan-2-carbonyl]-amino}-phenyl)-propionic acid (148);
(3-{[6-(4-Chloro-phenyl)-pyridine-2-carbonyl]-amino}-phenyl)-acetic acid (150);
3-(3-{[6-(4-Chloro-phenyl)-pyridine-2-carbonyl]-amino}-phenyl)-acrylic acid (151);
(3-{[6-(4-Fluoro-phenyl)-pyridine-2-carbonyl]-amino}-phenyl)-acetic acid (153);
(3-{[6-(4-Chloro-phenyl)-pyridine-2-carbonyl]-amino}-phenoxy)-acetic acid (154);
3-(3-{[6-(4-Fluoro-phenyl)-pyridine-2-carbonyl]-amino}-phenyl)-acrylic acid (155);
(3-{[5-(4-Chloro-phenyl)-furan-2-carbonyl]-amino}-phenoxy)-acetic acid (156);
(3-{[5-(4-Fluoro-phenyl)-furan-2-carbonyl]-amino}-phenoxy)-acetic acid (157);
(3-{[6-(4-Fluoro-phenyl)-pyridine-2-carbonyl]-amino}-phenoxy)-acetic acid (158);
3-(3-{[6-(4-Fluoro-phenyl)-pyridine-2-carbonyl]amino}-phenyl)-propionic acid (159);
{3-[(5-Phenyl-furan-2-carbonyl)-amino]-phenoxy}-acetic acid (160);
3-(3-{[6-(3-Fluoro-phenyl)-pyridine-2-carbonyl]-amino}-phenyl)-propionic acid (162);
3-(3-{[5-(3-Fluoro-phenyl)-furan-2-carbonyl]-amino}-phenyl)-propionic acid (163);
3-{3-[(6-Phenyl-pyridine-2-carbonyl)-amino]-phenyl}-propionic acid (164);
3-[(4-Fluoro-biphenyl-3-carbonyl)-amino]-phenoxy}-acetic acid (165);
3-{3-[(6-Phenyl-pyridine-2-carbonyl)-amino]-phenyl}-propionic acid (167);
(3-{[5-(3-Fluoro-phenyl)-furan-2-carbonyl]-amino}-phenoxy)-acetic acid (168);
{3-[(4,3'-Difluoro-biphenyl-3-carbonyl)-amino]-phenoxy}-acetic acid (169);
(3-{[6-(3-Fluoro-phenyl)-pyridine-2-carbonyl]-amino}-phenoxy)-acetic acid (170);
{3-[(4,4'-Difluoro-biphenyl-3-carbonyl)-amino]-phenoxy}-acetic acid (171);
5-Phenyl-furan-2-carboxylic acid [3-(1H-tetrazol-5-ylmethoxy)-phenyl]-amide (173);
6-Phenyl-pyridine-2-carboxylic acid [3-(1H-tetrazol-5-ylmethoxy)-phenyl]-amide (174);
6-Phenyl-pyridine-2-carboxylic acid {3-[2-(1H-tetrazol-5-yl)-vinyl]phenyl}-amide (175); and
4-Fluoro-biphenyl-3-carboxylic acid {3-[2-(1H-tetrazol-5-yl)-vinyl]phenyl}-amide (176).

The selectivity of the compound for modulating $EP_2$ receptors over one or more of the other EP receptors (i.e. $EP_1$, $EP_3$, $EP_4$) can be quantified by dividing the Ki for $EP_2$ (see below) by the Ki for the other EP receptors (see below). The resulting ratio is preferably 10 or more, more preferably 100 or more.

SYNTHESIS EXAMPLES

General Experimental Details

Petroleum ether refers to that fraction with a boiling point of 40-60° C.

Organic solutions were dried over magnesium sulphate unless otherwise specified.

General Experimental Details for Examples 1 to 5

All reactions were carried out under an inert atmosphere of nitrogen.

PS-TsCl refers to Polystyrene scavenger resin (loading 1.97 mmol/g)—Argonaut Technologies (P/N 800277)

LC/MS Systems

The Liquid Chromatography Mass Spectroscopy (LC/MS) systems used are as follows.

LC/MS System A:
  Mass Spectrometer—Platform LC with electrospray source operating in positive and negative ion mode. HP1100 system running at 2.0 mL/min, 200 μL/min split to the ESI source with inline HP1100 DAD detection and SEDEX ELS detection.
  Mobile Phase
  A) Water 0.1% Formic Acid
  B) acetonitrile 0.1% Formic Acid

| Gradient | | | |
|---|---|---|---|
| Time (min) | Flow (mL/min) | % A | % B |
| 0.00 | 2.0 | 95 | 5 |
| 0.50 | 2.0 | 95 | 5 |
| 4.50 | 2.0 | 5 | 95 |
| 5.00 | 2.0 | 5 | 95 |
| 5.50 | 2.0 | 95 | 5 |

Column—Luna 3u C18(2) 30×4.6 mm

LC/MS System B:
Mass Spectrometer—Platform II with electrospray source operating in negative ion mode. HP1100 system running at 2.0 mL/min, 200 μL/min split to the ESI source with inline HP1100 DAD detection and SEDEX ELS detection.
Mobile Phase
A) Water 0.1% Diethylamine
B) acetonitrile

| Gradient | | | |
|---|---|---|---|
| Time (min) | Flow (mL/min) | % A | % B |
| 0.00 | 2.0 | 95 | 5 |
| 0.50 | 2.0 | 95 | 5 |
| 4.00 | 2.0 | 5 | 95 |
| 4.50 | 2.0 | 5 | 95 |
| 5.00 | 2.0 | 95 | 5 |
| 20.00 | 2.0 | 95 | 5 |

Column—Xterra MS C18 3.5 μm 4.6×30 mm

LCMS System C:
Mass Spectrometer—Finnigan TSQ700 with electrospray source operating in negative ion mode.
HP1050 system running at 2.0 mL/min, 200 μL/min split to the ESI source with inline HP1050 Single wavelength UV detector at 254 nm.
Mobile Phase
A) Water 0.1% Diethylamine
B) acetonitrile

| Gradient | | | |
|---|---|---|---|
| Time (min) | Flow (mL/min) | % A | % B |
| 0.00 | 2.0 | 95 | 5 |
| 1.00 | 2.0 | 95 | 5 |
| 15.00 | 2.0 | 5 | 95 |
| 17.00 | 2.0 | 5 | 95 |
| 18.00 | 2.0 | 95 | 5 |
| 20.00 | 2.0 | 95 | 5 |

Column—Xterra MS C18 3.5 μm 4.6×30 mm

LC/MS System D:
Mass Spectrometer—Finnigan TSQ700 with electrospray source operating in positive or negative ion mode. HP1050 system running at 2.0 mL/min, 200 μL/min split to the ESI source with inline HP1050 Single Wavelength UV detector at 254 nm.
Mobile Phase
A) Water 0.1% formic Acid
B) acetonitrile 0.1% formic Acid

| Gradient | | | |
|---|---|---|---|
| Time (min) | Flow (mL/min) | % A | % B |
| 0.00 | 2.0 | 95 | 5 |
| 1.00 | 2.0 | 95 | 5 |
| 15.00 | 2.0 | 5 | 95 |
| 17.00 | 2.0 | 5 | 95 |
| 18.00 | 2.0 | 95 | 5 |
| 20.00 | 2.0 | 95 | 5 |

Column—Higgins Clipius C18 5 μm 100×3.0 mm

Example 1

Synthesis of {4-[(5-Phenyl-furan-2-carbonyl)-amino]-phenyl}-acetic acid (2)

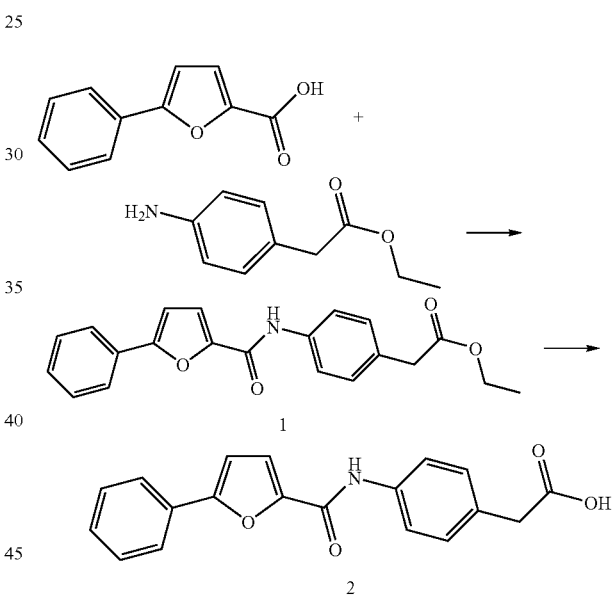

(a) {4-[(5-phenyl-furan-2-carbonyl)-amino]-phenyl}-acetic acid ethyl ester (1)

Diisopropylethylamine (300 μl) was added to a stirred solution of 5-phenyl-furan-2-carboxylic acid (73.5 mg, 0.39 mmol) and ethyl-4-aminophenyl acetate (70 mg, 0.39 mmoles) in N,N-dimethylformamide (10 ml). O-(7-Azabenzotriazol-1-yl)-N,N,N',N'-tetramethyluronium hexafluorophosphate (200 mg, 0.52 mmoles) was added and the solution was stirred at room temperature for 72 hours. The solvent was evaporated, the residue was dissolved in dichloromethane and washed with water, 10% aqueous sodium carbonate, 1 M aqueous hydrochloric acid and finally dried (MgSO$_4$). After evaporation of the solvent, the residue was triturated with cyclohexane and dried to afford (1) (82 mg) as a gum. LC/MS System A; R$_t$=3.80 mins, m/z (ES$^+$)=350 (M+H for $C_{21}H_{19}NO_4$).

(b) {4-[(5-Phenyl-furan-2-carbonyl)-amino]-phenyl}-acetic acid (2)

A solution of sodium hydroxide (100 mg) in water (5 ml) was added to a stirred solution of {4-[(5-phenyl-furan-2-carbonyl)-amino]-phenyl}-acetic acid ethyl ester (1) (75 mg, 0.214 mmoles) in ethanol (10 ml) and the mixture was stirred at room temperature for 1 hour. The solvent was evaporated and the residue was diluted with water (10 ml) and acidified to pH=2 with 1 M aqueous hydrochloric acid. The precipitate was collected, washed with water and the residue was triturated with cyclohexane to afford (2) (61.5 mg) as a white solid. LC/MS System D; $R_t$=3.01 mins, m/z (ES−)=320 (M−H for $C_{19}H_{15}NO_4$).

Example 2

Synthesis of 4-{[(5-Phenyl-furan-2-carbonyl)-amino]-methyl}-benzoic acid (4)

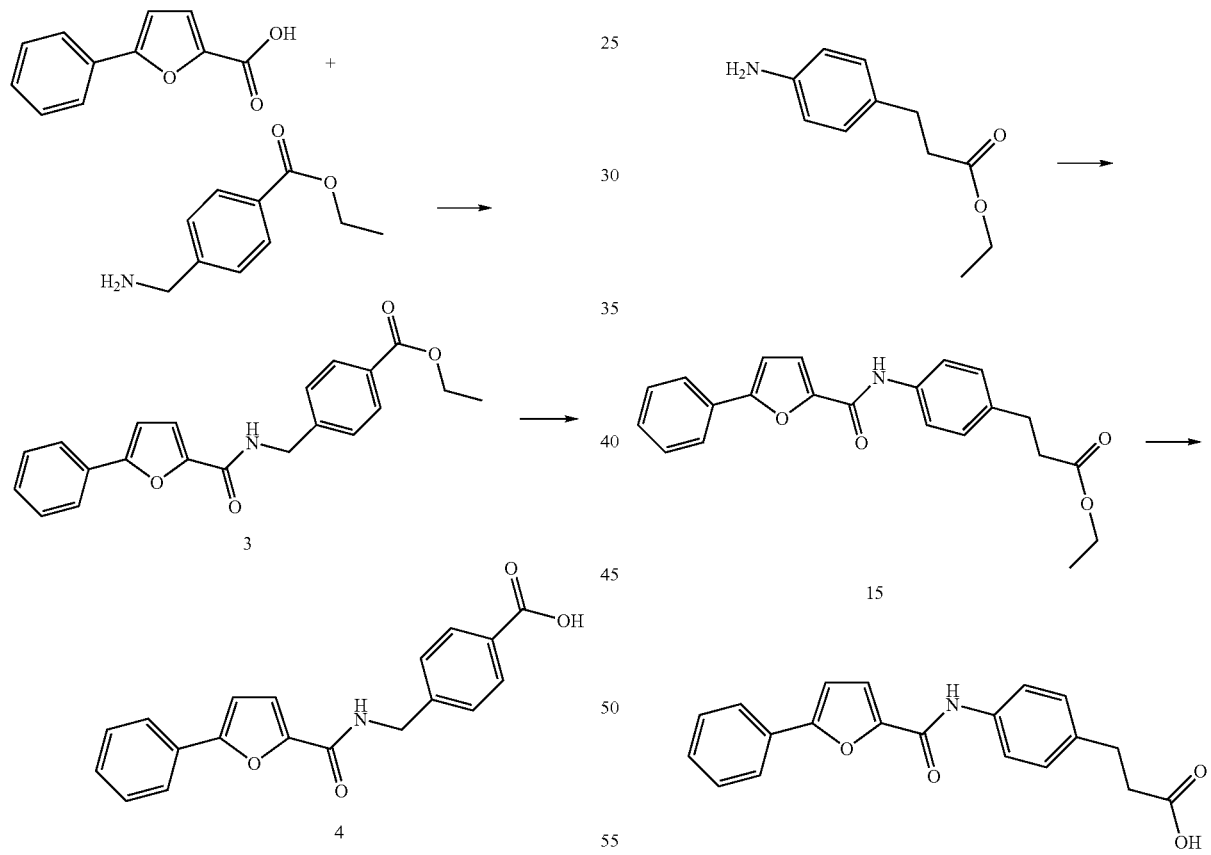

(a) 4-{[(5-Phenyl-furan-2-carbonyl)-amino]-methyl}-benzoic acid ethyl ester (3)

In an analogous manner to Example 1(a), compound (3) was synthesised from 5-phenyl-furan-2-carboxylic acid (73.5 mg, 0.39 mmol) and 4-aminomethyl-benzoic acid ethyl ester (70 mg, 0.39 mmoles). 80 mg of the product was obtained as a gum. LC/MS System A; $R_t$=3.69 mins, m/z (ES+)=350 (M+H for $C_{21}H_{19}NO_4$).

(b) 4-{[(5-Phenyl-furan-2-carbonyl)-amino]-methyl}-benzoic acid (4)

In an analogous manner to Example 1(b), compound (4) was synthesised from compound (3) (72 mg, 0.206 mmoles). 51 mg of the product was obtained as a white solid. LC/MS System C; $R_t$=2.74 mins, m/z (ES−)=320 (M−H for $C_{19}H_{15}NO_4$).

Example 3

Synthesis of 3-{4-[(5-Phenyl-furan-2-carbonyl)-amino]-phenyl}-propionic acid (16)

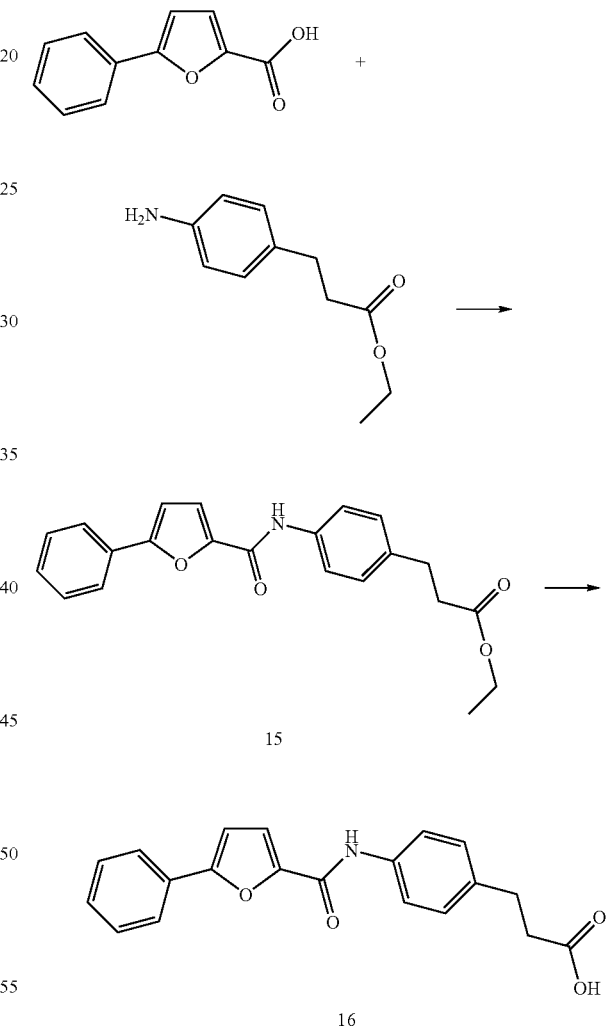

(a) 3-{4-[(5-Phenyl-furan-2-carbonyl)-amino]-phenyl}-propionic acid ethyl ester (15)

In an analogous manner to Example 2(a), compound (15) was synthesised from 5-phenyl-furan-2-carboxylic acid and 3-(4-amino-phenyl)-propionic acid ethyl ester.

(b) 3-{4-[(5-Phenyl-furan-2-carbonyl)-amino]-phenyl}-propionic acid (16)

In an analogous manner to Example 2(b), compound (16) was synthesised from compound (15).

Example 4

Synthesis of 4-{[(5-Phenyl-furan-2-carbonyl)-amino]-methyl}-benzoic acid (10)

(a) Ethyl-3-aminophenyl acetate (6)

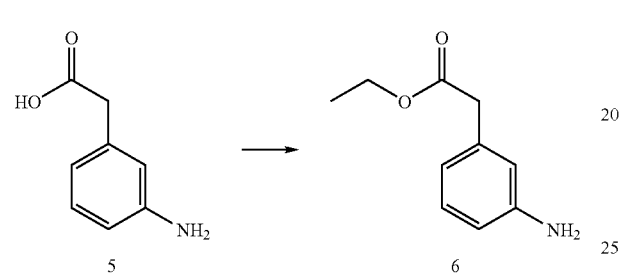

A stirred solution of 3-aminophenyl acetic acid (1 g, 6.6 mmoles) (5) and conc. sulphuric acid (2 ml) in ethanol (20 ml) was refluxed for 3 hours. The solvent was evaporated and the residue dissolved in ethyl acetate, washed with water, sodium carbonate, brine, water, and finally dried ($MgSO_4$). After concentrating in vacuo (6) (918 mg) was obtained as dark red oil.

(b) 5-phenyl-furan-2-carboxylic acid methyl ester (7)

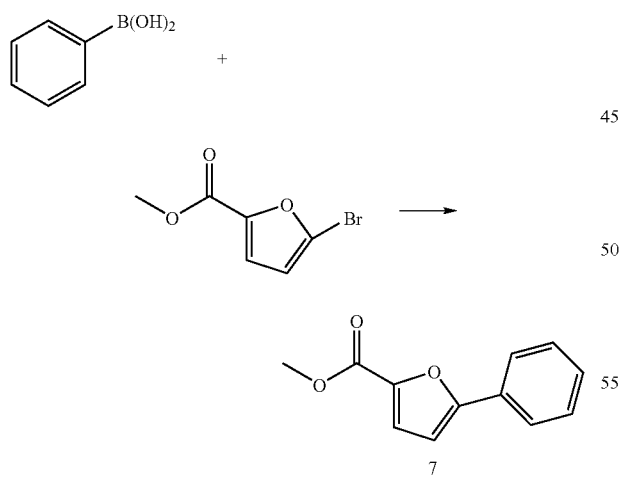

A mixture of methyl 5-bromofuroate (1 g, 5 mmoles), phenylboronic acid (1 g, 8.2 mmoles), tetrakis(triphenylphosphine)palladium(0) (0.2 g, 0.17 mmoles), sodium carbonate (1.5 g, 17.4 mmoles) in toluene (100 ml) was refluxed for 16 hours. After cooling, the solvent was evaporated and the yellow residue was partioned between water (50 ml) and ethyl acetate (50 ml). The aqueous layer was extracted with ethyl acetate (3×30 ml) and the combined organic layers washed with water (1×30 ml) and dried ($MgSO_4$). The residue was purified by flash chromatography (20% ethyl acetate/70% cyclohexane and 10% diethyl ether/90% cyclohexane) to afford (7) (384 mg). This ester was used directly in the next step.

(c) 5-phenyl-furan-2-carboxylic acid (8)

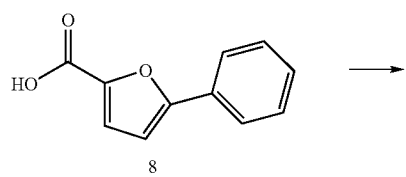

A solution of sodium hydroxide (200 mg) in water (5 ml) was added to a stirred solution of 5-phenyl-furan-2-carboxylic acid methyl ester (7) (384 mg, 1.90 mmoles) in methanol (20 ml) and the mixture was stirred at room temperature for 4 hours. The solvent was evaporated and the residue was diluted with water (10 ml) and acidified to pH=2 with 1 M aqueous hydrochloric acid. The precipitate was collected, washed with water and the residue was triturated with cyclohexane to afford (8) (350 mg) as a white solid. LC/MS System A; $R_t$=3.89 mins.

(d) {3-[(5-Phenyl-furan-2-carbonyl)-amino]-phenyl}-acetic acid ethyl ester (9)

-continued

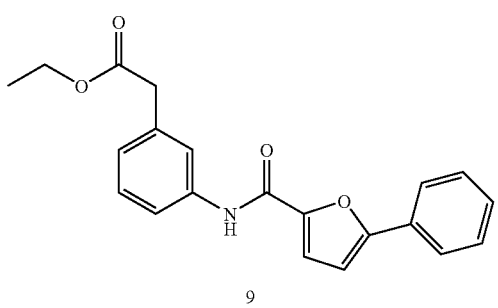

In an analogous manner to Example 1(a), compound (9) was synthesised from 5-phenyl-furan-2-carboxylic acid (8) (73.5 mg, 0.390 mmoles) and ethyl-3-aminophenyl acetate (6) (70 mg, 0.390 mmoles). 80 mg of the product was obtained as a gum. LC/MS System D; $R_t$=3.83 mins, m/z (ES$^+$)=350 (M+H for $C_{21}H_{19}NO_4$).

(e) (3-[(5-Phenyl-furan-2-carbonyl)-amino]-phenyl)-acetic acid (10)

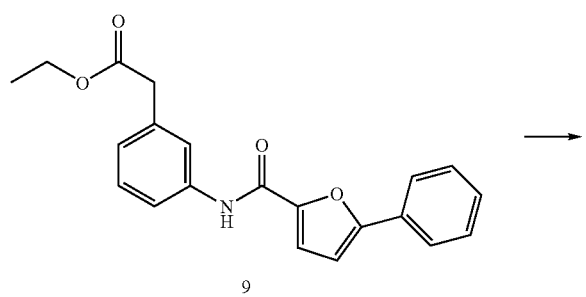

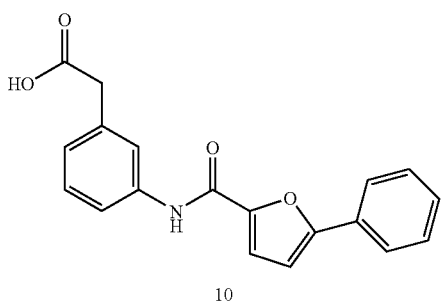

In an analogous manner to Example 1(b), compound (10) was synthesised from compound (9) (70 mg, 0.200 mmoles). 44 mg of the product was obtained as a white solid. LC/MS System D; $R_t$=2.90 mins, m/z (ES$^-$)=320 (M−H for $C_{19}H_{15}NO_4$).

Example 5

Synthesis of (3-[(5-(4-Methoxy-phenyl)-furan-2-carbonyl)-amino]-phenyl)-acetic acid (12) and (3-[(5-(4-Dimethylamino-phenyl)-furan-2-carbonyl)-amino]-phenyl)-acetic acid (14)

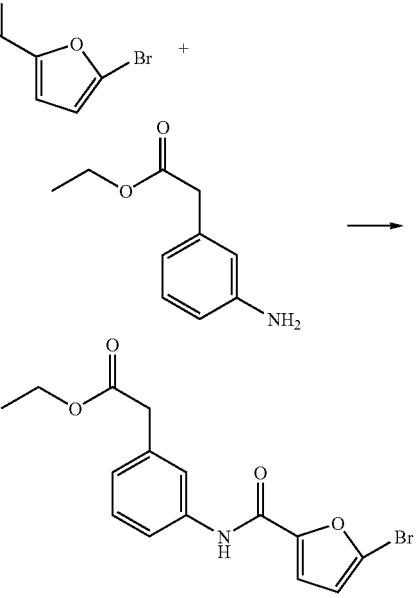

(a) (3-[(5-Bromo-furan-2-carbonyl)-amino]-phenyl)-acetic acid ethyl ester (11)

To a solution of 5-bromo-2-furoic acid (1.14 g) and 3-aminophenylacetic acid ethyl ester (1.06 g) in anhydrous DMF (15 ml) was added diisopropylamine (2.1 ml) and then O-(7-azabenzotriazol-1-yl)-N,N,N',N'-tetramethyluronium hexafluorophosphate (2.25 g). The solution was stirred at room temperature for 16 hours then partitioned between ethyl acetate and water. The organic layer was separated, washed twice with 1M hydrochloric acid, water, aqueous sodium carbonate solution, brine, dried over sodium sulphate and evaporated in vacuo. Compound 11 (1.8 g) was obtained following silica gel column chromatography of the residue in 2:1 ethyl acetate:petroleum ether.

$^1$H NMR (CDCl$_3$, δ): 1.2 (3H, t); 3.65 (2H, s); 4.2 (2H, q); 6.5 (1H, d); 7.1 (1H, d); 7.25 (1H, d); 7.35 (1H, t); 7.6 (2H, c); 8.0 (1H, broad s).

(b) (3-[(5-(4-Methoxy-phenyl)-furan-2-carbonyl)-amino]-phenyl)-acetic acid (12)

(i) To a previously degassed mixture of (3-[(5-bromo-furan-2-carbonyl)-amino]-phenyl)-acetic acid ethyl ester (11) (0.4 g), 4-methoxyphenylboronic acid (0.19 g), potassium carbonate (0.39 g) and tetra-n-butylammonium bromide (0.37 g) in water (2 ml) was added palladium II acetate (circa 10 mg). The mixture was heated to 70° C. for an hour, cooled and partitioned between ethyl acetate and water. The organic layer was separated, washed with brine, dried over sodium sulphate and evaporated in vacuo. (3-[(5-(4-Methoxy-phenyl)-furan-2-carbonyl)-amino]-phenyl)-acetic acid ethyl ester (0.4 g) was obtained following silica gel column chromatography of the residue in 2:1 ethyl acetate:petroleum ether.

(ii) The product of the previous step was hydrolysed in IMS (80 ml) by the addition of a solution of sodium hydroxide (0.65 g) in water (21 ml). The resulting solution was stirred at room temperature for 2 hours then evaporated in vacuo below 40° C. The residue was dissolved in dichloromethane, washed with 2M hydrochloric acid and the aqueous layer back-extracted with dichloromethane. The organic layers were combined, dried over sodium sulphate, filtered and evaporated in vacuo. Compound 12 (0.28 g; m.p. 179-180° C.) was obtained following trituration of the residue in a mixture of dichloromethane and pentane.

$^1$H NMR (d$_6$-DMSO, δ): 3.6 (2H, s); 3.8 (3H, s); 7.0 (4H, c); 7.25 (1H, t); 7.4 (1H, d); 7.65 (2H, c); 7.9 (2H, d); 10.1 (1H, s); 12.4 (1H, broad s); m/z=374.0 (M+Na)$^+$; microanalysis for C$_{20}$H$_{17}$NO$_5$.0.25H$_2$O: C expected 67.50 found 67.46; H expected 4.96 found 4.85; N expected 3.94 found 3.89.

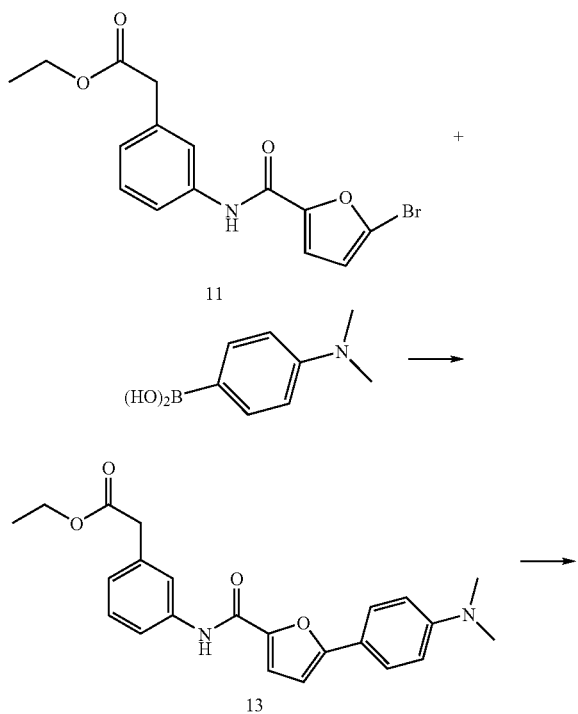

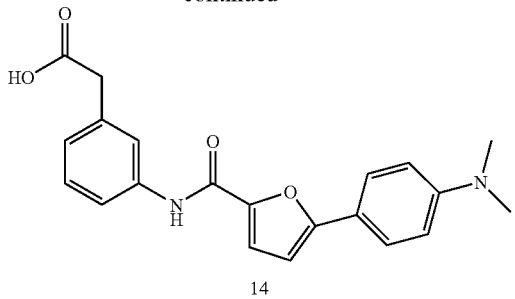

(c) (3-[(5-(4-Dimethylamino-phenyl)-furan-2-carbonyl)-amino]-phenyl)-acetic acid ethyl ester (13)

To a previously degassed mixture of (3-[(5-bromo-furan-2-carbonyl)-amino]-phenyl)-acetic acid ethyl ester (11) (0.4 g), 4-(dimethylamino)phenylboronic acid (0.23 g), potassium carbonate (0.39 g) and tetra-n-butylammonium bromide (0.37 g) in water (2 ml) was added palladium II acetate (circa 10 mg). The mixture was heated to 70° C. for an hour, cooled and partitioned between ethyl acetate and water. The organic layer was separated, washed with brine, dried over sodium sulphate and evaporated in vacuo. Compound 13 (0.33 g) was obtained following silica gel column chromatography of the residue in 2:3 ethyl acetate:petroleum ether.

$^1$H NMR (d$_6$-DMSO, δ): 1.2 (3H, t); 2.95 (6H, s); 3.6 (2H, s); 4.1 (2H, q); 6.75 (2H, d); 6.85 (1H, d); 7.0 (1H, m); 7.3 (1H, t); 7.35 (1H, d); 7.65 (2H, c); 7.8 (2H, d); 10.05 (1H, s).

(d) (3-[(5-(4-Dimethylamino-phenyl)-furan-2-carbonyl)-amino]-phenyl)-acetic acid (14)

To a solution of (3-[(5-(4-dimethylamino-phenyl)-furan-2-carbonyl)-amino]-phenyl)-acetic acid ethyl ester (13) (0.33 g) in IMS (80 ml) was added a solution of sodium hydroxide (0.65 g) in water (21 ml). The resulting solution was stirred at room temperature for 1 hour then concentrated in vacuo below 40° C. to circa 15 ml volume. Water (50 ml) then acetic acid (1.5 ml) were added and the resulting precipitate filtered, washed with water and triturated with dichloromethane/pentane to yield the title compound (0.26 g; m.p. 187-190° C.).

$^1$H NMR (d$_6$-DMSO, δ): 2.95 (6H, s); 3.6 (2H, s); 6.75 (2H, d); 6.85 (1H, d); 7.0 (1H, m); 7.3 (1H, t); 7.35 (1H, d); 7.65 (2H, c); 7.8 (2H, d); 10.05 (1H, s); m/z=387.1 (M+Na)$^+$; microanalysis for C$_{21}$H$_{20}$N$_2$O$_4$.0.2H$_2$O: C expected 68.54 found 68.77; H expected 5.59 found 5.83; N expected 7.61 found 7.26.

General Experimental Details for Examples 6 to 8

Commercially available reagents and solvents (HPLC grade) were used without further purification.

Microwave irradiation was carried out using a CEM Discover focused microwave reactor.

$^1$H NMR spectra were recorded on a Bruker 400 MHz AV spectrometer in deuterated solvents. Chemical shifts (δ) are in parts per million and coupling constants are expressed in Hz. Thin-layer chromatography (TLC) analysis was performed with Kieselgel 60 F$_{254}$ (Merck) plates and visualized using UV light.

Analytical HPLC-MS was performed on Agilent HP1100, Waters 600 or Waters 1525 LC systems using reverse phase Hypersil BDS C18 columns (5 μm, 2.1×50 mm), gradient 0-95% B (A=water/0.1% TFA, B=acetonitrile/0.1% TFA)

over 2.10 min, flow=1.0 ml/min. UV spectra were recorded at 215 nm using a Gilson G1315A Diode Array Detector, G1214A single wavelength UV detector, Waters 2487 dual wavelength UV detector, Waters 2488 dual wavelength UV detector, or Waters 2996 diode array UV detector. Mass spectra were obtained over the range m/z 150 to 850 at a sampling rate of 2 scans per second or 1 scan per 1.2 seconds using Micromass LCT with Z-spray interface or Micromass LCT with Z-spray or MUX interface. Data were integrated and reported using OpenLynx and OpenLynx Browser software.

Purification of compounds by preparative HPLC was performed on Gilson systems using reverse phase ThermoHypersil-Keystone Hyperprep HS C18 columns (12 μm, 100× 21.2 mm), gradient 20-100% B (A=water/0.1% TFA, B=acetonitrile/0.1% TFA) over 9.5 min, flow=30 ml/min, injection solvent 2:1 DMSO:acetonitrile (1.6 ml), UV detection at 215 nm.

Common Methods

In the following examples, the following common methods A to J are employed.

A)

Thionyl chloride (1 eq) was added dropwise to MeOH (15 vol) at 0° C. followed 10 min later by careful addition of a solution of carboxylic acid (1 eq) in MeOH (5 vol) at 0° C. The reaction mixture was allowed to warm to room temperature then stirred for 3 h. The reaction mixture was evaporated in vacuo to give the ester.

B)

A solution of carboxylic acid (1 eq) was heated under reflux for 18 h with $H_2SO_4$ (0.5 vol) in MeOH or EtOH (25 vol). The solvent was evaporated in vacuo and the residue partitioned between DCM and aqueous sodium bicarbonate. The DCM layer was washed with brine, dried ($Na_2SO_4$), filtered and the solvent removed in vacuo to give the ester.

C)
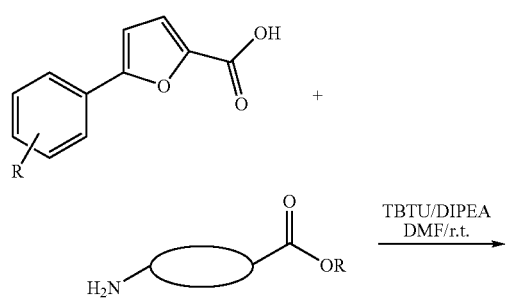

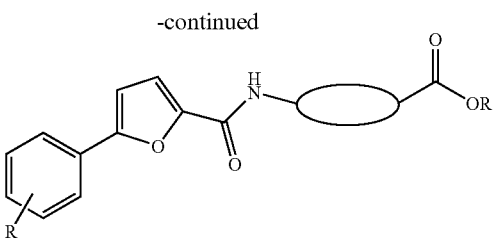

To a stirred solution of carboxylic acid (1 eq) and amino acid ester (1 eq) in DMF (20 vol) was added DIPEA (1 eq) followed by TBTU (1 eq). The reaction was stirred overnight, or until complete by LC/MS, at room temperature. To the reaction mixture was added EtOAc (30 vol) and the organic layer was washed with 2M HCl (2×50 vol), brine (2×50 vol), saturated aqueous $NaHCO_3$ (2×50 vol) and brine (2×50 vol). The organic layer was dried ($MgSO_4$), filtered and the solvent removed in vacuo to give the product.

D)
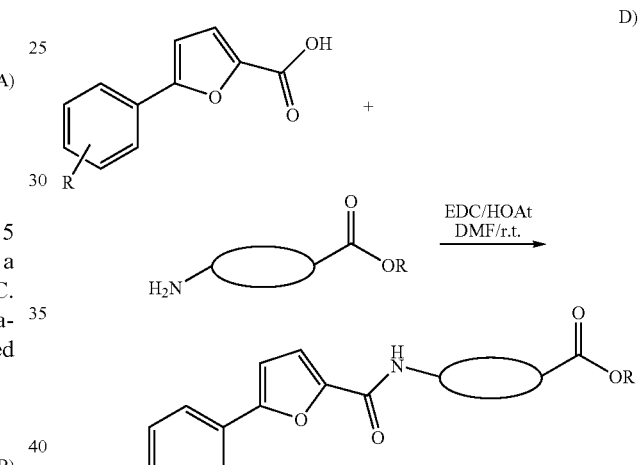

The carboxylic acid (1 eq), EDC (1.2 eq), and HOAt (1.2 eq) were added to a vial as solids. The amino ester was dissolved in DMF (10 vol) and added to the vial. The reaction was stirred at room temperature overnight or until complete by LC/MS. Water (20 vol) was added and the mixture was extracted with and EtOAc (3×10 vol). The organic layer was then washed with water (10 vol), dried ($MgSO_4$), filtered and concentrated in vacuo. Column chromatography using a stepped gradient of EtOAc in heptane gave the product.

E)
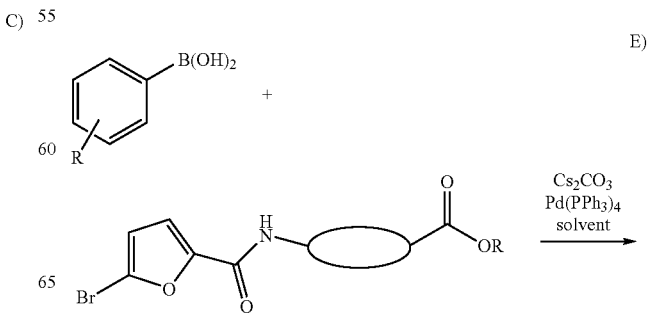

-continued

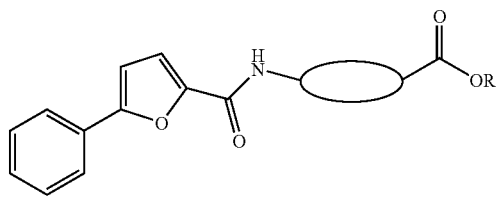

To a suspension of the aryl bromide (1 eq), Cs$_2$CO$_3$ (1.2 eq) and boronic acid (1.1 eq) in toluene (15 vol) and MeOH (4 vol) was added Pd(PPh$_3$)$_4$ (0.1 eq). The resulting mixture was heated in a CEM discover microwave for 30 mins at 120° C. (150 W, 250 psi). Analysis was carried out by LC-MS and, if required, the reaction was heated again to drive the reaction to completion. Once complete, the reaction mixture was filtered through celite and the solvents removed in vacuo. The crude residue was re-dissolved in EtOAc and washed with water (3×5 vol). The combined organic layers were dried (Na$_2$SO$_4$), filtered and the solvents removed in vacuo. The compounds were then purified by column chromatography.

If the ester group present was ethyl ester then EtOH was, used instead of MeOH

E1) In some cases, LC-MS analysis showed that partial hydrolysis occurred during reaction. In this case, after the solvents were removed in vacuo, the residue was re-dissolved in EtOAc (1.5 vol) and the organic layer was washed with 1M HCl (2×1 vol), dried (Na$_2$SO$_4$), filtered and the solvent removed in vacuo. The residue was triturated with TBME (1.5 vol).

F)

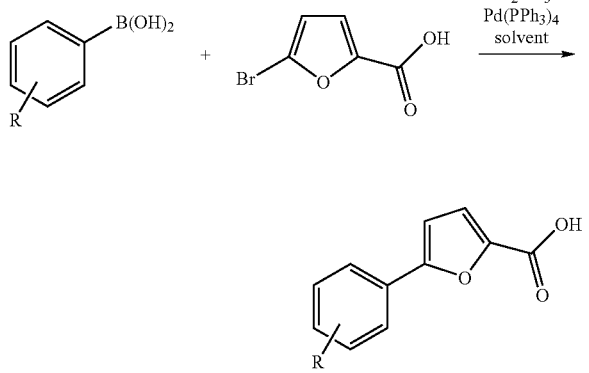

To a suspension of the aryl bromide (1.2 eq), Cs$_2$CO$_3$ (4.0 eq) and boronic acid (1 eq) in toluene (5 vol) and EtOH (5 vol) under N$_2$ was added Pd(PPh$_3$)$_4$ (0.05 eq) and the resulting mixture was heated to 85° C. for 3 h. The solvents were removed in vacuo and the solids re-suspended in EtOAc (10 vol). Water (10 vol) was then added and all the solids dissolved. The layers were separated and the aqueous layer was washed with EtOAc (3×5 vol) and acidified to pH 4 with 2M HCl upon which a precipitate formed. This was then extracted with EtOAc (2×10 vol). The combined organic layers were dried (Na$_2$SO$_4$) and removed in vacuo to give the product.

G)

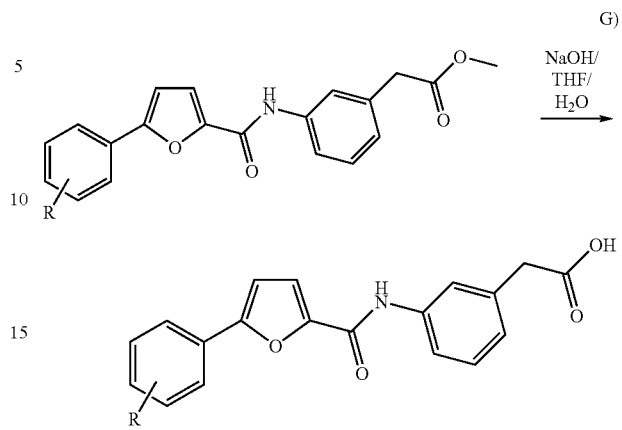

To a solution of the ester in THF (1.5 ml) was added NaOH (18 eq) in water (0.5 ml) and the resulting solution was stirred for 1 h at room temperature. The THF was removed under a stream of N$_2$ then EtOAc (2 ml) and water (1 ml) were added. The aqueous layer was extracted with EtOAc (2×2 ml) and acidified with 2M HCl until a white precipitate formed. This was then extracted with EtOAc (3×2 ml). The solvent was removed in vacuo to give the product.

H)

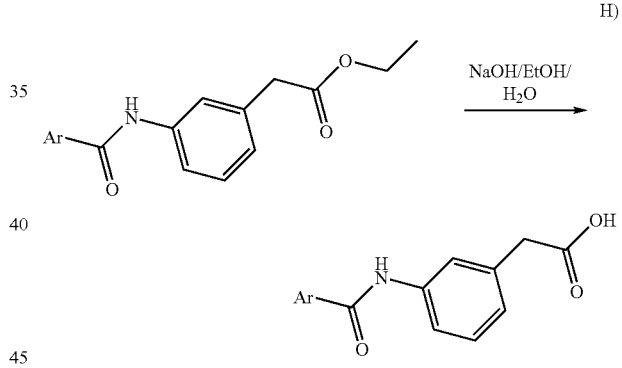

To a solution of ethyl ester in EtOH (2 ml) was added 1M NaOH (2 ml) and the resulting solution was stirred for 30 min at room temperature. The EtOH was then removed in vacuo and the residue re-dissolved in TBME (20 ml) and water (20 ml). The aqueous layer was extracted with TBME (2×20 ml) then acidified with 2M HCl until a white precipitate formed. This was then extracted with EtOAc (3×20 ml). The combined organic layers were washed with brine, dried (Na$_2$SO$_4$), filtered and the solvent removed in vacuo to give the product.

I)

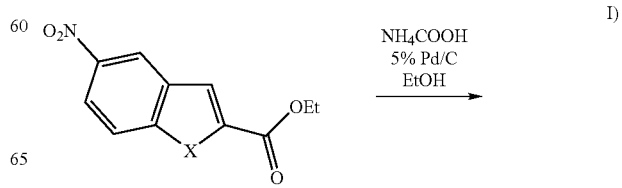

-continued

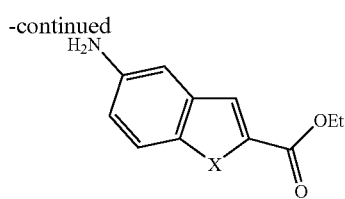

The nitro ester was dissolved in EtOH (6 vol) and NH₄COOH (4 eq) was added as a solid. 5% Palladium on carbon (10% by weight) was then added under N₂ and the resulting mixture heated to reflux under N₂ for 30 min. The reaction mixture was filtered through celite and the celite was washed with EtOH (20 vol). The solvent was removed in vacuo to give the product.

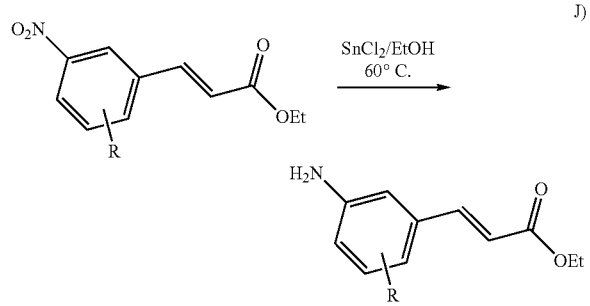

J)

The nitro derivative was dissolved in EtOH (5 vol) and SnCl₂.2H₂O (50 eq) was added as a solid. The resulting solution was then stirred at 60° C. for 2 h. After cooling to room temperature, a pre-mixed solution of saturated Rochelle's salt (10 vol) and saturated NaHCO₃ (10 vol) was added to the reaction mixture and the aqueous layer was extracted with EtOAc (3×20 vol). The combined organic layers were dried (MgSO₄) and the solvent removed in vacuo to afford the product.

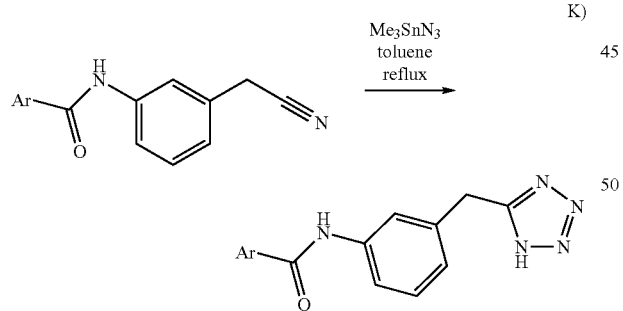

K)

To a solution of nitrile (1 eq) in toluene (4 vol) was added Me₃SnN₃ (1.1 eq). After heating to reflux for 18 h, analysis was carried out by LC-MS. If required, additional Me₃SnN₃ (1.1 eq) and toluene (3 vol) were added and the reaction heated again to drive the reaction to completion. 2M NaOH (3 vol) and hexane (3 vol) were then added to the reaction mixture and stirred for 10 min. Water (1.5 vol) was added and the organic layer separated. EtOAc (3 vol) was added to the aqueous layer and the solution stirred for 2 min before the organic layer was separated. The combined organic layers were discarded. The aqueous layer was then acidified to pH 5 with 2M HCl then EtOAc (3.5 vol) was added and the solution stirred for 10 min after which time the organic layer was separated. Further EtOAc (3.5 vol) was added to the aqueous layer and the solution stirred for 1 hour. The EtOAc layer was separated and these combined organic layers were evaporated in vacuo.

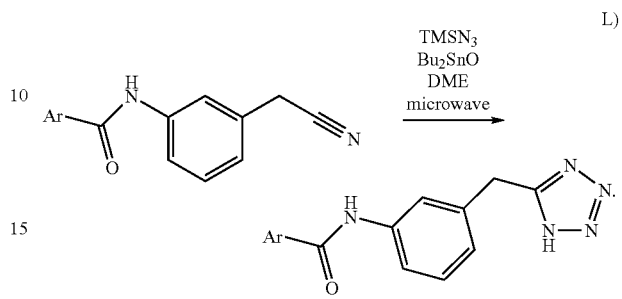

L)

To a suspension of the nitrile (1 eq) in DME (2 vol) were added TMSN₃ (4 eq) and Bu₂SnO (0.2 eq). The resulting mixture was heated in a CEM Discover microwave for 40 min at 150° C. (150 W, 250 psi). Analysis was carried out by LC-MS and, if required, the mixture was heated again to drive the reaction to completion. Once complete, EtOAc (3.5 vol) and H₂O (3.5 vol) were added. The layers were separated, and the organic layer was washed with a saturated NaHCO₃ solution (3×3.5 vol). The aqueous layer was acidified with 2M HCl until a white precipitate appeared, then extracted with EtOAc (3×3.5 vol). The solvent was removed under a stream of N₂.

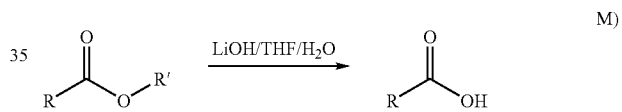

M)

To a solution of ester in EtOH or MeOH (5 vol), water (5 vol) and THF (10 vol) was added LiOH (20 eq.) and the resulting solution was stirred for 4 h at room temperature. ROH and THF were removed under a stream of N₂ and the remaining aqueous layer acidified using 1M HCl until a white precipitate appeared. The aqueous layer was then extracted using EtOAc (2×20 vol). This organic layer was dried (Na₂SO₄), filtered and the solvent removed in vacuo.

Example 6 a) (3-{[5-(2-Methoxy-phenyl)-furan-2-carbonyl]-amino}-phenyl)-acetic acid (17)

(i) (3-Amino-phenyl)-acetic acid methyl ester (15)

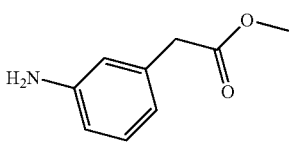

3-Aminophenylacetic acid (5 g, 33.1 mmol) was esterified with MeOH using Method B to give the title compound Yield: 4.22 g, 77%; LC/MS t, 0.70 min; MS (ES+) m/z 166 (M+H)

(ii) (3-[(5-Bromo-furan-2-carbonyl)-amino]-phenyl)-
acetic acid methyl ester (16)

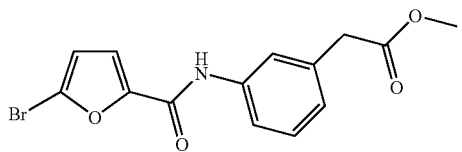

Methyl ester (15) (1 g, 6.06 mmol) was coupled to 5-bromo-furan-2-carboxylic acid (1.16 g, 6.07 mmol) using Method C to give the title compound Yield: 1.83 g, 89%; LC/MS $t_r$ 1.34 min; MS (ES+) m/z 338, 340 (M+H)

(iii) (3-([5-(2-Methoxy-phenyl)-furan-2-carbonyl]-
amino)-phenyl)-acetic acid methyl ester

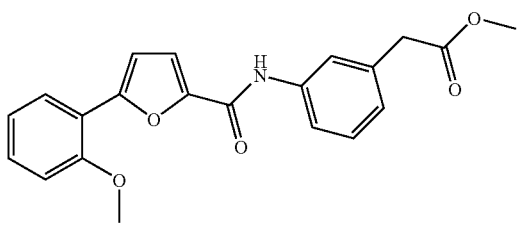

Methyl ester (16) (100 mg, 0.30 mmol) was coupled to 2-methoxy-phenylboronic acid (49 mg, 0.33 mmol) using Method E. The crude compound was purified by column chromatography, eluting in 17% EtOAc in heptane to give the title compound.

Yield: 18 mg, 17%; LC/MS $t_r$ 1.54 min; MS (ES+) m/z 366 (M+H)

(iv) (3-{[5-(2-Methoxy-phenyl)-furan-2-carbonyl]-
amino}-phenyl)-acetic acid (17)

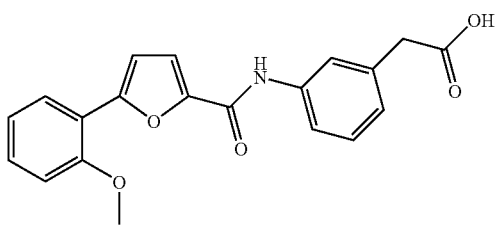

The ester (18.4 mg, 0.050 mmol) was hydrolysed with NaOH (36 mg, 0.9 mmol) using Method G to give the title compound.

Yield: 5.6 mg, 32%; LC/MS $t_r$ 1.45 min; MS (ES+) m/z 352 (M+H); HPLC Purity: 99%; $^1$H NMR (250 MHz; MeOD): δ 3.65 (s, 2H), 4.05 (s, 3H), 7.1-7.2 (m, 4H), 7.3-7.45 (m, 3H), 7.65-7.75 (m, 2H), 8.25 (s, 1H)

b) (3-{[5-(3-Methoxy-phenyl)-furan-2-carbonyl]-
amino}-phenyl)-acetic acid (18)

(i) (3-{[5-(3-Methoxy-phenyl)-furan-2-carbonyl]-
amino}-phenyl)-acetic acid methyl ester

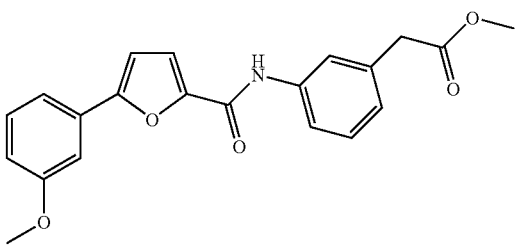

Methyl ester (16) (100 mg, 0.30 mmol) was coupled to 3-methoxy-phenylboronic acid (49 mg, 0.33 mmol) using Method E. The crude compound was purified by column chromatography, eluting in 17% EtOAc in heptane to give the title compound.

Yield: 13 mg, 12%; LC/MS $t_r$ 1.48 min; MS (ES+) m/z 366 (M+H)

(ii) (3-{[5-(3-Methoxy-phenyl)-furan-2-carbonyl]-
amino}-phenyl)-acetic acid (18)

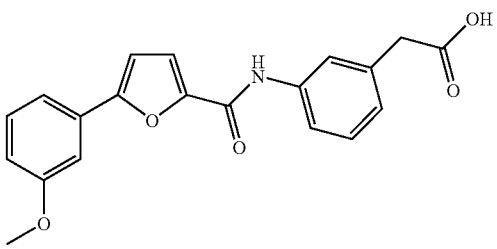

The ester (13 mg, 0.035 mmol) was hydrolysed with NaOH (25 mg, 0.63 mmol using Method G to give the title compound.

Yield: 8.2 mg, 66%; LC/MS $t_r$ 1.41 min; MS (ES+) m/z 352 (M+H); HPLC Purity: 99%; $^1$H NMR (250 MHz; MeOD): δ 3.70 (s, 2H), 3.95 (s, 3H), 6.95-7.05 (m, 2H), 7.10-7.15 (m, 1H), 7.3-7.45 (m, 3H), 7.50-7.6 (m, 2H), 7.65-7.75 (m, 2H)

c) (3-([5-(3-Acetyl-phenyl)-furan-2-carbonyl]-
amino)-phenyl)-acetic acid (19)

(i) (3-{[5-(3-Acetyl-phenyl)-furan-2-carbonyl]-
amino}-phenyl)-acetic acid methyl ester

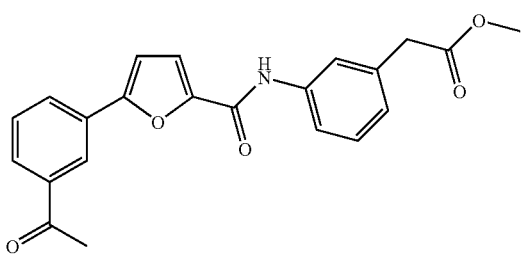

Methyl ester (16) (100 mg, 0.30 mmol) was coupled to 3-acetyl-phenylboronic acid (53 mg, 0.33 mmol) using Method E. The crude compound was purified by column chromatography, eluting in 17% EtOAc in heptane to give the title compound.

Yield: 11 mg, 10%; LC/MS t$_r$ 1.46 min; MS (ES+) m/z 378 (M+H)

(ii) (3-{[5-(3-Acetyl-phenyl)-furan-2-carbonyl]-amino}-phenyl)-acetic acid (19)

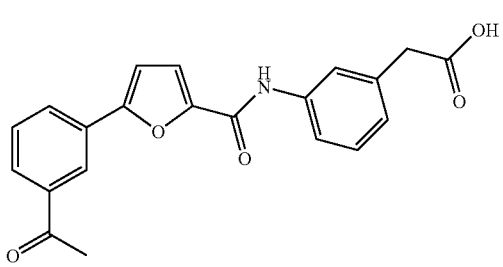

The ester (11 mg, 0.028 mmol) was hydrolysed with NaOH (20 mg, 0.5 mmol) using Method G to give the title compound.

Yield: 10 mg, 98%; LC/MS t$_r$ 1.34 min; MS (ES+) m/z 364 (M+H) HPLC Purity: 92%; $^1$H NMR (250 MHz; MeOD): δ 2.5 (s, 3H), 3.45 (s, 2H), 6.9 (s, 2H), 7.10-7.20 (m, 2H), 7.35-7.5 (m, 3H), 7.8 (d, 1H), 7.95 (d, 1H), 8.35 (s, 1H)

d) (3-{[5-(4-Acetyl-phenyl)-furan-2-carbonyl]-amino}-phenyl)-acetic acid (20)

(i) (3-{[5-(4-Acetyl-phenyl)-furan-2-carbonyl]-amino}-phenyl)-acetic acid methyl ester

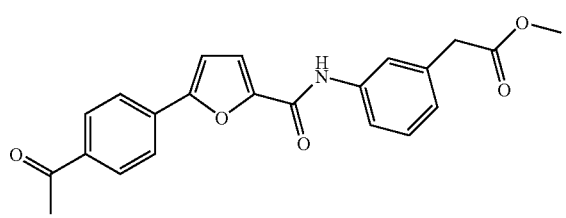

Methyl ester (16) (100 mg, 0.30 mmol) was coupled to 4-acetyl-phenylboronic acid (53 mg, 0.33 mmol) using Method E. The crude compound was purified by column chromatography, eluting in 17% EtOAc in heptane to give the title compound.

Yield: 26 mg, 23%; LC/MS t$_r$ 1.45 min; MS (ES+) m/z 378 (M+H)

(ii) (3-{[5-(4-Acetyl-phenyl)-furan-2-carbonyl]-amino}-phenyl)-acetic acid (20)

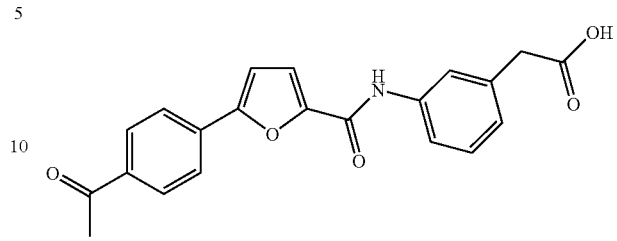

The ester (26 mg, 0.068 mmol) was hydrolysed with NaOH (49 mg, 1.22 mmol) using Method G to give the title compound.

Yield: 22 mg, 87%; LC/MS t$_r$ 1.35 min; MS (ES+) m/z 364 (M+H) HPLC Purity: 87%; $^1$H NMR (400 MHz; MeOD): δ 2.6 (s, 3H), 3.65 (s, 2H), 7.10-7.20 (m, 2H), 7.30-7.40 (m, 2H), 7.70 (s, 2H), 8.05-8.10 (m, 4H)

(e) (3-{[5-(3-Methyl-phenyl)-furan-2-carbonyl]-amino}-phenyl)-acetic acid (21)

(i) (3-{[5-(3-Methyl-phenyl)-furan-2-carbonyl]-amino}-phenyl)-acetic acid methyl ester

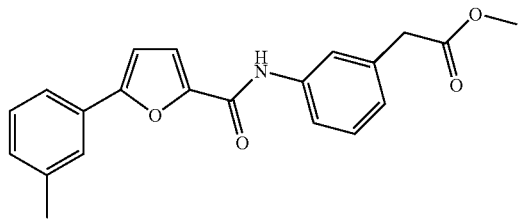

Methyl ester (16) (100 mg, 0.30 mmol) was coupled to 3-methyl-phenylboronic acid (44 mg, 0.33 mmol) using Method E. The crude compound was purified by column chromatography, eluting in 17% EtOAc in heptane to give the title compound.

Yield: 20 mg, 19%; LC/MS t$_r$ 1.59 min; MS (ES+) m/z 350 (M+H)

(ii) (3-{[5-(3-Methyl-phenyl)-furan-2-carbonyl]-amino}-phenyl)-acetic acid (21)

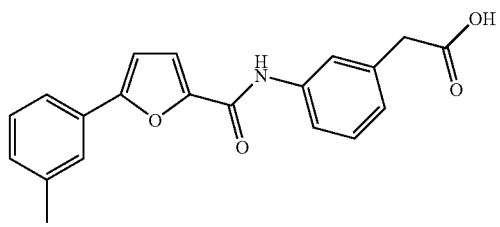

The ester (20 mg, 0.057 mmol) was hydrolysed with NaOH (41 mg, 1.03 mmol) using Method G to give the title compound.

Yield: 15 mg, 78%; LC/MS t$_r$ 1.41 min; MS (ES+) m/z 336 (M+H); HPLC Purity: 100%; $^1$H NMR (400 MHz; MeOD): δ 2.35 (s, 3H), 3.5 (s, 2H), 6.9 (s, 1H), 7.0-7.05 (m, 1H), 7.1-7.15 (m, 1H), 7.20-7.30 (m, 3H), 7.5 (s, 1H), 7.60-7.65 (m, 2H), 7.7 (s, 1H)

(f) (3-{[5-(4-Methyl-phenyl)-furan-2-carbonyl]-amino}-phenyl)-acetic acid (22)

(i) (3-{[5-(4-Methyl-phenyl)-furan-2-carbonyl]-amino}-phenyl)-acetic acid methyl ester

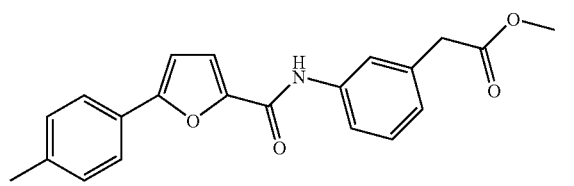

Methyl ester (16) (100 mg, 0.30 mmol) was coupled to 4-methyl-phenylboronic acid (44 mg, 0.33 mmol) using Method E. The crude compound was purified by column chromatography, eluting in 17% EtOAc in heptane to give the title compound.

Yield: 45 mg, 44%; LC/MS t$_r$ 1.60 min; MS (ES+) m/z 350 (M+H)

(ii) (3-{[5-(4-Methyl-phenyl)-furan-2-carbonyl]-amino}-phenyl)-acetic acid (22)

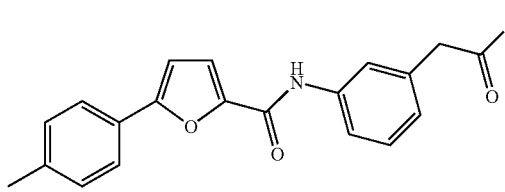

The ester (45 mg, 0.13 mmol) was hydrolysed with NaOH (94 mg, 2.34 mmol) using Method G.

Yield: 36 mg, 84%; LC/MS t$_r$ 1.41 min; MS (ES+) m/z 336 (M+H); HPLC Purity: 100%; $^1$H NMR (400 MHz; MeOD): δ 2.2 (s, 3H), 3.45 (s, 2H), 6.7 (d, 1H), 6.9 (d, 1H), 7.05-7.15 (m, 4H), 7.45-7.50 (m, 2H), 7.65 (d, 2H)

(g) (3-{[5-(2-Trifluoromethyl-phenyl)-furan-2-carbonyl]-amino}-phenyl)-acetic acid (23)

(i) (3-{[5-(2-Trifluoromethyl-phenyl)-furan-2-carbonyl]-amino}-phenyl)-acetic acid methyl ester

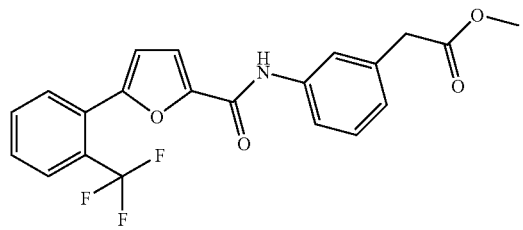

Methyl ester (16) (100 mg, 0.30 mmol) was coupled to 2-trifluoromethyl-phenylboronic acid (44 mg, 0.33 mmol) using Method E. The crude compound was purified by column chromatography, eluting in 17% EtOAc in heptane to give the title compound.

Yield: 55 mg, 46%; LC/MS t$_r$ 1.62 min; MS (ES+) m/z 404 (M+H)

(ii) (3-{[5-(2-Trifluoromethyl-phenyl)-furan-2-carbonyl]-amino}-phenyl)-acetic acid (23)

The ester (55 mg, 0.14 mmol) was hydrolysed with NaOH (100 mg, 2.52 mmol) using Method G to give the title compound.

Yield: 47 mg, 89%; LC/MS t$_r$ 1.42 min; MS (ES+) m/z 390 (M+H); HPLC Purity: 100%; $^1$H NMR (400 MHz; MeOD): δ 3.8 (s, 2H), 7.05-7.10 (m, 1H), 7.25-7.30 (m, 1H), 7.45-7.60 (m, 2H), 7.75-7.85 (m, 3H), 7.90-7.95 (m, 1H), 8.00-8.05 (m, 1H), 8.15-8.2 (m, 1H)

(h) (3-{[5-(3-Trifluoromethyl-phenyl)-furan-2-carbonyl]-amino}-phenyl)-acetic acid (24)

(i) (3-([5-(3-Trifluoromethyl-phenyl)-furan-2-carbonyl]-amino)-phenyl)-acetic acid methyl ester Methyl ester (16) (100 mg, 0.30 mmol) was coupled to 3-trifluoromethyl-phenylboronic acid (44 mg, 0.33 mmol) using Method E. The crude compound was purified by column chromatography, eluting in 17% EtOAc in heptane to give the title compound.

Yield: 30 mg, 25%; LC/MS t$_r$ 1.65 min; MS (ES+) m/z 404 (M+H)

(ii) (3-{[5-(3-Trifluoromethyl-phenyl)-furan-2-carbonyl]-amino}-phenyl)-acetic acid (24)

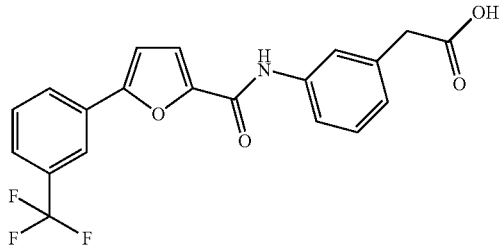

The ester (30 mg, 0.074 mmol) was hydrolysed with NaOH (53 mg, 1.33 mmol) using Method G to give the title compound.

Yield: 25 mg, 87%; LC/MS t$_r$ 1.46 min; MS (ES+) m/z 390 (M+H); HPLC Purity: 92%; $^1$H NMR (400 MHz; MeOD): δ 3.45 (s, 2H), 7.00-7.05 (m, 2H), 7.15-7.20 (m, 1H), 7.3 (d, 1H), 7.45 (s, 1H), 7.55-7.60 (m, 3H), 8.05-8.10 (m, 1H), 8.25 (s, 1H)

(j) (3-{[5-(2,4-Dichloro-phenyl)-furan-2-carbonyl]-amino}-phenyl)-acetic acid (25)

(i) (3-{[5-(2,4-Dichloro-phenyl)-furan-2-carbonyl]-amino}-phenyl)-acetic acid methyl ester

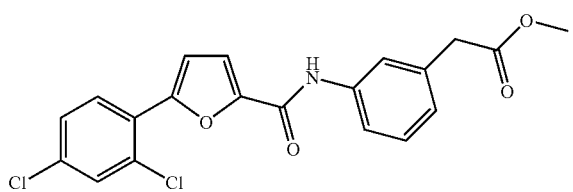

Methyl ester (16) (100 mg, 0.30 mmol) was coupled to 2,4-dichloro-phenylboronic acid (61 mg, 0.33 mmol) using Method E. The crude compound was purified by column chromatography, eluting in 17% EtOAc in heptane to give the title compound.

Yield: 37 mg, 31%; LC/MS t$_r$ 1.76 min; MS (ES+) m/z 404, 406 (M+H)

(ii) (3-{[5-(2,4-Dichloro-phenyl)-furan-2-carbonyl]-amino}-phenyl)-acetic acid (25)

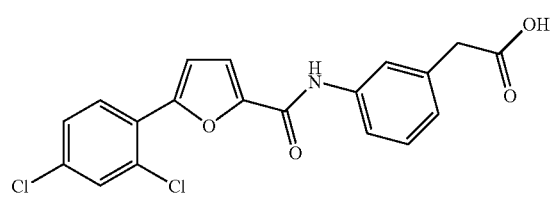

The ester (37 mg, 0.091 mmol) was hydrolysed with NaOH (66 mg, 1.64 mmol) using Method G to give the title compound.

Yield: 9.1 mg, 25%; LC/MS t$_r$ 1.96 min; MS (ES+) m/z 390, 392 (M+H); HPLC Purity: 100%; $^1$H NMR (400 MHz; MeOD): δ 3.5 (s, 2H), 7.0 (d, 1H), 7.2-7.25 (m, 2H), 7.3 (d, 1H), 7.4 (d, 1H), 7.5 (s, 1H), 7.6 (2H), 8.1 (1H)

(k) (3-{[5-(3,5-Dichloro-phenyl)-furan-2-carbonyl]-amino}-phenyl)-acetic acid (26)

(i) (3-{[5-(3,5-Dichloro-phenyl)-furan-2-carbonyl]-amino}-phenyl)-acetic acid methyl ester

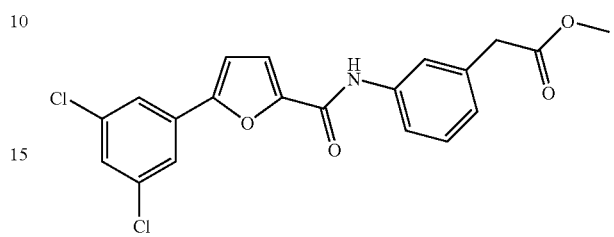

Methyl ester (16) (100 mg, 0.30 mmol) was coupled to 3,5-dichloro-phenylboronic acid (61 mg, 0.33 mmol) using Method E. The crude compound was purified by column chromatography, eluting in 17% EtOAc in heptane to give the title compound.

Yield: 11 mg, 9%; LC/MS t$_r$ 1.76 min; MS (ES+) m/z 404, 406 (M+H)

(ii) (3-{[5-(3,5-Dichloro-phenyl)-furan-2-carbonyl]-amino}-phenyl)-acetic acid (26)

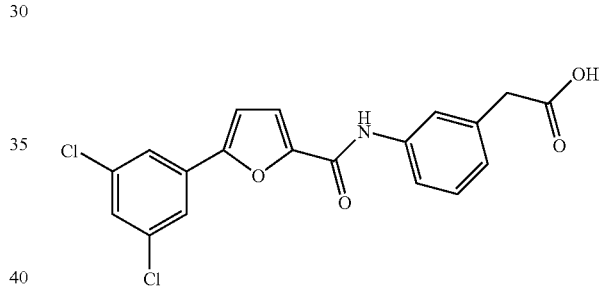

The ester (11 mg, 0.027 mmol) was hydrolysed with NaOH (20 mg, 0.49 mmol) using Method G to give the title compound.

Yield: 9.6 mg, 91%; LC/MS t$_r$ 1.97 min; MS (ES+) m/z 390, 392 (M+H); HPLC Purity: 100%; $^1$H NMR (400 MHz; MeOD): δ 3.55 (s, 2H), 7.00-7.05 (m, 2H), 7.20-7.30 (m, 2H), 7.35 (s, 1H), 7.55-7.60 (m, 2H), 7.9 (s, 2H)

(l) (3-{[5-(3,4-Dichloro-phenyl)-furan-2-carbonyl]-amino}-phenyl)-acetic acid (27)

(i) (3-{[5-(3,4-Dichloro-phenyl)-furan-2-carbonyl]-amino}-phenyl)-acetic acid methyl ester

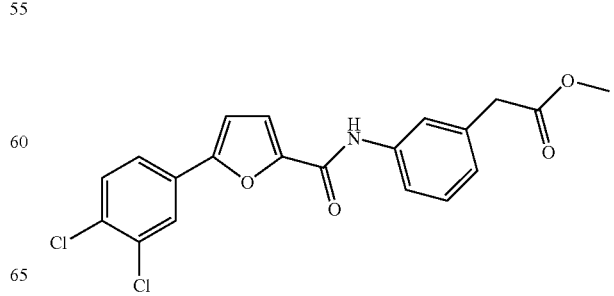

Methyl ester (16) (100 mg, 0.30 mmol) was coupled to 3,4-dichloro-phenylboronic acid (61 mg, 0.33 mmol) using Method E. The crude compound was purified by column chromatography, eluting in 17% EtOAc in heptane to give the title compound.

Yield: 33 mg, 27%; LC/MS $t_r$ 1.70 min; MS (ES+) m/z 404, 406 (M+H)

(ii) (3-{[5-(3,4-Dichloro-phenyl)-furan-2-carbonyl]-amino}-phenyl)-acetic acid 27)

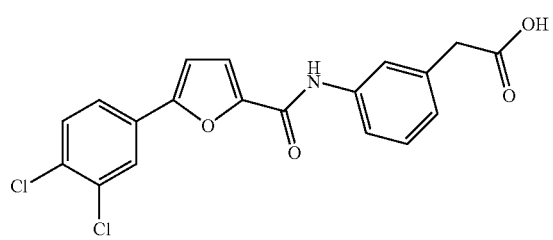

The ester (33 mg, 0.081 mmol) was hydrolysed with NaOH (58 mg, 1.46 mmol) using Method G to give the title compound.

Yield: 24 mg, 76%; LC/MS t, 1.92 min; MS (ES+) m/z 390, 392 (M+H); HPLC Purity: 87%; $^1$H NMR (400 MHz; MeOD): δ 3.5 (s, 2H), 6.95-7.05 (m, 2H), 7.20-7.25 (m, 2H), 7.45-7.50 (m, 1H), 7.55-7.60 (m, 2H), 7.7 (d, 1H), 8.1 (s, 1H).

(m) (3-{[5-(2-Methyl-phenyl)-furan-2-carbonyl]-amino}-phenyl)-acetic acid (28)

(i) (3-{[5-(2-Methyl-phenyl)-furan-2-carbonyl]-amino}-phenyl)-acetic acid methyl ester

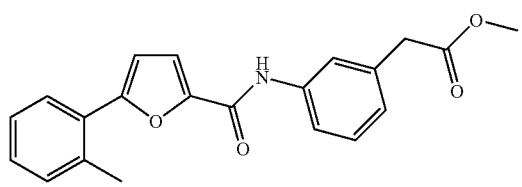

Methyl ester (16) (100 mg, 0.30 mmol) was coupled to 2-methyl-phenylboronic acid (44 mg, 0.33 mmol) using Method E. The crude compound was purified by column chromatography, eluting in 17% EtOAc in heptane to give the title compound.

Yield: 60 mg, 58%; LC/MS $t_r$: 1.55 min; MS (ES+) m/z 350 (M+H)

(ii) (3-{[5-(2-Methyl-phenyl)-furan-2-carbonyl]-amino}-phenyl)-acetic acid (28)

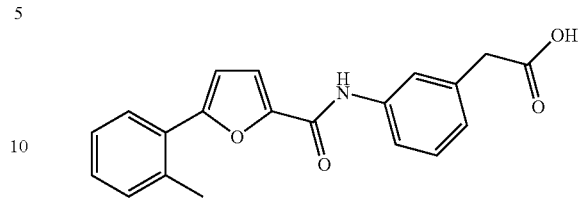

The ester (60 mg, 0.17 mmol) was hydrolysed with NaOH (122 mg, 3.06 mmol) using Method G to give the title compound.

Yield: 41 mg, 71%; LC/MS $t_r$ 1.84 min; MS (ES+) m/z 336 (M+H); HPLC Purity: 100%; $^1$H NMR (400 MHz; MeOD): δ 2.4 (s, 3H), 3.5 (s, 2H), 6.7 (d, 1H), 7.0 (d, 1H), 7.15-7.20 (m, 4H), 7.28-7.30 (m, 1H), 7.50-7.60 (m, 2H), 7.75-7.85 (m, 1H).

(n) (3-{[5-(4-Methoxy-phenyl)-furan-2-carbonyl]-amino}-phenyl)-acetic acid (29)

(i) (3-{[5-(4-Methoxy-phenyl)-furan-2-carbonyl]-amino}-phenyl)-acetic acid methyl ester

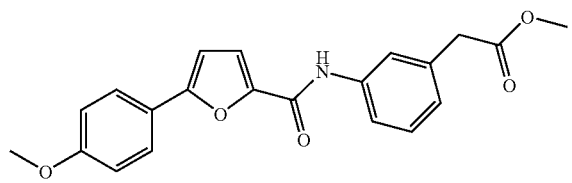

Methyl ester (16) (100 mg, 0.30 mmol) was coupled to 4-methoxy-phenylboronic acid (49 mg, 0.33 mmol) using Method E. The crude compound was purified by column chromatography, eluting in 17% EtOAc in heptane to give the title compound.

Yield: 50 mg, 46%; LC/MS $t_r$ 1.49 min; MS (ES+) m/z 366 (M+H)

(ii) (3-{[5-(4-Methoxy-phenyl)-furan-2-carbonyl]-amino}-phenyl)-acetic acid (29)

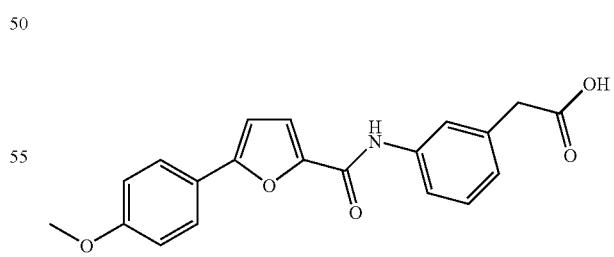

The ester (50 mg, 0.14 mmol) was hydrolysed with NaOH (100 mg, 2.52 mmol) using Method G to give the title compound.

Yield: 45 mg, 93%; LC/MS $t_r$ 1.79 min; MS (ES+) m/z 352 (M+H); HPLC Purity: 100%; $^1$H NMR (400 MHz; MeOD): δ 3.5 (s, 2H), 3.7 (s, 3H), 6.7 (s, 1H), 6.9 (d, 2H), 7.0 (d, 1H), 7.20-7.25 (m, 2H), 7.55-7.60 (m, 2H), 7.70-7.80 (m, 2H)

(o) (3-{[5-(2-Chloro-phenyl)-furan-2-carbonyl]-amino}-phenyl)-acetic acid (30)

(i) (3-{[5-(2-Chloro-phenyl)-furan-2-carbonyl]-amino}-phenyl)-acetic acid methyl ester

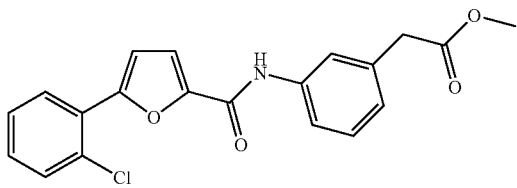

Methyl ester (16) (100 mg, 0.30 mmol) was coupled to 2-chloro-phenylboronic acid (51 mg, 0.33 mmol) using Method E. The crude compound was purified by column chromatography, eluting in 17% EtOAc in heptane to give the title compound.

Yield: 38 mg, 34%; LC/MS $t_r$ 1.58 min; MS (ES+) m/z 370, 372 (M+H)

(ii) (3-{[5-(2-Chloro-phenyl)-furan-2-carbonyl]-amino}-phenyl)-acetic acid (30)

The ester (38 mg, 0.10 mmol) was hydrolysed with NaOH (72 mg, 1.8 mmol) using Method G to give the title compound.

Yield: 35 mg, 95%; LC/MS $t_r$ 1.86 min; MS (ES+) m/z 356, 358 (M+H); HPLC Purity: 97%; $^1$H NMR (400 MHz; MeOD): δ 3.5 (s, 2H), 6.95-7.00 (m, 1H), 7.20-7.30 (m, 4H), 7.30-7.38 (m, 1H), 7.40-7.45 (m, 1H), 7.55-7.60 (m, 2H), 8.10 (d, 1H).

(p) {3-[(5-Naphthalen-1-yl-furan-2-carbonyl)-amino]-phenyl}-acetic acid (31)

(i) {3-[(5-Naphthalen-1-yl-furan-2-carbonyl)-amino]-phenyl}-acetic acid methyl ester

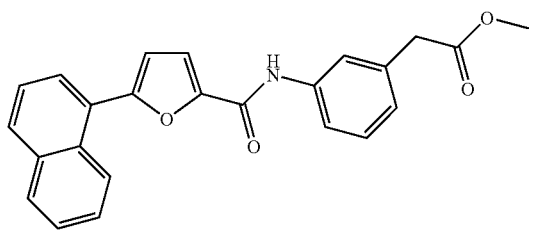

Methyl ester (16) (100 mg, 0.30 mmol) was coupled to 1-naphthaleneboronic acid (56 mg, 0.33 mmol) using Method E. The crude compound was purified by column chromatography, eluting in 17% EtOAc in heptane to give the title compound.

Yield: 12 mg, 10%; LC-MS $t_r$ 1.62 min; MS (ES+) m/z 386 (M+H)

(ii) {3-[(5-Naphthalen-1-yl-furan-2-carbonyl)-amino]-phenyl}-acetic acid (31)

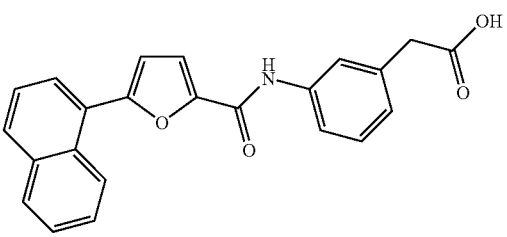

The ester (12 mg, 0.031 mmol) was hydrolysed with NaOH (22 mg, 0.56 mmol) using Method G to give the title compound.

Yield: 8.7 mg, 76%; LC/MS $t_r$ 1.87 min; MS (ES+) m/z 372 (M+H); HPLC Purity: 89%; $^1$H NMR (250 MHz; MeOD) δ 4.52 (s, 2H), 6.88 (d, 1H), 7.00 (d, 1H), 7.18-7.27 (t, 1H), 7.39 (d, 1H), 7.43-7.58 (m, 5H), 7.80-7.89 (m, 3H), 8.29 (d, 1H).

(q) (3-([5-(3-Trifluoromethoxy-phenyl)-furan-2-carbonyl]-amino)-phenyl)-acetic acid (32)

(i) (3-([5-(3-Trifluoromethoxy-phenyl)-furan-2-carbonyl]-amino)-phenyl)-acetic acid methyl ester

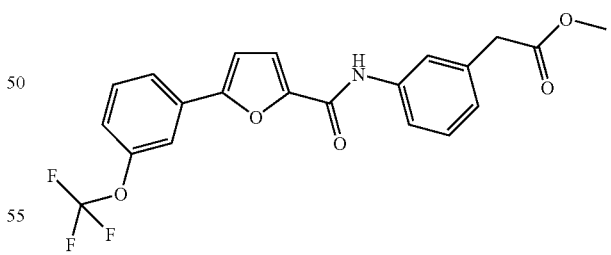

Methyl ester (16) (100 mg, 0.30 mmol) was coupled to 3-(trifluoromethoxy)-phenylboronic acid (67 mg, 0.33 mmol) using Method E. The crude compound was purified by column chromatography, eluting in 17% EtOAc in heptane to give the title compound.

Yield: 23 mg, 18%; LC-MS $t_r$ 1.63 min; MS (ES+) m/z 420 (M+H)

(ii) (3-([5-(3-Trifluoromethoxy-phenyl)-furan-2-carbonyl]-amino)-phenyl)-acetic acid (32)

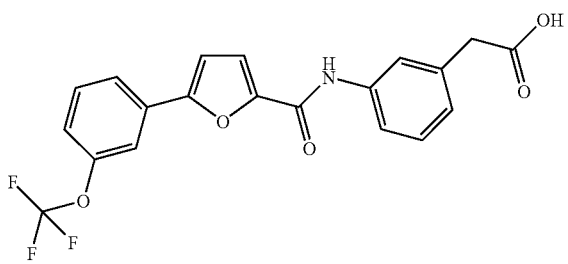

The ester (23 mg, 0.055 mmol) was hydrolysed with NaOH (40 mg, 0.99 mmol) using Method G to give the title compound.

Yield: 22 mg, 100%; LC/MS $t_r$ 1.90 min; MS (ES+) m/z 406 (M+H); HPLC Purity: 100%; $^1$H NMR (250 MHz; MeOD) δ 3.66 (s, 2H), 7.10-7.16 (m, 2H), 7.28-7.40 (m, 3H), 7.59 (t, 1H), 7.67-7.73 (m, 2H), 7.90-7.98 (m, 2H).

(r) (3-{[5-(4-Trifluoromethoxy-phenyl)-furan-2-carbonyl]-amino}-phenyl)-acetic acid (33)

(i) (3-{[5-(4-Trifluoromethoxy-phenyl)-furan-2-carbonyl]-amino}-phenyl)-acetic acid methyl ester

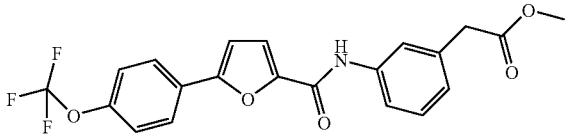

The methyl ester (16) (100 mg, 0.30 mmol) was coupled to 4-(trifluoromethoxy)-phenylboronic acid (67 mg, 0.33 mmol) using Method E. The crude compound was purified by column chromatography, eluting in 17% EtOAc in heptane to give the title compound.

Yield: 65 mg, 52%; LC-MS $t_r$ 1.62 min; MS (ES+) m/z 420 (M+H)

(ii) (3-{[5-(4-Trifluoromethoxy-phenyl)-furan-2-carbonyl]-amino}-phenyl)-acetic acid (33)

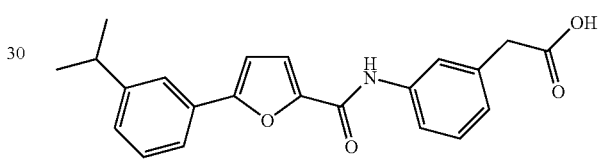

The ester (65 mg, 0.15 mmol) was hydrolysed with NaOH (0.11 mg, 2.7 mmol) using Method G to give the title compound.

Yield: 47 mg, 75%; LC/MS $t_r$ 1.91 min; MS (ES+) m/z 406 (M+H); HPLC Purity: 100%; $^1$H NMR (250 MHz; MeOD) δ 3.65 (s, 2H), 7.06 (d, 1H), 7.12 (d, 1H), 7.31-7.42 (m, 4H), 7.66-7.72 (m, 2H), 8.08 (d, 2H).

(s) (3-{[5-(3-Isopropyl-phenyl)-furan-2-carbonyl]-amino}-phenyl)-acetic acid (34)

(i) (3-{[5-(3-Isopropyl-phenyl)-furan-2-carbonyl]-amino}-phenyl)-acetic acid methyl ester

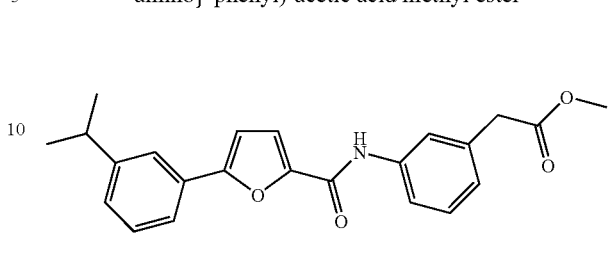

Methyl ester (16) (100 mg, 0.30 mmol) was coupled to 3-isopropyl-phenylboronic acid (53 mg, 0.33 mmol) using Method E. The crude compound was purified by column chromatography, eluting in 17% EtOAc in heptane to give the title compound.

Yield: 30 mg, 27%; LC-MS $t_r$ 1.70 min; MS (ES+) m/z 378 (M+H)

(ii) (3-{[5-(3-Isopropyl-phenyl)-furan-2-carbonyl]-amino}-phenyl)-acetic acid (34)

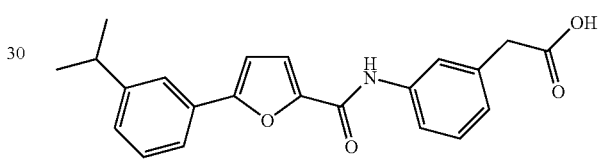

The ester (30 mg, 0.080 mmol) was hydrolysed with NaOH (58 mg; 1.44 mmol) using Method G to give the title compound.

Yield: 29 mg, 100%; LC/MS $t_r$ 1.54 min; MS (ES+) m/z 364 (M+H); HPLC Purity: 100%; $^1$H NMR (400 MHz; MeOD) δ 1.20 (d, 6H), 2.90 (sept, 1H), 3.53 (s, 2H), 6.87 (d, 1H), 7.00 (d, 1H), 7.17 (d, 1H), 7.20-7.29 (m, 3H), 7.52-7.59 (m, 2H), 7.63 (d, 1H), 7.72 (s, 1H).

(t) (3-{[5-(4-Isopropyl-phenyl)-furan-2-carbonyl]-amino}-phenyl)-acetic acid (35)

(i) (3-{[5-(4-Isopropyl-phenyl)-furan-2-carbonyl]-amino}-phenyl)-acetic acid methyl ester

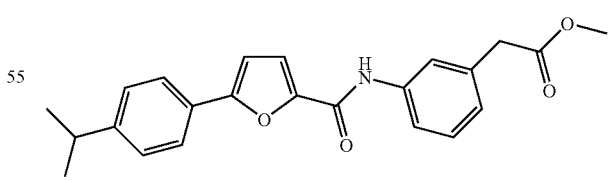

Methyl ester (16) (100 mg, 0.30 mmol) was coupled to 4-isopropyl-phenylboronic acid (53 mg, 0.33 mmol) using Method E. The crude compound was purified by column chromatography, eluting in 17% EtOAc in heptane to give the title compound.

Yield: 33 mg, 30%; LC-MS $t_r$ 1.70 min; MS (ES+) m/z 378 (M+H)

(ii) (3-{[5-(4-Isopropyl-phenyl)-furan-2-carbonyl]-amino}-phenyl)-acetic acid (35)

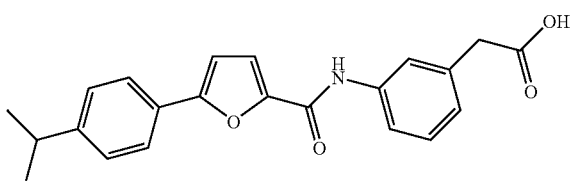

The ester (33 mg, 0.087 mmol) was hydrolysed with NaOH (63 mg, 1.57 mmol) using Method G to give the title compound.
Yield: 32 mg, 100%; LC/MS $t_r$ 1.56 min; MS (ES+) m/z 364 (M+H); HPLC Purity: 100%; $^1$H NMR (400 MHz; MeOD) δ 1.19 (d, 6H), 2.86 (sept, 1H), 3.52 (s, 2H), 6.82 (d, 1H), 7.00 (d, 1H), 7.18-7.27 (m, 4H), 7.53-7.60 (m, 2H), 7.75 (d, 2H).

(u) {3-[(5-Benzo[1,3]dioxol-5-yl-furan-2-carbonyl)-amino]-phenyl}-acetic acid (36)

(i) {3-[(5-Benzo[1,3]dioxol-5-yl-furan-2-carbonyl)-amino]-phenyl}-acetic acid methyl ester

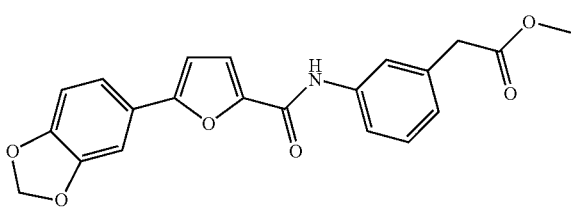

Methyl ester (16) (100 mg, 0.30 mmol) was coupled to 3,4-(methylenedioxy)-phenylboronic acid (54 mg, 0.33 mmol) using Method E. The crude compound was purified by column chromatography, eluting in 17% EtOAc in heptane to give the title compound.
Yield: 25 mg, 22%; LC-MS $t_r$ 1.46 min; MS (ES+) m/z 380 (M+H)

(ii) {3-[(5-Benzo[1,3]dioxol-5-yl-furan-2-carbonyl)-amino]-phenyl}-acetic acid (36)

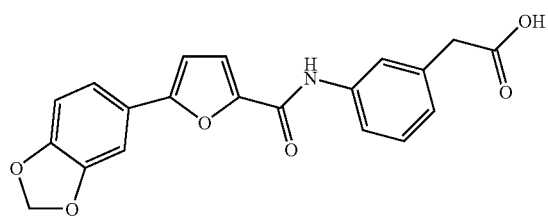

The ester (25 mg, 0.066 mmol) was hydrolysed with NaOH (48 mg, 1.19 mmol) using Method G to give the title compound.
Yield: 16 mg, 66%; LC/MS $t_r$: 1.32 min; MS (ES+) m/z 366 (M+H); HPLC Purity: 97%; $^1$H NMR (250 MHz; MeOD) δ 3.67 (s, 2H), 6.03 (s, 2H), 6.85 (d, 1H), 6.93 (d, 1H), 7.12 (d, 1H), 7.31-7.39 (m, 2H), 7.45-7.51 (m, 2H), 7.65-7.72 (m, 2H).

(v) (3-{[5-(2,3-Dichloro-phenyl)-furan-2-carbonyl]-amino}-phenyl)-acetic acid (37)

(i) (3-{[5-(2,3-Dichloro-phenyl)-furan-2-carbonyl]-amino}-phenyl)-acetic acid methyl ester

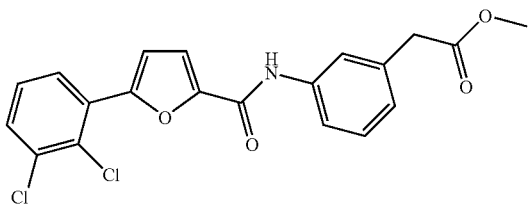

Methyl ester (16) (100 mg, 0.30 mmol) was coupled to 2,3-dichloro-phenylboronic acid (62 mg, 0.33 mmol) using Method E. The crude compound was purified by column chromatography, eluting in 17% EtOAc in heptane to give the title compound.
Yield: 15 mg, 13%; LC-MS $t_r$ 1.72 min; MS (ES+) m/z 404, 406 (M+H)

(ii) (3-{[5-(2,3-Dichloro-phenyl)-furan-2-carbonyl]-amino}-phenyl)-acetic acid (37)

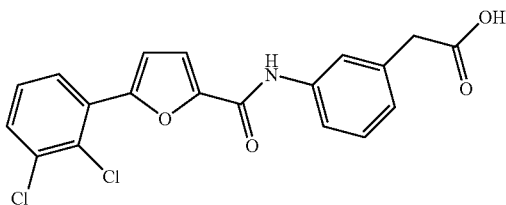

The ester (15 mg, 0.037 mmol) was hydrolysed with NaOH (27 mg, 0.67 mmol) using Method G to give the title compound.
Yield: 12 mg, 80%; LC/MS $t_r$ 1.91 min; MS (ES+) m/z 390, 392 (M+H); HPLC Purity: 96%; $^1$H NMR (400 MHz; MeOD) δ 3.54 (s, 2H), 7.01 (d, 1H), 7.20-7.28 (m, 2H), 7.29-7.37 (m, 2H), 7.49 (d, 1H), 7.53-7.59 (m, 2H), 8.03 (d, 1H).

(w) {3-[([2,2']Bifuranyl-5-carbonyl)-amino]-phenyl}-acetic acid (38)

(i) {3-[([2,2']Bifuranyl-5-carbonyl)-amino]-phenyl}-acetic acid methyl ester

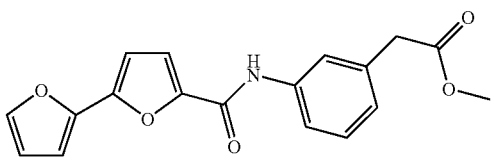

Methyl ester (16) (100 mg, 0.30 mmol) was coupled to furan-2-boronic acid (37 mg, 0.33 mmol) using Method E. The crude compound was purified by column chromatography, eluting in 17% EtOAc in heptane to give the title compound.

Yield: 13 mg, 13%; LC-MS $t_r$ 1.41 min; MS (ES+) m/z 326 (M+H)

(ii) (3-[([2,2']Bifuranyl-5-carbonyl)-amino]-phenyl)-acetic acid (38)

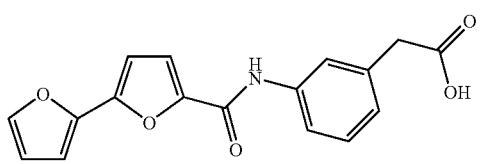

The ester (13 mg, 0.040 mmol) was hydrolysed with NaOH (29 mg, 0.72 mmol) using Method G to give the title compound.

Yield: 11 mg, 88%; LC/MS $t_r$ 1.70 min; MS (ES+) m/z 312 (M+H); HPLC Purity: 94%; $^1$H NMR (400 MHz; MeOD) δ 3.56 (s, 2H), 6.50 (d, 1H), 6.67 (d, 1H), 6.88 (d, 1H), 7.00 (d, 1H), 7.19-7.23 (m, 2H), 7.49-7.58 (m, 3H).

(x) (3-{[5-(3-Chloro-phenyl)-furan-2-carbonyl]-amino}-phenyl)-acetic acid (39)

(i) (3-{[5-(3-Chloro-phenyl)-furan-2-carbonyl]-amino}-phenyl)-acetic acid methyl ester

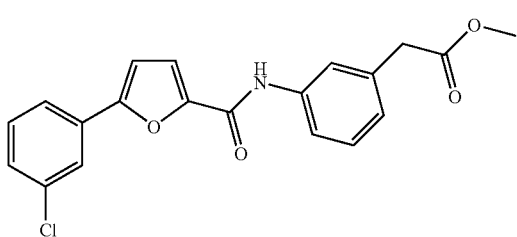

Methyl ester (16) (100 mg, 0.30 mmol) was coupled to 3-chlorophenylboronic acid (51 mg, 0.33 mmol) using Method E. The crude compound was purified by column chromatography, eluting in 17% EtOAc in heptane to give the title compound.

Yield: 29 mg, 26%; LC/MS $t_r$ 1.58 min; MS (ES+) m/z 370, 372 (M+H)

(ii) (3-{[5-(3-Chloro-phenyl)-furan-2-carbonyl]-amino}-phenyl)-acetic acid (39)

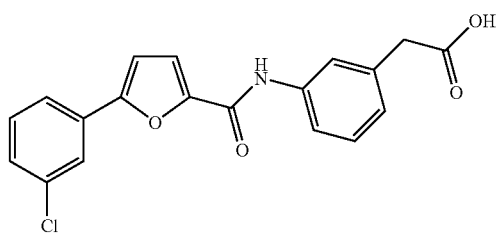

The ester (29 mg, 0.076 mmol) was hydrolysed with NaOH (55 mg, 1.37 mmol) using Method G to give the title compound.

Yield: 27 mg, 100%; LC/MS $t_r$ 1.86 min; MS (ES+) m/z 356, 358 (M+H); HPLC Purity: 100%; $^1$H NMR (250 MHz; MeOD): δ 3.66 (s, 2H), 7.06-7.14 (m, 2H), 7.32-7.49 (m, 4H), 7.69-7.70 (m, 2H), 7.86 (d, 1H), 8.07 (s, 1H)

(y) (3-{[5-(4-Chloro-phenyl)-furan-2-carbonyl]-amino}-phenyl)-acetic acid (40)

(i) (3-{[5-(4-Chloro-phenyl)-furan-2-carbonyl]-amino}-phenyl)-acetic acid methyl ester

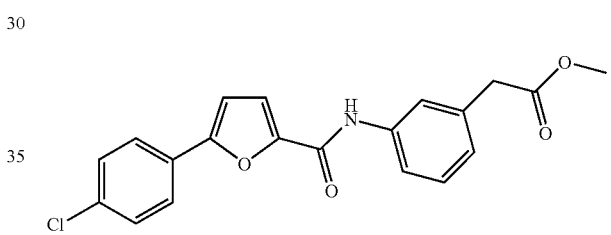

Methyl ester (16) (100 mg, 0.30 mmol) was coupled to 4-chloro-phenylboronic acid (51 mg, 0.33 mmol) using Method E. The crude compound was purified by column chromatography, eluting in 17% EtOAc in heptane to give the title compound.

Yield: 34 mg, 31%; LC/MS $t_r$ 1.59 min; MS (ES+) m/z 370, 372 (M+H)

(ii) (3-{[5-(4-Chloro-phenyl)-furan-2-carbonyl]-amino}-phenyl)-acetic acid (40)

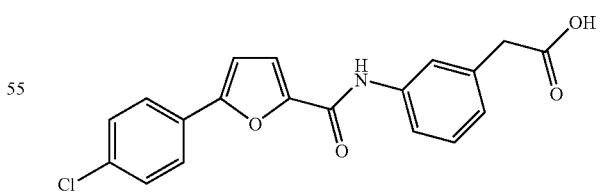

The ester (34 mg, 0.092 mmol) was hydrolysed with NaOH (66 mg, 1.66 mmol) using Method G to give the title compound.

Yield: 23 mg, 70%; LC/MS $t_r$ 1.86 min; MS (ES+) m/z 356, 358 (M+H); HPLC Purity: 94%; $^1$H NMR (250 MHz; MeOD): δ 3.34 (s, 2H), 7.15 (d, 1H), 7.12 (d, 1H), 7.36 (m, 2H), 7.48 (m, 2H), 7.69 (m, 2H), 7.94 (m, 2H)

(z) 3-{[5-(1H-Indol-5-yl)-furan-2-carbonyl]-amino}-phenyl)-acetic acid (41)

(i) 3-([5-(1H-Indol-5-yl)-furan-2-carbonyl]-amino)-phenyl)-acetic acid methyl ester

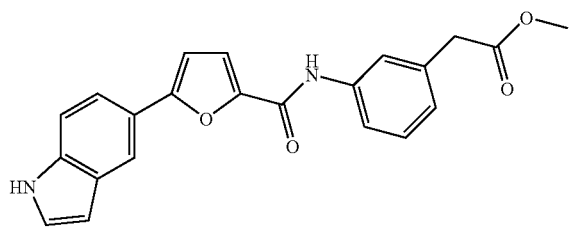

Methyl ester (16) (100 mg, 0.30 mmol) was coupled to 1H-indole-5-boronic acid (52 mg, 0.33 mmol) using Method E. The crude compound was purified by column chromatography, eluting in 20% EtOAc in heptane to give the title compound.

Yield: 22 mg, 20%; LC/MS $t_r$ 1.14 min; MS (ES+) m/z 375 (M+H)

(ii) 3-{[5-(1H-Indol-5-yl)-furan-2-carbonyl]-amino}-phenyl)-acetic acid (41)

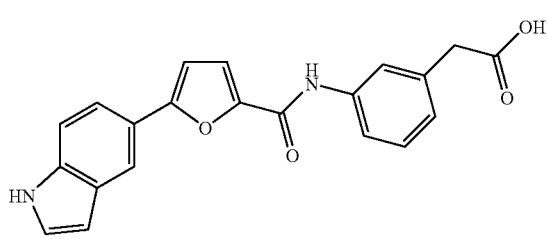

The ester (22 mg, 0.059 mmol) was hydrolysed with NaOH (42 mg, 1.06 mmol) using Method G to give the title compound.

Yield: 8.8 mg, 41%; LC/MS $t_r$ 1.29 min; MS (ES+) m/z 361 (M+H); HPLC Purity: 94%; $^1$H NMR (400 MHz; DMSO): δ 3.60 (s, 2H), 6.65 (s, 1H), 7.03 (d, 2H), 7.32 (t, 1H), 7.43 (d, 2H), 7.50 (d, 1H), 7.70 (m, 3H), 8.22 (s, 1H), 10.15 (s, 1H), 11.30 (s, 1H)

(aa) (3-{[5-(4-Fluoro-phenyl)-furan-2-carbonyl]-amino}-phenyl)-acetic acid (42)

(i) Alternate Synthesis of (3-Amino-phenyl)-acetic acid ethyl ester (6)

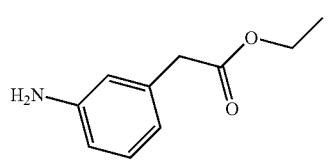

3-Aminophenylacetic acid (2 g, 13 mmol) was esterified with EtOH using Method B to give the title compound.

Yield: 2.1 g, 89%; LC/MS $t_r$ 0.78 min; MS (ES+) m/z 180 (M+H)

(ii) 5-(4-Fluoro-phenyl)-furan-2-carboxylic acid (76)

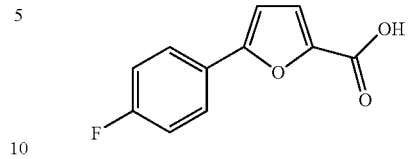

4-Fluoro-phenylboronic acid (611 mg, 4.4 mmol) was coupled to 5-bromo-2-furoic acid (1 g, 5.2 mmol) using Method F to give the title compound.

Yield: 350 mg, 38%; LC/MS $t_r$ 1.24 min; MS (ES+) m/z 207 (M+H)

(iii) (3-{[5-(4-Fluoro-phenyl)-furan-2-carbonyl]-amino}-phenyl)-acetic acid ethyl ester

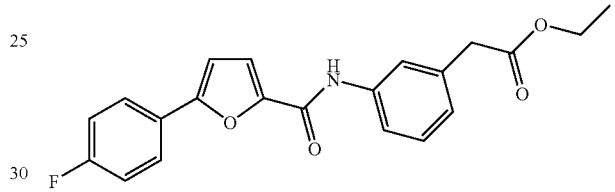

(3-Amino-phenyl)-acetic acid ethyl ester (44 mg, 0.24 mmol) was coupled to 5-(4-fluoro-phenyl)-furan-2-carboxylic acid (76) (50 mg, 0.24 mmol) using Method C. The crude compound was purified by column chromatography, eluting in 20% EtOAc in heptane to give the title compound.

Yield: 90 mg, 100%; LC/MS $t_r$ 1.59 min; MS (ES+) m/z 368 (M+H)

(iv) (3-{[5-(4-Fluoro-phenyl)-furan-2-carbonyl]-amino}-phenyl)-acetic acid (42)

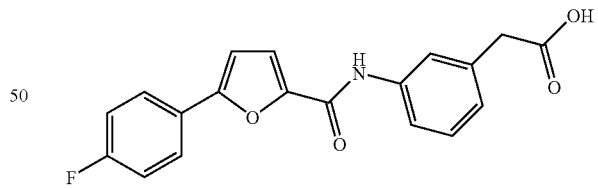

To a solution of ester (90 mg, 0.25 mmol) in MeOH (0.09 ml) was added 1M NaOH (1 ml) and the reaction mixture was stirred for 3 h at room temperature. The MeOH was evaporated under a stream of $N_2$. The aqueous layer was washed with DCM (0.5 ml) and acidified to pH 4 with 2M HCl until a white precipitate formed. This was then extracted with EtOAc (0.5 ml). The organic layer was dried ($Na_2SO_4$), filtered, and the solvent removed in vacuo to give the title compound.

Yield: 25 mg, 30%; LC/MS $t_r$ 1.42 min; MS (ES+) m/z 339 (M+H); HPLC Purity: 95%; $^1$H NMR (360 MHz; MeOD): δ

3.53 (s, 2H), 6.84 (d, 1H), 7.00 (d, 1H), 7.10 (m, 2H), 7.23 (m, 2H), 7.56 (m, 2H), 7.87 (m, 2H).

(bb) Alternate Synthesis of (3-([5-(phenyl)-furan-2-carbonyl]-amino)-phenyl)-acetic acid (10)

(i) (3-([5-(phenyl)-furan-2-carbonyl]-amino)-phenyl)-acetic acid methyl ester

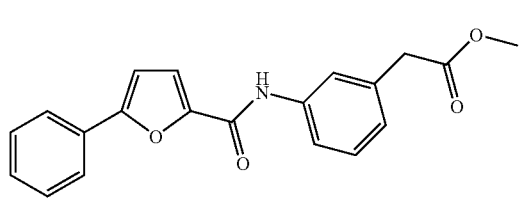

Methyl ester (16) (500 mg, 1.48 mmol) was coupled to phenylboronic acid (150 mg, 1.23 mmol) using Method E. The crude compound was purified by column chromatography, eluting with a stepped gradient of 20-25% EtOAc in heptane to give the title compound.

Yield: 120 mg, 29%; LC/MS $t_r$ 1.51 min; MS (ES+) m/z 336 (M+H)

(ii) (3-{[5-(phenyl)-furan-2-carbonyl]-amino}-phenyl)-acetic acid (10)

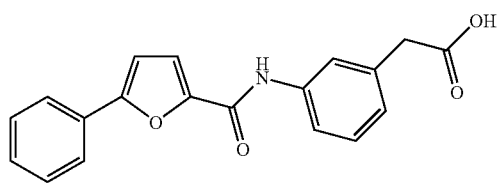

To a solution of ester (112 mg, 0.33 mmol) in THF (1.1 ml) was added NaOH (112 mg, 2.8 mmol) in water (1.1 ml) and the resulting solution was stirred for 6 h at room temperature. The THF was removed under a stream of $N_2$ and the aqueous layer was acidified to pH 4 using 1M HCl. The aqueous layer was extracted with DCM (2×2 ml) and the combined organic layers evaporated in vacuo to give the title compound.

Yield: 97 mg, 91%; LC/MS $t_r$ 1.36 min; MS (ES+) m/z 322 (M+H); HPLC Purity: 99%; $^1$H NMR (360 MHz; DMSO): δ 3.63 (s, 2H), 7.08 (d, 1H), 7.25 (d, 2H), 7.37 (t, 1H), 7.47 (m, 2H), 7.56 (t, 2H), 7.71 (s, 1H), 7.77 (d, 2H), 8.04 (d, 2H), 10.24 (s, 1H), 12.45 (s, 1H)

Example 7

(a) {3-[(5-Phenyl-thiophene-2-carbonyl)-amino]-phenyl}-acetic acid (43)

(i) {3-[(5-Bromo-thiophene-2-carbonyl)-amino]-phenyl}-acetic acid ethyl ester

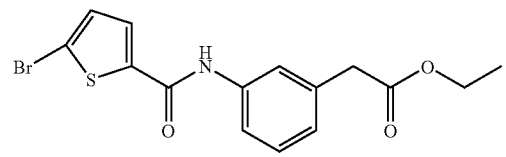

5-Bromothiophene-2-carboxylic acid (232 mg, 1.1 mmol) was coupled with ethyl ester (6) (201 mg, 1.1 mmol) following Method C to give the title compound.

Yield: 220 mg, 54%; LC/MS $t_r$ 1.54 min; MS (ES+) m/z 368, 370 (M+H)

(ii) {3-[(5-Phenyl-thiophene-2-carbonyl)-amino]-phenyl}-acetic acid ethyl ester

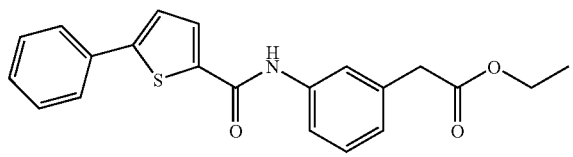

{3-[(5-Bromo-thiophene-2-carbonyl)-amino]-phenyl}-acetic acid ethyl ester (220 mg, 0.60 mmol) was coupled to phenylboronic acid using Method E except that the reaction mixture was heated at 80° C. for 25 min under microwave conditions. The crude product was purified by column chromatography using 33% EtOAc in heptane to give the title compound.

Yield: 128 mg, 58%; LC/MS $t_r$ 1.61 min; MS (ES+) m/z 366 (M+H)

(iii) {3-[(5-Phenyl-thiophene-2-carbonyl)-amino]-phenyl}-acetic acid (43)

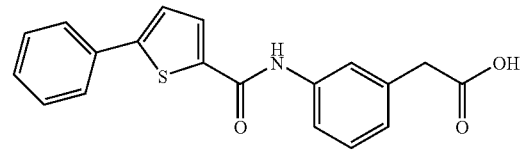

The ethyl ester (75 mg, 0.21 mmol) was hydrolysed using Method H to give the title compound.

Yield: 44 mg, 63%; LC/MS $t_r$ 1.50 min; MS (ES+) m/z 338 (M+H); HPLC Purity: 100%; $^1$H NMR (400 MHz, MeOD) δ 3.62 (s, 2H), 7.08-7.10 (m, 1H), 7.29-7.46 (m, 5H), 7.60-7.62 (m, 2H), 7.70-7.72 (m, 2H), 7.88 (d, 1H).

(b) (3-[(4-Chloro-biphenyl-3-carbonyl)-amino]-phenyl)-acetic acid (44)

(i) [3-(5-Bromo-2-chloro-benzoylamino)-phenyl]-acetic acid ethyl ester

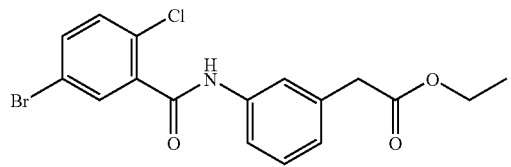

5-Bromo-2-chlorobenzoic acid (132 mg, 0.56 mmol) was coupled with ethyl ester (6) (100 mg, 0.56 mmol) following Method C to give the title compound.

Yield: 198 mg, 89%; LC/MS $t_r$ 1.55 min; MS (ES+) m/z 396, 398 (M+H)

(ii) {3-[(4-Chloro-biphenyl-3-carbonyl)-amino]-phenyl}-acetic acid ethyl ester

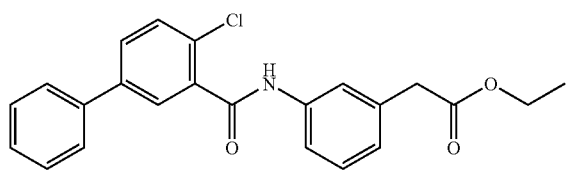

[3-(5-Bromo-2-chloro-benzoylamino)-phenyl]-acetic acid ethyl ester (198 mg, 0.50 mmol) was coupled to phenylboronic acid using Method E, except that the reaction mixture was heated at 80° C. for 25 min. The crude product was purified by column chromatography using 20% EtOAc in heptane to give the title compound.

Yield: 86 mg, 44%; LC/MS $t_r$ 1.66 min; MS (ES+) m/z 394, 396 (M+H)

(iii) {3-[(4-Chloro-biphenyl-3-carbonyl)-amino]-phenyl}-acetic acid (44)

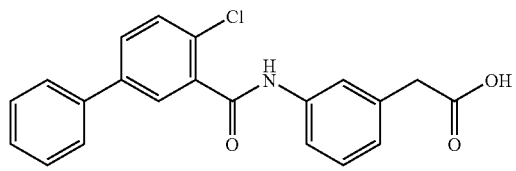

The ethyl ester (86 mg, 0.22 mmol) was hydrolysed using Method H to give the title compound.

Yield: 62 mg, 78%; LC/MS $t_r$ 1.48 min; MS (ES+) m/z 366, 368 (M+H); HPLC Purity: 92%; $^1$H NMR (400 MHz, MeOD) δ 3.65 (s, 2H), 7.13 (d, 1H), 7.33-7.50 (m, 4H), 7.58-7.82 (m, 7H).

(c) {3-[(6-Phenyl-pyridine-2-carbonyl)-amino]-phenyl}-acetic acid (45)

(i) {3-[(6-Bromo-pyridine-2-carbonyl)-amino]-phenyl}-acetic acid ethyl ester (77)

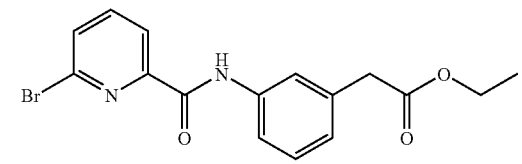

6-Bromo-2-pyridinecarboxylic acid (113 mg, 0.56 mmol) was coupled with ethyl ester (6) (100 mg, 0.56 mmol) following Method C to give the title compound.

Yield: 198 mg, 97%; LC/MS $t_r$ 1.52 min; MS (ES+) m/z 363, 365 (M+H)

(ii) {3-[(6-Phenyl-pyridine-2-carbonyl)-amino]-phenyl}-acetic acid ethyl ester

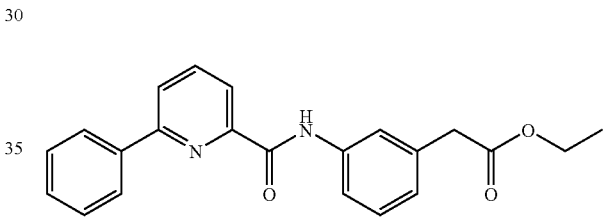

{3-[(6-Bromo-pyridine-2-carbonyl)-amino]-phenyl}-acetic acid ethyl ester (77)(198 mg, 0.54 mmol) was coupled to phenylboronic acid using Method E, except that the reaction mixture was heated at 80° C. for 25 min. The crude product was purified by column chromatography using 20% EtOAc in heptane to give the title compound.

Yield: 129 mg, 66%; LC/MS $t_r$ 1.70 min; MS (ES+) m/z 361 (M+H)

(iii) {3-[(6-Phenyl-pyridine-2-carbonyl)-amino]-phenyl}-acetic acid (45)

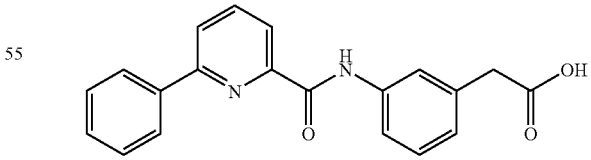

The ethyl ester (129 mg, 0.36 mmol) was hydrolysed using Method H to give the title compound.

Yield: 100 mg, 84%; LC/MS $t_r$ 1.49 min; MS (ES+) m/z 333 (M+H); HPLC Purity: 96%; $^1$H NMR (400 MHz, MeOD) δ 3.69 (s, 2H), 7.15 (d, 1H), 7.37-7.42 (m, 1H), 7.50-7.60 (m, 3H), 7.78-7.80 (m, 2H), 8.08-8.23 (m, 5H)

(d) {3-[(6-Fluoro-biphenyl-3-carbonyl)-amino]-phenyl}-acetic acid (46)

(i) [3-(3-Bromo-4-fluoro-benzoylamino)-phenyl]-acetic acid ethyl ester

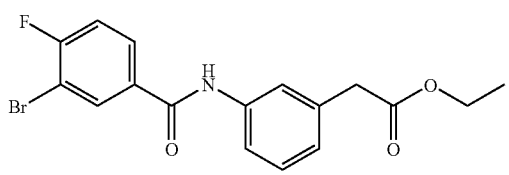

3-Bromo-4-fluorobenzoic acid (123 mg, 0.56 mmol) was coupled with ethyl ester (6) (100 mg, 0.56 mmol) following Method C to give the title compound.

Yield: 190 mg, 89%; LC/MS t$_r$ 1.55 min; MS (ES+) m/z 380, 382 (M+H)

(ii) {3-[(6-Fluoro-biphenyl-3-carbonyl)-amino]-phenyl}-acetic acid ethyl ester

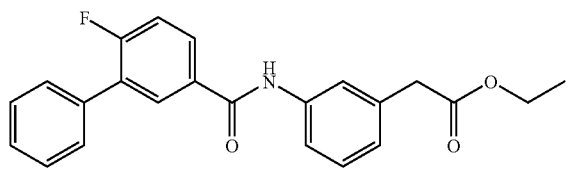

[3-(3-Bromo-4-fluoro-benzoylamino)-phenyl]-acetic acid ethyl ester (190 mg, 0.50 mmol) was coupled to phenylboronic acid using Method E, except that the reaction mixture was heated at 80° C. for 25 min. The crude product was purified by column chromatography using 20% EtOAc in heptane to give the title compound.

Yield: 106 mg, 56%; LC/MS t$_r$ 1.67 min; MS (ES+) m/z 378 (M+H)

(iii) {3-[(6-Fluoro-biphenyl-3-carbonyl)-amino]-phenyl}-acetic acid (46)

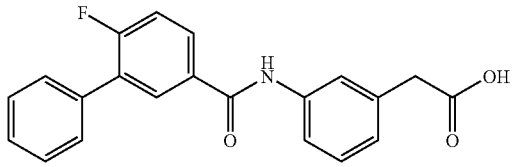

The ethyl ester (106 mg, 0.28 mmol) was hydrolysed using Method H to give the title compound.

Yield: 83 mg, 84%; LC/MS t$_r$ 1.51 min; MS (ES+) m/z 350 (M+H); HPLC Purity: 92%; $^1$H NMR (400 MHz, MeOD) δ 3.65 (s, 2H), 7.12 (d, 1H), 7.33-7.53 (m, 5H), 7.63-7.67 (m, 4H), 7.97-8.01 (m, 1H), 8.10-8.12 (m, 1H).

(e) {3-[(3-Methyl-biphenyl-4-carbonyl)-amino]-phenyl}-acetic acid (47)

(i) [3-(4-Bromo-2-methyl-benzoylamino)-phenyl]-acetic acid ethyl ester

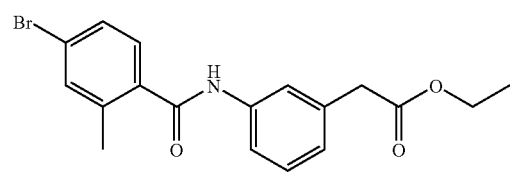

4-Bromo-2-methylbenzoic acid (120 mg, 0.56 mmol) was coupled with ethyl ester (6) (100 mg, 0.56 mmol) following Method C to give the title compound Yield: 188 mg, 89%; LC/MS t$_r$ 1.53 min; MS (ES+) m/z 376, 378 (M+H)

(ii) {3-[(3-Methyl-biphenyl-4-carbonyl)-amino]-phenyl}-acetic acid ethyl ester

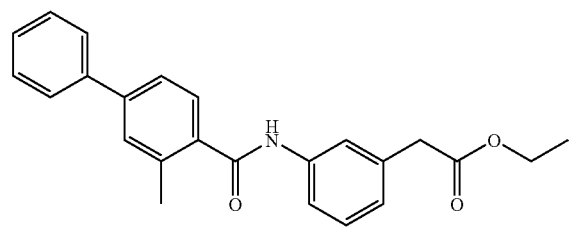

[3-(4-Bromo-2-methyl-benzoylamino)-phenyl]-acetic acid ethyl ester (188 mg, 0.50 mmol) was coupled to phenylboronic acid using Method E, except that the reaction mixture was heated at 80° C. The crude residue was purified by column chromatography using 20% EtOAc in heptane to give the title compound.

Yield: 87 mg, 47%; LC/MS t$_r$ 1.73 min; MS (ES+) m/z 374 (M+H)

(iii) {3-[(3-Methyl-biphenyl-4-carbonyl)-amino]-phenyl}-acetic acid (47)

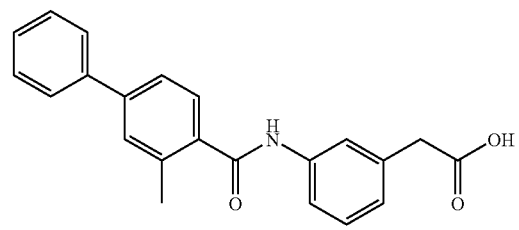

The ethyl ester (87 mg, 0.23 mmol) was hydrolysed using Method H to give the title compound.

Yield: 52 mg, 65%; LC/MS t$_r$ 1.84 min; MS (ES+) m/z 346 (M+H); HPLC Purity: 96%; $^1$H NMR (400 MHz, MeOD) δ 2.56 (s, 3H), 3.64 (s, 2H), 7.13 (d, 1H), 7.33-7.41 (m, 2H), 7.46-7.51 (m, 2H), 7.58-7.69 (m, 7H).

(f) {3-[(3-Chloro-biphenyl-4-carbonyl)-amino]-phenyl}-acetic acid (48)

(i) [3-(4-Bromo-2-chloro-benzoylamino)-phenyl]-acetic acid ethyl ester

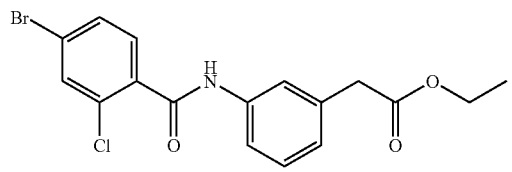

4-Bromo-2-chlorobenzoic acid (132 mg, 0.56 mmol) was coupled with ethyl ester (6) (100 mg, 0.56 mmol) following Method C to give the title compound.

Yield: 198 mg, 89%; LC/MS $t_r$ 1.57 min; MS (ES+) m/z 396, 398 (M+H)

(ii) {3-[(3-Chloro-biphenyl-4-carbonyl)-amino]-phenyl}-acetic acid ethyl ester

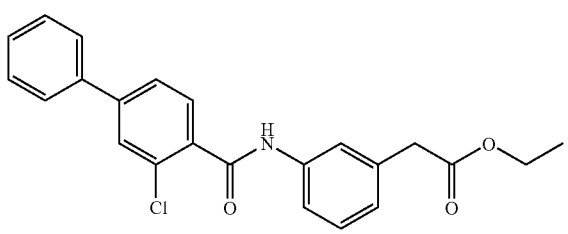

[3-(4-Bromo-2-chloro-benzoylamino)-phenyl]-acetic acid ethyl ester (198 mg, 0.50 mmol) was coupled to phenylboronic acid using Method E, except that the reaction mixture was heated at 80° C. The crude residue was purified by column chromatography using 20% EtOAc in heptane to give the title compound.

Yield: 100 mg, 51%; LC/MS $t_r$ 1.67 min; MS (ES+) m/z 394, 396 (M+H)

(iii) {3-[(3-Chloro-biphenyl-4-carbonyl)-amino]-phenyl}-acetic acid (48)

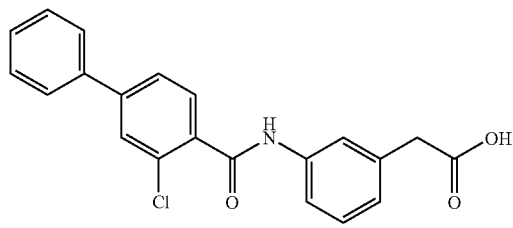

The ethyl ester (100 mg, 0.25 mmol) was hydrolysed using Method H to give the title compound.

Yield: 90 mg, 97%; LC/MS $t_r$ 1.84 min; MS (ES+) m/z 366, 368 (M+H); HPLC Purity: 96%; $^1$H NMR (250 MHz, MeOD) δ 3.64 (s, 2H), 7.13 (d, 1H), 7.32-7.55 (m, 4H), 7.64-7.79 (m, 7H).

(g) {3-[(Biphenyl-3-carbonyl)-amino]-phenyl}-acetic acid (49)

(i) [3-(3-Bromo-benzoylamino)-phenyl]-acetic acid ethyl ester

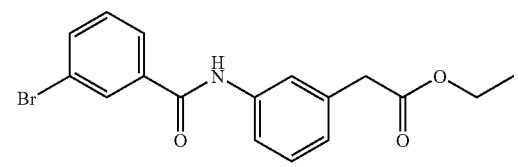

3-Bromo-benzoic acid (112 mg, 0.56 mmol) was coupled with ethyl ester (6) (100 mg, 0.56 mmol) following Method C to give the title compound.

Yield: 203 mg, 100%; LC/MS $t_r$ 1.56 min; MS (ES+) m/z 362, 364 (M+H)

(ii) {3-[(Biphenyl-3-carbonyl)-amino]-phenyl}-acetic acid ethyl ester

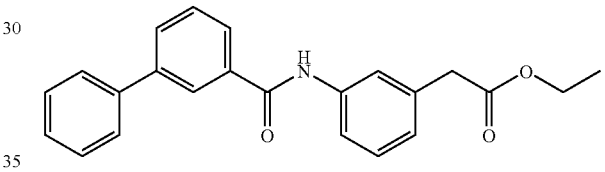

[3-(3-Bromo-benzoylamino)-phenyl]-acetic acid ethyl ester (203 mg, 0.56 mmol) was coupled to phenylboronic acid using Method E, except that the reaction mixture was heated at 80° C. The crude residue was purified by column chromatography using 20% EtOAc in heptane to give the title compound.

Yield: 142 mg, 70%; LC/MS $t_r$ 1.65 min; MS (ES+) m/z 360 (M+H)

(iii) (3-[(Biphenyl-3-carbonyl)-amino]-phenyl)-acetic acid (49)

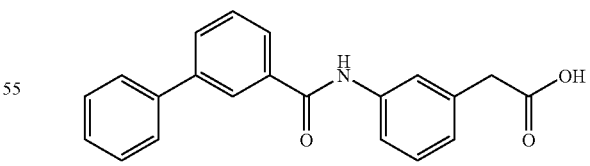

The ethyl ester (140 mg, 0.39 mmol) was hydrolysed using Method H to give the title compound.

Yield: 85 mg, 66%; LC/MS $t_r$ 1.49 min; MS (ES+) m/z 332 (M+H); HPLC Purity: 97%; $^1$H NMR (250 MHz, MeOD) δ 3.65 (s, 2H), 7.13 (d, 1H), 7.32-7.44 (m, 2H), 7.47-7.54 (m, 2H), 7.59-7.75 (m, 5H), 7.85-7.96 (m, 2H), 8.21-8.22 (m, 1H).

(h) {3-[(4-Methyl-5-phenyl-thiophene-2-carbonyl)-amino]-phenyl}-acetic acid (50)

(i) 4-Methyl-5-phenyl-thiophene-2-carboxylic acid (methyl and ethyl) ester

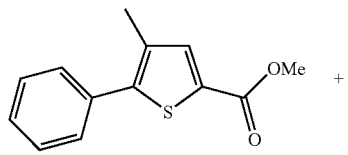
+
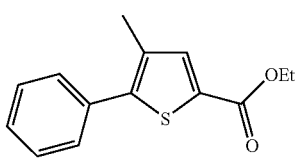

5-Bromo-4-methyl-thiophene-2-carboxylic acid methyl ester (120 mg, 0.51 mmol) was coupled to phenylboronic acid using Method E, except that the reaction mixture was heated at 80° C. in EtOH/toluene. The crude residue was purified by column chromatography using 10% EtOAc in heptane to give the title compound as a mixture of the methyl and ethyl esters.

Yield: 108 mg (combined); LC/MS $t_r$: 1.69 min (Me), 1.78 min (Et); MS (ES+) m/z 233 [(M+H) Me]; 247 [(M+H) Et]; HPLC Purity: 98% (59% Me, 39% Et)

(ii) 4-Methyl-5-phenyl-thiophene-2-carboxylic acid

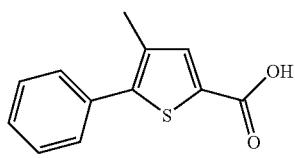

To a solution of 4-methyl-5-phenyl-thiophene-2-carboxylic acid (methyl and ethyl) ester (106 mg, ~0.45 mmol) in MeOH (5 ml) was added 1M NaOH (5 ml) and the resulting solution was stirred for 30 min at room temperature. The MeOH was then removed in vacuo. DCM (20 ml) and water (20 ml) were added and the aqueous layer extracted with DCM (2×20 ml). The aqueous layer was acidified with 2M HCl until a white precipitate formed. This was then extracted with EtOAc (3×20 ml). The combined organic layers were washed with brine (20 ml), dried (Na$_2$SO$_4$), filtered and the solvent removed in vacuo to give the title compound.

Yield: 25 mg, 25%; LC/MS $t_r$ 1.42 min; MS (ES+) m/z 260 (M+H+MeCN)

(iii) {3-[(4-Methyl-5-phenyl-thiophene-2-carbonyl)-amino]-phenyl}-acetic acid ethyl ester

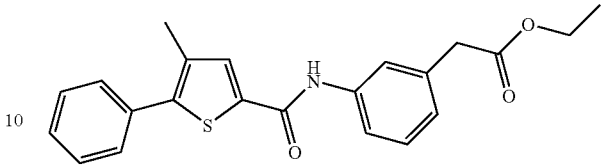

4-Methyl-5-phenyl-thiophene-2-carboxylic acid (25 mg, 0.11 mmol) was coupled with ethyl ester (4) (20 mg, 0.11 mmol) following Method C. The crude residue was purified by column chromatography using 20% EtOAc in heptane to give the title compound.

Yield: 29 mg, 67%; LC/MS $t_r$ 1.70 min; MS (ES+) m/z 380 (M+H)

(iv) {3-[(4-Methyl-5-phenyl-thiophene-2-carbonyl)-amino]-phenyl}-acetic acid (50)

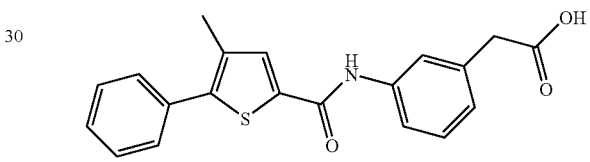

The ethyl ester (29 mg, 0.08 mmol) was hydrolysed using Method H to give the title compound.

Yield: 24 mg, 85%; LC/MS $t_r$ 1.55 min; MS (ES+) m/z 352 (M+H); HPLC Purity: 84%; $^1$H NMR (250 MHz, MeOD) δ 2.38 (s, 3H), 3.62 (s, 2H), 7.12 (d, 1H), 7.30-7.60 (m, 7H), 7.64-7.67 (m, 1H), 7.77 (s, 1H)

(j) {3-[(4-Fluoro-biphenyl-3-carbonyl)-amino]-phenyl}-acetic acid (51)

(i) [3-(5-Bromo-2-fluoro-benzoylamino)-phenyl]-acetic acid ethyl ester (78)

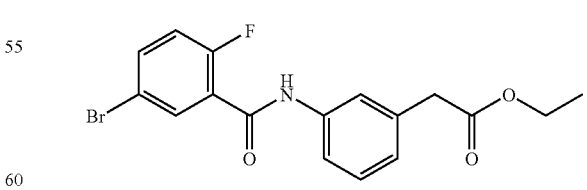

2-Fluoro-5-bromobenzoic acid (123 mg, 0.56 mmol) was coupled with ethyl ester (6) (100 mg, 0.56 mmol) following Method C to give the title compound.

Yield: 209 mg, 98%; LC/MS $t_r$ 1.63 min; MS (ES+) m/z 380, 382 (M+H)

(ii) {3-[(4-Fluoro-biphenyl-3-carbonyl)-amino]-phenyl}-acetic acid ethyl ester

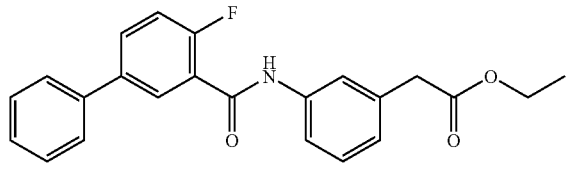

[3-(5-Bromo-2-fluoro-benzoylamino)-phenyl]-acetic acid ethyl ester (78) (209 mg, 0.55 mmol) was coupled to phenylboronic acid using Method E, except that the reaction mixture was heated at 80° C. The crude reside was purified by column chromatography using 20% EtOAc in heptane to give the title compound.

Yield: 98 mg, 47%; LC/MS $t_r$ 1.71 min; MS (ES+) m/z 378 (M+H)

(iii) {3-[(4-Fluoro-biphenyl-3-carbonyl)-amino]-phenyl}-acetic acid (51)

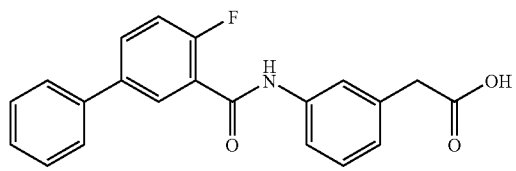

The ethyl ester (98 mg, 0.26 mmol) was hydrolysed using Method H to give the title compound.

Yield: 89 mg, 98%; LC/MS $t_r$: 1.47 min; MS (ES+) m/z 350 (M+H); HPLC Purity: 100%; $^1$H NMR (250 MHz, MeOD) δ 3.55 (s, 2H), 7.16 (d, 1H), 7.28-7.35 (m, 1H), 7.40-7.55 (m, 4H), 7.60-7.78 (m, 5H) 8.07-8.08 (m, 1H)

(k) ({3-[(5-Fluoro-biphenyl-3-carbonyl)-amino]-phenyl}-acetic acid (52)

(i) [3-(3-Bromo-5-fluoro-benzoylamino)-phenyl]-acetic acid ethyl ester

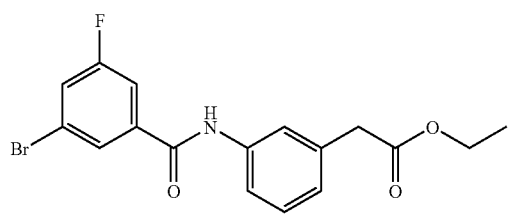

3-Fluoro-5-bromobenzoic acid (123 mg, 0.56 mmol) was coupled with ethyl ester (6) (100 mg, 0.56 mmol) following Method C to give the title compound.

Yield: 209 mg, 98%; LC/MS $t_r$ 1.52 min; MS (ES+) m/z 380, 382 (M+H)

(ii) {3-[(5-Fluoro-biphenyl-3-carbonyl)-amino]-phenyl}-acetic acid ethyl ester

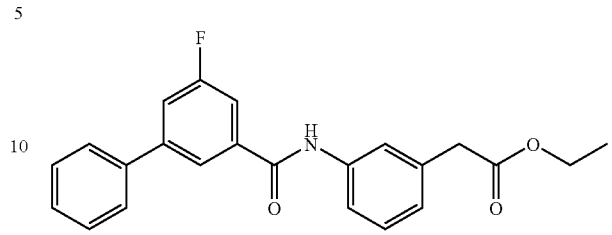

[3-(3-Bromo-5-fluoro-benzoylamino)-phenyl]-acetic acid ethyl ester (209 mg, 0.55 mmol) was coupled to phenylboronic acid using Method E, except that the reaction mixture was heated at 80° C. The crude residue was purified by column chromatography using 20% EtOAc in heptane to give the title compound.

Yield: 104 mg, 50%; LC/MS $t_r$ 1.66 min; MS (ES+) m/z 378 (M+H)

(iii) {3-[(5-fluoro-biphenyl-3-carbonyl)-amino]-phenyl}-acetic acid (52)

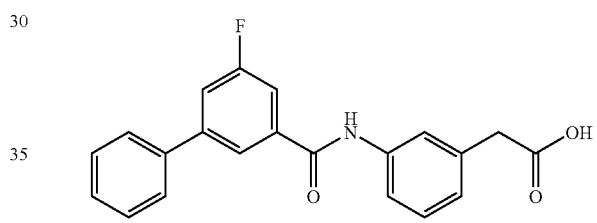

The ethyl ester (104 mg, 0.28 mmol) was hydrolysed using Method H to give the title compound.

Yield: 91 mg, 95%; LC/MS $t_r$ 1.42 min; MS (ES+) m/z 350 (M+H); HPLC Purity: 94%; $^1$H NMR (250 MHz, MeOD) δ 3.60 (s, 2H), 7.14 (d, 1H), 7.30-7.36 (m, 5H), 7.60 (s, 1H), 7.65-7.72 (m, 3H) 7.80-7.86 (m, 1H) 7.97-8.00 (m, 1H)

(l) {3-[(2-Phenyl-1H-imidazole-5-carbonyl)-amino]-phenyl}-acetic acid (53)

(i) {3-[(2-Phenyl-1H-imidazole-5-carbonyl)-amino]-phenyl}-acetic acid ethyl ester

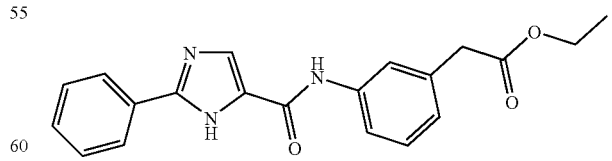

2-Phenyl-1H-imidazole-5-carboxylic acid (105 mg, 0.56 mmol) was coupled with ethyl ester (6) (100 mg, 0.56 mmol) following Method C to give the title compound.

Yield: 116 mg, 59%; LC/MS $t_r$ 1.19 min; MS (ES+) m/z 350 (M+H)

(ii) {3-[(2-Phenyl-1H-imidazole-5-carbonyl)-amino]-phenyl}-acetic acid (53)

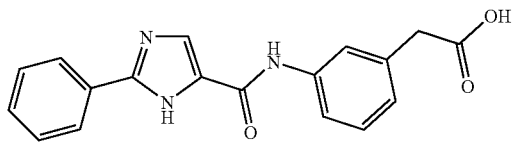

The ethyl ester (50 mg, 0.14 mmol) was hydrolysed using Method H to give the title compound.
Yield: 29 mg, 63%; LC/MS $t_r$ 1.39 min; MS (ES+) m/z 322 (M+H); HPLC Purity: 89%; $^1$H NMR (250 MHz, MeOD) δ 3.66 (s, 2H), 7.10 (d, 1H), 7.31-7.37 (m, 1H), 7.43-7.56 (m, 3H), 7.67-7.68 (m, 2H), 7.87 (s, 1H), 7.97-8.00 (m, 2H).

(m) (3-[(2-Phenyl-thiazole-4-carbonyl)-amino]-phenyl)-acetic acid (54)

(i) 2-Amino-thiazole-4-carboxylic acid ethyl ester hydrobromide salt

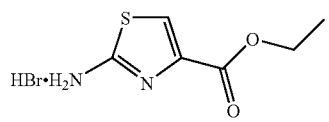

Thiourea (1.5 g, 20 mmol) and ethyl bromopyruvate (2.8 ml, 22 mmol) were heated at 100° C. for 1 h. The reaction was cooled and acetone (10 ml) was added. The mixture was then filtered to give a yellow/brown solid and the crude material was crystallised from hot ethanol (20 ml) to give the title compound as the HBr salt (2.63 g). The liquor was concentrated and recrystallised from hot EtOH (5 ml) to give further product (0.63 g).
Yield: 3.26 g, 64%; LC/MS $t_r$ 0.67 min; MS (ES+) m/z 173 (M+H); $^1$H NMR (400 MHz, MeOD) δ 1.42 (t, 3H), 4.43 (q, 2H), 7.74 (s, 1H).

(ii) 2-Chloro-thiazole-4-carboxylic acid ethyl ester

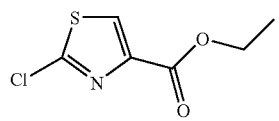

2-Amino-thiazole-4-carboxylic acid ethyl ester hydrobromide salt (506 mg, 2 mmol) was converted to the free base by partitioning between aqueous saturated K$_2$CO$_3$ solution and EtOAc. The organic layer was washed with brine, dried (Na$_2$SO$_4$), filtered and the solvent removed in vacuo to give the free base (306 mg, 89%).
The free based 2-amino-thiazole-4-carboxylic acid ethyl ester (306 mg, 1.78 mmol) and CuCl (238 mg, 2.4 mmol) were suspended in conc. HCl (8 ml) and the mixture cooled on a salt/ice bath. A pre-cooled solution of NaNO$_2$ (166 mg, 2.4 mmol) in water (2 ml) was added over a period of 10 min. The mixture was allowed to warm to room temperature over 1 h and was stirred for a further 1 h. Water was added and the aqueous layer extracted with EtOAc (3×10 ml). The combined EtOAc layers were washed with brine, dried (Na$_2$SO$_4$), filtered and the solvent removed in vacuo to give the title compound.
Yield: 251 mg, 74%; LC/MS $t_r$ 1.06 min; MS (ES+) m/z 192, 194 (M+H); $^1$H NMR (250 MHz, CDCl$_3$) δ 1.41 (t, 3H), 4.43 (q, 2H), 8.08 (s, 1H).

(iii) 2-Chloro-thiazole-4-carboxylic acid (79)

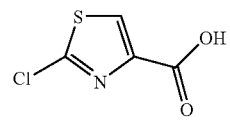

The ethyl ester (120 mg, 0.63 mmol) was hydrolysed using Method H to give the title compound.
Yield: 75 mg, 73%; LC/MS $t_r$ 0.77 min; MS (ES+) m/z 164, 166 (M+H)

(iv) {3-[(2-Chloro-thiazole-4-carbonyl)-amino]-phenyl}-acetic acid ethyl ester

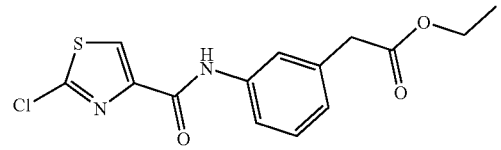

2-Chloro-thiazole-4-carboxylic acid (79) (70 mg, 0.43 mmol) was coupled with ethyl ester (6) (77 mg, 0.43 mmol) following Method C to give the title compound.
Yield: 114 mg, 82%; LC/MS $t_r$ 1.44 min; MS (ES+) m/z 325, 327 (M+H)

(v) (3-[(2-Phenyl-thiazole-4-carbonyl)-amino]-phenyl)-acetic acid ethyl ester

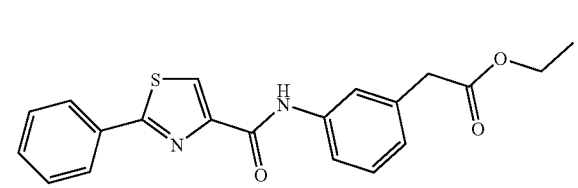

{3-[(2-Chloro-thiazole-4-carbonyl)-amino]-phenyl}-acetic acid ethyl ester (114 mg, 0.35 mmol) was coupled to phenylboronic acid using Method E, except that the reaction mixture was heated for 140 min. The crude residue was purified by column chromatography using 33% EtOAc in heptane to give the title compound.
Yield: 37 mg, 29%; LC/MS $t_r$ 1.64 min; MS (ES+) m/z 367 (M+H)

(vi) {3-[(2-Phenyl-thiazole-4-carbonyl)-amino]-phenyl}-acetic acid (54)

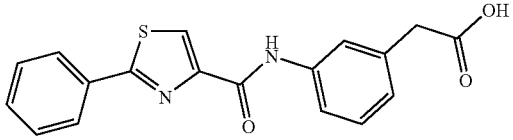

The ethyl ester (37 mg, 0.10 mmol) was hydrolysed using Method H to give the title compound.

Yield: 23 mg, 67%; LC/MS $t_r$ 1.62 min; MS (ES+) m/z 339 (M+H); HPLC Purity: 100%; $^1$H NMR (400 MHz, MeOD) δ 3.68 (s, 2H), 7.15 (d, 1H), 7.36-7.40 (m, 1H), 7.54-7.58 (m, 3H), 7.74-7.75 (m, 2H), 8.15-8.16 (m, 2H), 8.35 (s, 1H)

(n) 3-{[(5-Phenyl-furan-2-carbonyl)-amino]-methyl}-benzoic acid (57)

(i) 5-Bromo-furan-2-carboxylic acid methyl ester (55)

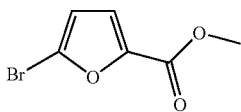

5-Bromo-furan-2-carboxylic acid (2 g, 10.5 mmol) was esterified with MeOH using Method B to give the title compound.

Yield: 1.54 g, 72%; LC-MS $t_r$ 1.24 min; MS (ES+) m/z 205, 207 (M+H)

(ii) 5-Phenyl-furan-2-carboxylic acid (56)

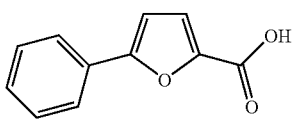

5-Bromo-furan-2-carboxylic acid methyl ester (5) (205 mg, 1 mmol) was coupled to phenylboronic acid (146 mg, 1.2 mmol) using Method E except that once the reaction was complete, the solvents were removed in vacuo. The crude residue was re-dissolved in EtOAc (10 ml) and 1M NaOH (20 ml) was added. The aqueous layer was extracted with EtOAc (3×10 ml), and the organic layer was discarded. The aqueous layer was acidified to pH 1 with conc. HCl, and extracted with EtOAc (3×10 ml). The combined organic layers were dried (MgSO$_4$), filtered, and the solvent removed in vacuo to give the title compound.

Yield: 190 mg, 100%; LC-MS $t_r$ 1.23 min; MS (ES+) m/z 189 (M+H)

(iii) 3-[(9H-Fluoren-9-ylmethoxycarbonylamino)-methyl]-benzoic acid methyl ester

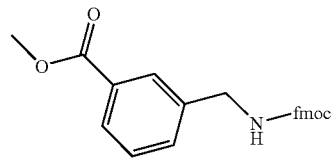

3-[(9H-Fluoren-9-ylmethoxycarbonylamino)-methyl]-benzoic acid (200 mg, 0.54 mmol) was esterified with MeOH using Method B to give the title compound.

Yield: 193 mg, 93%; LC-MS $t_r$ 1.64 min; MS (ES+) m/z 388 (M+H)

(iv) 3-Aminomethyl-benzoic acid methyl ester

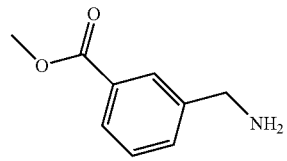

A 20% solution of piperidine in DMF (5 ml) was added to 3-[(9H-Fluoren-9-ylmethoxycarbonylamino)-methyl]-benzoic acid methyl ester (193 mg, 0.5 mmol) and the reaction was stirred at room temperature for 30 min. Water (10 ml) was added to the crude reaction mixture, followed by 1M HCl (10 ml). The aqueous layer was washed with EtOAc (3×10 ml) then basified to pH 9 with saturated NaHCO$_3$. The basic layer was extracted with EtOAc (3×10 ml) and the aqueous layer was evaporated down to a small volume, then further extracted with EtOAc (5×10 ml). The combined organic layers were dried (MgSO$_4$), filtered and the solvent evaporated in vacuo to give the title compound.

Yield: 17 mg, 21%; LC-MS $t_r$ 0.77 min; MS (ES+) m/z 166 (M+H)

(v) 3-{[(5-Phenyl-furan-2-carbonyl)-amino]-methyl}-benzoic acid methyl ester

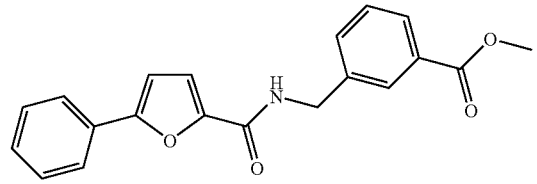

5-Phenyl-furan-2-carboxylic acid (6) (17 mg, 0.10 mmol) was coupled to 3-aminomethyl-benzoic acid methyl ester (19.4 mg, 0.10 mmol) using Method D to give the title compound Yield: 18 mg, 52%; LC-MS $t_r$ 1.90 min; MS (ES+) m/z 336 (M+H)

(vi) 3-{[(5-Phenyl-furan-2-carbonyl)-amino]-methyl}-benzoic acid (57)

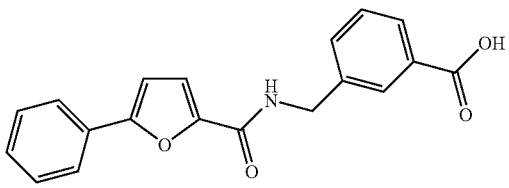

The ester (10 mg, 0.03 mmol) was dissolved in THF (0.1 ml) and NaOH (20 mg, 0.5 mmol) was dissolved in H$_2$O (0.1 ml). The solutions were combined and stirred at room temperature for 6 h. Further NaOH (50 mg, 1.25 mmol) was added and the reaction was stirred overnight. The THF was removed under a stream of N$_2$ and the aqueous layer was acidified to pH 3 with 2M HCl before extracting with EtOAc (3×1 ml). The combined organic layers were dried (MgSO$_4$), filtered and the solvent removed in vacuo to give the title compound as a white solid.

Yield: 5 mg, 52%; LC-MS $t_r$ 1.76 min; MS (ES+) m/z 322 (M+H); HPLC Purity: 100%; $^1$H NMR (400 MHz; MeOD) δ 4.53 (s, 2H), 6.82 (d, 1H), 7.12 (d, 1H), 7.24 (t, 1H), 7.30-7.37 (m, 3H), 7.51 (d, 1H), 7.76 (d, 2H), 7.82 (d, 1H), 7.95 (s, 1H).

(o) 5-[(5-Phenyl-furan-2-carbonyl)-amino]-1H-indole-2-carboxylic acid (59)

(i) 5-Amino-1H-indole-2-carboxylic acid ethyl ester (58)

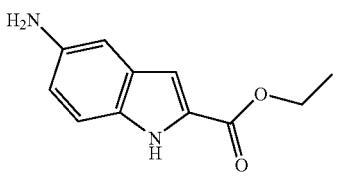

5-Nitro-1H-indole-2-carboxylic acid ethyl ester (500 mg, 2.1 mmol) was reduced using Method I to give the title compound.

Yield: 433 mg, 100%; LC-MS $t_r$ 0.84 min; MS (ES+) m/z 205 (M+H)

(ii) 5-[(5-Phenyl-furan-2-carbonyl)-amino]-1H-indole-2-carboxylic acid ethyl ester

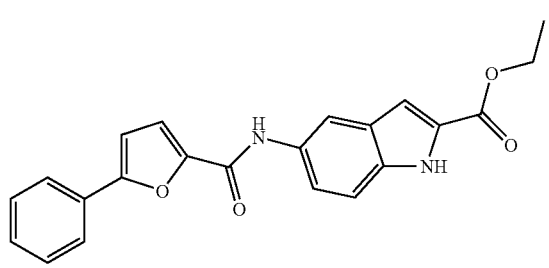

5-Phenyl-furan-2-carboxylic acid (56) (35 mg, 0.19 mmol) was coupled to 5-amino-1H-indole-2-carboxylic acid ethyl ester (42 mg, 0.20 mmol) using Method D to give the title compound.

Yield: 10 mg, 14%; LC-MS $t_r$ 1.55 min; MS (ES+) m/z 375 (M+H)

(iii) 5-[(5-Phenyl-furan-2-carbonyl)-amino]-1H-indole-2-carboxylic acid (59)

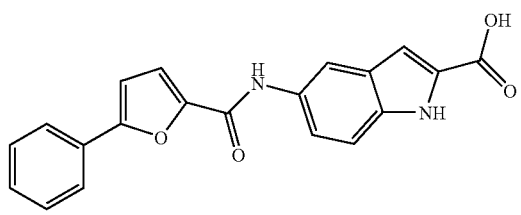

The ester (10 mg, 0.027 mmol) was dissolved in THF (0.5 ml) and water (2 ml). LiOH.H$_2$O (11 mg, 0.27 mmol) was then added as a solid. The resulting solution was stirred for 48 h at room temperature and then heated to 40° C. for 3 h with a few drops of MeOH. The THF was removed in vacuo and the basic solution was extracted with EtOAc (3×1 ml). The aqueous layer was acidified to pH 1 with conc. HCl and then extracted with EtOAc (3×1 ml). The combined organic layers were evaporated in vacuo to give the title compound.

Yield: 5.4 mg, 58%; LC/MS $t_r$ 1.34 min; MS (ES+) m/z 347 (M+H); HPLC Purity: 100%; $^1$H NMR (400 MHz; MeOD) δ 6.83-6.89 (m, 1H), 7.03-7.07 (m, 1H), 7.20-7.29 (m, 2H), 7.30-7.38 (m, 3H), 7.40-7.45 (m, 1H), 7.78-7.85 (m, 2H), 7.90 (s, 1H).

(p) 3-{3-[(5-Phenyl-furan-2-carbonyl)-amino]-phenyl}-acrylic acid (61)

(i) 3-(3-Amino-phenyl)-acrylic acid ethyl ester (60)

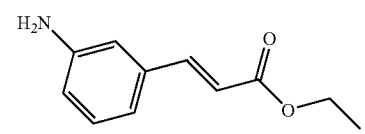

3-(3-Nitro-phenyl)-acrylic acid ethyl ester (500 mg, 2.3 mmol) was reduced using Method J to give the title compound.

Yield: 430 mg, 100%; LC-MS $t_r$ 0.92 min; MS (ES+) m/z 192 (M+H)

(ii) 3-{3-[(5-Phenyl-furan-2-carbonyl)-amino]-phenyl}-acrylic acid ethyl ester

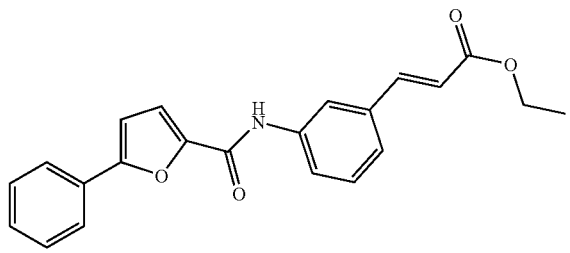

5-Phenyl-furan-2-carboxylic acid (56) (35 mg, 0.19 mmol) was coupled to 3-(3-amino-phenyl)-acrylic acid ethyl ester (60) (39 mg, 0.20 mmol) using Method D to give the title compound.

Yield: 13 mg, 18%; LC-MS $t_r$ 1.65 min; MS (ES+) m/z 362 (M+H)

(iii) 3-{3-[(5-Phenyl-furan-2-carbonyl)-amino]-phenyl}-acrylic acid (61)

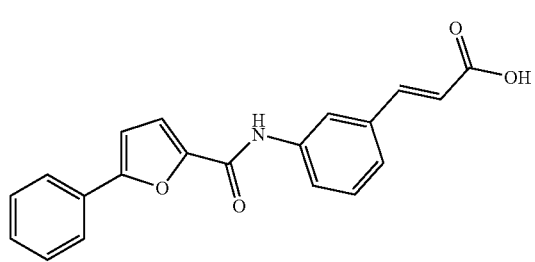

The ester (13 mg, 0.036 mmol) was dissolved in THF (0.5 ml) and water (2 ml). LiOH.H$_2$O (15 mg, 0.36 mmol) was then added as a solid and the resulting solution was stirred at room temperature for 18 h. The THF was removed in vacuo and the basic solution was extracted with EtOAc (3×1 ml). The aqueous layer was acidified to pH 1 with conc. HCl and then extracted with EtOAc (3×1 ml). The combined organic layers were evaporated in vacuo to give the title compound.

Yield: 3.4 mg, 28%; LC/MS $t_r$ 1.34 min; MS (ES+) m/z 334 (M+H); HPLC Purity: 94%; $^1$H NMR (400 MHz; MeOD) δ 6.43 (d, 1H), 6.92 (d, 1H), 7.25-7.41 (m, 6H), 7.59 (d, 1H), 7.72 (d, 1H), 7.86 (m, 2H), 7.91 (s, 1H).

(q) 3-{3-[(5-Phenyl-furan-2-carbonyl)-amino]-phenyl}-propionic acid (62)

(i) 3-(3-Amino-phenyl)-propionic acid methyl ester

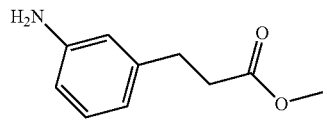

3-(3-Amino-phenyl)-propionic acid (495 mg, 3 mmol) was esterified with MeOH using Method A, except that the residue was partitioned between EtOAc (10 ml) and saturated aqueous NaHCO$_3$ (10 ml). The organic layer was dried (MgSO$_4$), filtered and evaporated in vacuo to give the title compound.

Yield: 448 mg, 83%; LC-MS $t_r$ 0.78 min; MS (ES+) m/z 180 (M+H)

(ii) 3-{3-[(5-Phenyl-furan-2-carbonyl)-amino]-phenyl}-propionic acid methyl ester

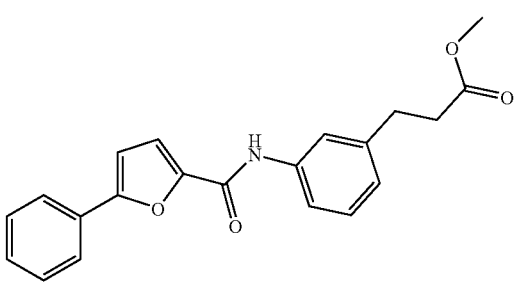

5-Phenyl-furan-2-carboxylic acid (56) (40 mg, 0.21 mmol) was coupled to 3-(3-amino-phenyl)-propionic acid methyl ester (41 mg, 0.23 mmol) using Method D to give the title compound.

Yield: 38 mg, 52%; LC-MS $t_r$ 1.51 min; MS (ES+) m/z 350 (M+H)

(iii) 3-{3-[(5-Phenyl-furan-2-carbonyl)-amino]-phenyl}-propionic acid (62)

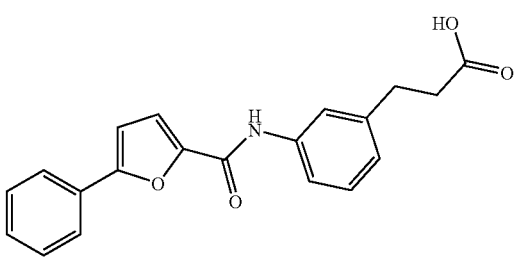

The ester (38 mg, 0.11 mmol) was dissolved in THF (1.5 ml) and NaOH (76 mg, 1.9 mmol) was dissolved in H$_2$O (1 ml). The solutions were combined and stirred at room temperature for 1 h. The THF was removed in vacuo and the aqueous layer was extracted with EtOAc (3×1 ml). The aqueous layer was then acidified to pH 1 with 1M HCl and then extracted with EtOAc (3×1 ml). The combined organic layers were dried (MgSO$_4$), filtered, and the solvent removed in vacuo to give the title compound.

Yield: 31 mg, 86%; LC/MS $t_r$ 1.39 min; MS (ES+) m/z 336 (M+H); HPLC Purity: 93%; $^1$H NMR (250 MHz; CDCl$_3$) δ 2.71 (t, 2H), 3.01 (t, 2H), 6.81 (d, 1H), 7.01 (d, 1H), 7.22-7.58 (m, 7H), 7.74 (d, 2H), 8.08 (s, 1H).

(r) 6-[(5-Phenyl-furan-2-carbonyl)-amino]-naphthalene-2-carboxylic acid (63)

(i) 6-Amino-naphthalene-2-carboxylic acid methyl ester

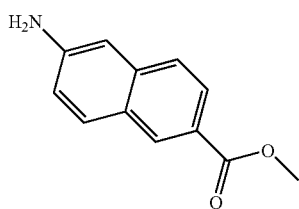

6-Amino-naphthalene-2-carboxylic acid (561 mg, 3 mmol) was esterified with MeOH using Method B to give the title compound.
Yield: 360 mg, 59%; MS (ES+) m/z 203 (M+H)

(ii) 6-[(5-Phenyl-furan-2-carbonyl)-amino]-naphthalene-2-carboxylic acid methyl ester

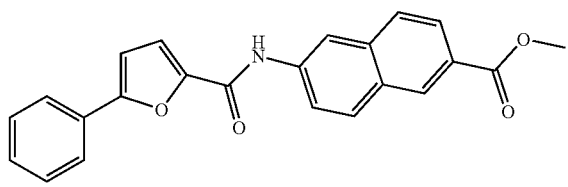

5-Phenyl-furan-2-carboxylic acid (56) (50 mg, 0.26 mmol) was coupled to 6-amino-naphthalene-2-carboxylic acid methyl ester (53 mg, 0.26 mmol) using Method C to give the title compound.
Yield: 17 mg, 17%; MS (ES+) m/z 372 (M+H)

(iii) 6-[(5-Phenyl-furan-2-carbonyl)-amino]-naphthalene-2-carboxylic acid (63)

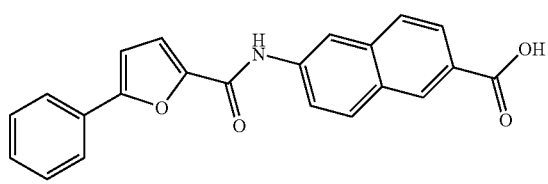

The ester (17 mg, 0.046 mmol) was dissolved in THF (1.5 ml) and MeOH (2 ml). NaOH (34 mg, 0.85 mmol) was dissolved in H$_2$O (1 ml). The solutions were combined and stirred at room temperature for 3.5 h. Further NaOH (34 mg, 0.85 mmol) was then added and the reaction mixture was stirred for 18 h at room temperature. The THF was removed under a stream of N$_2$, then MeOH (2 ml) was added and the resulting solution was heated at 40° C. for 2 h. The reaction was cooled to room temperature and stirred for 18 h. The MeOH was removed under a stream of N$_2$ and the aqueous layer extracted with EtOAc (3×1 ml). The aqueous layer was then acidified to pH 1 with 1M HCl and extracted with EtOAc (3×1 ml). The combined organic layers were dried (MgSO$_4$), filtered, and the solvents removed in vacuo to give the title compound.
Yield: 15 mg, 86%; LC/MS t$_r$ 1.53 min; MS (ES+) m/z 378 (M+H); HPLC Purity: 100%; $^1$H NMR (250 MHz; d-DMSO) δ 7.22 (s, 1H), 7.40-7.48 (m, 1H), 7.50-7.57 (m, 3H), 7.92-8.02 (m, 5H), 8.13 (d, 1H), 8.55 (d, 2H), 10.52 (s, 1H), 13.01 (s, 1H).

(s) (3-{[5-(3-Chloro-phenyl)-furan-2-carbonyl]-amino}-phenoxy)-acetic acid (66)

(i) (3-Acetylamino-phenoxy)-acetic acid ethyl ester

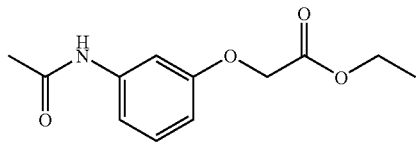

To a solution of N-(3-hydroxy-phenyl)-acetamide (0.5 g, 3.3 mmol) in acetone (5 ml) was added K$_2$CO$_3$ (0.46 g, 3.3 mmol), ethyl bromoacetate (0.67 g, 4.0 mmol) and 10 4 A molecular sieves. The reaction mixture was then heated in the microwave for 1 h at 100° C. (150 W, 200 psi). The reaction mixture was filtered and the acetone layer evaporated in vacuo. This residue was dissolved in EtOAc (10 ml) and washed with 2M KOH (5 ml×2). The organic layer was dried (Na$_2$SO$_4$), filtered and the solvent removed in vacuo to give the title compound as a colourless oil which solidified upon standing.
Yield: 700 mg, 89%; LC/MS t$_r$ 1.04 min; MS (ES+) m/z 238 (M+H)

(ii) (3-Amino-phenoxy)-acetic acid

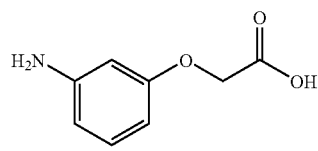

The ester (0.25 g, 1 mmol) was suspended in 1.2 M HCl and heated to 100° C. for 80 min. The water was removed in vacuo to give the title compound as the hydrochloride salt.
Yield: 170 mg, 83%; LC/MS t$_r$ 0.17 and 0.56 min; MS (ES+) m/z 168 (M+H)

(iii) (3-Amino-phenoxy)-acetic acid ethyl ester (64)

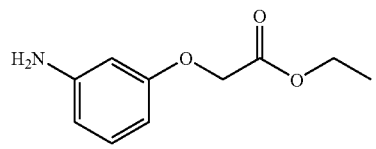

The carboxylic acid (100 mg, 0.6 mmol) was suspended in EtOH (1 ml) at 0° C. and SOCl$_2$ (78 mg, 0.7 mmol) was added dropwise. The reaction mixture was allowed to warm to room temperature and stirred for 18 h. The solvent was removed in vacuo to give the title compound as the hydrochloride salt.

Yield: 139 mg, 100%; LC/MS t$_r$ 0.79 min; MS (ES+) m/z 196 (M+H); $^1$H NMR (400 MHz; CDCl$_3$) δ 1.26 (t, 3H), 4.23 (q, 2H), 4.58 (s, 2H), 6.86 (d, 1H), 7.15 (s, 2H), 7.25 (t, 1H)

(iv) 5-(3-Chloro-phenyl)-furan-2-carboxylic acid (65)

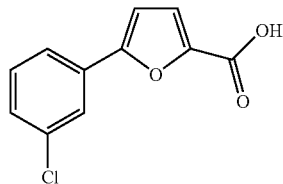

5-Bromo-2-furoic acid (1 g, 5.8 mmol) was coupled to 3-chloro-phenylboronic acid (683 g, 4.4 mmol) acid using Method F to give the title compound.

Yield: 510 mg, 52%; LC/MS t$_r$ 1.24 min; MS (ES+) m/z 223, 225 (M+H)

(v) (3-{[5-(3-Chloro-phenyl)-furan-2-carbonyl]-amino}-phenoxy)-acetic acid ethyl ester

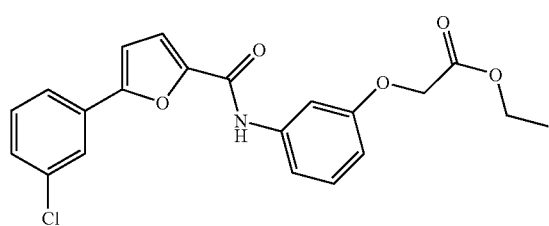

Carboxylic acid (65) (67 mg, 0.3 mmol) was coupled to ethyl ester (64) (58 mg, 0.25 mmol) using Method C. The crude residue was purified by column chromatography eluting with a stepped gradient of 10-20% EtOAc in heptane to give the title compound.

Yield: 75 mg, 75%; LC/MS t$_r$ 1.65 min; MS (ES+) m/z 400, 402 (M+H)

(vi) (3-{[5-(3-Chloro-phenyl)-furan-2-carbonyl]-amino}-phenoxy)-acetic acid (66)

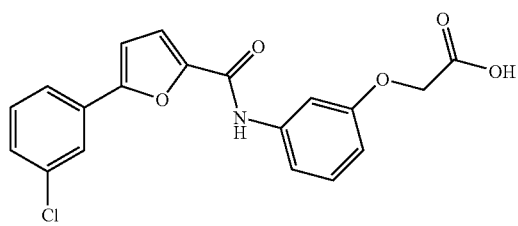

The ester (64 mg, 0.16 mmol) was dissolved in MeOH (1.5 ml), and a solution of NaOH (128 mg, 3.2 mmol) in water (0.5 ml) was added. The reaction mixture was stirred for 1 h at room temperature before the MeOH was removed in vacuo. The aqueous layer was washed with EtOAc (2×2 ml) and then acidified with 2M HCl until a white precipitate formed. This was then extracted with EtOAc (2 ml). The organic layer was dried (Na$_2$SO$_4$), filtered and the solvent removed in vacuo to give the title compound.

Yield: 30 mg, 50%; LC/MS t$_r$ 1.45 min; MS (ES+) m/z 372, 374 (M+H); HPLC Purity: 99%; $^1$H NMR (400 MHz; DMSO) δ 4.24 (s, 2H), 6.69 (d, 1H), 7.31 (t, 1H), 7.42 (m, 3H), 7.55 (m, 2H), 7.64 (t, 1H), 8.05 (d, 1H), 8.21 (s, 1H), 10.38 (s, 1H)

(t) (3-{[5-(3,5-Dichloro-phenyl)-furan-2-carbonyl]-amino}-phenoxy)-acetic acid (68)

(i) 5-(3,5-Dichloro-phenyl)-furan-2-carboxylic acid (67)

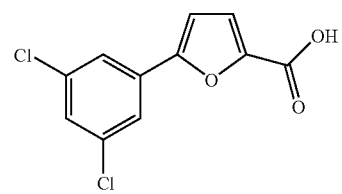

5-Bromo-2-furoic acid (1 g, 4.8 mmol) was coupled to 3,5-dichloro-phenylboronic acid (833 g, 4.4 mmol) acid using Method F to give the title compound.

Yield: 500 mg, 44%; LC/MS t$_r$ 1.48 min; MS (ES+) m/z 257, 259 (M+H)

(ii) (3-{[5-(3,5-Dichloro-phenyl)-furan-2-carbonyl]-amino}-phenoxy)-acetic acid ethyl ester

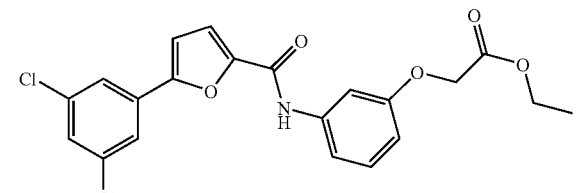

Carboxylic acid (67) (77 mg, 0.3 mmol) was coupled to ethyl ester (9) (58 mg, 0.25 mmol) using Method C. The crude residue was purified by column chromatography eluting with 10% EtOAc in heptane to give the title compound.

Yield: 109 mg, 100%; LC/MS t$_r$ 1.78 min; MS (ES+) m/z 434, 436 (M+H)

(iii) (3-{[5-(3,5-Dichloro-phenyl)-furan-2-carbonyl]-amino}-phenoxy)-acetic acid (68)

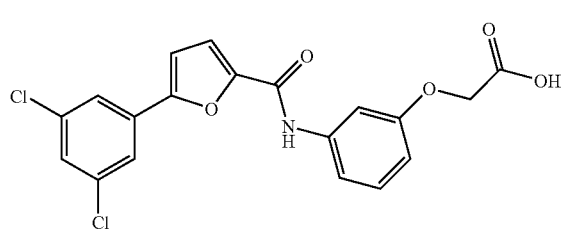

The ester (70 mg, 0.16 mmol) was dissolved in MeOH (1.5 ml) and a solution of NaOH (140 mg, 3.5 mmol) in water (0.5 ml) was added. The reaction mixture was stirred for 1 h at room temperature and the MeOH was removed in vacuo. The aqueous layer was washed with EtOAc (2×2 ml) and then acidified with 2M HCl until a white precipitate formed. This was then extracted with EtOAc (2 ml). The organic layer was dried (Na$_2$SO$_4$), filtered and the solvent removed in vacuo to give the title compound.

Yield: 40 mg, 61%; LC/MS t$_r$ 1.58 min; MS (ES+) m/z 406, 408 (M+H); HPLC Purity: 99%; $^1$H NMR (400 MHz; DMSO) δ 4.20 (s, 2H), 6.65 (d, 1H), 7.25 (t, 1H), 7.35 (s, 2H), 7.47 (d, 2H), 7.69 (s, 1H), 8.15 (s, 2H)

(u) 3-(3-{[5-(3-Chloro-phenyl)-furan-2-carbonyl]-amino}-phenyl)-acrylic acid (69)

(i) 3-(3-{[5-(3-Chloro-phenyl)-furan-2-carbonyl]-amino}-phenyl)-acrylic acid ethyl ester

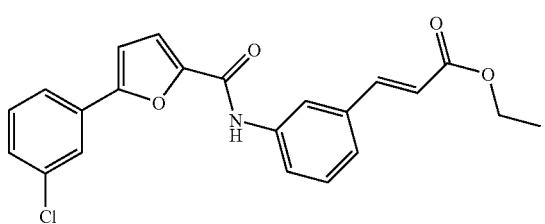

Carboxylic acid (65) (58 mg, 0.26 mmol) was coupled to ethyl ester (60) (50 mg, 0.26 mmol) using Method C. The crude residue was purified by column chromatography eluting with a stepped gradient of 10-15% EtOAc in heptane to give the title compound.

Yield: 67 mg, 65%; LC/MS t$_r$ 1.72 min; MS (ES+) m/z 396, 398 (M+H)

(ii) 3-(3-{[5-(3-Chloro-phenyl)-furan-2-carbonyl]-amino}-phenyl)-acrylic acid (69)

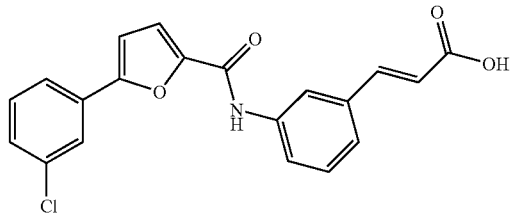

The ester (67 mg, 0.17 mmol) was dissolved in THF (1 ml) and water (0.25 ml). To this was added LiOH.H$_2$O (20 mg, 0.48 mmol) and the reaction was stirred for 2 h at room temperature. The THF was removed in vacuo and the aqueous layer was washed twice with EtOAc (2×2 ml) then acidified with 2M HCl until a white precipitate formed. This was then extracted with EtOAc (2 ml). The organic layer was dried (Na$_2$SO$_4$), filtered and the solvent removed in vacuo to give the title compound.

Yield: 23 mg, 37%; LC/MS t$_r$ 1.51 min; MS (ES+) m/z 367, 369 (M+H); HPLC Purity: 98%; $^1$H NMR (400 MHz; DMSO) δ 6.41 (d, 1H), 7.24 (d, 1H), 7.36 (m, 4H), 7.45 (t, 1H), 7.51 (d, 1H), 7.74 (m, 1H), 7.87 (m, 1H), 7.92 (s, 1H), 8.04 (t, 1H), 10.25 (s, 1H)

(v) 3-(3-{[5-(3,5-Dichloro-phenyl)-furan-2-carbonyl]-amino}-phenyl)-acrylic acid (70)

(i) 3-(3-{[5-(3,5-Dichloro-phenyl)-furan-2-carbonyl]-amino}-phenyl)-acrylic acid ethyl ester

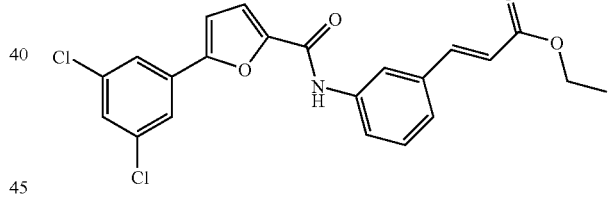

Carboxylic acid (67) (67 mg, 0.26 mmol) was coupled to ethyl ester (60) (50 mg, 0.26 mmol) using Method C. The crude residue was purified by column chromatography eluting with 10% EtOAc in heptane to give the title compound.

Yield: 90 mg, 80%; LC/MS t$_r$ 1.84 min; MS (ES+) m/z 430, 432 (M+H)

(ii) 3-(3-{[5-(3,5-Dichloro-phenyl)-furan-2-carbonyl]-amino}-phenyl)-acrylic acid (70)

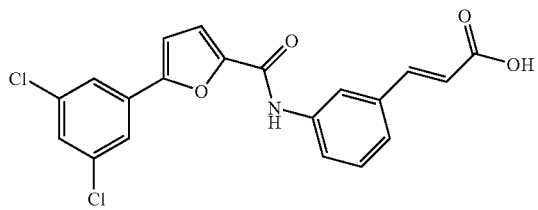

The ester (90 mg, 0.21 mmol) was dissolved in THF (1 ml) and water (0.25 ml). To this was added LiOH.H₂O (30 mg, 0.71 mmol) and the resulting solution was stirred for 2 h at room temperature. The THF was removed in vacuo and the aqueous layer was washed twice with EtOAc (2×2 ml) then acidified with 2M HCl until a white precipitate formed. This was then extracted with EtOAc (2 ml). The organic layer was dried (Na₂SO₄), filtered and the solvent removed in vacuo to give the title compound.

Yield: 41 mg, 48%; LC/MS $t_r$ 1.63 min; MS (ES+) m/z 402, 404 (M+H); HPLC Purity: 98%; ¹H NMR (400 MHz; DMSO) δ 6.42 (d, 1H), 7.37 (m, 4H), 7.51 (d, 1H), 7.55 (t, 1H), 7.73 (d, 1H), 7.91 (s, 1H), 8.04 (d, 2H), 10.29 (s, 1H)

(x) 3-(3-{[5-(4-Fluoro-phenyl)-furan-2-carbonyl]-amino}-phenyl)-acrylic acid (71)

(i) 5-(4-Fluoro-phenyl)-furan-2-carboxylic acid

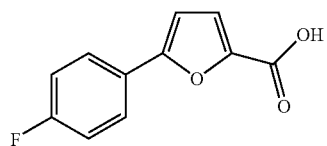

4-Fluoro-phenylboronic acid (611 mg, 4.4 mmol) was coupled to 5-bromo-2-furoic acid (1 g, 4.8 mmol) using Method F to give the title compound.

Yield: 350 mg, 39%; LC/MS $t_r$ 1.24 min; MS (ES+) m/z 207 (M+H)

(ii) 3-(3-{[5-(4-Fluoro-phenyl)-furan-2-carbonyl]-amino}-phenyl)-acrylic acid ethyl ester

5-(4-Fluoro-phenyl)-furan-2-carboxylic acid (54 mg, 0.26 mmol) was coupled to ethyl ester (60) (50 mg, 0.26 mmol) using Method C. The crude residue was purified by column chromatography eluting with 10% EtOAc in heptane to give the title compound.

Yield: 98 mg, 100%; LC/MS $t_r$ 1.67 min; MS (ES+) m/z 380 (M+H)

(iii) 3-(3-{[5-(4-Fluoro-phenyl)-furan-2-carbonyl]-amino}-phenyl)-acrylic acid (71)

The ester (109 mg, 0.29 mmol) was dissolved in THF (0.4 ml) and water (0.1 ml). To this was added LiOH.H₂O (126 mg, 3.1 mmol) and the resulting solution was stirred for 2 h at room temperature. The THF was removed in vacuo and the aqueous layer was washed twice with EtOAc (2×2 ml) then acidified with 2M HCl until a white precipitate formed. This was then extracted with EtOAc (2 ml). The combined organic layers were dried (Na₂SO₄), filtered and the solvent removed in vacuo to give the title compound.

Yield: 48 mg, 47%; LC/MS $t_r$ 1.42 min; MS (ES+) m/z 352 (M+H); HPLC Purity: 98%; ¹H NMR (400 MHz; DMSO) δ 6.47 (d, 1H), 7.18 (d, 1H), 7.23 (d, 1H), 7.29 (d, 1H), 7.41 (q, 3H), 7.54 (d, 1H), 7.80 (d, 1H), 7.93 (s, 1H), 8.11 (q, 2H), 10.42 (s, 1H)

(y) 5-{[5-(3-Chloro-phenyl)-furan-2-carbonyl]-amino}-1H-indole-2-carboxylic acid (72)

(i) 5-{[5-(3-Chloro-phenyl)-furan-2-carbonyl]-amino}-1H-indole-2-carboxylic acid ethyl ester

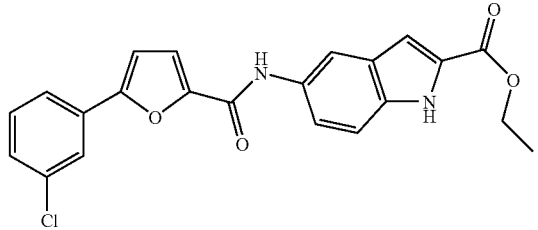

5-(3-Chloro-phenyl)-furan-2-carboxylic acid (65) (54 mg, 0.24 mmol) was coupled to ethyl ester (58) (50 mg, 0.24 mmol) using Method C. The crude residue was purified by column chromatography eluting with 20% EtOAc in heptane to give the title compound.

Yield: 42 mg, 43%; LC/MS $t_r$ 1.64 min; MS (ES+) m/z 409, 411 (M+H); HPLC Purity: 92%

(ii) 5-{[5-(3-Chloro-phenyl)-furan-2-carbonyl]-amino}-1H-indole-2-carboxylic acid (72)

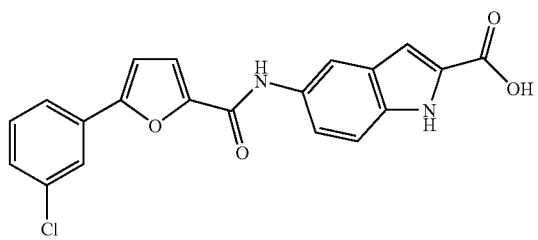

The ester (42 mg, 0.10 mmol) was dissolved in THF (0.2 ml) and water (0.05 ml). To this was added LiOH.H₂O (42 mg, 1 mmol) and the resulting solution was stirred for 2 h at room temperature then at 35° C. for 2 h. The THF was removed under a stream of N₂ and the aqueous layer acidified with 2M HCl until a white precipitate formed. This was then extracted with EtOAc (2 ml). The organic layer was dried (Na₂SO₄), filtered, and the solvent removed in vacuo to give the title compound which was re-suspended in hot DCM (1.5 ml), then hot MeCN (1.5 ml), filtered, and dried in vacuo.

Yield: 30 mg, 79%; LC/MS $t_r$ 1.46 min; MS (ES+) m/z 380, 382 (M+H); HPLC Purity: 97%; ¹H NMR (360 MHz; DMSO): δ 6.55 (s, 1H), 7.22-7.42 (m, 6H), 7.48 (t, 1H), 7.80 (s, 1H), 7.91 (d, 1H), 8.10 (s, 1H), 10.08 (s, 1H), 11.07 (s, 1H)

Example 8

(a) 5-Phenyl-furan-2-carboxylic acid (3-carbamoyl-methyl-phenyl)-amide (73)

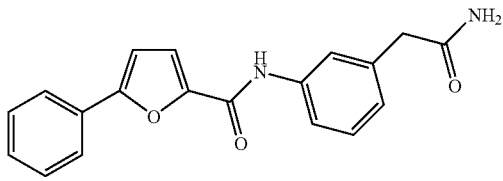

The carboxylic acid (10) (50 mg, 0.15 mmol) was coupled to NH₄OH (0.01 ml, 0.15 mmol) using Method C. The crude compound was purified by column chromatography, eluting with a stepped gradient of 80-100% EtOAc in heptane to give the title compound.

Yield: 15 mg, 31%; LC/MS $t_r$ 1.23 min; MS (ES+) m/z 321 (M+H); HPLC Purity: 95%; ¹H NMR (400 MHz; CDCl₃) δ 3.44 (m, 2H), 6.98 (brs, 2H), 7.08 (d, 1H), 7.24 (d, 1H), 7.35 (t, 1H), 7.46 (t, 2H), 7.56 (t, 2H), 7.70 (s, 1H), 7.74 (d, 1H), 8.04 (d, 2H), 10.23 (s, 1H)

(b) Phenyl-furan-2-carboxylic acid [3-(2-hydroxy-ethyl)-phenyl]-amide (74)

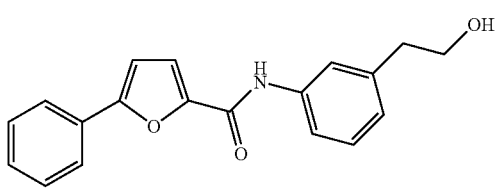

The carboxylic acid (10) (50 mg, 0.15 mmol) was dissolved in anhydrous THF (0.1 ml) and placed under an atmosphere of N₂. The solution was cooled to −78° C. using acetone/dry ice and stirred for 10 min. LiAlH₄ (1M in THF) was added dropwise (0.31 ml, 0.31 mmol) and the resulting solution was stirred for 10 min at −78° C., then allowed to warm to room temperature and stirred for a further 2 h. After cooling to 5° C. using ice/water, the reaction mixture was quenched by dropwise addition of water (1 ml) then neutralised to pH 7 with 1M NaOH and extracted with EtOAc (2×1 ml). The combined organic layers were dried (Na₂SO₄), filtered and the solvent removed in vacuo. The crude residue was purified by column chromatography, eluting in 60% EtOAc in heptane to give the title compound.

Yield: 34 mg, 74%; LC/MS $t_r$ 1.35 min; MS (ES+) m/z 308 (M+H); HPLC Purity: 92%; ¹H NMR (400 MHz; CDCl₃) δ 2.90 (t, 2H), 3.91 (t, 2H), 6.80 (d, 1H), 7.05 (d, 1H), 7.03 (d, 1H), 7.29-7.41 (m, 3H), 7.46 (t, 2H), 7.58 (d, 2H), 7.76 (d, 2H), 8.09 (s, 1H)

(c) 5-Phenyl-furan-2-carboxylic acid [3-(1H-tetrazol-5-ylmethyl)-phenyl]-amide (75)

(i) (3-Amino-phenyl)-acetonitrile (80)

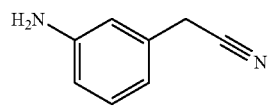

A solution of 3-nitrophenyl acetonitrile (500 mg, 3.1 mmol) in 5% AcOH (10 ml) was heated to 80° C. Iron powder (1.5 g, 27 mmol) was then added and the resulting mixture stirred for 2 h. The reaction mixture was filtered through celite and the filter cake washed with MeCN (4×50 ml). The combined MeCN layers were evaporated in vacuo and the residue was re-dissolved in EtOAc (30 ml) followed by 2M HCl (30 ml). The aqueous layer was separated, basified to pH 10 with 6M NaOH, and extracted with EtOAc (3×80 ml). The combined organic layers were dried (MgSO₄), filtered and the solvent removed in vacuo to give the title compound.

Yield: 140 mg, 34%; ¹H NMR (400 MHz, CDCl₃): δ 3.65 (s, 2H), 3.75 (s, 2H), 6.60-6.70 (m, 3H), 7.15 (t, 1H)

(ii) 5-Phenyl-furan-2-carboxylic acid (3-cyanom-ethyl-phenyl)-amide

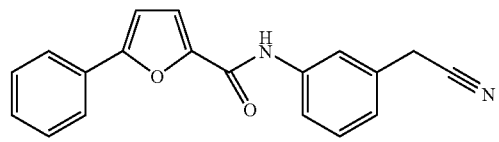

5-Phenyl-2-furoic acid (56) (223 mg, 1.2 mmol) was coupled to 3-aminophenyl acetonitrile (80) (157 mg, 1.19 mmol), using Method C. The crude residue was purified by column chromatography, eluting in 17% EtOAc in heptane to give the title compound.

Yield: 70 mg, 19%; LC/MS $t_r$ 1.47 min; MS (ES+) m/z 303 (M+H)

(iii) 5-Phenyl-furan-2-carboxylic acid [3-(1H-tetra-zol-5-ylmethyl)-phenyl]-amide

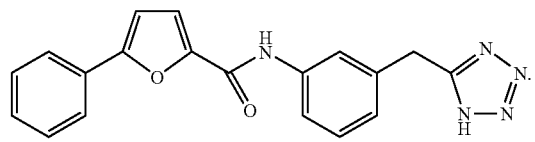

To a solution of 5-phenyl-furan-2-carboxylic acid (3-cya-nomethyl-phenyl)-amide (70 mg, 0.23 mmol) in toluene (3 ml) was added Me₃SnN₃ (56 mg, 0.28 mmol). After heating to reflux for 18 h, additional Me₃SnN₃ (56 mg, 0.28 mmol) and toluene (2 ml) were added and the reaction was heated to reflux for a further 18 h. After this time, 2M NaOH (2 ml) and hexane (2 ml) were added to the reaction mixture and stirred for 10 min. Water (1 ml) was added and the organic layer separated. EtOAc (2 ml) was added to the aqueous layer and the solution stirred for 2 min before the organic layer was separated. The combined organic layers were discarded. The aqueous layer was then acidified to pH 5 with 2M HCl then EtOAc (2.5 ml) was added and the solution stirred for 10 min after which time the organic layer was separated. EtOAc (2.5 ml) was added to the aqueous layer and the solution stirred for 1 hour. The EtOAc layer was separated and these combined organic layers were evaporated in vacuo to give the title compound.

Yield: 16 mg, 20%; LC/MS t$_r$ 1.31 min; MS (ES+) m/z 346 (M+H); HPLC Purity: 98%; ¹H NMR (400 MHz, DMSO): δ 4.2 (s, 2H), 7.1 (d, 1H), 7.25 (s, 1H), 7.35 (t, 1H), 7.4-7.49 (m, 2H), 7.55 (t, 2H), 7.65 (s, 1H), 7.75 (d, 1H), 8.0 (d, 2H), 10.25 (s, 1H).

(d) 5-Phenyl-furan-2-carboxylic acid [3-(1H-tetrazol-5-yl)-phenyl]-amide (177)

(i) 5-Phenyl-furan-2-carboxylic acid (3-cyano-phenyl)-amide

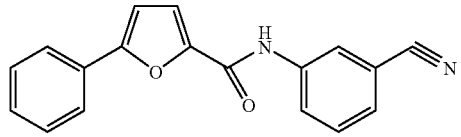

Carboxylic acid (56) (150 mg, 0.80 mmol) was coupled to 3-amino-benzonitrile (94 mg, 0.80 mmol) using Method C. The residue was purified by column chromatography eluting with 17% EtOAc in heptane to give the title compound.

Yield: 80 mg, 35%; LC/MS t$_r$ 1.51 min; MS (ES+) m/z 289 (M+H)

(ii) 5-Phenyl-furan-2-carboxylic acid [3-(1H-tetrazol-5-yl)-phenyl]-amide (177)

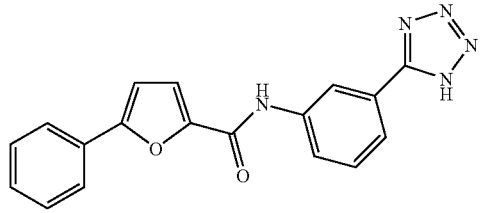

The nitrile (80 mg, 0.28 mmol) was reacted with Me₃SnN₃ using Method K. The solid was then re-dissolved in EtOAc (2 ml) and 2M NaOH (2 ml). The layers were separated and the aqueous layer was acidified to pH 5 with 2M HCl and extracted with EtOAc (2 ml). The combined organic layers were evaporated in vacuo and the residue triturated with TBME (2×2 ml). The solid was dissolved in MeOH (1.5 ml) and washed with heptane (2×2 ml). MeOH was removed in vacuo to give the title compound.

Yield: 15 mg, 16%; LC/MS t$_r$ 1.42 min; MS (ES+) m/z 332 (M+H); HPLC Purity: 98%; ¹H NMR (400 MHz, DMSO): δ 7.07 (d, 1H), 7.19-7.42 (m, 5H), 7.60 (d, 1H), 7.69 (d, 1H), 7.89 (d, 2H), 8.18-8.20 (m, 1H), 10.13 (s, 1H).

(e) 5-(3-Chloro-phenyl)-furan-2-carboxylic acid [3-(1H-tetrazol-5-ylmethyl)-phenyl]-amide (81)

(i) {3-[5-(3-Chloro-phenyl)-furan-2-carbonyl]-phenyl}-acetonitrile

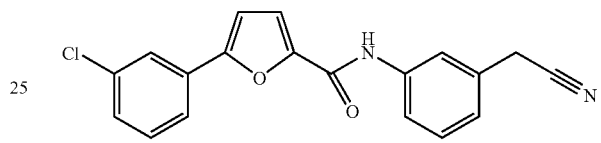

Carboxylic acid (65) (127 mg, 0.57 mmol) was coupled to aniline (80) (75 mg, 0.57 mmol) using Method C. The crude residue was purified by column chromatography eluting with 17% EtOAc in heptane to give the title compound.

Yield: 65 mg, 34%; LC/MS t$_r$ 1.57 min; MS (ES+) m/z 337, 339 (M+H)

(ii) 5-(3-Chloro-phenyl)-furan-2-carboxylic acid [3-(1H-tetrazol-5-ylmethyl)-phenyl]-amide (81)

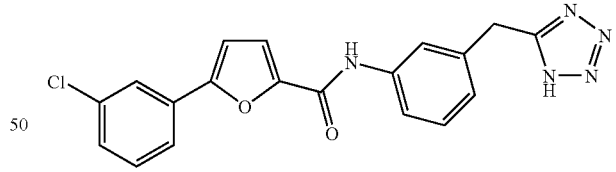

The nitrile (65 mg, 0.19 mmol) was reacted with Me₃SnN₃ using Method K. The solid was re-dissolved in MeOH (2.5 ml) and washed with heptane (5×3 ml). The product was further purified by column chromatography eluting with a stepped gradient of 10-100% EtOAc in heptane to give the title compound.

Yield: 1.2 mg, 2%; LC/MS t$_r$ 1.48 min; MS (ES+) m/z 380, 382 (M+H); HPLC Purity: 98%; ¹H NMR (400 MHz, DMSO): δ 4.38 (s, 2H), 7.11 (d, 1H), 7.35-7.57 (m, 3H), 7.49-7.53 (m, 1H), 7.56-7.62 (t, 1H), 7.69 (s, 1H), 7.79 (d, 1H), 8.00 (d, 1H), 8.19 (s, 1H), 10.32 (s, 1H).

(f) 5-(3,5-Dichloro-phenyl)-furan-2-carboxylic acid [3-(1H-tetrazol-5-ylmethyl)-phenyl]-amide (82)

(i) 5-(3,5-Dichloro-phenyl)-furan-2-carboxylic acid (3-cyanomethyl-phenyl)-amide

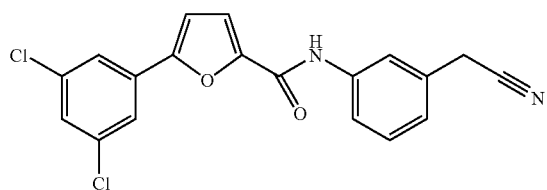

Carboxylic acid (67) (62 mg, 0.24 mmol) was coupled to aniline (80) (32 mg, 0.24 mmol) using Method C. After workup, the solid was recrystallised from MeCN (3 ml) to give the title compound.

Yield: 63 mg, 71%; LC/MS $t_r$ 1.73 min; MS (ES+) m/z 371, 373 (M+H)

(ii) 5-(3,5-Dichloro-phenyl)-furan-2-carboxylic acid [3-(1H-tetrazol-5-ylmethyl)-phenyl]-amide (82)

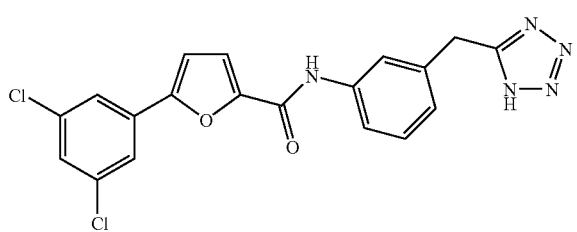

The nitrile (63 mg, 0.17 mmol) was reacted with Me₃SnN₃ using Method K. The residue was purified by column chromatography, flushing with heptane (200 ml) and eluting with 50% MeOH in EtOAc. The solid was then triturated with MeOH (3 ml) to give the title compound.

Yield: 4.2 mg, 6%; LC/MS $t_r$ 1.53 min; MS (ES+) m/z 414, 416 (M+H); HPLC Purity: 92%; ¹H NMR (400 MHz, DMSO): δ 4.48 (s, 2H), 7.21 (d, 1H), 7.43-7.60 (m, 3H), 7.75-7.81 (m, 2H), 7.88 (d, 1H), 8.26 (s, 2H), 10.45 (s, 1H).

(g) 5-(4-Fluoro-phenyl)-furan-2-carboxylic acid [3-(1H-tetrazol-5-ylmethyl)-phenyl]-amide (85)

(i) 5-Bromo-furan-2-carboxylic acid (3-cyanomethyl-phenyl)-amide (83)

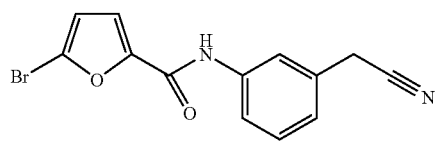

5-Bromo-furan-2-carboxylic acid (1.68 g, 8.80 mmol) was coupled to aniline (80) (1.16 g, 8.80 mmol), using Method C. The residue was purified by column chromatography eluting with 20% EtOAc in heptane to give the title compound.

Yield: 399 mg, 15%; LC/MS $t_r$ 1.31 min; MS (ES+) m/z 305, 307 (M+H)

(ii) 5-Bromo-furan-2-carboxylic acid [3-(1H-tetrazol-5-ylmethyl)-phenyl]-amide (84)

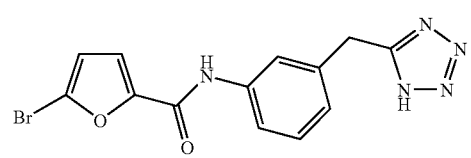

Nitrile (83) (162 mg, 0.53 mmol) was treated with Me₃SnN₃ using Method K. The residue was purified by column chromatography, flushing with heptane (200 ml) and eluting with 50% EtOAc in heptane to give the title compound.

Yield: 35 mg, 19%; LC/MS $t_r$ 1.11 min; MS (ES+) m/z 348, 350 (M+H)

(iii) 5-(4-Fluoro-phenyl)-furan-2-carboxylic acid [3-(1H-tetrazol-5-ylmethyl)-phenyl]-amide (85)

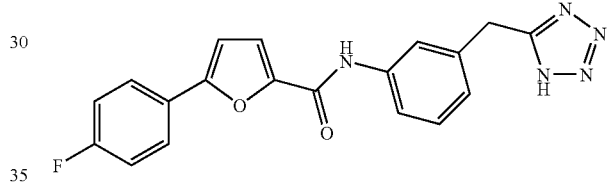

The furyl bromide (84) (100 mg, 0.29 mmol) was coupled to 4-fluoro-phenylboronic acid (44 mg, 0.32 mmol) using Method E. The solvents were removed in vacuo as described, but the residue was dissolved in 2M NaOH (10 ml) and washed with EtOAc (2×10 ml). The aqueous layer was acidified to pH 1 with 2M HCl until a white precipitate formed and extracted with EtOAc (2×10 ml). The organic layer was dried (MgSO₄), filtered and the solvent removed in vacuo to give the title compound.

Yield: 13 mg, 12%; LC/MS $t_r$ 1.32 min; MS (ES+) m/z 364 (M+H); HPLC Purity: 87%; ¹H NMR (400 MHz, DMSO): δ 4.31 (s, 2H), 7.04 (d, 1H), 7.17 (d, 1H), 7.32-7.41 (m, 4H), 7.61 (s, 1H), 7.73 (d, 1H), 8.02 (t, 2H), 10.21 (s, 1H).

(h) 5-(3-Fluoro-phenyl)-furan-2-carboxylic acid [3-(1H-tetrazol-5-ylmethyl)-phenyl]-amide (86)

(i) 5-(3-Fluoro-phenyl)-furan-2-carboxylic acid (3-cyanomethyl-phenyl)-amide

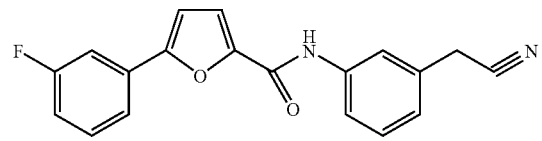

The furyl bromide (83) (135 mg, 0.44 mmol) was coupled to 3-fluoro-phenylboronic acid (68 mg, 0.49 mmol) using Method E. The crude residue was purified by column chromatography eluting with 20% EtOAc in heptane to give the title compound.

Yield: 40 mg, 28%; LC/MS $t_r$ 1.47 min; MS (ES+) m/z 321 (M+H)

(ii) 5-(3-Fluoro-phenyl)-furan-2-carboxylic acid [3-(1H-tetrazol-5-ylmethyl)-phenyl]-amide (86)

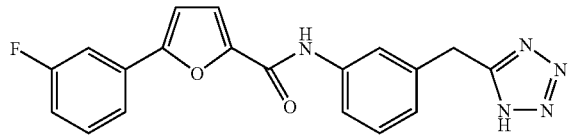

The nitrile (40 mg, 0.13 mmol) was treated with TMSN$_3$ and Bu$_2$SnO using Method L. After a first treatment, TMSN$_3$ (58 mg, 0.50 mmol) and Bu$_2$SnO (6 mg, 0.025 mmol) were added, and the mixture was heated in the microwave for a further 20 min. After work-up, the residue was dissolved in MeOH (2 ml) and washed with heptane (3×3 ml). The layers were separated and the MeOH was removed in vacuo. The solid was then triturated with heptane (4×2 ml) to give the title compound.

Yield: 16 mg, 34%; LC/MS $t_r$ 1.42 min; MS (ES+) m/z 364 (M+H); HPLC Purity: 100%; $^1$H NMR (400 MHz, DMSO): δ 4.24 (s, 2H), 7.02 (d, 1H), 7.18-7.34 (m, 3H), 7.37 (d, 1H), 7.52 (q, 1H), 7.59 (s, 1H), 7.69 (d, 1H), 7.81 (d, 1H), 7.89 (d, 1H), 10.21 (s, 1H).

(i) 5-(4-Chloro-phenyl)-furan-2-carboxylic acid [3-(1H-tetrazol-5-ylmethyl)-phenyl]-amide (87)

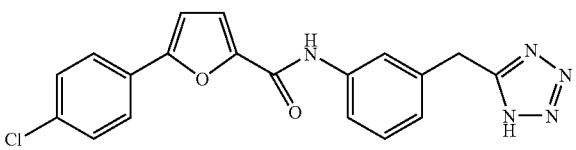

The bromo-derivative (84) (100 mg, 0.29 mmol) was coupled to 4-chloro-phenylboronic acid (49 mg, 0.32 mmol) using Method E. After reaction, the solvents were removed under a stream of N$_2$, and the residue was dissolved in saturated NaHCO$_3$ solution (5 ml) and washed with EtOAc (5 ml). The aqueous layer was acidified to pH 1 with 2M HCl until a white precipitate formed and extracted with EtOAc (2×5 ml). The organic layer was dried (MgSO$_4$), filtered and the solvent removed in vacuo. The residue was triturated with MeCN (4 ml) and further purified by preparative HPLC to give the title compound.

Yield: 11 mg, 10%; LC/MS $t_r$ 1.52 min; MS (ES+) m/z 380, 382 (M+H); HPLC Purity: 100%; $^1$H NMR (400 MHz, DMSO): δ 4.20 (s, 2H), 6.92 (d, 1H), 7.12 (d, 1H), 7.20-7.29 (m, 2H), 7.42-7.50 (m, 3H), 7.60 (d, 1H), 7.89 (d, 2H), 10.11 (s, 1H).

(j) 5-Phenyl-furan-2-carboxylic acid (3-[2-(1H-tetrazol-5-yl)-vinyl]-phenyl)-amide (89)

(i) 3-(3-Amino-phenyl)-acrylonitrile (88)

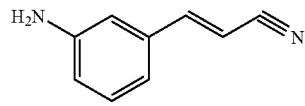

A solution of 3-(3-nitro-phenyl)-acrylonitrile (500 mg, 2.87 mmol) in 5% aqueous AcOH (10 ml) was heated to 80° C. Iron powder (1.44 g, 25.8 mmol) was then added and the resulting mixture was stirred for 3 h. The reaction mixture was filtered through celite and the filter cake washed with MeCN (4×50 ml). The combined MeCN layers were evaporated in vacuo and the residue was re-dissolved in EtOAc (30 ml) and HCl (30 ml). The aqueous layer was separated, basified to pH 10 with 6M NaOH, and extracted with EtOAc (3×80 ml). The combined organic layers were dried (MgSO$_4$), filtered and the solvent removed in vacuo to give the title compound.

Yield: 297 mg, 71%; LC/MS $t_r$ 0.70 min; MS (ES+) m/z 186 (M+MeCN+H)

(ii) 5-Phenyl-furan-2-carboxylic acid [3-(2-cyano-vinyl)-phenyl]-amide

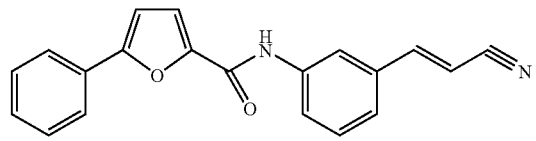

Carboxylic acid (56) (120 mg, 0.64 mmol) was coupled to aniline (88) (92 mg, 0.64 mmol), using Method C to give the title compound.

Yield: 113 mg, 56%; LC/MS $t_r$ 1.55 min; MS (ES+) m/z 315 (M+H)

(iii) 5-Phenyl-furan-2-carboxylic acid {3-[2-(1H-tetrazol-5-yl)-vinyl]-phenyl}-amide (89)

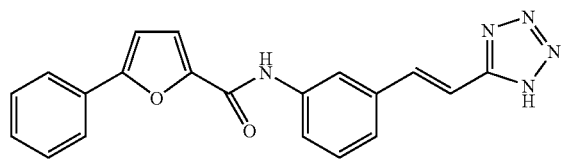

The nitrile (113 mg, 0.36 mmol) was treated with Me$_3$SnN$_3$ using Method K. After work-up, the residue was purified by column chromatography, flushing with heptane (200 ml) and eluting with 50% MeOH in EtOAc. Column chromatography was repeated eluting with 100% EtOAc. The solid was further purified by preparative HPLC to give the title compound.

Yield: 4.7 mg, 4%; LC/MS $t_r$ 1.40 min; MS (ES+) m/z 358 (M+H); HPLC Purity: 100%; $^1$H NMR (400 MHz, DMSO): δ 7.22 (d, 1H), 7.33 (d, 1H), 7.41-7.58 (m, 6H), 7.69 (d, 1H), 7.83 (d, 1H), 8.02 (d, 2H), 8.10 (s, 1H), 10.32 (s, 1H).

(k) 5-(3-Chloro-phenyl)-furan-2-carboxylic acid {3-[2-(1H-tetrazol-5-yl)-vinyl]-phenyl}-amide (90)

(i) 5-Bromo-furan-2-carboxylic acid [3-(2-cyano-vinyl)-phenyl]-amide

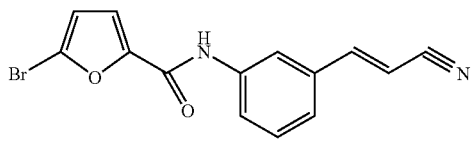

5-Bromo-furan-2-carboxylic acid (716 mg, 3.75 mmol) was coupled to aniline (88) (540 mg, 3.75 mmol) using Method C. The residue was purified by column chromatography eluting with 20% EtOAc in heptane, to give the title compound.

Yield: 451 mg, 38%; LC/MS $t_r$ 1.39 min; MS (ES+) m/z 317, 319 (M+H)

(ii) 5-(3-Chloro-phenyl)-furan-2-carboxylic acid [3-(2-cyano-vinyl)-phenyl]-amide

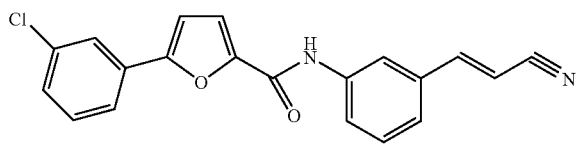

The furyl bromide (150 mg, 0.47 mmol) was coupled to 3-chloro-phenylboronic acid (81 mg, 0.52 mmol) using Method E. The crude residue was purified by column chromatography eluting with 20% EtOAc in heptane to give the title compound.

Yield: 61 mg, 37%; LC/MS $t_r$ 1.65 min; MS (ES+) m/z 349, 351 (M+H)

(iii) 5-(3-Chloro-phenyl)-furan-2-carboxylic acid {3-[2-(1H-tetrazol-5-yl)-vinyl]-phenyl}-amide (90)

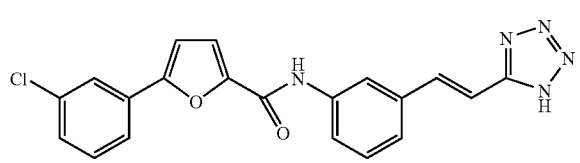

The nitrile (61 mg, 0.18 mmol) was treated with TMSN$_3$ and Bu$_2$SnO using Method L. After work-up, the residue was dissolved in MeOH (2 ml) and washed with heptane (3×3 ml). The layers were separated and the MeOH was removed in vacuo to give the title compound.

Yield: 18 mg, 26%; LC/MS $t_r$ 1.48 min; MS (ES+) m/z 392, 394 (M+H); HPLC Purity: 98%; $^1$H NMR (400 MHz, DMSO): δ 7.20-7.27 (m, 2H), 7.48-7.70 (m, 5H), 7.67 (d, 1H), 7.77 (d, 1H), 7.90 (d, 1H), 8.05 (d, 2H), 10.34 (s, 1H).

(l) 6-Phenyl-pyridine-2-carboxylic acid [3-(1H-tetrazol-5-ylmethyl)-phenyl]-amide (92)

(i) 6-Bromo-pyridine-2-carboxylic acid (3-cyanomethyl-phenyl)-amide (91)

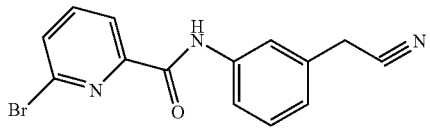

6-Bromo-pyridine-2-carboxylic acid (1.60 g, 12.1 mmol) was coupled to aniline (91) (2.44 g, 12.1 mmol) using Method C. The residue was purified by column chromatography eluting with 20% EtOAc in heptane to give the title compound.

Yield: 1.20 g, 31%; LC/MS $t_r$ 1.38 min; MS (ES+) m/z 316, 318 (M+H)

(ii) 6-Phenyl-pyridine-2-carboxylic acid (3-cyanomethyl-phenyl)-amide

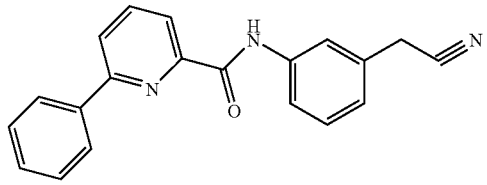

The pyridyl bromide (91) (150 mg, 0.47 mmol) was coupled to phenylboronic acid (64 mg, 0.52 mmol) using Method E. The crude residue was purified by column chromatography eluting with 20% EtOAc in heptane to give the title compound.

Yield: 50 mg, 34%; LC/MS $t_r$ 1.58 min; MS (ES+) m/z 314 (M+H)

(iii) 6-Phenyl-pyridine-2-carboxylic acid [3-(1H-tetrazol-5-ylmethyl)-phenyl]-amide (92)

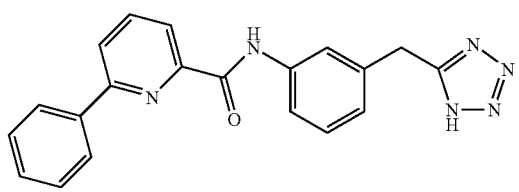

The nitrile (50 mg, 0.16 mmol) was treated with TMSN$_3$ and Bu$_2$SnO using Method L. After a first treatment, TMSN$_3$ (73 mg, 0.64 mmol) and Bu$_2$SnO (8 mg, 0.032 mmol) were added, and the mixture was heated in the microwave for a further 20 min. After work-up, the residue was dissolved in MeOH (2 ml) and washed with heptane (3×3 ml). The layers were separated and the MeOH was removed in vacuo. The solid was then triturated with heptane (4×2 ml) to give the title compound.

Yield: 14 mg, 25%; LC/MS $t_r$ 1.47 min; MS (ES+) m/z 357 (M+H); HPLC Purity: 98%; $^1$H NMR (400 MHz, DMSO): δ

4.09 (s, 2H), 6.85 (d, 1H), 7.15 (t, 1H), 7.27-7.39 (m, 3H), 7.58-7.63 (m, 2H), 7.86-7.96 (m, 2H), 8.03 (d, 1H), 8.12 (d, 2H), 10.31 (s, 1H).

(m) 6-(4-Fluoro-phenyl)-pyridine-2-carboxylic acid [3-(1H-tetrazol-5-ylmethyl)-phenyl]-amide (93)

(i) 6-(4-Fluoro-phenyl)-pyridine-2-carboxylic acid (3-cyanomethyl-phenyl)-amide

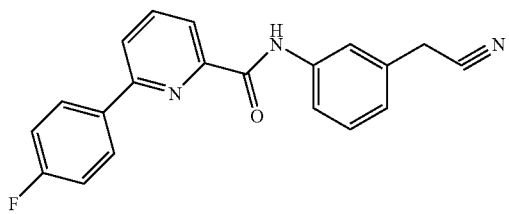

The pyridyl bromide (91) (150 mg, 0.47 mmol) was coupled to 4-fluoro-phenylboronic acid (73 mg, 0.52 mmol) using Method E. The crude residue was purified by column chromatography eluting with 20% EtOAc in heptane to give the title compound.

Yield: 90 mg, 58%; LC/MS $t_r$ 1.55 min; MS (ES+) m/z 332 (M+H)

(ii) 6-(4-Fluoro-phenyl)-pyridine-2-carboxylic acid [3-(1H-tetrazol-5-ylmethyl)-phenyl]-amide (93)

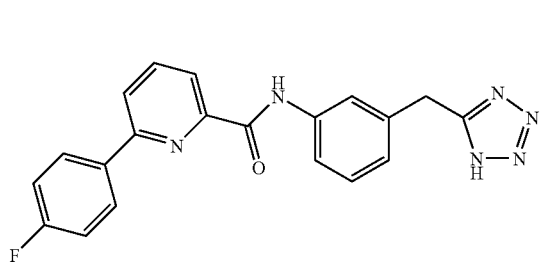

The nitrile (90 mg, 0.27 mmol) was treated with TMSN$_3$ and Bu$_2$SnO using Method L. After a first treatment, further TMSN$_3$ (125 mg, 1.08 mmol) and Bu$_2$SnO (14 mg, 0.054 mmol) were added and the mixture was heated in the microwave for a further 20 min. After work-up, the residue was dissolved in MeOH (2 ml) and washed with heptane (3×3 ml). The layers were separated and the MeOH was removed in vacuo. The solid was then triturated with heptane (4×2 ml) to give the title compound.

Yield: 59 mg, 58%; LC/MS $t_r$ 1.48 min; MS (ES+) m/z 375 (M+H); HPLC Purity: 100%; $^1$H NMR (400 MHz, DMSO): δ 4.25 (s, 2H), 7.02 (d, 1H), 7.29-7.36 (m, 3H), 7.71-7.78 (m, 2H), 7.99-8.11 (m, 2H), 8.19 (d, 1H), 8.34-8.40 (m, 2H), 10.49 (s, 1H).

(n) 6-(3-Fluoro-phenyl)-pyridine-2-carboxylic acid [3-(1H-tetrazol-5ylmethyl)-phenyl]-amide (94)

(i) 6-(3-Fluoro-phenyl)-pyridine-2-carboxylic acid (3-cyanomethyl-penyl)-amide

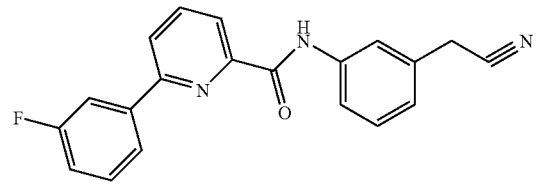

The pyridyl bromide (91) (150 mg, 0.47 mmol) was coupled to 3-fluoro-phenylboronic acid (73 mg, 0.52 mmol) using Method E. The crude residue was purified by column chromatography eluting with 20% EtOAc in heptane to give the title compound.

Yield: 144 mg, 93%; LC/MS $t_r$ 1.56 min; MS (ES+) m/z 332 (M+H)

(ii) 6-(3-Fluoro-phenyl)-pyridine-2-carboxylic acid [3-(1H-tetrazol-5-ylmethyl)-phenyl]-amide (93)

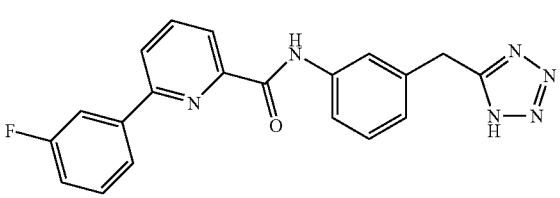

The nitrile (144 mg, 0.44 mmol) was treated with TMSN$_3$ and Bu$_2$SnO using Method L. After a first treatment, TMSN$_3$ (200 mg, 1.74 mmol) and Bu$_2$SnO (21 mg, 0.087 mmol) were added and the mixture was heated in the microwave for a further 20 min. After work-up, the residue was dissolved in MeOH (2 ml) and washed with heptane (3×3 ml). The layers were separated and the MeOH was removed in vacuo. The solid was then triturated with heptane (4×2 ml) to give the title compound.

Yield: 92 mg, 56%; LC/MS $t_r$ 1.58 min; MS (ES+) m/z 375 (M+H); HPLC Purity: 100%; $^1$H NMR (400 MHz, DMSO): δ 4.53 (s, 2H), 7.29 (d, 1H), 7.51-7.62 (m, 2H), 7.75-7.83 (m, 1H), 7.99-8.05 (m, 2H), 8.29-8.40 (m, 3H), 8.49-8.55 (m, 2H), 10.78 (s, 1H).

(o) 6-(4-Chloro-phenyl)-pyridine-2-carboxylic acid [3-(1H-tetrazol-5ylmethyl)-phenyl]-amide (95)

(i) 6-(4-Chloro-phenyl)-pyridine-2-carboxylic acid (3-cyanomethyl-phenyl)-amide

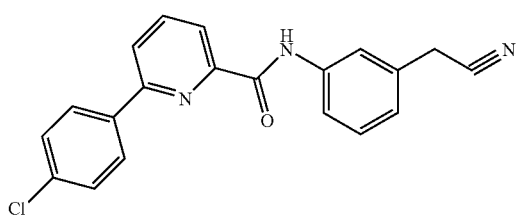

The pyridyl bromide (91) (150 mg, 0.47 mmol) was coupled to 4-chloro-phenylboronic acid (81 mg, 0.52 mmol) using Method E. The crude residue was purified by column chromatography eluting with 20% EtOAc in heptane to give the title compound.

Yield: 113 mg, 69%; LC/MS $t_r$ 1.62 min; MS (ES+) m/z 348, 350 (M+H)

(ii) 6-(4-Chloro-phenyl)-pyridine-2-carboxylic acid [3-(1H-tetrazol-5ylmethyl)-phenyl]-amide (95)

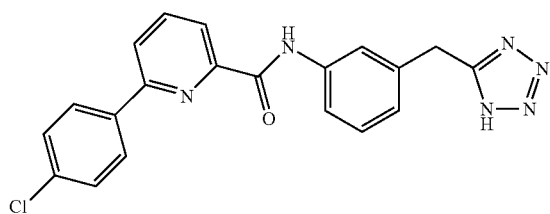

The nitrile (113 mg, 0.33 mmol) was treated with TMSN₃ and Bu₂SnO using Method L. After a first treatment, TMSN₃ (150 mg, 1.30 mmol) and Bu₂SnO (16 mg, 0.065 mmol) were added and the mixture was heated in the microwave for a further 20 min. After work-up, the residue was dissolved in MeOH (2 ml) and washed with heptane (3×3 ml). The layers were separated and the MeOH was removed in vacuo. The solid was then triturated with heptane (4×2 ml) to give the title compound.

Yield: 78 mg, 60%; LC/MS $t_r$ 1.53 min; MS (ES+) m/z 391, 393 (M+H); HPLC Purity: 97%; ¹H NMR (400 MHz, DMSO): δ 4.23 (s, 2H), 6.96 (d, 1H), 7.27 (t, 1H), 7.50 (d, 2H), 7.68-7.74 (m, 2H), 7.99-8.08 (m, 2H), 8.15 (d, 1H), 8.31 (d, 2H), 10.45 (s, 1H).

Example 9

(a) 5-[(5-Phenyl-furan-2-carbonyl)-amino]-benzofuran-2-carboxylic acid (96)

(i) 5-Nitro-benzofuran-2-carboxylic acid ethyl ester

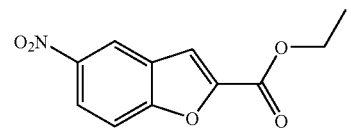

5-Nitro-benzofuran-2-carboxylic acid (500 mg, 2.41 mmol) was esterified with EtOH using Method A to give the title compound.

Yield: 488 mg, 86%; LC-MS $t_r$ 1.44 min; MS (ES+) m/z (M+H) not present (ii) 5-Amino-benzofuran-2-carboxylic acid ethyl ester

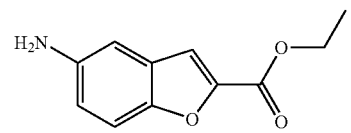

5-Nitro-benzofuran-2-carboxylic acid ethyl ester (150 mg, 0.64 mmol) was reduced using Method J to give the title compound.

Yield: 65 mg, 50%; LC-MS $t_r$ 0.87 min; MS (ES+) m/z 206 (M+H)

(iii) 5-[(5-Phenyl-furan-2-carbonyl)-amino]-benzofuran-2-carboxylic acid ethyl ester

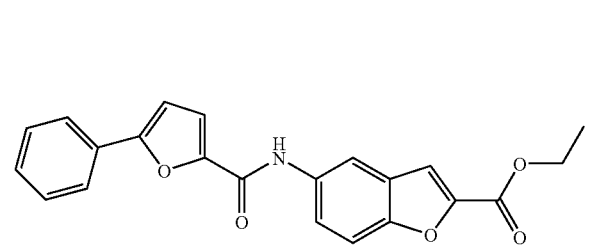

Carboxylic acid (56) (60 mg, 0.32 mmol) was coupled to 5-amino-benzofuran-2-carboxylic acid ethyl ester (65 mg, 0.32 mmol) using Method C to give the title compound.

Yield: 35 mg, 29%; LC-MS $t_r$ 1.63 min; MS (ES+) m/z 376 (M+H)

(iv) 5-[(5-Phenyl-furan-2-carbonyl)-amino]-benzofuran-2-carboxylic acid (96)

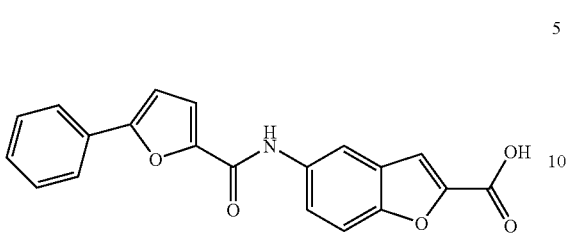

The ester (35 mg, 0.093 mmol) was hydrolysed using Method H to give the title compound.

Yield: 25 mg, 77%; LC/MS $t_r$ 1.38 min; MS (ES+) m/z 348 (M+H); HPLC Purity: 100%; $^1$H NMR (250 MHz, MeOD) δ 7.02 (d, 1H), 7.36-7.53 (m, 4H), 7.61-7.64 (m, 2H), 7.75-7.80 (m, 1H) 7.95-7.99 (m, 2H), 8.20-8.21 (m, 1H).

(b) 5-[(5-Phenyl-furan-2-carbonyl)-amino]-benzo[b]thiophene-2-carboxylic acid (97)

(i) 5-Nitro-benzo[b]thiophene-2-carboxylic acid ethyl ester

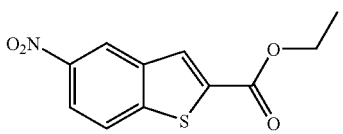

5-Nitro-benzofuran-2-carboxylic acid (500 mg, 2.24 mmol) was esterified with EtOH using Method A to give the title compound.

Yield: 497 mg, 88%; LC-MS $t_r$ 1.58 min; MS (ES+) m/z (M+H) not present

(ii) 5-Amino-benzo[b]thiophene-2-carboxylic acid ethyl ester

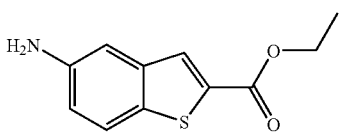

5-Nitro-benzothiophene-2-carboxylic acid ethyl ester (160 mg, 0.64 mmol) was reduced using Method J to give the title compound.

Yield: 123 mg, 87%; LC-MS $t_r$ 0.98 min; MS (ES+) m/z 222 (M+H)

(iii) 5-[(5-Phenyl-furan-2-carbonyl)-amino]-benzo[b]thiophene-2-carboxylic acid ethyl ester

Carboxylic acid (56) (105 mg, 0.56 mmol) was coupled to 5-amino-benzothiophene-2-carboxylic acid ethyl ester (123 mg, 0.56 mmol) using Method C to give the title compound.

Yield: 75 mg, 34%; LC-MS $t_r$ 1.72 min; MS (ES+) m/z 392 (M+H)

(iv) 5-[(5-Phenyl-furan-2-carbonyl)-amino]-benzo[b]thiophene-2-carboxylic acid (97)

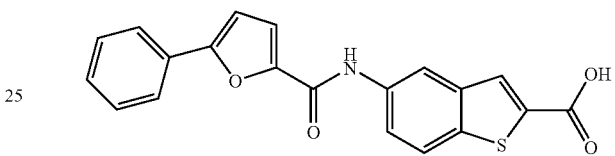

The ester (75 mg, 0.19 mmol) was hydrolysed using Method H to give the title compound.

Yield: 43 mg, 62%; LC/MS $t_r$ 1.47 min; MS (ES+) m/z 363 (M+H); HPLC Purity: 100%; $^1$H NMR (400 MHz, MeOD) δ 7.03 (d, 1H), 7.39-7.42 (m, 2H), 7.48-7.52 (m, 2H), 7.82-7.85 (m, 1H), 7.94-7.99 (m, 3H) 8.07-8.10 (m, 1H), 8.42-8.43 (m, 1H).

(c) 2-{3-[(5-Phenyl-furan-2-carbonyl)-amino]-benzylidene}-butyric acid (98)

(i) 2-(3-Nitro-benzylidene)-butyric acid ethyl ester

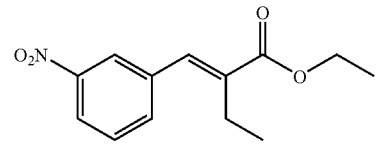

2-(3-Nitro-benzylidene)-butyric acid (500 mg, 2.27 mmol) was esterified by dissolving in EtOH (12.5 ml), adding conc HCl (0.25 ml) and heating to reflux for 8 h. The solvents were evaporated in vacuo to give the title compound.

Yield: 440 mg, 78%; LC-MS $t_r$ 1.64 min; MS (ES+) m/z (M+H) not present

(ii) 2-(3-Amino-benzylidene)-butyric acid ethyl ester

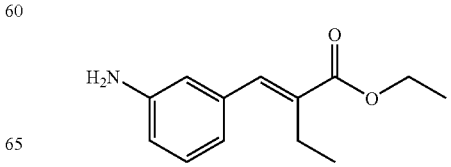

2-(3-Nitro-benzylidene)-butyric acid ethyl ester (230 mg, 0.92 mmol) was reduced using Method J to give the title compound.

Yield: 186 mg, 92%; LC-MS $t_r$ 1.06 min; MS (ES+) m/z 220 (M+H)

(iii) 2-{3-[(5-Bromo-furan-2-carbonyl)-amino]-benzylidene}-butyric acid ethyl ester

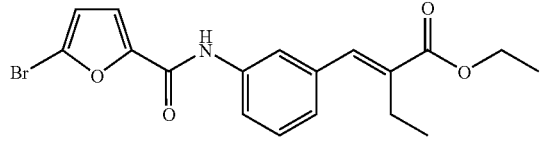

5-Bromo-furan-2-carboxylic acid (88 mg, 0.46 mmol) was coupled to 2-(3-amino-benzylidene)-butyric acid ethyl ester (100 mg, 0.46 mmol) using Method C to give the title compound.

Yield: 132 mg, 73%; LC-MS $t_r$ 1.66 min; MS (ES+) m/z 392, 394 (M+H)

(iv) 2-{3-[(5-Phenyl-furan-2-carbonyl)-amino]-benzylidene}-butyric acid ethyl ester

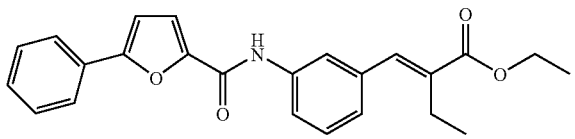

The furyl bromide (132 mg, 0.34 mmol) was coupled to phenylboronic acid (45 mg, 0.37 mmol) using Method E. The residue was purified by column chromatography eluting with 10% EtOAc in heptane to give the title compound.

Yield: 36 mg, 27%; LC-MS $t_r$ 1.78 min; MS (ES+) m/z 390 (M+H)

(v) 2-{3-[(5-Phenyl-furan-2-carbonyl)-amino]-benzylidene}-butyric acid (98)

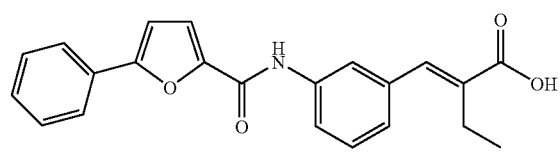

The ester (35 mg, 0.090 mmol) was hydrolysed using Method H to give the title compound.

Yield: 7.6 mg, 23%; LC/MS $t_r$ 1.49 min; MS (ES+) m/z 362 (M+H); HPLC Purity: 100%; $^1$H NMR (250 MHz, MeOD) δ 1.23 (t, 3H), 3.33 (q, 2H) 7.01 (d, 1H), 7.20-7.23 (m, 1H), 7.39-7.52 (m, 5H), 7.67-7.70 (m, 2H) 7.95-7.98 (m, 3H).

(d) 3-(3-{[5-(3-Fluoro-phenyl)-furan-2-carbonyl]-amino}-phenyl)-acrylic acid (100)

(i) 3-{3-[(5-Bromo-furan-2-carbonyl)-amino]-phenyl}-acrylic acid ethyl ester (99)

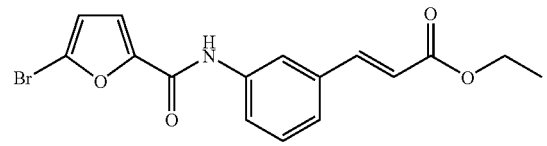

5-Bromo-furan-2-carboxylic acid (150 mg, 0.78 mmol) was coupled to aniline (60) (150 mg, 0.78 mmol) using Method C to give the title compound.

Yield: 125 mg, 44%; LC-MS $t_r$ 1.53 min; MS (ES+) m/z 364, 366 (M+H)

(ii) 3-{3-([5-(3-Fluoro-phenyl)-furan-2-carbonyl]-amino}-phenyl)-acrylic acid ethyl ester

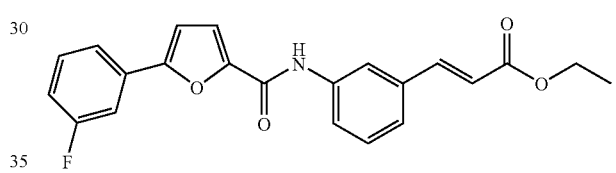

The furyl bromide (99) (125 mg, 0.34 mmol) was coupled to 3-fluoro-phenylboronic acid (48 mg, x 0.41 mmol) acid using Method E. The residue was purified by column chromatography eluting with 20% EtOAc in heptane to give the title compound.

Yield: 96 mg, 74%; LC-MS $t_r$ 1.68 min; MS (ES+) m/z 380 (M+H)

(iii) 3-(3-{[5-(3-Fluoro-phenyl)-furan-2-carbonyl]-amino}-phenyl)-acrylic acid (100)

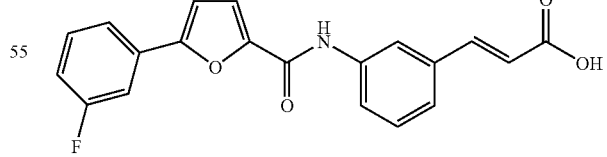

The ester (96 mg, 0.25 mmol) was hydrolysed using Method H to give the title compound.

Yield: 58 mg, 66%; LC/MS $t_r$ 1.42 min; MS (ES+) m/z 352 (M+H); HPLC Purity: 100%; $^1$H NMR (250 MHz, DMSO) δ 6.51 (d, 1H), 7.22-7.63 (m, 7H), 7.83-8.01 (m, 4H), 10.31 (s, 1H), 12.43 (s, 1H).

(e) 3-{3-[(5-Benzo[1,3]dioxol-5-yl-furan-2-carbonyl)-amino]-phenyl}-acrylic acid (101)

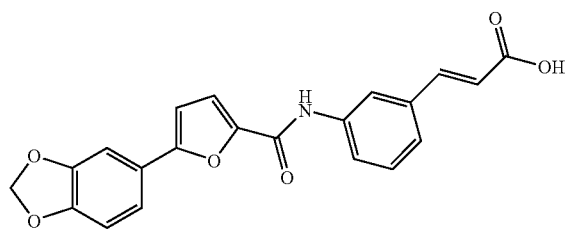

The furyl bromide (99) (100 mg, 0.30 mmol) was coupled to 3,4-(methylenedioxy)-phenylboronic acid (54 mg, 0.33 mmol) using Method E. During this reaction, hydrolysis occurred. The crude reaction mixture was diluted with $H_2O$ (4 ml) and extracted with EtOAc (3×1 ml), then the aqueous layer was acidified with 2M HCl until a white precipitate appeared and extracted with DCM (3×1 ml). The organic layer was dried ($MgSO_4$), filtered and the solvent removed in vacuo. The solid was triturated with TBME (2×2 ml) to give the title compound.

Yield: 27 mg, 24%; LC/MS $t_r$ 1.99 min; MS (ES+) m/z 378 (M+H); HPLC Purity: 93%; $^1$H NMR (250 MHz; DMSO): δ 6.10 (s, 2H), 6.50 (d, 1H), 7.02-7.05 (m, 2H), 7.33-7.68 (m, 6H), 7.78-7.88 (m, 1H), 8.00 (s, 1H), 10.21 (s, 1H).

(f) 3-(3-{[5-(3,5-Bis-trifluoromethyl-phenyl)-furan-2-carbonyl]-amino}phenyl)-acrylic acid (102)

(i) 3-(3-{[5-(3,5-Bis-trifluoromethyl-phenyl)-furan-2-carbonyl]-amino}phenyl)-acrylic acid ethyl ester

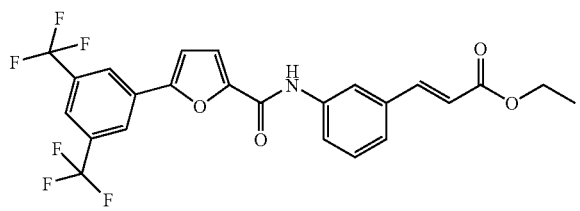

The furyl bromide (99) (70 mg, 0.19 mmol) was coupled to 3,5-bis-trifluoromethyl-phenylboronic acid (55 mg, 0.21 mmol) acid using Method E, except that the reaction was heated at 100° C. The crude product was purified by column chromatography eluting with a stepped gradient of 0-10% EtOAc in heptane to give the title compound.

Yield: 45 mg, 47%; LC-MS $t_r$ 1.87 min; MS (ES+) m/z 498 (M+H)

(ii) 3-{3-([5-(3,5-Bis-trifluoromethyl-phenyl)-furan-2-carbonyl]-amino}phenyl)-acylic acid (102)

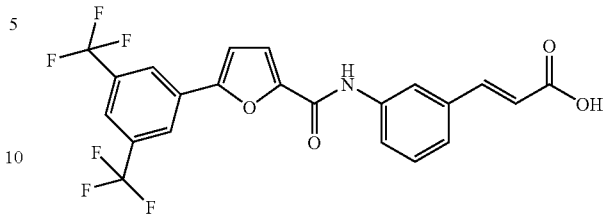

To a solution of the ester (45 mg, 0.09 mmol) in THF (1 ml) and MeOH (1 ml) was added 1M NaOH (2 ml) and the resulting solution was stirred for 1 h at 40° C. The THF and MeOH were removed in vacuo then 2M HCl was added until a white precipitate formed. The aqueous layer was extracted with DCM (3×1 ml). The organic layer was dried ($MgSO_4$), filtered and the solvent was removed in vacuo. The solid was triturated with 50% DCM in heptane (2×2 ml) and 50% MeOH in $H_2O$ (2×2 ml) to give the title compound.

Yield: 15 mg, 36%; LC/MS $t_r$ 2.23 min; MS (ES+) m/z 470 (M+H); HPLC Purity: 100%; $^1$H NMR (400 MHz; MeOD): δ 6.52 (d, 1H), 7.25-7.28 (m, 1H), 7.30-7.37 (m, 3H), 7.59 (d, 1H), 7.69-7.73 (m, 1H), 7.38 (d, 2H), 8.50 (s, 2H).

(g) 3-{3-[(5-Biphenyl-3-yl-furan-2-carbonyl)-amino]-phenyl}-acrylic acid (103)

(i) 3-{3-[(5-Biphenyl-3-yl-furan-2-carbonyl)-amino]-phenyl}-acrylic acid ethyl ester

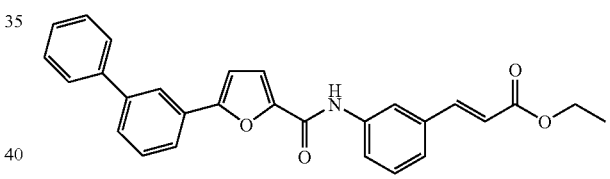

Bromo-derivative (99) (70 mg, 0.19 mmol) was coupled to biphenyl-3-boronic acid (42 mg, 0.21 mmol) acid using Method E, except that the reaction was heated at 100° C. The crude product was purified by column chromatography eluting with a stepped gradient of 0-10% EtOAc in heptane to give the title compound.

Yield: 33 mg, 39%; LC-MS $t_r$ 1.86 min; MS (ES+) m/z 438 (M+H)

(ii) 3-{3-[(5-Biphenyl-3-yl-furan-2-carbonyl)-amino]-phenyl}-acrylic acid (103)

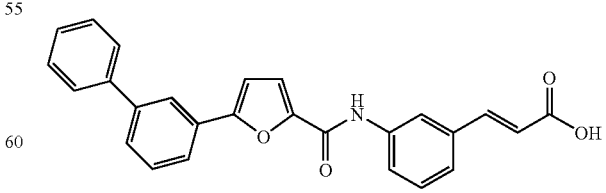

To a solution of the ester (33 mg, 0.075 mmol) in THF (2 ml) and MeOH (2 ml) was added 1M NaOH (4 ml) and the resulting solution was stirred for 1 h at 40° C. The THF and MeOH were removed in vacuo and the aqueous layer was extracted with TBME (2×2 ml). The aqueous layer was acidified with 6M HCl until a white precipitate formed. This was then extracted with TBME (3×2 ml). The organic layer was dried (MgSO$_4$), filtered and the solvent was removed in vacuo. The residue was suspended in H$_2$O (1 ml), MeOH (1 ml) and heptane (1 ml) and the resulting solid was filtered and dried in vacuo to give the title compound.

Yield: 15 mg, 46%; LC/MS t$_r$ 2.21 min; MS (ES+) m/z 410 (M+H); HPLC Purity: 100%; $^1$H NMR (400 MHz; MeOD): δ 6.72 (d, 1H), 7.29 (d, 1H), 7.56-7.72 (m, 6H), 7.73-7.79 (t, 1H), 7.83-7.97 (m, 4H), 8.01 (d, 1H), 8.12 (d, 1H), 8.19 (s, 1H), 8.43 (s, 1H).

(h) 3-(3-{[5-(3-Benzyloxy-phenyl)-furan-2-carbonyl]-amino}-phenyl)-acrylic acid (104)

(i) 3-(3-{[5-(3-Benzyloxy-phenyl)-furan-2-carbonyl]-amino}-phenyl)-acrylic acid ethyl ester

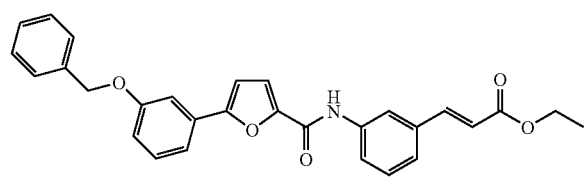

The furyl bromide (99) (100 mg, 0.28 mmol) was coupled to 3-benzyloxy-phenylboronic acid (69 mg, 0.30 mmol) acid using Method E, except that the reaction was heated at 85° C. The crude product was purified by column chromatography eluting with 20% EtOAc in heptane to give the title compound.

Yield: 86 mg, 67%; LC-MS t$_r$ 1.83 min; MS (ES+) m/z 468 (M+H)

(ii) 3-(3-{[5-(3-Benzyloxy-phenyl)-furan-2-carbonyl]-amino}-phenyl)-acrylic acid (104)

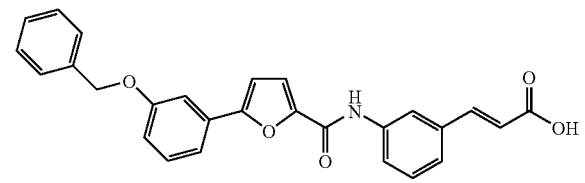

The ester (86 mg, 0.18 mmol) was hydrolysed using Method H to give the title compound.

Yield: 36 mg, 45%; LC/MS t$_r$ 1.65 min; MS (ES+) m/z 440 (M+H); HPLC Purity: 100%; $^1$H NMR (250 MHz, DMSO) δ 5.19 (s, 2H), 6.51 (d, 1H), 6.67-7.05 (m, 2H), 7.28-7.45 (m, 7H), 7.46-7.54 (m, 3H), 7.62-7.73 (m, 2H), 7.80-7.88 (m, 1H), 8.01 (s, 1H).

(i) 3-(3-{[5-(2-Fluoro-biphenyl-4-yl)-furan-2-carbonyl]-amino}-phenyl)-acrylic acid (105)

(i) 3-(3-{[5-(2-Fluoro-biphenyl-4-yl)-furan-2-carbonyl]-amino}-phenyl)-acrylic acid ethyl ester

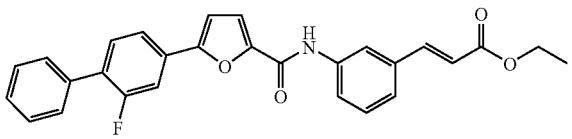

The furyl bromide (99) (100 mg, 0.28 mmol) was coupled to 2-Fluoro-biphenyl-4-boronic acid (65 mg, 0.30 mmol) acid using Method E, except that the reaction was heated at 85° C. The crude product was purified by column chromatography eluting with 20% EtOAc in heptane to give the title compound.

Yield: 67 mg, 54%; LC-MS t$_r$ 1.89 min; MS (ES+) m/z 456 (M+H)

(ii) 3-(3-{[5-(2-Fluoro-biphenyl-4-yl)-furan-2-carbonyl]-amino}-phenyl)-acrylic acid (105)

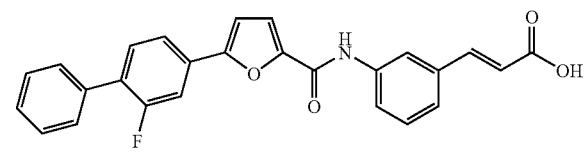

The ester (67 mg, 0.15 mmol) was hydrolysed using Method H to give the title compound.

Yield: 43 mg, 67%; LC/MS t$_r$ 2.23 min; MS (ES+) m/z 440 (M+H); HPLC Purity: 100%; $^1$H NMR (250 MHz, DMSO) δ 6.53 (d, 1H), 7.38 (d, 1H), 7.42-7.59 (m, 6H), 7.60-7.73 (m, 4H), 7.87 (d, 1H), 7.94 (d, 1H), 8.01-8.09 (m, 2H), 10.35 (s, 1H), 12.52 (broad s, 1H).

(j) 3-{3-[(4-Fluoro-biphenyl-3-carbonyl)-amino]-phenyl}-acrylic acid (107)

(i) 3-[3-(5-Bromo-2-fluoro-benzoylamino)-phenyl]-acrylic acid ethyl ester (106)

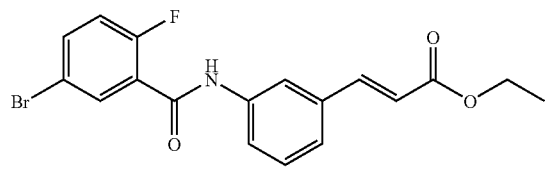

5-Bromo-2-fluorobenzoic acid (330 mg, 1.5 mmol) was coupled to aniline (99) (290 mg, 1.5 mmol) using Method C to give the title compound.

Yield: 525 mg, 89%; LC-MS t$_r$ 1.61 min; MS (ES+) m/z 392, 394 (M+H)

(ii) 3-{3-[(4-Fluoro-biphenyl-3-carbonyl)-amino]-phenyl}-acrylic acid ethyl ester

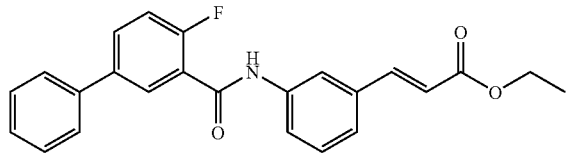

The phenyl bromide (106) (100 mg, 0.25 mmol) was coupled to phenylboronic acid (34 mg, x 0.28 mmol) using Method E. The residue was purified by column chromatography eluting with 20% EtOAc in heptane to give the title compound.

Yield: 38 mg, 39%; LC-MS $t_r$ 1.72 min; MS (ES+) m/z 390 (M+H)

(iii) 3-{3-[(4-Fluoro-biphenyl-3-carbonyl)-amino]-phenyl}-acrylic acid (107)

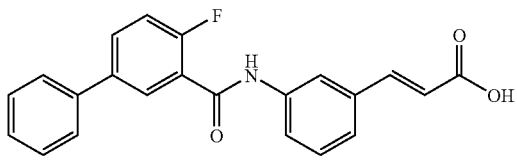

The ester (38 mg, 0.098 mmol) was hydrolysed using Method H to give the title compound.

Yield: 29 mg, 82%; LC-MS $t_r$ 1.46 min; MS (ES+) m/z 362 (M+H); HPLC Purity: 100%; $^1$H NMR (250 MHz, MeOD) δ 6.54 (d, 1H), 7.34-7.53 (m, 6H), 7.66-7.88 (m, 5H), 7.99-8.03 (m, 2H).

(k) 3-{3-[(4,3'-Difluoro-biphenyl-3-carbonyl)-amino]-phenyl}-acrylic acid (108)

(i) 3-{3-[(4,3'-Difluoro-biphenyl-3-carbonyl)-amino]-phenyl}-acrylic acid ethyl ester

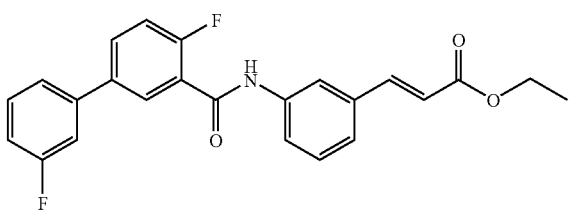

The phenyl bromide (106) (100 mg, 0.25 mmol) was coupled to 3-fluoro-phenylboronic acid (39 mg, 0.28 mmol) using Method E. The crude product was purified by column chromatography eluting with 20% EtOAc in heptane to give the title compound.

Yield: 17 mg, 17%; LC-MS $t_r$ 1.73 min; MS (ES+) m/z 408 (M+H)

(ii) 3-{3-[(4,3'-Difluoro-biphenyl-3-carbonyl)-amino]-phenyl}-acrylic acid (108)

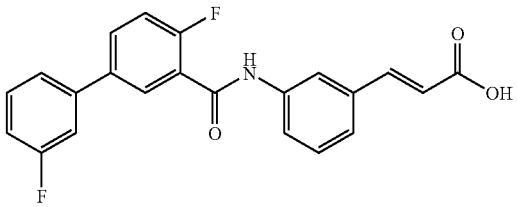

The ester (17 mg, 0.042 mmol) was hydrolysed using Method H to give the title compound.

Yield: 13 mg, 82%; LC/MS $t_r$ 1.46 min; MS (ES+) m/z 380 (M+H) HPLC Purity: 100%; $^1$H NMR (250 MHz, MeOD) δ 6.54 (d, 1H), 7.08-7.20 (m, 1H), 7.35-7.53 (m, 6H), 7.69 (d, 1H), 7.78-7.90 (m, 2H), 7.99-8.04 (m, 2H).

(l) 3-(3-{[6-(3-Fluoro-phenyl)-pyridine-2-carbonyl]-amino}-phenyl)-acrylic acid (110)

(i) 3-{3-[(6-Bromo-pyridine-2-carbonyl)-amino]-phenyl}-acrylic acid ethyl ester (109)

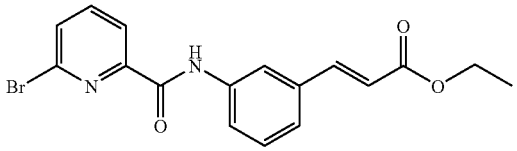

6-Bromo-pyridine-2-carboxylic acid (127 mg, 0.63 mmol) was coupled to aniline (60) (120 mg, 0.63 mmol) using Method C to give the title compound.

Yield: 201 mg, 85%; LC-MS $t_r$ 1.62 min; MS (ES+) m/z 375, 377 (M+H)

(ii) 3-(3-{[6-(3-Fluoro-phenyl)-pyridine-2-carbonyl]-amino}-phenyl)-acrylic acid ethyl ester

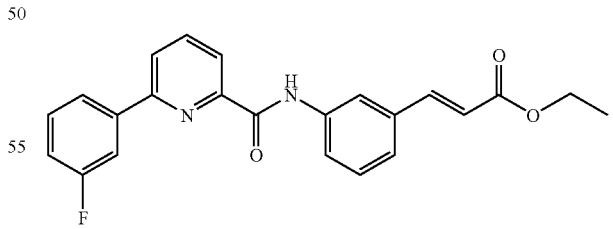

The pyridyl bromide (109) (100 mg, 0.27 mmol) was coupled to 3-fluoro-phenylboronic acid (41 mg, 0.29 mmol) using Method E. The residue was purified by column chromatography eluting with 20% EtOAc in heptane to give the title compound.

Yield: 36 mg, 34%; LC-MS $t_r$ 1.79 min; MS (ES+) m/z 391 (M+H)

(iii) 3-(3-{[6-(3-Fluoro-phenyl)-pyridine-2-carbo-nyl]-amino}-phenyl)-acrylic acid (110)

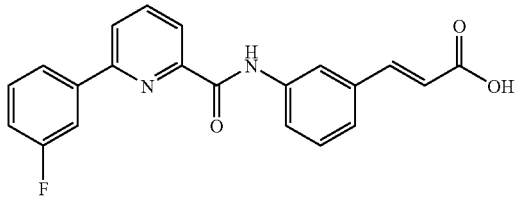

The ester (36 mg, 0.092 mmol) was hydrolysed using Method H to give the title compound.

Yield: 23 mg, 69%; LC/MS $t_r$ 1.53 min; MS (ES+) m/z 363 (M+H); HPLC Purity: 100%; $^1$H NMR (250 MHz, MeOD) δ 6.54-6.64 (m, 1H), 7.22-7.30 (m, 1H), 7.43-7.60 (m, 3H), 7.70-7.76 (m, 1H), 7.89-7.93 (m, 1H), 8.05-8.13 (m, 6H).

(m) 3-[(4,3'-Difluoro-biphenyl-3-carbonyl)-amino]-phenyl}-acetic acid (111)

(i) {3-[(4,3'-Difluoro-biphenyl-3-carbonyl)-amino]-phenyl}-acetic acid ethyl ester

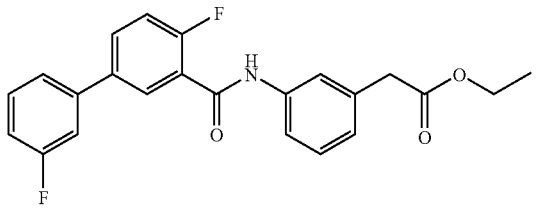

The phenyl bromide (78) (106 mg, 0.28 mmol) was coupled to 3-fluoro-phenylboronic acid (42 mg, 0.30 mmol) using Method E. The crude product was purified by column chromatography eluting with 20% EtOAc in heptane to give the title compound.

Yield: 66 mg, 60%; LC-MS $t_r$ 1.63 min; MS (ES+) m/z 396 (M+H)

(ii) 3-[(4,3'-Difluoro-biphenyl-3-carbonyl)-amino]-phenyl}-acetic acid (111)

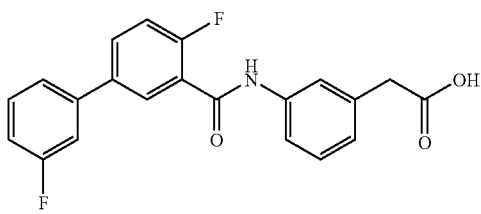

The ester (66 mg, 0.17 mmol) was hydrolysed using Method H to give the title compound.

Yield: 52 mg, 85%; LC/MS $t_r$ 1.58 min; MS (ES+) m/z 368 (M+H); HPLC Purity: 100%; $^1$H NMR (250 MHz, MeOD) δ 3.65 (s, 2H), 7.07-7.19 (m, 2H), 7.32-7.51 (m, 5H), 7.65-7.68 (m, 2H), 7.80-7.86 (m, 1H), 7.96-8.00 (m, 1H).

(n) 3-{3-[(4,4'-Difluoro-biphenyl-3-carbonyl)-amino]-phenyl}-acrylic acid (112)

(i) 4,4'-Difluoro-biphenyl-3-carboxylic acid

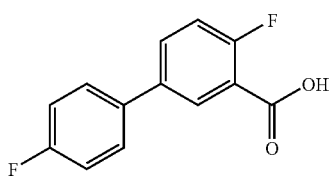

5-Bromo-2-fluorobenzoic acid (250 mg, 1.14 mmol) was coupled to 4-fluoro-phenylboronic acid (192 mg, 1.37 mmol) using Method E to give the title compound. No chromatography was necessary.

Yield: 209 mg, 78%; LC-MS $t_r$ 1.36 min; MS (ES+) m/z (M+H) not present (ii) 3-(3-[(4,4'-Difluoro-biphenyl-3-carbonyl)-amino]-phenyl)-acrylic acid ethyl ester

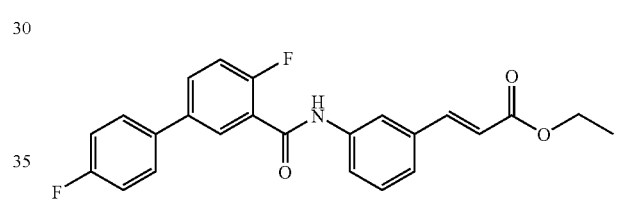

4,4'-Difluoro-biphenyl-3-carboxylic acid (100 mg, 0.43 mmol) was coupled to aniline (60) (82 mg, 0.43 mmol) using Method C to give the title compound.

Yield: 119 mg, 68%; LC-MS $t_r$ 1.73 min; MS (ES+) m/z 408 (M+H)

(iii) 3-{3-[(4,4'-Difluoro-biphenyl-3-carbonyl)-amino]-phenyl}-acrylic acid (112)

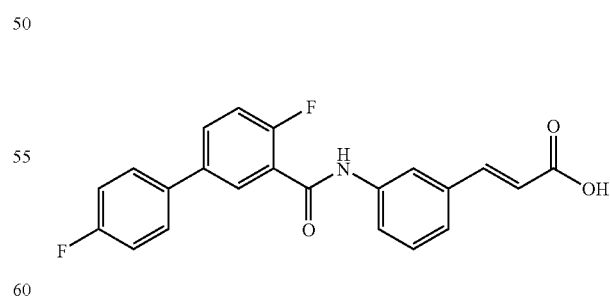

The ester (119 mg, 0.29 mmol) was hydrolysed using Method H to give the title compound.

Yield: 85 mg, 77%; LC/MS $t_r$ 1.56 min; MS (ES+) m/z 380 (M+H); HPLC Purity: 98%; $^1$H NMR (250 MHz, MeOD) δ 6.53 (d, 1H), 7.19-7.27 (m, 2H), 7.33-7.49 (m, 3H), 7.67-7.86 (m, 5H), 7.96-8.00 (m, 2H).

(o) (3-{[6-(3-Fluoro-phenyl)-pyridine-2-carbonyl]-amino}-phenyl)-acetic acid (113)

(i) (3-{[6-(3-Fluoro-phenyl)-pyridine-2-carbonyl]-amino}-phenyl)-acetic acid ethyl ester

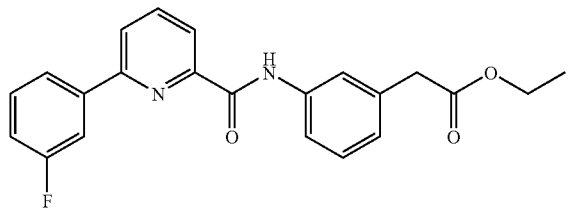

The pyridyl bromide (77) (100 mg, 0.28 mmol) was coupled to 3-fluoro-phenylboronic acid (42 mg, 0.30 mmol) using Method E. The crude product was purified by column chromatography eluting with 20% EtOAc in heptane to give the title compound.

Yield: 95 mg, 90%; LC-MS $t_r$ 1.69 min; MS (ES+) m/z 379 (M+H)

(ii) (3-{[6-(3-Fluoro-phenyl)-pyridine-2-carbonyl]-amino}-phenyl)-acetic acid (113)

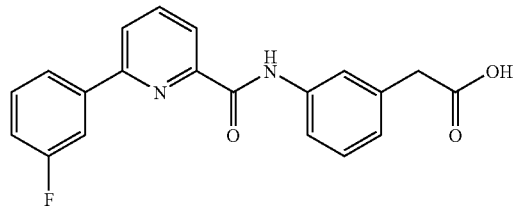

The ester (95 mg, 0.25 mmol) was hydrolysed using Method H to give the title compound.

Yield: 57 mg, 65%; LC/MS $t_r$ 1.54 min; MS (ES+) m/z 351 (M+H); HPLC Purity: 100%; $^1$H NMR (250 MHz, MeOD) δ 3.68 (s, 2H), 7.13-7.28 (m, 2H), 7.35-7.41 (m, 1H), 7.52-7.61 (m, 1H), 7.76-7.79 (m, 2H), 8.01-8.21 (m, 5H).

(p) 3-{3-[(2-Phenyl-thiazole-4-carbonyl)-amino]-phenyl}-acrylic acid (115)

(i) 3-{3-[(2-Chloro-thiazole-4-carbonyl)-amino]-phenyl}-acrylic acid ethyl ester (114)

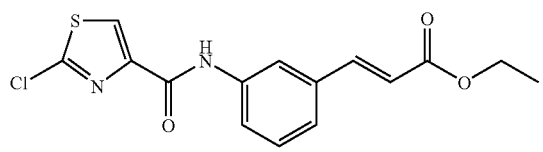

Carboxylic acid (79) (220 mg, 1.34 mmol) was coupled to aniline (60) (257 mg, 1.34 mmol) using Method C to give the title compound.

Yield: 260 mg, 57%; LC/MS $t_r$ 1.54 min; MS (ES+) m/z 337 (M+H)

(ii) 3-{3-[(2-Phenyl-thiazole-4-carbonyl)-amino]-phenyl}-acrylic acid ethyl ester

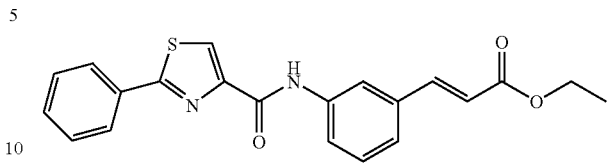

The chloro thiazole (114) (80 mg, 0.24 mmol) was coupled to phenylboronic acid (32 mg, 0.26 mmol) using Method E, except that the reaction mixture was heated for a total of 4 h. The crude residue was purified by column chromatography eluting with 25% EtOAc in heptane to give the title compound.

Yield: 52 mg, 57%; LC/MS $t_r$ 1.76 min; MS (ES+) m/z 379 (M+H)

(iii) 3-{3-[(2-Phenyl-thiazole-4-carbonyl)-amino]-phenyl}-acrylic acid (115)

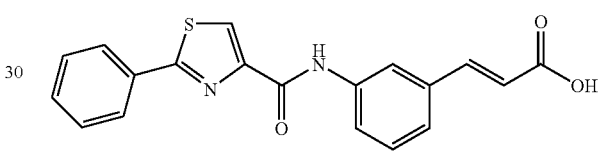

The ester (52 mg, 0.14 mmol) was hydrolysed using Method H to give the title compound.

Yield: 31 mg, 63%; LC/MS $t_r$ 2.06 min; MS (ES+) m/z 351 (M+H); HPLC Purity: 100%; $^1$H NMR (250 MHz, DMSO) δ 6.53 (d, 1H), 7.44-7.47 (m, 2H), 7.55-7.61 (m, 4H), 7.96-8.01 (m, 1H), 8.13-8.21 (m, 3H), 8.53 (s, 1H), 10.33 (s, 1H).

(q) 3-(3-{[2-(3-Fluoro-phenyl)-thiazole-4-carbonyl]-amino}-phenyl)-acrylic acid (116)

(i) 3-(3-{[2-(3-Fluoro-phenyl)-thiazole-4-carbonyl]-amino}-phenyl)-acrylic acid ethyl ester

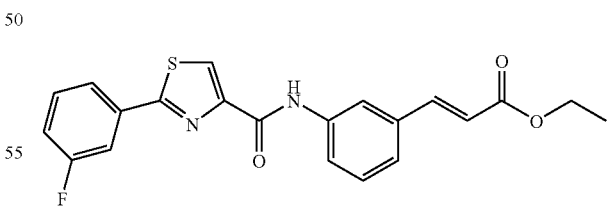

The chloro thiazole (114) (80 mg, 0.24 mmol) was coupled to 3-fluoro-phenylboronic acid (42 mg, 0.30 mmol) using Method E, except that the reaction mixture was heated for a total of 12 h. The crude residue was purified by column chromatography eluting with 20% EtOAc in heptane to give the title compound.

Yield: 35 mg, 37%; LC/MS $t_r$ 1.76 min; MS (ES+) m/z 397 (M+H)

(ii) 3-(3-{[2-(3-Fluoro-phenyl)-thiazole-4-carbonyl]-amino}-phenyl)-acrylic acid (116)

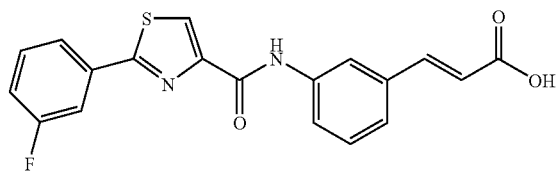

The ester (35 mg, 0.088 mmol) was hydrolysed using Method H to give the title compound.

Yield: 6.3 mg, 19%; LC/MS $t_r$ 1.45 min; MS (ES+) m/z 369 (M+H); HPLC Purity: 100%; $^1$H NMR (250 MHz, d$^6$-Acetone) δ 6.57 (d, 1H), 7.52-7.40 (m, 1H), 7.49 (d, 2H), 7.56-7.74 (m, 2H), 7.93-8.06 (m, 3H), 8.22 (s, 1H), 8.48 (s, 1H), 10.14 (s, 1H).

(r) [3-(Biphenyl-3-ylcarbamoyl)-phenyl]-acetic acid (117)

(i) Biphenyl-3-ylamine

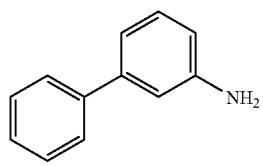

Bromobenzene (300 mg, 1.91 mmol) was coupled to 3-amino-phenylboronic acid (355 mg, 2.29 mmol) using Method E. The crude residue was re-dissolved in EtOAc (8 ml) and washed with saturated NaHCO$_3$ (3×8 ml). The organic layer was extracted with 1.2M HCl (1×8 ml) then basified with 6M NaOH until a white precipitate formed. This was then extracted with EtOAc (3×10 ml). The combined organic layers were dried (MgSO$_4$), filtered and the solvent removed in vacuo to give the title compound.

Yield: 297 mg, 92%; LC/MS $t_r$ 0.96 min; MS (ES+) m/z 170 (M+H)

(ii) 3-Cyanomethyl-benzonitrile

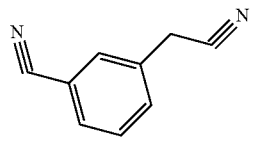

3-Bromomethyl-benzonitrile (150 mg, 0.76 mmol) was dissolved in DMF (2 ml). KCN (55 mg, 0.84 mmol) was dissolved in the minimum amount of water and was added to the reaction. The resulting solution was stirred at 85° C. overnight. The reaction mixture was allowed to cool to room temperature, EtOAc (5 ml) was added, and the solution was washed with saturated NaHCO$_3$ (4×10 ml). The organic layer was dried (MgSO$_4$), filtered and the solvent removed in vacuo to give the title compound.

Yield: 90 mg, 83%; LC/MS $t_r$ 1.04 min; MS (ES+) m/z 143 (M+H)

(iii) 3-Carboxymethyl-benzoic acid

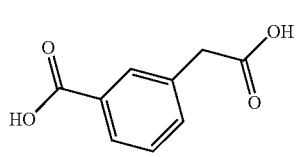

3-Cyanomethyl-benzonitrile (90 mg, 0.63 mmol) was suspended in conc. HCl (3 ml), and heated to 80° C. for 2 h. The solvent was then removed in vacuo to give the crude product, which was used without further purification.

Yield: 110 mg, 97%; LC/MS $t_r$ 0.71 min; MS (ES+) m/z 181 (M+H)

(iv) 3-Ethoxycarbonylmethyl-benzoic acid

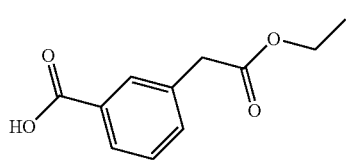

The phenylacetic acid (110 mg, 0.61 mmol) was esterified with EtOH using Method A to give the crude product, which was used without further purification.

Yield: 126 mg, 99%; LC/MS $t_r$ 1.13 min; MS (ES+) m/z 209 (M+H)

(v) [3-(Biphenyl-3-ylcarbamoyl)-phenyl]-acetic acid ethyl ester

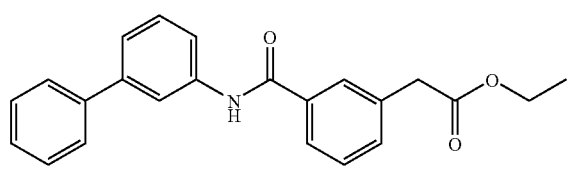

3-Ethoxycarbonylmethyl-benzoic acid (126 mg, 0.61 mmol) was coupled to biphenyl-3-ylamine (105 mg, 0.62 mmol) using Method C. The residue was purified by column chromatography eluting with 100% DCM to give the title compound.

Yield: 17 mg, 8%; LC/MS $t_r$ 1.64 min; MS (ES+) m/z 360 (M+H)

(vi) [3-(Biphenyl-3-ylcarbamoyl)-phenyl]-acetic acid (117)

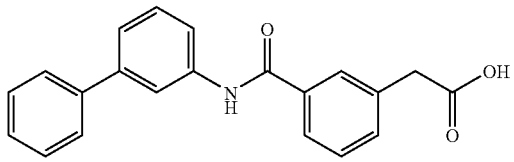

The ester (17 mg, 0.047 mmol) was hydrolysed with NaOH (34 mg, 0.85 mmol using Method G to give the title compound.

Yield: 7.8 mg, 50%; LC/MS $t_r$ 1.46 min; MS (ES+) m/z 332 (M+H); HPLC Purity: 96%; $^1$H NMR (400 MHz; CDCl$_3$): δ 3.78 (s, 2H), 7.37-7.42 (m, 1H), 7.44-7.59 (m, 6H), 7.66-7.76 (m, 3H), 7.88-7.94 (m, 2H), 8.04 (s, 1H).

(s) 1-Methyl-5-[(5-phenyl-furan-2-carbonyl)-amino]-1H-indole-2-carboxylic acid (118)

(i) 1-Methyl-5-nitro-1H-indole-2-carboxylic acid

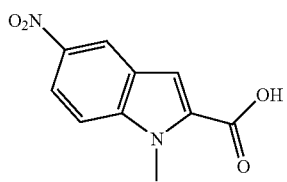

5-Nitro-1H-indole-2-carboxylic acid ethyl ester (234 mg, 1 mmol) was dissolved in DMF (2 ml). NaH (32 mg, 1.4 mmol) was added as a suspension in heptane (0.5 ml) and the mixture was stirred at room temperature for 10 min. Iodomethane (170 mg, 1.2 mmol) was added drop-wise and the solution was left stirring for 1 h. During this reaction, hydrolysis occurred. The reaction mixture was quenched with H$_2$O (2 ml) and washed with EtOAc (3×1 ml). The aqueous layer was acidified to pH 1 with conc. HCl until a white precipitate formed and extracted with EtOAc (3×1 ml). These organic layer were combined, dried (MgSO$_4$), filtered and the solvent removed in vacuo to give the title compound.

Yield: 99 mg, 45%; LC/MS $t_r$ 1.24 min; MS (ES+) m/z (M+H) not present; $^1$H NMR (400 MHz; DMSO) δ 4.10 (s, 3H), 7.52 (s, 1H), 7.81 (d, 1H), 8.16-8.20 (m, 1H), 8.74 (d, 1H).

(ii) 1-Methyl-5-nitro-1H-indole-2-carboxylic acid methyl ester

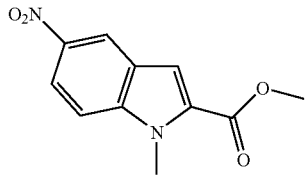

1-Methyl-5-nitro-1H-indole-2-carboxylic acid (99 mg, 0.45 mmol) was esterified with MeOH using Method A to give the title compound.

Yield: 70 mg, 66%; LC/MS $t_r$ 1.45 min; MS (ES+) m/z 235 (M+H)

(iii) 5-Amino-1-methyl-1H-indole-2-carboxylic acid methyl ester

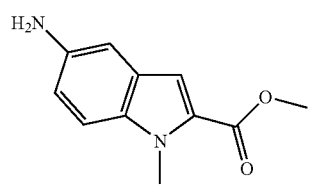

1-Methyl-5-nitro-1H-indole-2-carboxylic acid methyl ester (70 mg, 0.3 mmol) was dissolved in DMF (5 ml) and SnCl$_2$.2H$_2$O (339 mg, 1.5 mmol) was added as a solid. The resulting solution was stirred at 60° C. for 4 h. After cooling to room temperature, a pre-mixed aqueous solution of saturated Rochelle's salt (3 ml) and saturated NaHCO$_3$ (3 ml) was added to the reaction mixture and the aqueous layer was extracted with EtOAc (3×6 ml). The organic layer was washed with H$_2$O (3 ml), 1:1 NaHCO$_3$: Rochelle's salt solution (3 ml), dried (MgSO$_4$), filtered and the solvent was removed in vacuo to give the title compound.

Yield: 25 mg, 41%; LC-MS $t_r$ 0.85 min; MS (ES+) m/z 205 (M+H)

(iv) 1-Methyl-5-[(5-phenyl-furan-2-carbonyl)-amino]-1H-indole-2-carboxylic acid methyl ester

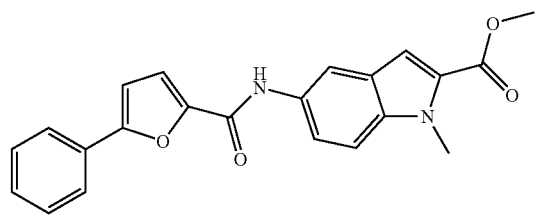

Carboxylic acid (56) (23 mg, 0.12 mmol) was coupled to 5-amino-1-methyl-1H-indole-2-carboxylic acid methyl ester (25 mg, 0.12 mmol) using Method D to give the title compound.

Yield: 31 mg, 69%; LC-MS $t_r$ 1.59 min; MS (ES+) m/z 375 (M+H)

(v) 1-Methyl-5-[(5-phenyl-furan-2-carbonyl)-amino]-1H-indole-2-carboxylic acid (118)

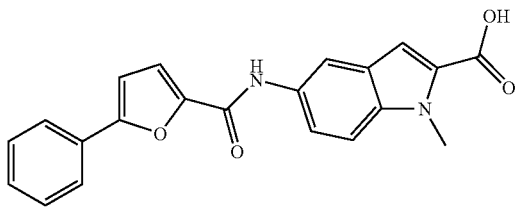

The ester (31 mg, 0.08 mmol) was dissolved in MeOH (2 ml) and 1M NaOH (1 ml). The suspension was stirred at room temperature for 1 h, upon which THF (2 ml) was added. 1M NaOH (1 ml) was added after 1 h. The resulting solution was stirred for 30 min at room temperature, then THF and MeOH were removed in vacuo. The basic solution was extracted with EtOAc (2×1 ml) and DCM (2×1 ml). The organic layers were dried (MgSO$_4$), filtered, combined, and evaporated in vacuo to give the title compound.

Yield: 19 mg, 66%; LC/MS $t_r$ 1.50 min; MS (ES+) m/z 361 (M+H); HPLC Purity: 95%; $^1$H NMR (400 MHz; MeOD) δ 4.00 (s, 3H), 6.89 (s, 1H), 6.92-7.02 (m, 1H), 7.25 (d, 1H), 7.22-7.46 (m, 4H), 7.42 (d, 1H), 7.80-7.88 (m, 3H).

Example 10

(a) 3-{3-[2-Oxo-2-(5-phenyl-furan-2-yl)-ethyl]-phenyl}-acrylic acid (120)

(i) 2-Phenyl-furan (119)

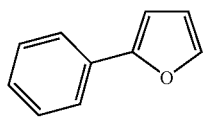

Bromobenzene (1.5 g, 9.55 mmol) was coupled to 2-furylboronic acid (1.75 g, 15.6 mmol) using Method E. The crude compound was purified by column chromatography using a stepped gradient of 5-10% EtOAc in heptane to give the title compound.

Yield: 1.23 g, 89%; LC/MS $t_r$ 1.55 min; MS (ES+) m/z (M+H) not present; $^1$H NMR (400 MHz; DMSO) δ 6.46-6.48 (m, 1H), 6.65 (d, 1H), 7.25 (t, 1H), 7.38 (t, 2H), 7.46-7.47 (m, 1H), 7.67 (d, 2H).

(ii) 2-(3-Bromo-phenyl)-1-(5-phenyl-furan-2-yl)-ethanone

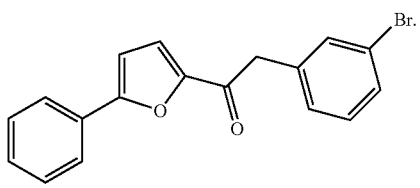

2-Phenyl-furan (119) (50 mg, 0.28 mmol) and (3-bromophenyl)-acetic acid (134 mg, 0.63 mmol) were dissolved in ortho-dichlorobenzene (4 ml). P$_2$O$_5$ (202 mg, 1.42 mmol) was added as a suspension in ortho-dichlorobenzene (2 ml). The reaction mixture was heated to 80° C. for 2 h and cooled to room temperature overnight. After the addition of further P$_2$O$_5$ (202 mg, 1.42 mmol), heating was resumed at 90° C. for 3 h. The reaction mixture was cooled to 0° C. and quenched with H$_2$O (15 ml). The organic layer was separated and the aqueous layer was washed with DCM (3×10 ml). The combined organic layers were dried (MgSO$_4$), filtered and the DCM removed in vacuo. The ortho-dichlorobenzene solution was loaded to a silica-gel column and flushed with heptane (100 ml). The title compound was then eluted with 10% EtOAc in heptane.

Yield: 60 mg, 63%; LC/MS $t_r$ 1.72 min; MS (ES+) m/z 341, 343 (M+H)

(iii) 3-{3-[2-Oxo-2-(5-phenyl-furan-2-yl)-ethyl]-phenyl}-acrylic acid methyl ester

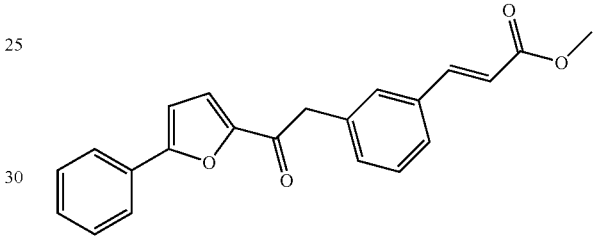

Acrylic acid methyl ester (15 mg, 0.18 mmol) and Et$_3$N (59 mg, 0.59 mmol) were added to a microwave tube. Palladium (II) acetate (1.6 mg, 0.05 mmol) in MeCN solution (0.5 ml), tri-o-tolyl-phosphine (4.5 mg, 0.015 mmol) in MeCN solution (0.5 ml), and the phenyl bromide (50 mg, 0.15 mmol) in MeCN solution (3 ml) were then added. The solution was heated in a CEM Discover microwave for 2×15 min at 90° C. (150 W, 250 psi). The solvent was removed in vacuo and the residue was purified by column chromatography eluting with 10% EtOAc in heptane to give the title compound.

Yield: 22 mg, 42%; LC/MS $t_r$ 1.61 min; MS (ES+) m/z 347 (M+H)

(iv) 3-{3-[2-Oxo-2-(5-phenyl-furan-2-yl)-ethyl]-phenyl}-acrylic acid (120)

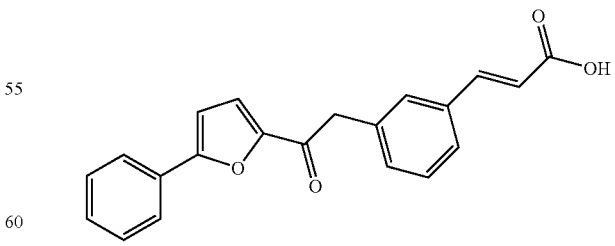

The ester (22 mg, 0.063 mmol) was dissolved in MeOH (1 ml), THF (0.2 ml) and 1M NaOH (1 ml). The suspension was stirred at room temperature for 1 h. The solution was extracted with EtOAc (2×1 ml). Further 1M NaOH was added (1 ml) and extraction was repeated with EtOAc (2×1 ml). The aqueous layer was acidified to pH1 with conc.HCl and extracted with EtOAc (2×1 ml). The organic layer was filtered through MgSO$_4$ and the solvent removed in vacuo. The solid was triturated with DCM (0.5 ml) to give the title compound.

Yield: 1.3 mg, 6%; LC/MS t$_r$ 1.44 min; MS (ES+) m/z 333 (M+H); HPLC Purity: 97%; $^1$H NMR (250 MHz; MeOD) δ 4.29 (s, 2H), 6.53 (d, 1H), 7.05 (d, 1H), 7.38-7.53 (m, 6H), 7.59 (d, 1H), 7.62-7.74 (m, 2H), 7.85-7.92 (m, 2H).

(b) 3-[3-(2-Phenyl-thiazol-4-ylmethoxy)-phenyl]-acrylic acid (121)

(i) 3-(3-Hydroxy-phenyl)-acrylic acid methyl ester

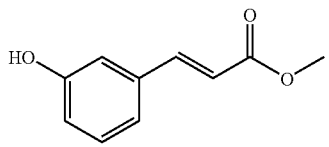

3-(3-Hydroxy-phenyl)-acrylic acid (2 g, 12.2 mmol) was esterified with MeOH using Method B to give the title compound.

Yield: 2.09 g, 96%; LC/MS t$_r$ 1.13 min; MS (ES+) m/z 179 (M+H)

(ii) 3-[3-(2-Phenyl-thiazol-4-ylmethoxy)-phenyl]-acrylic acid methyl ester

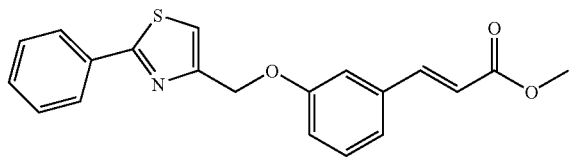

3-(3-Hydroxy-phenyl)-acrylic acid methyl ester (85 mg, 0.48 mmol) was dissolved in dry DMF (1.5 ml) and NaH (14 mg, 0.60 mmol) was added as a suspension in heptane (0.5 ml). The mixture was stirred at room temperature for 10 min. 4-Chloromethyl-2-phenyl-thiazole (100 mg, 0.48 mmol) was added portion-wise and the solution left stirring for 4 h. The reaction mixture was quenched with H$_2$O (2 ml) and extracted with EtOAc (3×1 ml). The combined organic layers were washed with H$_2$O (3×1 ml), dried (MgSO$_4$), filtered and the solvent removed in vacuo to give a mixture of acid and ester, which was used without further purification.

For the ester: LC/MS t$_r$ 1.64 min; MS (ES+) m/z 352 (M+H)

(iii) 3-[3-(2-Phenyl-thiazol-4-ylmethoxy)-phenyl]-acrylic acid (122)

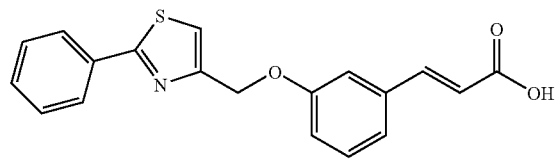

The mixture (167 mg, 0.47 mmol) was stirred in MeOH (3 ml), 4M NaOH (3 ml) and THF (3 ml) for 30 min. The solution was extracted with EtOAc (3×5 ml) and the aqueous layer was acidified with conc. HCl until a white precipitate formed. This was extracted with EtOAc (3×5 ml). The combined organic layers were dried (MgSO$_4$), filtered and the solvent removed in vacuo to give the title compound.

Yield: 156 mg, 98% over 2 steps; LC/MS t$_r$ 1.58 min; MS (ES+) m/z 338 (M+H); HPLC Purity: 100%; $^1$H NMR (250 MHz; DMSO): δ 5.23 (s, 2H), 6.5 (broad d, 1H), 7.02 (broad d, 1H), 7.09-7.18 (m, 2H), 7.22-7.35 (m, 2H), 7.42-7.58 (m, 3H), 7.78 (s, 1H), 7.89-7.99 (m, 2H).

(c) 3-[3-(2-Phenyl-thiazol-4-ylmethylsulfanyl)-phenyl]-acrylic acid (122)

(i) 4-(3-Bromo-phenylsulfanylmethyl)-2-phenyl-thiazole

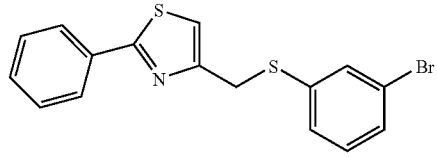

NaH (53 mg, 2.2 mmol) was suspended in dry THF (1.5 ml) under a stream of N$_2$ and 3-bromo-benzenethiol (378 mg, 2 mmol) was added dropwise to the suspension over 5 min. 4-Chloromethyl-2-phenyl-thiazole (419 mg, 2 mmol) was added and the solution left stirring overnight. The reaction mixture was quenched with a saturated K$_2$CO$_3$ solution (8 ml) and extracted with EtOAc (3×4 ml). The combined organic layers were washed with saturated K$_2$CO$_3$ solution (4 ml), dried (MgSO$_4$), filtered and the solvent removed in vacuo. The residue was purified by column chromatography eluting with 20% EtOAc in heptane to give the title compound.

Yield: 630 mg, 87%; LC/MS t$_r$ 1.85 min; MS (ES+) m/z 362, 364 (M+H)

(ii) 3-[3-(2-Phenyl-thiazol-4-ylmethylsulfanyl)-phenyl]-acrylic acid methyl ester

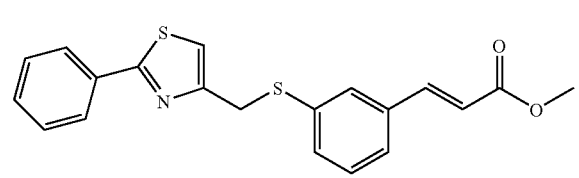

Acrylic acid methyl ester (28 mg, 0.33 mmol) and Et$_3$N (113 mg, 1.12 mmol) were added to a microwave tube. Palladium (II) acetate (3 mg, 0.014 mmol) in MeCN solution (0.5 ml), tri-o-tolyl-phosphine (4.5 mg, 0.028 mmol) in MeCN solution (0.5 ml), and the bromo-derivative (100 mg, 0.28 mmol) in MeCN solution (1 ml) were then added. The solution was heated in a CEM Discover microwave at 90° C. (150 W, 250 psi) for a total of 4 h. During this time, further palladium (II) acetate (4×3 mg, 0.056 mmol) was added. The solvent was removed under a stream of N$_2$ and H$_2$O (3 ml) was added. The aqueous layer was extracted with EtOAc (3×1 ml) and the organic layer washed with H$_2$O (1 ml), dried (MgSO$_4$), filtered and the solvent removed in vacuo. The residue was purified by column chromatography eluting with 20% EtOAc in heptane to give the title compound.

Yield: 67 mg, 65%; LC/MS t$_r$ 1.78 min; MS (ES+) m/z 368 (M+H)

(iii) 3-[3-(2-Phenyl-thiazol-4-ylmethylsulfanyl)-phenyl]-acrylic acid (122)

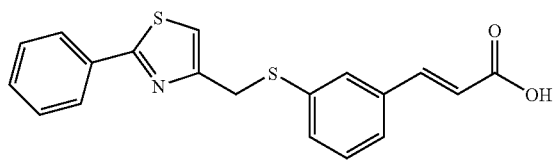

The ester (67 mg, 0.18 mmol) was hydrolysed using Method H to give the title compound.

Yield: 39 mg, 61%; LC/MS t$_r$ 1.61 min; MS (ES+) m/z 354 (M+H); HPLC Purity: 100%; $^1$H NMR (250 MHz; MeOD): δ 4.38 (s, 2H), 6.48 (d, 1H), 7.25-7.53 (m, 7H), 7.57-7.70 (m, 2H), 7.89-7.99 (m, 2H).

(d) 3-{3-[(5-Adamantan-1-yl-furan-2-carbonyl)-amino]-phenyl}-acrylic acid (123)

(i) 5-Adamantan-1-yl-furan-2-carboxylic acid methyl ester

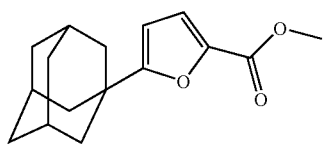

Furan-2-carboxylic acid methyl ester (500 mg, 3.97 mmol) and 1-bromo-adamantane (853 mg, 3.97 mmol) were dissolved in ortho-dichlorobenzene (6 ml) and cooled to 0° C. before adding AlCl$_3$ (1.06 g, 7.94 mmol) as a solid. The reaction mixture was allowed to warm up to room temperature, stirred for 4 h, then heated to 40° C. for 2 h and left standing at room temperature overnight. The reaction mixture was cooled to 0° C. and quenched with H$_2$O (10 ml). The organic layer was separated and the aqueous layer was extracted with DCM (3×20 ml). The combined organic layers were dried (MgSO$_4$), filtered and the DCM removed in vacuo. The ortho-dichlorobenzene solution was loaded to a silica-gel column and flushed with heptane (100 ml). The title compound was then eluted using a stepped gradient of 0-10% EtOAc in heptane.

Yield: 503 mg, 49%; LC/MS t$_r$ 1.84 min; MS (ES+) m/z 261 (M+H)

(ii) 5-Adamantan-1-yl-furan-2-carboxylic acid

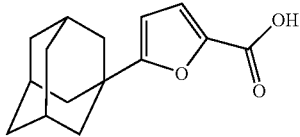

The ester (503 mg, 1.93 mmol) was dissolved in THF (3 ml) and 1M NaOH (3 ml). The suspension was stirred at room temperature for 2 h. MeOH (3 ml) and 1M NaOH (3 ml) were added, and the suspension was heated to 40° C. for 1.5 h. THF and MeOH were removed in vacuo upon which a precipitate appeared. The solid was filtered, washed with 2M HCl (10 ml), and dried in vacuo to give the title compound.

Yield: 458 mg, 96%; LC/MS t$_r$ 1.57 min; MS (ES+) m/z 288 (M+MeCN+H)

(iii) 3-{3-[(5-Adamantan-1-yl-furan-2-carbonyl)-amino]-phenyl}-acrylic acid ethyl ester

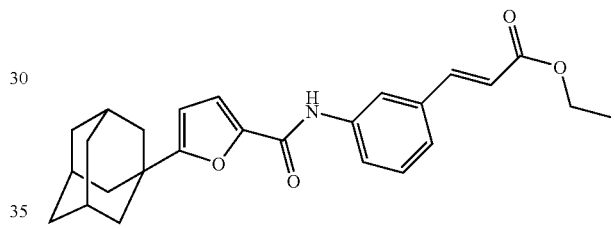

5-Adamantan-1-yl-furan-2-carboxylic acid (50 mg, 0.20 mmol) was coupled to aniline (60) (43 mg, 0.22 mmol) using Method D to give the title compound.

Yield: 84 mg, 100%; LC-MS t$_r$ 1.97 min; MS (ES+) m/z 420 (M+H)

(iv) 3-{3-[(5-Adamantan-1-yl-furan-2-carbonyl)-amino]-phenyl}-acrylic acid (123)

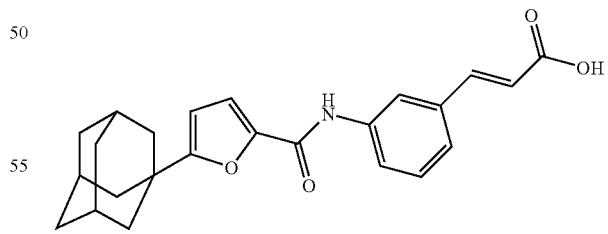

The ester (84 mg, 0.20 mmol) was dissolved in MeOH (2 ml), THF (2 ml) and 1M NaOH (4 ml). The suspension was heated to 40° C. for 1 h. THF and MeOH were removed in vacuo, the solution was acidified with 2M HCl (3 ml) and extracted with DCM (3×2 ml). The organic layer was dried (MgSO$_4$), filtered and the solvent removed in vacuo. The solid was triturated with DCM (2 ml) to give the title compound.

Yield: 35 mg, 45%; LC/MS $t_r$ 2.29 min; MS (ES+) m/z 392 (M+H); HPLC Purity: 97%; $^1$H NMR (250 MHz; DMSO) δ 1.52 (s, 6H), 1.72 (s, 6H), 1.82 (s, 3H), 6.05 (s, 1H), 6.26 (d, 1H), 7.04 (d, 1H), 7.13-7.22 (m, 2H), 7.34 (d, 1H), 7.54 (d, 1H), 7.72 (s, 1H), 9.72 (s, 1H), 12.25 (broad s, 1H).

(e) 3-(3-{[5-(3-Chloro-phenyl)-furan-2-carbonyl]-amino}-phenyl)-propionic acid (125)

(i) 3-(3-Amino-phenyl)-propionic acid ethyl ester (124)

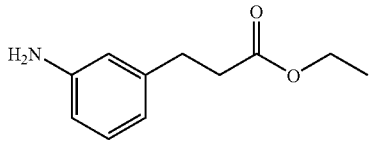

3-(3-Aminophenyl)propionic acid (250 mg, 1.52 mmol) was esterified with EtOH using Method A to give the title compound.

Yield: 260 mg, 89%; LC-MS $t_r$ 0.78 min; MS (ES+) m/z 194 (M+H)

(ii) 3-(3-{[5-(3-Chloro-phenyl)-furan-2-carbonyl]-amino}-phenyl)-propionic acid ethyl ester

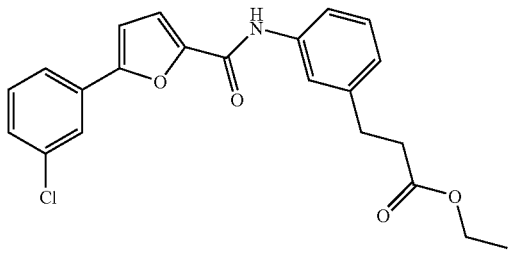

Carboxylic acid (67) (58 mg, 0.26 mmol) was coupled to aniline (124) (50 mg, 0.26 mmol) using Method C. The residue was purified by column chromatography eluting with 10% EtOAc in heptane to give the title compound.

Yield: 62 mg, 60%; LC/MS $t_r$ 1.72 min; MS (ES+) m/z 398, 400 (M+H)

(iii) 3-(3-{[5-(3-Chloro-phenyl)-furan-2-carbonyl]-amino}-phenyl)-propionic acid (125)

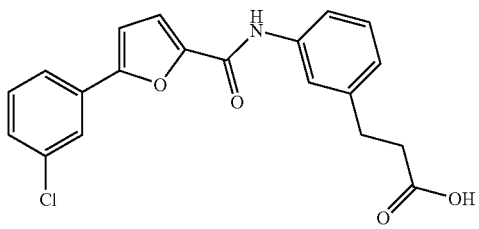

The ester (62 mg, 0.16 mmol) was hydrolysed using Method H to give the title compound.

Yield: 42 mg, 71%; LC/MS $t_r$ 1.53 min; MS (ES+) m/z 369, 371 (M+H); HPLC purity: 100%; $^1$H NMR (400 MHz; DMSO): δ 2.51 (t, 2H), 2.79 (t, 2H), 6.96 (d, 1H), 7.2-7.3 (m, 2H), 7.35 (d, 1H), 7.41 (d, 1H), 7.48 (t, 1H), 7.54 (s, 1H), 7.59 (d, 1H), 7.90 (d, 1H), 8.07 (s, 1H), 10.15 (s, 1H).

(f) 3-(3-{[5-(3,5-Dichloro-phenyl)-furan-2-carbonyl]-amino}-phenyl)-propionic acid (126)

(i) 3-(3-{[5-(3,5-Dichloro-phenyl)-furan-2-carbonyl]-amino}-phenyl)-propionic acid ethyl ester

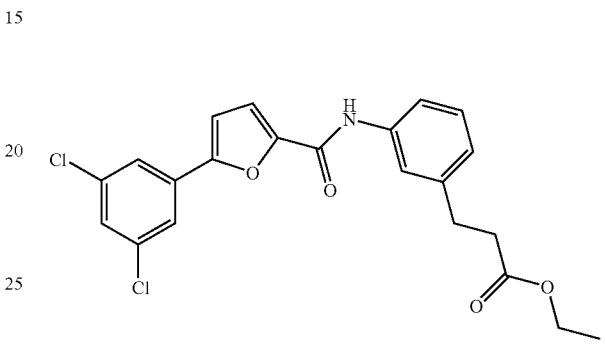

Carboxylic acid (67) (67 mg, 0.26 mmol) was coupled to aniline (124) (50 mg, 0.26 mmol) using Method C. The residue was purified by column chromatography eluting with 10% EtOAc in heptane to give the title compound.

Yield: 65 mg, 58%; LC/MS $t_r$ 1.86 min; MS (ES+) m/z 432, 434 (M+H)

(ii) 3-(3-([5-(3,5-Dichloro-phenyl)-furan-2-carbonyl]-amino)-phenyl)-propionic acid (126)

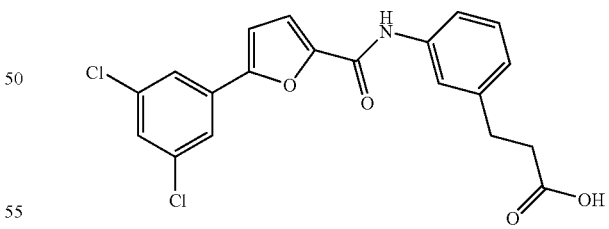

The ester (65 mg, 0.15 mmol) was hydrolysed using Method H to give the title compound.

Yield: 46 mg, 76%; LC/MS $t_r$ 1.64 min; MS (ES+) m/z 404, 406 (M+H); HPLC purity: 90%; $^1$H NMR (400 MHz; DMSO): δ 2.55 (t, 2H), 2.83 (t, 2H), 7.01 (d, 1H), 7.28 (t, 1H), 7.38 (d, 1H), 7.43 (d, 1H), 7.56 (s, 1H), 7.60 (t, 2H), 8.11 (s, 2H), 10.23 (s, 1H).

(g) (3-{[5-(3,5-Difluoro-phenyl)-furan-2-carbonyl]-amino}-phenyl)-acetic acid (127)

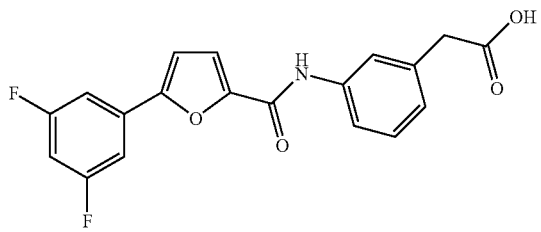

The furyl bromide (16) (100 mg, 0.30 mmol) was coupled to 3,5-difluoro-phenylboronic acid (48 mg, 0.30 mmol) using Method E. During this reaction, hydrolysis occurred. The residue was extracted using Work-up E1 to give the acid. The residue was purified by column chromatography eluting with 20% heptane:75% EtOAc:5% AcOH to give the title compound.

Yield: 25 mg, 23%; LC/MS $t_r$ 1.47 min; MS (ES+) m/z 358 (M+H); HPLC Purity: 92%; $^1$H NMR (400 MHz; DMSO): δ 3.64 (s, 2H), 7.10 (d, 1H), 7.31-7.41 (m, 2H), 7.44 (q, 2H), 7.68 (s, 1H), 7.75 (d, 1H), 7.87 (d, 2H), 10.29 (s, 1H).

(h) (3-{[5-(3-fluoro-phenyl)-furan-2-carbonyl]-amino}-phenyl)-acetic acid (128)

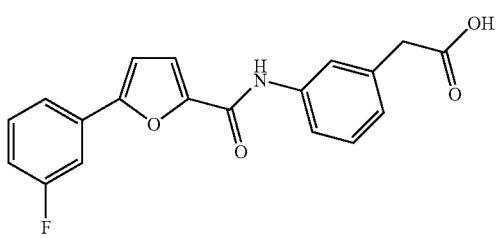

The furyl bromide (16) (100 mg, 0.30 mmol) was coupled to 3-fluoro-phenylboronic acid (42 mg, 0.30 mmol) using Method E. During this reaction, hydrolysis occurred. The residue was extracted using Work-up E1 to give the title compound.

Yield: 26 mg, 25%; LC/MS $t_r$ 1.45 min; MS (ES+) m/z 339 (M+H); HPLC Purity: 91%; $^1$H NMR (400 MHz; DMSO): δ 3.50 (s, 2H), 6.95 (d, 1H), 7.15 (t, 1H), 7.20 (d, 1H), 7.24 (t, 1H), 7.32 (d, 1H), 7.46 (q, 1H), 7.56 (s, 1H), 7.62 (d, 1H), 7.74 (d, 1H), 7.83 (d, 1H), 10.13 (s, 1H).

(i) (3-{[6-(3-Chloro-phenyl)-pyridine-2-carbonyl]-amino}-phenyl)-acetic acid (129)

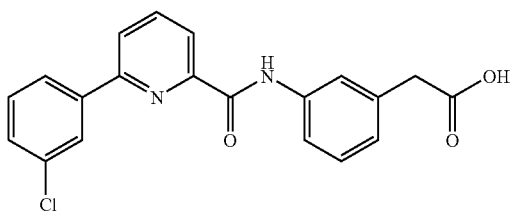

The pyridyl bromide (77) (44 mg, 0.12 mmol) was coupled to 3-chloro-phenylboronic acid (20 mg, 0.13 mmol) using Method E. During this reaction, hydrolysis occurred. The residue was extracted using Work-up E1 to give the acid. The solid was further purified by preparative HPLC to give the title compound.

Yield: 8 mg, 18%; LC/MS $t_r$ 1.51 min; MS (ES+) m/z 367, 369 (M+H); HPLC Purity: 99%; $^1$H NMR (400 MHz; DMSO): δ 3.63 (s, 2H), 7.09 (d, 1H), 7.37 (t, 1H), 7.60 (m, 2H), 7.82 (m, 2H), 8.17 (m, 2H), 8.33 (m, 2H), 8.52 (s, 1H), 10.60 (s, 1H).

(j) (3-{[6-(3,5-Dichloro-phenyl)-pyridine-2-carbonyl]-amino}-phenyl)-acetic acid (130)

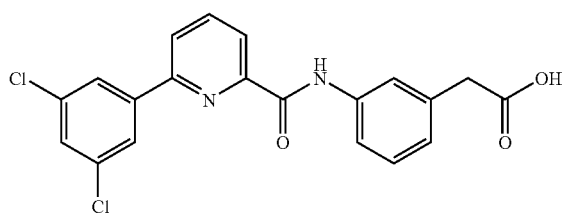

The pyridyl bromide (77) (44 mg, 0.12 mmol) was coupled to 3,5-dichloro-phenylboronic acid (20 mg, 0.10 mmol) using Method E. During this reaction, hydrolysis occurred. The residue was extracted using Work-up E1 to give the acid. The solid was further purified by preparative HPLC to give the title compound.

Yield: 30 mg, 62%; LC/MS $t_r$ 1.63 min; MS (ES+) m/z 401, 403 (M+H); HPLC Purity: 99%; $^1$H NMR (400 MHz; DMSO): δ 3.60 (s, 2H), 7.07 (d, 1H), 7.35 (t, 1H), 7.77 (m, 3H), 8.17 (m, 2H), 8.37 (d, 1H), 8.49 (s, 2H), 10.64 (s, 1H).

(k) 3-(3-{[6-(3,5-Dichloro-phenyl)-pyridine-2-carbonyl]-amino}-phenyl)-acrylic acid (132)

(i) 6-(3,5-Dichloro-phenyl)-pyridine-2-carboxylic acid (131)

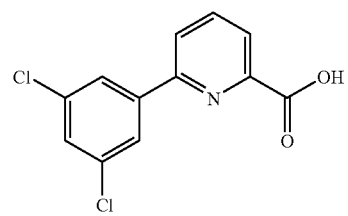

6-Bromo-pyridine-2-carboxylic acid (500 mg, 2.47 mmol) was coupled to 3,5-dichloro-phenylboronic acid (473 mg, 2.47 mmol) acid using Method F to give the title compound.

Yield: 400 mg, 60%; LC/MS $t_r$ 1.47 min; MS (ES+) m/z 268, 270 (M+H)

(ii) 3-(3-{[6-(3,5-Dichloro-phenyl)-pyridine-2-carbonyl]-amino}-phenyl)-acrylic acid ethyl ester

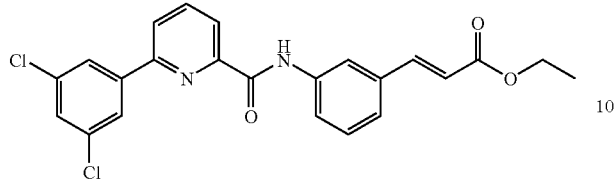

Carboxylic acid (131) (50 mg, 0.19 mmol) was coupled to aniline (60) (40 mg, 0.21 mmol) using Method D. The residue was triturated with TBME (3 ml) to give the title compound.

Yield: 61 mg, 72%; LC/MS $t_r$ 1.98 min; MS (ES+) m/z 441, 443 (M+H)

(iii) 3-(3-{[6-(3,5-Dichloro-phenyl)-pyridine-2-carbonyl]-amino}-phenyl)-acrylic acid (132)

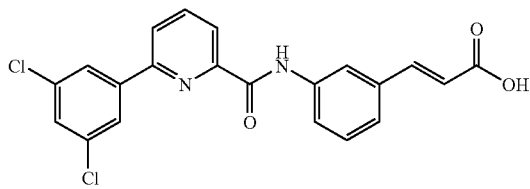

The ester (61 mg, 0.14 mmol) was hydrolysed using Method M to give the title compound.

Yield: 50 mg, 87%; LC/MS $t_r$ 1.73 min; MS (ES+) m/z 412, 414 (M+H); HPLC Purity: 89%; $^1$H NMR (250 MHz; DMSO): δ 6.44 (d, 1H), 7.17 (d, 1H), 7.29 (d, 1H), 7.40 (t, 1H), 7.75 (s, 1H), 7.82 (d, 1H), 8.02 (s, 1H), 8.18 (d, 2H), 8.38 (q, 1H), 8.50 (s, 2H), 10.66 (s, 1H).

(l) (3-{[6-(3,5-Dichloro-phenyl)-pyridine-2-carbonyl]-amino}-phenoxy)-acetic acid (133)

(i) (3-{[6-(3,5-Dichloro-phenyl)-pyridine-2-carbonyl]-amino}-phenoxy)-acetic acid ethyl ester

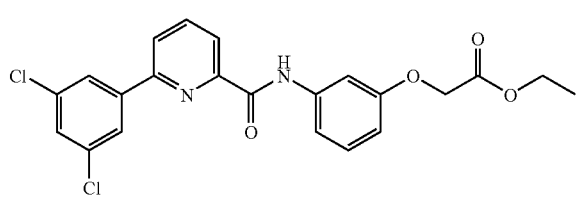

Carboxylic acid (131) (50 mg, 0.19 mmol) was coupled to aniline (64) (40 mg, 0.21 mmol) using Method D. The residue was triturated with TBME (3 ml) to give the title compound.

Yield: 29 mg, 34%; LC/MS $t_r$ 1.86 min; MS (ES+) m/z 445, 447 (M+H)

(ii) (3-{([6-(3,5-Dichloro-phenyl)-pyridine-2-carbonyl]-amino}-phenoxy)-acetic acid (133)

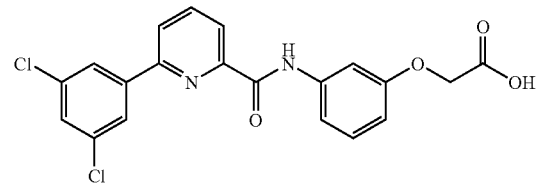

The ester (29 mg, 0.07 mmol) was hydrolysed using Method M. The solid was triturated with DCM (3 ml) to give the title compound.

Yield: 27 mg, 100%; LC/MS $t_r$ 1.67 min; MS (ES+) m/z 416, 418 (M+H); HPLC Purity: 92%; $^1$H NMR (250 MHz; DMSO): δ 3.82 (s, 2H), 6.07 (broad s, 1H), 6.85 (broad t, 3H), 7.50 (s, 1H), 7.78 (m, 4H), 8.11 (broad s, 1H), 8.32 (s, 1H).

(m) 3-(3-{[6-(3,5-Dichloro-phenyl)-pyridine-2-carbonyl]-amino}-phenyl)-propionic acid (134)

(i) 3-(3-{[6-(3,5-Dichloro-phenyl)-pyridine-2-carbonyl]-amino}-phenyl)-propionic acid ethyl ester

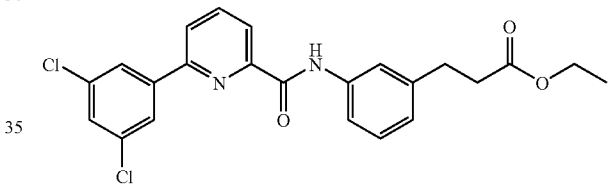

Carboxylic acid (131) (50 mg, 0.19 mmol) was coupled to aniline (124) (40 mg, 0.21 mmol) using Method D to give the product, which was used without further purification.

Yield: 83 mg, 99%; LC/MS $t_r$ 1.90 min; MS (ES+) m/z 443, 445 (M+H)

(ii) 3-(3-{[6-(3,5-Dichloro-phenyl)-pyridine-2-carbonyl]-amino}-phenyl)-propionic acid (134)

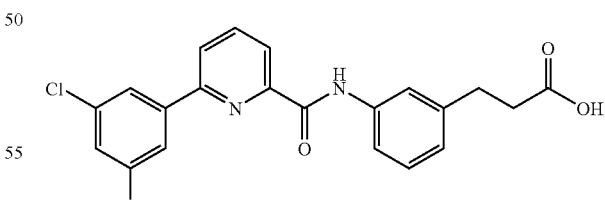

The ester (83 mg, 0.19 mmol) was hydrolysed using Method M. The residue was purified by preparative HPLC to give the title compound.

Yield: 42 mg, 53%; LC/MS $t_r$ 1.66 min; MS (ES+) m/z 415, 417 (M+H); HPLC Purity: 96%; $^1$H NMR (400 MHz; DMSO): δ 2.69 (t, 2H), 2.98 (t, 2H), 7.16 (d, 1H), 7.44 (t, 1H), 7.80-7.88 (m, 3H), 8.25-8.32 (m, 2H), 8.47 (d, 1H), 8.59 (s, 2H), 10.70 (s, 1H), 12.28 (s, 1H).

(n) 5-{[6-(3,5-Dichloro-phenyl)-pyridine-2-carbonyl]-amino}-1H-indole-2-carboxylic acid (135)

(i) 5-{[6-(3,5-Dichloro-phenyl)-pyridine-2-carbonyl]-amino}-1H-indole-2-carboxylic acid ethyl ester

Carboxylic acid (131) (50 mg, 0.19 mmol) was coupled to aniline (58) (42 mg, 0.21 mmol) using Method D to give the crude product.
Yield: 85 mg, 99%; LC/MS $t_r$ 1.82 min; MS (ES+) m/z 454, 456 (M+H)

(ii) 5-{[6-(3,5-Dichloro-phenyl)-pyridine-2-carbonyl]-amino}-1H-indole-2-carboxylic acid (135)

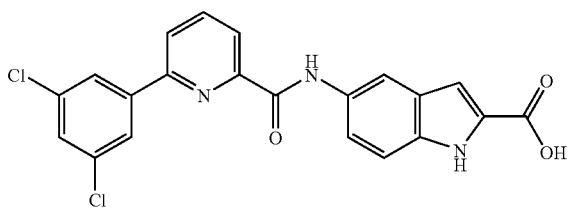

The ester (85 mg, 0.19 mmol) was hydrolysed using Method M. The residue was purified by preparative HPLC to give the title compound.
Yield: 16 mg, 20%; LC/MS $t_r$ 1.61 min; MS (ES+) m/z 426, 428 (M+H); HPLC Purity: 99%; $^1$H NMR (400 MHz; DMSO): δ 7.23 (s, 1H), 7.56 (d, 1H), 7.75 (dd, 1H), 7.85 (t, 1H), 8.27 (m, 3H), 8.47 (q, 1H), 8.61 (d, 2H), 10.73 (s, 1H).

(o) 3-(3-{[6-(3-Chloro-phenyl)-pyridine-2-carbonyl]-amino}-phenyl)-acrylic acid (137)

(i) 6-(3-chloro-phenyl)-pyridine-2-carboxylic acid (136)

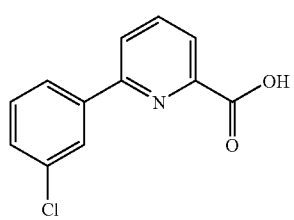

6-Bromo-pyridine-2-carboxylic acid (200 mg, 0.99 mmol) was coupled to 3-chloro-phenylboronic acid (130 mg, 0.83 mmol) using Method F to give the title compound.
Yield: 182 mg, 98%; LC/MS $t_r$ 1.32 min; MS (ES+) m/z 234, 236 (M+H)

(ii) 3-(3-{[6-(3-Chloro-phenyl)-pyridine-2-carbonyl]-amino}-phenyl)-acrylic acid ethyl ester

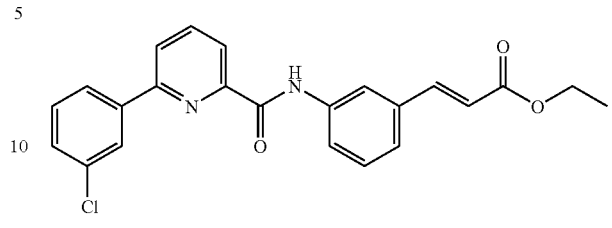

Carboxylic acid (136) (44 mg, 0.19 mmol) was coupled with aniline (60) (40 mg, 0.21 mmol) using Method D. The residue was purified by column chromatography eluting with a stepped gradient of 10-15% EtOAc in heptane to give the title compound.
Yield: 64 mg, 83%; LC/MS $t_r$ 1.87 min; MS (ES+) m/z 407, 409 (M+H)

(iii) 3-{3-([6-(3-Chloro-phenyl)-pyridine-2-carbonyl]-amino}-phenyl)-acrylic acid (137)

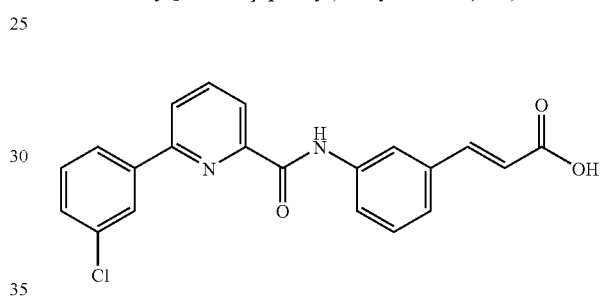

The ester (64 mg, 0.16 mmol) was hydrolysed using Method M. The residue was purified by preparative HPLC to give the title compound.
Yield: 7 mg, 11%; LC/MS $t_r$ 1.98 min; MS (ES+) m/z 379, 381 (M+H); HPLC Purity: 97%; $^1$H NMR (250 MHz; DMSO): δ 6.54 (d, 1H), 7.43-7.67 (m, 5H), 7.99 (d, 1H), 8.17 (m, 3H), 8.34 (m, 2H), 8.50 (s, 1H), 10.66 (s, 1H).

(p) (3-{[6-(3-Chloro-phenyl)-pyridine-2-carbonyl]-amino}-phenoxy)-acetic acid (138)

(i) (3-{[6-(3-Chloro-phenyl)-pyridine-2-carbonyl]-amino}-phenoxy)-acetic acid ethyl ester

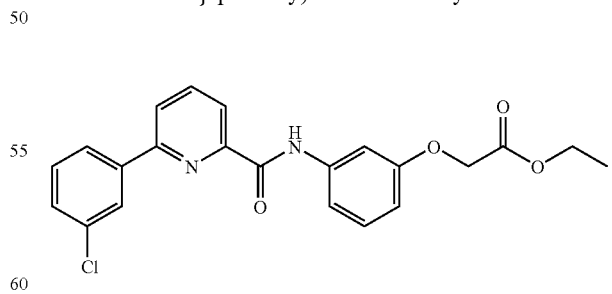

Carboxylic acid (136) (44 mg, 0.19 mmol) was coupled with aniline (64) (40 mg, 0.2 mmol) using Method D. The residue was purified by column chromatography eluting with 10% EtOAc in heptane to give the title compound.
Yield: 50 mg, 64%; LC/MS $t_r$ 1.77 min; MS (ES+) m/z 411, 413 (M+H)

(ii) (3-{[6-(3-Chloro-phenyl)-pyridine-2-carbonyl]-amino}-phenoxy)-acetic acid (138)

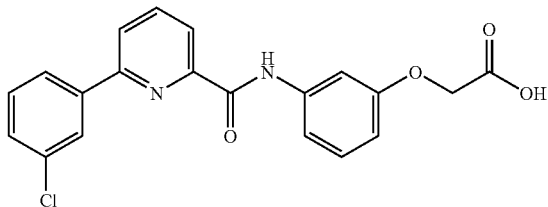

The ester (50 mg, 0.12 mmol) was hydrolysed using Method M. The residue was purified by preparative HPLC to give the title compound.

Yield: 30 mg, 65%; LC/MS $t_r$ 1.51 min; MS (ES+) m/z 383, 385 (M+H); HPLC Purity: 99%; $^1$H NMR (400 MHz; DMSO): δ 4.63 (s, 2H), 6.66 (dd, 1H), 7.24 (t, 1H), 7.44 (d, 1H), 7.53 (m, 3H), 8.03 (m, 2H), 8.25 (m, 2H), 8.41 (s, 1H), 10.49 (s, 1H).

(q) {3-[(3'-Chloro-4-fluoro-biphenyl-3-carbonyl)-amino]-phenoxy}-acetic acid (140)

(i) [3-(5-Bromo-2-fluoro-benzoylamino)-phenoxy]-acetic acid ethyl ester (139)

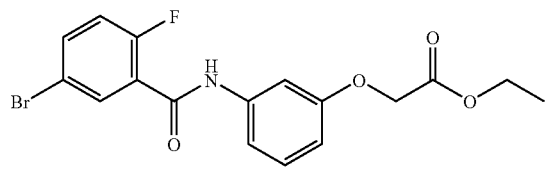

5-Bromo-2-fluoro-benzoic acid (250 mg, 1.14 mmol) was coupled to aniline (64) (245 mg, 1.25 mmol) using Method D. The residue was purified by column chromatography eluting with a stepped gradient of 10-15% EtOAc in heptane to give the title compound.

Yield: 144 mg, 36%; LC/MS $t_r$ 1.52 min; MS (ES+) m/z 396, 398 (M+H)

(ii) {3-[(3'-Chloro-4-fluoro-biphenyl-3-carbonyl)-amino]-phenoxy}-acetic acid (140)

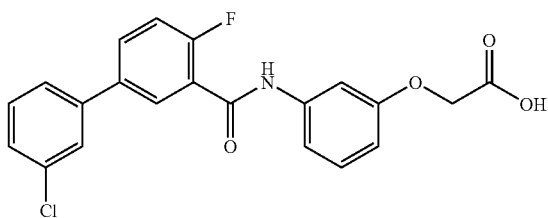

The phenyl bromide (139) (50 mg, 0.13 mmol) was coupled to 3-chloro-phenylboronic acid (20 mg, 0.13 mmol) using Method E. During this reaction, hydrolysis occurred and the residue was extracted using Work-up E1. The crude product was then triturated with TBME (2 ml), DCM (2 ml), and recrystallised from a hot 10% EtOH in H$_2$O mixture to give the title compound.

Yield: 2 mg, 4%; LC/MS $t_r$ 1.89 min; MS (ES+) m/z 400, 402 (M+H); HPLC Purity: 88%; $^1$H NMR (400 MHz; DMSO) δ 3.95 (s, 2H), 6.45 (d, 1H), 7.10 (m, 2H), 7.20 (m, 1H), 7.30-7.50 (m, 3H), 7.65 (d, 1H), 7.75 (s, 1H), 7.80 (m, 1H), 7.90 (d, 1H), 10.35 (s, 1H).

(r) 3-{3-[(3'-Chloro-4-fluoro-biphenyl-3-carbonyl)-amino]-phenyl}-acrylic acid (142)

(i) 3-[3-(5-Bromo-2-fluoro-benzoylamino)-phenyl]-acrylic acid ethyl ester (141)

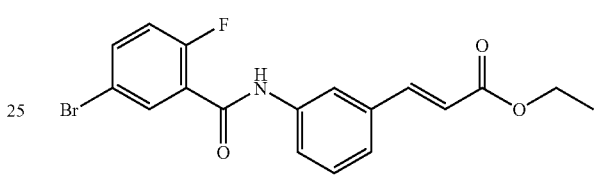

5-Bromo-2-fluoro-benzoic acid (250 mg, 1.14 mmol) was coupled to aniline (60) (240 mg, 1.26 mmol) using Method D. The residue was purified by column chromatography eluting with a stepped gradient of 10-15% EtOAc in heptane to give the title compound.

Yield: 402 mg, 90%; LC/MS $t_r$ 1.64 min; MS (ES+) m/z 392, 394 (M+H)

(ii) 3-{3-[(3'-Chloro-4-fluoro-biphenyl-3-carbonyl)-amino]-phenyl}-acrylic acid ethyl ester

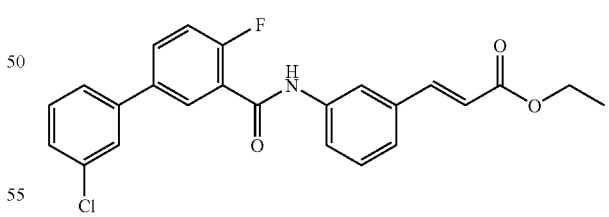

The phenyl bromide (141) (100 mg, 0.26 mmol) was coupled to 3-chloro-phenylboronic acid (40 mg, 0.26 mmol) using Method E. The residue was purified by column chromatography eluting with 10% EtOAc in heptane to give the title compound.

Yield: 109 mg, 99%; LC/MS $t_r$ 1.82 min; MS (ES+) m/z 424, 426 (M+H)

(iii) 3-{3-[(3'-Chloro-4-fluoro-biphenyl-3-carbonyl)-amino]-phenyl}-acrylic acid (142)

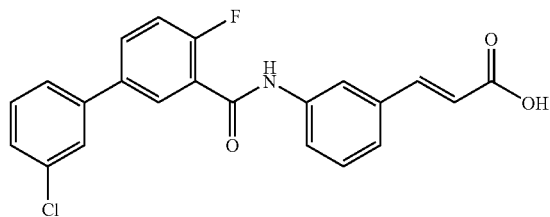

The ester (109 mg, 0.26 mmol) was hydrolysed using Method M to give the title compound.
Yield: 80 mg, 78%; LC/MS $t_r$ 1.05 min; MS (ES+) m/z 396, 398 (M+H); HPLC Purity: 95%; $^1$H NMR (400 MHz, DMSO): δ 6.60 (d, 1H), 7.40-7.75 (m, 6H), 7.90 (d, 2H), 8.00 (s, 1H), 8.10 (broad s, 2H), 8.20 (d, 1H), 10.80 (s, 1H).

(s) {3-[(3',5'-Dichloro-4-fluoro-biphenyl-3-carbonyl)-amino]-phenoxy}-acetic acid (143)

(i) (3-[(3',5'-Dichloro-4-fluoro-biphenyl-3-carbonyl)-amino]-phenoxy)-acetic acid ethyl ester

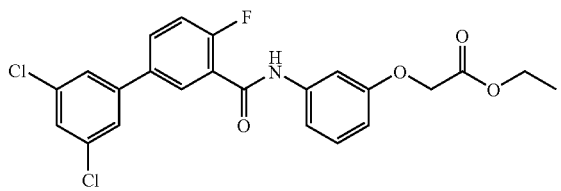

The phenyl bromide (139) (50 mg, 0.13 mmol) was coupled to 3,5-dichloro-phenylboronic acid (24 mg, 0.13 mmol) using method E. The residue was purified by column chromatography eluting with 10% EtOAc in heptane to give the title compound.
Yield: 10 mg, 17%; LC/MS $t_r$ 1.79 min; MS (ES+) m/z 462, 464 (M+H)

(ii) {3-[(3',5'-Dichloro-4-fluoro-biphenyl-3-carbonyl)-amino]-phenoxy}-acetic acid (143)

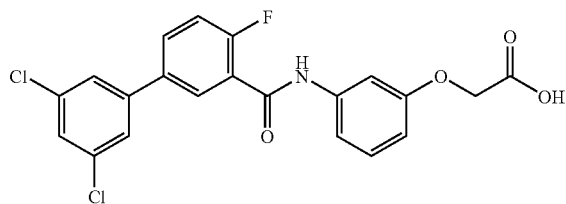

The ester (10 mg, 0.02 mmol) was hydrolysed using Method M to give the title compound.
Yield: 4 mg, 46%; LC/MS $t_r$ 1.09 min; MS (ES+) m/z 434, 436 (M+H); HPLC Purity: 91%; $^1$H NMR (400 MHz; DMSO) δ 4.50 (s, 2H), 6.65 (d, 1H), 7.20 (t, 1H), 7.30 (broad s, 2H), 7.45 (t, 1H), 7.65 (s, 1H), 7.85 (s, 2H), 8.00 (m, 1H), 8.05 (d, 1H), 10.50 (s, 1H).

(t) 3-{3-[(3',5'-Dichloro-4-fluoro-biphenyl-3-carbonyl)-amino]-phenyl}-acrylic acid (144)

(i) 3-{3-[(3',5'-Chloro-4-fluoro-biphenyl-3-carbonyl)-amino]-phenyl}-acrylic acid ethyl ester

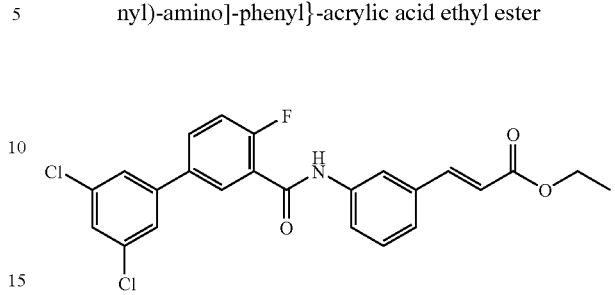

The phenyl bromide (141) (100 mg, 0.26 mmol) was coupled to 3,5-dichloro-phenylboronic acid (40 mg, 0.21 mmol) using method E. The residue was purified by column chromatography eluting with 10% EtOAc in heptane to give the title compound.
Yield: 75 mg, 78%; LC/MS $t_r$ 1.90 min; MS (ES+) m/z 458, 460 (M+H)

(ii) 3-{3-[(3',5'-Chloro-4-fluoro-biphenyl-3-carbonyl)-amino]-phenyl}-acrylic acid (144)

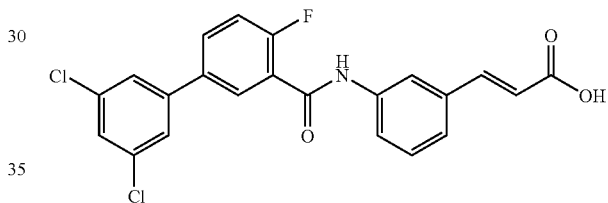

The ester (75 mg, 0.16 mmol) was hydrolysed using Method M to give the title compound.
Yield: 58 mg, 84%; LC/MS $t_r$ 1.66 min; MS (ES+) m/z 430, 432 (M+H); HPLC Purity: 89%; $^1$H NMR (400 MHz, DMSO): δ 6.50 (d, 1H), 7.35-7.70 (m, 5H), 7.80 (d, 1H), 7.90 (s, 2H), 8.00 (broad s, 2H), 8.10 (m, 1H), 10.60 (s, 1H).

(u) 3-(3-{[5-(4-Chloro-phenyl)-furan-2-carbonyl]-amino}-phenyl)-acrylic acid (146)

(i) 5-(4-Chloro-phenyl)-furan-2-carboxylic acid (145)

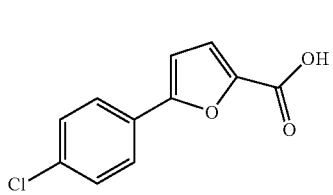

5-Bromo-2-furoic acid (1 g, 5.25 mmol) was coupled to 4-chloro-phenylboronic acid (819 mg, 5.23 mmol) acid using Method F to give the title compound.
Yield: 250 mg, 22%; LC/MS $t_r$ 1.34 min; MS (ES+) m/z 223, 225 (M+H)
$^1$H NMR (400 MHz, DMSO): δ 7.05 (d, 1H), 7.20 (d, 1H), 7.40 (d, 2H), 7.70 (d, 2H).

(ii) 3-(3-{[5-(4-Chloro-phenyl)-furan-2-carbonyl]-amino}-phenyl)-acrylic acid ethyl ester

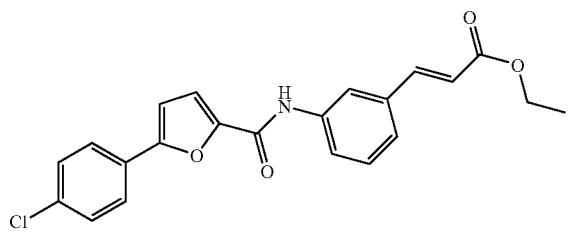

Carboxylic acid (145) (50 mg, 0.19 mmol) was coupled to aniline (60) (43 mg, 0.23 mmol) using Method C. The residue was purified by column chromatography eluting with 10% EtOAc in heptane to give the title compound.
Yield: 66 mg, 87%; LC/MS $t_r$ 1.77 min; MS (ES+) m/z 396, 398 (M+H)

(iii) 3-(3-{[5-(4-Chloro-phenyl)-furan-2-carbonyl]-amino}-phenyl)-acrylic acid (146)

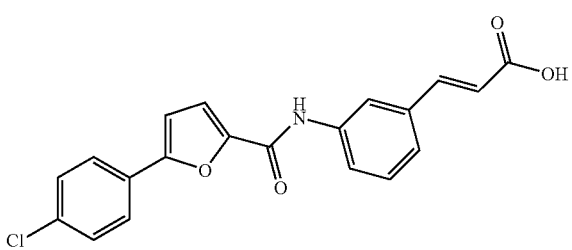

The ester (66 mg, 0.17 mmol) was hydrolysed using Method M. The residue was recrystallised from a hot 10% EtOH in H$_2$O mixture to give the title compound.
Yield: 40 mg, 64%; LC/MS $t_r$ 1.49 min; MS (ES+) m/z 368, 370 (M+H); HPLC Purity: 100%; $^1$H NMR (400 MHz, DMSO): δ 6.50 (d, 1H), 7.30 (d, 1H), 7.35-7.65 (m, 6H), 7.85 (m, 1H), 8.00 (m, 3H).

(v) 3-(3-{[5-(4-Chloro-phenyl)-furan-2-carbonyl]-amino}-phenyl)-propionic acid (147)

(i) 3-(3-{[5-(4-Chloro-phenyl)-furan-2-carbonyl]-amino}-phenyl)-propionic acid ethyl ester

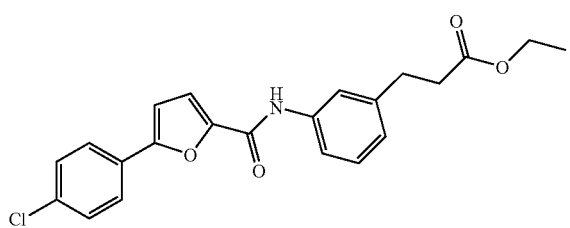

Carboxylic acid (145) (58 mg, 0.26 mmol) was coupled to aniline (124) (50 mg, 0.26 mmol) using Method C. During this reaction, partial hydrolysis occurred. The acid was re-dissolved in EtOAc (2 ml) and the organic layer was washed with 1M HCl (2×1 ml), dried (Na$_2$SO$_4$), filtered and the solvent removed in vacuo to give a mixture of acid and ester, which was used without further purification.
For the ester: LC/MS $t_r$ 1.72 min; MS (ES+) m/z 398, 400 (M+H)

(ii) 3-(3-{[5-(4-Chloro-phenyl)-furan-2-carbonyl]-amino}-phenyl)-propionic acid (147)

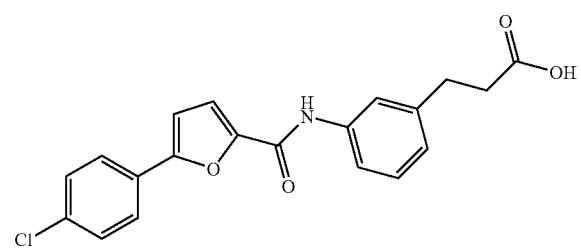

The mixture (103 mg, 0.26 mmol) was hydrolysed using Method M. The solid was recrystallised from a hot 10% EtOH in H$_2$O mixture to give the title compound.
Yield: 40 mg, 41% over 2 steps; LC/MS $t_r$ 1.48 min; MS (ES+) m/z 370, 372 (M+H); HPLC Purity: 100%; $^1$H NMR (400 MHz, DMSO): δ 2.60 (t, 2H), 2.90 (t, 2H), 7.00 (d, 1H), 7.20-7.35 (m, 2H), 7.40 (1H), 7.50-7.70 (m, 4H), 8.05 (d, 2H), 10.20 (s, 1H).

(x) 3-(3-{[5-(4-Fluoro-phenyl)-furan-2-carbonyl]-amino}-phenyl)-propionic acid (148)

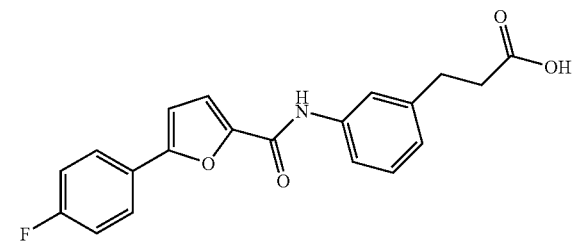

Carboxylic acid (76) (53 mg, 0.26 mmol) was coupled to aniline (124) (50 mg, 0.26 mmol) using Method C. During this reaction, hydrolysis occurred. The acid was re-dissolved in EtOAc (2 ml) and the organic layer was washed with 1M HCl (2×1 ml), dried (Na$_2$SO$_4$), filtered and the solvent removed in vacuo. The solid was recrystallised from a hot 10% EtOH in H$_2$O mixture to give the title compound.
Yield: 40 mg, 43%; LC/MS $t_r$ 1.39 min; MS (ES+) m/z 354 (M+H); HPLC Purity: 93%; $^1$H NMR (400 MHz, DMSO): δ 2.57 (t, 2H), 2.85 (t, 2H), 7.01 (d, 1H), 7.17 (d, 1H), 7.24-7.42 (m, 4H), 7.63 (t, 2H), 8.05 (2H), 10.14 (s, 1H).

(y) (3-{[6-(4-Chloro-phenyl)-pyridine-2-carbonyl]-amino}-phenyl)-acetic acid (150)

(i) 6-(4-Chloro-phenyl)-pyridine-2-carboxylic acid (149)

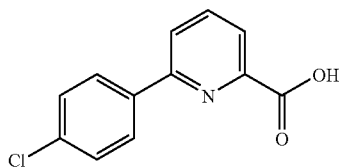

6-Bromo-pyridine-2-carboxylic acid (1 g, 4.95 mmol) was coupled to 4-chloro-phenylboronic acid (775 mg, 4.96 mmol) acid using Method F to give the title compound.

Yield: 900 mg, 78%; LC/MS $t_r$ 1.29 min; MS (ES+) m/z 234, 236 (M+H); $^1$H NMR (400 MHz, DMSO): δ 7.50 (d, 2H), 8.00 (t, 1H), 8.05 (d, 1H), 8.15 (t, 3H).

(ii) (3-{[6-(4-Chloro-phenyl)-pyridine-2-carbonyl]-amino}-phenyl)-acetic acid ethyl ester

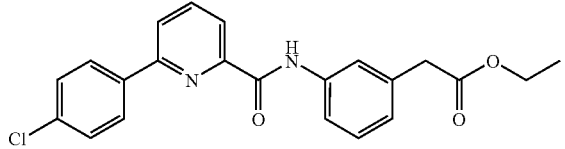

Carboxylic acid (149) (50 mg, 0.22 mmol) was coupled to aniline (6) (39 mg, 0.22 mmol) using Method C. The residue was purified by column chromatography eluting with 10% EtOAc in heptane to give the title compound.

Yield: 28 mg, 32%; LC/MS $t_r$ 1.77 min; MS (ES+) m/z 395, 397 (M+H)

(iii) (3-{[6-(4-Chloro-phenyl)-pyridine-2-carbonyl]-amino}-phenyl)-acetic acid (150)

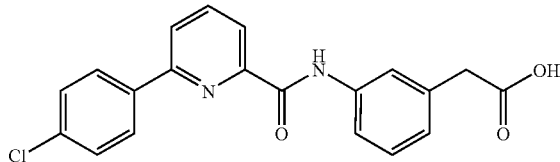

The ester (28 mg, 0.07 mmol) was hydrolysed using Method M to give the title compound.

Yield: 17 mg, 66%; LC/MS $t_r$ 1.54 min; MS (ES+) m/z 367, 369 (M+H); HPLC Purity: 99%; $^1$H NMR (250 MHz; DMSO): δ 3.60 (s, 2H), 7.10 (d, 1H), 7.40 (t, 1H), 7.60 (d, 2H), 7.80 (s, 2H), 8.10-8.20 (m, 2H), 8.30 (d, 1H), 8.45 (d, 2H).

(z) 3-(3-{[6-(4-Chloro-phenyl)-pyridine-2-carbonyl]-amino}-phenyl)-acrylic acid (151)

(i) 3-(3-{[6-(4-Chloro-phenyl)-pyridine-2-carbonyl]-amino}-phenyl)-acrylic acid ethyl ester

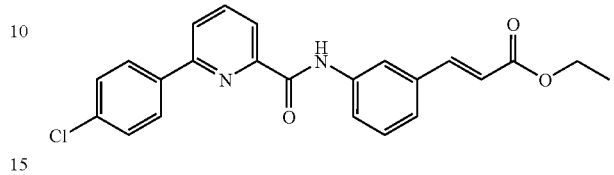

Carboxylic acid (149) (50 mg, 0.21 mmol) was coupled to aniline (60) (41 mg, 0.21 mmol) using Method C. The residue was purified by column chromatography eluting with 10% EtOAc in heptane to give the title compound.

Yield: 34 mg, 40%; LC/MS $t_r$ 1.88 min; MS (ES+) m/z 407, 409 (M+H)

(ii) 3-(3-{[6-(4-Chloro-phenyl)-pyridine-2-carbonyl]-amino}-phenyl)-acrylic acid (151)

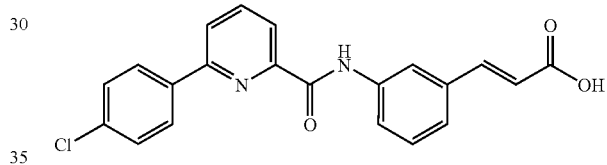

The ester (34 mg, 0.08 mmol) was hydrolysed using Method M to give the title compound.

Yield: 15 mg, 50%; LC/MS $t_r$ 1.62 min; MS (ES+) m/z 379, 381 (M+H); HPLC Purity: 99%; $^1$H NMR (250 MHz; DMSO): δ 6.60 (d, 1H), 7.45-7.60 (m, 2H), 7.60-7.70 (m, 3H), 8.05 (m, 1H), 8.10-8.25 (m, 3H), 8.35 (m, 1H), 8.50 (d, 2H), 10.65 (s, 1H).

(aa) (3-{[6-(4-Fluoro-phenyl)-pyridine-2-carbonyl]-amino}-phenyl)-acetic acid (153)

(i) 6-(4-Fluoro-phenyl)-pyridine-2-carboxylic acid (152)

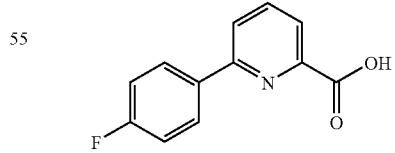

6-Bromo-pyridine-2-carboxylic acid (1 g, 4.95 mmol) was coupled 4-fluoro-phenylboronic acid (693 mg, 4.95 mmol) acid using Method F to give the title compound.

Yield: 900 mg, 83%; LC/MS $t_r$ 1.14 min; MS (ES+) m/z 218 (M+H); $^1$H NMR (400 MHz, DMSO): δ 7.42 (t, 2H), 8.05 (d, 1H), 8.13 (t, 1H), 8.27 (d, 1H), 8.32 (t, 2H).

(ii) (3-{[6-(4-Fluoro-phenyl)-pyridine-2-carbonyl]-amino}-phenyl)-acetic acid ethyl ester

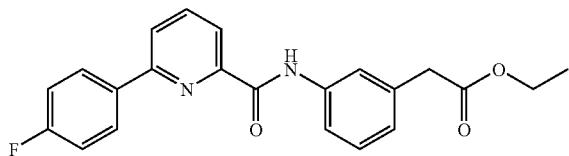

Carboxylic acid (152) (50 mg, 0.23 mmol) was coupled to aniline (6) (42 mg, 0.23 mmol) using Method C. The residue was purified by column chromatography eluting with 10% EtOAc in heptane to give the title compound.

Yield: 53 mg, 61%; LC/MS $t_r$ 1.69 min; MS (ES+) m/z 379 (M+H)

(iii) (3-{[6-(4-Fluoro-phenyl)-pyridine-2-carbonyl]-amino}-phenyl)-acetic acid (153)

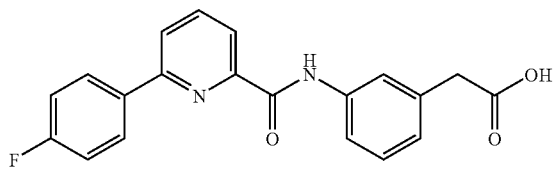

The ester (48 mg, 0.13 mmol) was hydrolysed using Method M to give the title compound.

Yield: 40 mg, 88%; LC/MS $t_r$ 1.46 min; MS (ES+) m/z 351 (M+H); HPLC Purity: 99%; $^1$H NMR (250 MHz; DMSO): δ 3.60 (s, 2H), 7.31-7.43 (m, 3H), 7.81 (d, 2H), 8.07-8.18 (2H), 8.25 (d, 2H), 8.45 (m, 2H), 10.52 (s, 1H).

(bb) (3-{[6-(4-Chloro-phenyl)-pyridine-2-carbonyl]-amino}-phenoxy)-acetic acid (154)

(i) (3-{[6-(4-Chloro-phenyl)-pyridine-2-carbonyl]-amino}-phenoxy)-acetic acid ethyl ester

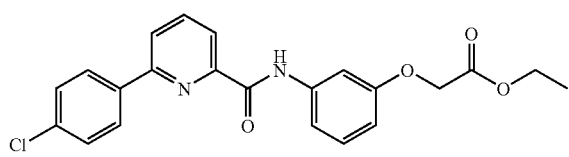

Carboxylic acid (149) (50 mg, 0.21 mmol) was coupled to aniline (64) (42 mg, 0.21 mmol) using Method C. During this reaction, partial hydrolysis occurred. The residue was re-dissolved in EtOAc (2 ml) and the organic layer was washed with 1M HCl (2×1 ml), dried (Na$_2$SO$_4$), filtered and the solvent removed in vacuo to give a mixture of acid and ester, which was used without further purification.

For the ester: LC/MS $t_r$ 1.76 min; MS (ES+) m/z 411, 413 (M+H)

(ii) (3-{[6-(4-Chloro-phenyl)-pyridine-2-carbonyl]-amino}-phenoxy)-acetic acid (154)

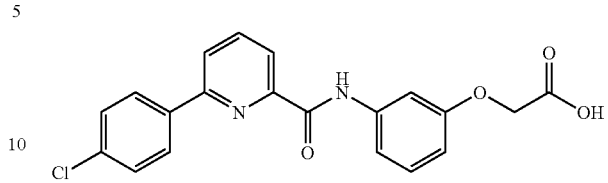

The mixture (86 mg, 0.21 mmol) was hydrolysed using Method M. The residue was purified by column chromatography eluting with 47.5% EtOAc:47.5% heptane:5% AcOH to give the title compound.

Yield: 3 mg, 4% over 2 steps; LC/MS $t_r$ 1.55 min; MS (ES+) m/z 383, 385 (M+H); $^1$H NMR (250 MHz; DMSO): δ 4.70 (s, 2H), 6.70 (d, 1H), 7.30 (t, 1H), 7.50 (d, 1H), 7.60 (m, 3H), 8.10-8.35 (m, 3H), 8.45 (d, 2H).

(cc) 3-(3-{[6-(4-Fluoro-phenyl)-pyridine-2-carbonyl]-amino}-phenyl)-acrylic acid (155)

(i) 3-(3-{[6-(4-Fluoro-phenyl)-pyridine-2-carbonyl]-amino}-phenyl)-acrylic acid ethyl ester

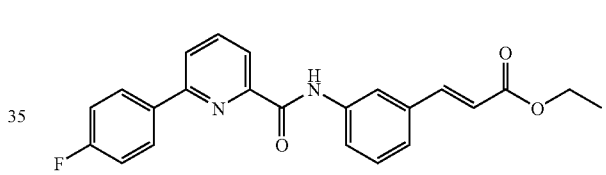

Carboxylic acid (152) (50 mg, 0.23 mmol) was coupled to aniline (60) (44 mg, 0.23 mmol) using Method C. The crude residue was purified by column chromatography eluting with 10% EtOAc in heptane to give the title compound.

Yield: 78 mg, 87%; LC/MS $t_r$ 1.79 min; MS (ES+) m/z 391 (M+H)

(ii) 3-(3-{[6-(4-Fluoro-phenyl)-pyridine-2-carbonyl]-amino}-phenyl)-acrylic acid (155)

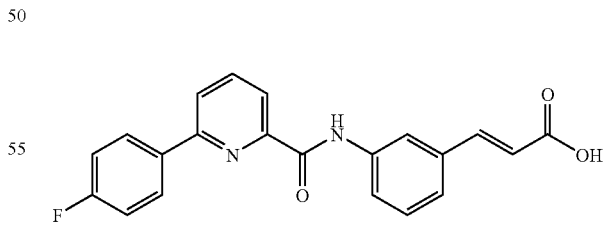

The ester (65 mg, 0.17 mmol) was hydrolysed using Method M to give the title compound.

Yield: 54 mg, 88%; LC/MS $t_r$ 1.53 min; MS (ES+) m/z 363 (M+H); HPLC Purity: 99%; $^1$H NMR (250 MHz; DMSO): δ 6.44 (d, 1H), 7.13 (d, 1H), 7.26 (d, 1H), 7.40 (m, 3H), 7.86 (d, 1H), 8.01 (s, 1H), 8.08-8.30 (m, 3H), 8.47 (m, 2H), 10.55 (s, 1H).

(dd) (3-{[5-(4-Chloro-phenyl)-furan-2-carbonyl]-amino}-phenoxy)-acetic acid (156)

(i) (3-{[5-(4-Chloro-phenyl)-furan-2-carbonyl]-amino}-phenoxy)-acetic acid ethyl ester

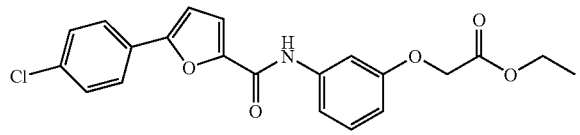

Carboxylic acid (145) (57 mg, 0.26 mmol) was coupled to aniline (64) (50 mg, 0.26 mmol) using Method C to give the title compound.

Yield: 61 mg, 59%; LC/MS $t_r$ 1.64 min; MS (ES+) m/z 400, 402 (M+H)

(ii) (3-{[5-(4-Chloro-phenyl)-furan-2-carbonyl]-amino}-phenoxy)-acetic acid (156)

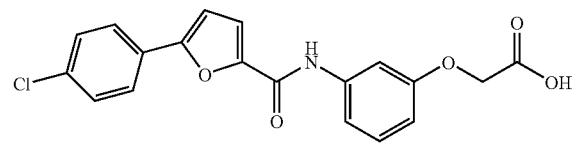

The ester (61 mg, 0.15 mmol) was hydrolysed using Method M to give the title compound.

Yield: 42 mg, 75%; LC/MS $t_r$ 1.50 min; MS (ES+) m/z 372, 374 (M+H); HPLC Purity: 100%; $^1$H NMR (400 MHz, DMSO) δ 4.14 (s, 2H), 6.57-6.60 (m, 1H), 7.17-7.24 (m, 2H), 7.30-7.33 (m, 2H), 7.45 (d, 1H) 7.57-7.60 (m, 2H), 8.01-8.03 (m, 2H), 10.25 (s, 1H).

(ee) (3-{[5-(4-Fluoro-phenyl)-furan-2-carbonyl]-amino}-phenoxy)-acetic acid (157)

(i) (3-{[5-(4-fluoro-phenyl)-furan-2-carbonyl]-amino}-phenoxy)-acetic acid ethyl ester

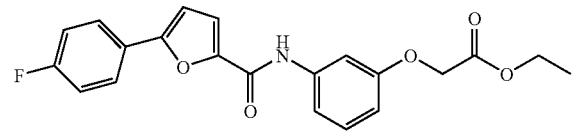

Carboxylic acid (76) (53 mg, 0.26 mmol) was coupled to aniline (64) (56 mg, 0.26 mmol) using Method C to give the title compound.

Yield: 40 mg, 40%; LC/MS $t_r$ 1.54 min; MS (ES+) m/z 384 (M+H)

(ii) (3-{[5-(4-Fluoro-phenyl)-furan-2-carbonyl]-amino}-phenoxy)-acetic acid (157)

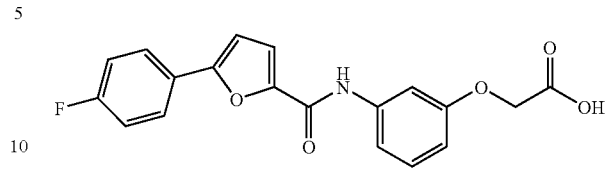

The ester (40 mg, 0.10 mmol) was hydrolysed using Method M to give the title compound.

Yield: 20 mg, 54%; LC/MS $t_r$ 1.44 min; MS (ES+) m/z 356 (M+H); HPLC Purity: 98%; $^1$H NMR (250 MHz, DMSO) δ 4.68 (s, 2H), 6.67-6.71 (m, 1H), 7.14-7.45 (m, 7H), 8.01-8.05 (m, 2H).

(ff) (3-{[6-(4-Fluoro-phenyl)-pyridine-2-carbonyl]-amino}-phenoxy)-acetic acid (158)

(i) (3-{[6-(4-Fluoro-phenyl)-pyridine-2-carbonyl]-amino}-phenoxy)-acetic acid ethyl ester

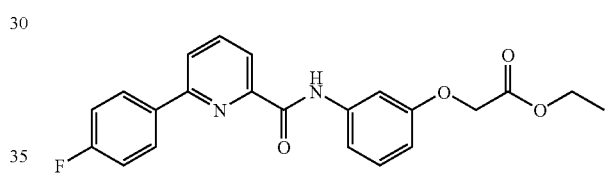

Carboxylic acid (152) (50 mg, 0.23 mmol) was coupled to aniline (64) (45 mg, 0.23 mmol) using Method C to give the title compound.

Yield: 35 mg, 39%; LC/MS $t_r$ 1.67 min; MS (ES+) m/z 395 (M+H)

(ii) (3-{[6-(4-Fluoro-phenyl)-pyridine-2-carbonyl]-amino}-phenoxy)-acetic acid (158)

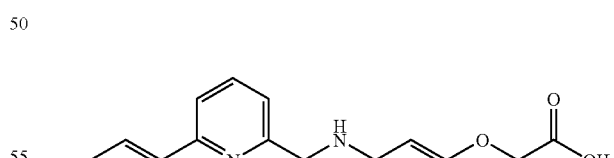

The ester (35 mg, 0.09 mmol) was hydrolysed using Method M to give the title compound.

Yield: 17 mg, 52%; LC/MS $t_r$ 1.45 min; MS (ES+) m/z 367 (M+H); HPLC Purity: 100%; $^1$H NMR (400 MHz, DMSO) δ 4.71 (s, 2H), 6.72-6.75 (m, 1H), 7.30-7.42 (m, 3H), 7.52-7.54 (m, 1H), 7.62 (s, 1H), 8.10-8.18 (m, 2H), 8.25-8.27 (m, 1H), 8.44-8.48 (m, 2H), 10.52 (s, 1H), 13.06 (s, 1H).

(gg) 3-(3-{[6-(4-Fluoro-phenyl)-pyridine-2-carbonyl]amino}-phenyl)-propionic acid (159)

(i) 3-(3-{[6-(4-Fluoro-phenyl)-pyridine-2-carbonyl]amino}-phenyl)-propionic acid ethyl ester

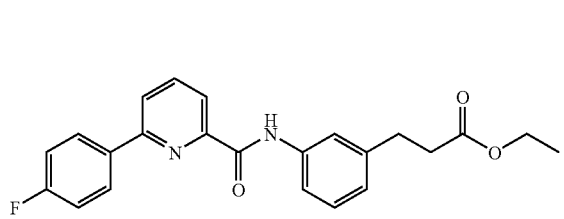

Carboxylic acid (152) (50 mg, 0.23 mmol) was coupled to aniline (124) (45 mg, 0.23 mmol) using Method C. The residue was purified by column chromatography eluting with 30% EtOAc in heptane to give the title compound.

Yield: 11 mg, 12%; LC/MS $t_r$ 1.77 min; MS (ES+) m/z 393 (M+H)

(j) 3-(3-{[6-(4-Fluoro-phenyl)-pyridine-2-carbonyl]amino}-phenyl)-propionic acid (159)

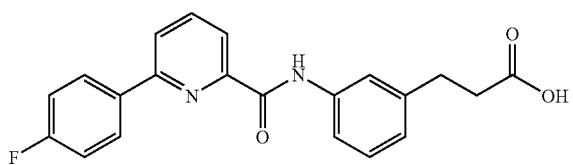

The ester (11 mg, 0.028 mmol) was hydrolysed using Method M to give the title compound.

Yield: 5 mg, 49%; LC/MS $t_r$ 1.49 min; MS (ES+) m/z 365 (M+H); HPLC Purity: 100%; $^1$H NMR (400 MHz, DMSO) δ 2.59 (t, 2H), 2.88 (t, 2H), 7.05 (d, 1H), 7.31-7.43 (m, 3H), 7.76-7.80 (m, 2H), 8.10-8.18 (m, 2H), 8.25-8.27 (m, 1H), 8.45-8.48 (m, 2H), 10.49 (s, 1H), 12.19 (s, 1H).

(hh) {3-[(5-Phenyl-furan-2-carbonyl)-amino]-phenoxy}-acetic acid (160)

(i) {3-[(5-Phenyl-furan-2-carbonyl)-amino]-phenoxy}-acetic acid ethyl ester

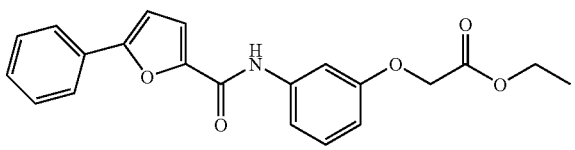

Carboxylic acid (56) (50 mg, 0.27 mmol) was coupled to aniline (64) (52 mg, 0.27 mmol) using Method C. During this reaction, partial hydrolysis occurred. The residue was re-dissolved in EtOAc (2 ml) and the organic layer was washed with 1M HCl (2×1 ml), dried (Na$_2$SO$_4$), filtered and the solvent removed in vacuo to give a mixture of acid and ester, which was used without further purification.

For the ester: LC/MS $t_r$ 1.47 min; MS (ES+) m/z 352 (M+H)

(ii) {3-[(5-Phenyl-furan-2-carbonyl)-amino]-phenoxy}-acetic acid (160)

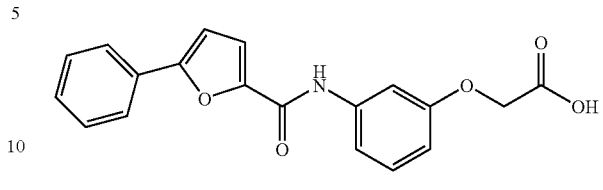

The mixture (95 mg, 0.27 mmol) was hydrolysed using Method M. The solid was recrystallised from a hot 10% EtOH in H$_2$O mixture and triturated with DCM (2 ml) to give the title compound.

Yield: 20 mg, 22% over 2 steps; LC/MS $t_r$ 1.35 min; MS (ES+) m/z 338 (M+H); HPLC Purity: 93%; $^1$H NMR (400 MHz, DMSO) δ 4.70 (s, 2H), 6.69-6.72 (m, 1H), 7.21-7.31 (m, 2H), 7.41-7.55 (m, 6H), 7.99-8.01 (m, 2H), 10.18 (s, 1H), 13.10 (s, 1H).

(ii) 3-(3-{[6-(3-Fluoro-phenyl)-pyridine-2-carbonyl]-amino}-phenyl)-propionic acid (162)

(i) 3-{3-[(6-Bromo-pyridine-2-carbonyl)-amino]-phenyl}-propionic acid ethyl ester (161)

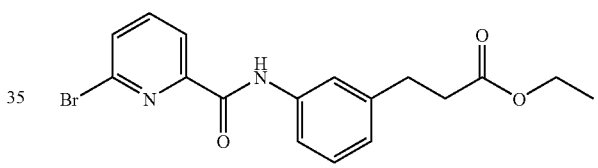

6-Bromo-pyridine-2-carboxylic acid (261 mg, 1.29 mmol) was coupled to aniline (124) (250 mg, 1.29 mmol) using Method C to give the title compound.

Yield: 308 mg, 63%; LC/MS $t_r$ 1.58 min; MS (ES+) m/z 377, 379 (M+H)

(ii) 3-(3-{[6-(3-Fluoro-phenyl)-pyridine-2-carbonyl]-amino}-phenyl)-propionic acid ethyl ester

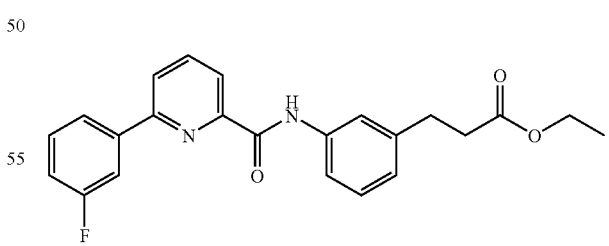

The pyridyl bromide (161) (100 mg, 0.27 mmol) was coupled to 3-fluoro-phenylboronic acid (34 mg, 0.24 mmol) using Method E. The residue was purified by column chromatography eluting with 15% EtOAc in heptane to give the title compound.

Yield: 75 mg, 80%; LC-MS $t_r$ 1.72 min; MS (ES+) m/z 393 (M+H)

(iii) 3-(3-{[6-(3-Fluoro-phenyl)-pyridine-2-carbonyl]-amino}-phenyl)-propionic acid (162)

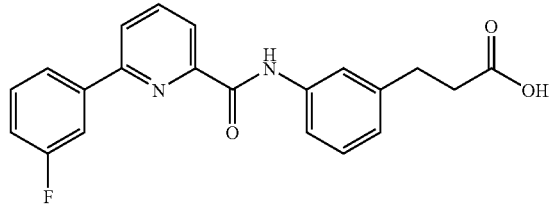

The ester (75 mg, 0.19 mmol) was hydrolysed using Method M to give the title compound.

Yield: 60 mg, 87%; LC/MS $t_r$ 1.49 min; MS (ES+) m/z 365 (M+H); HPLC Purity: 100%; $^1$H NMR (400 MHz, DMSO) δ 2.59 (t, 2H), 2.88 (t, 2H), 7.06 (d, 1H), 7.31-7.39 (m, 2H), 7.59-7.64 (m, 1H), 7.76-7.80 (m, 2H), 8.14-8.19 (m, 3H), 8.30-8.36 (m, 2H), 10.52 (s, 1H), 12.21 (s, 1H).

(jj) 3-(3-{[5-(3-Fluoro-phenyl)-furan-2-carbonyl]-amino}-phenyl)-propionic acid (163)

(i) 3-{3-[(5-Bromo-furan-2-carbonyl)-amino]-phenyl}-propionic acid ethyl ester

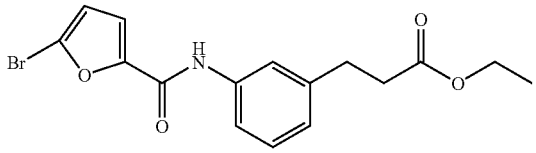

5-Bromo-2-furoic acid (247 mg, 1.29 mmol) was coupled to aniline (124) (250 mg, 1.29 mmol) using Method C to give the title compound.

Yield: 247 mg, 52%; LC/MS $t_r$ 1.46 min; MS (ES+) m/z 366, 368 (M+H)

(ii) 3-(3-{[5-(3-Fluoro-phenyl)-furan-2-carbonyl]-amino}-phenyl)-propionic acid ethyl ester

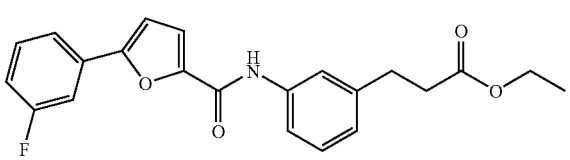

The furyl bromide (100 mg, 0.27 mmol) was coupled to 3-fluoro-phenylboronic (35 mg, 0.25 mmol) acid using Method E. The residue was purified by column chromatography eluting with 15% EtOAc in heptane to give the title compound.

Yield: 77 mg, 81%; LC-MS $t_r$ 1.62 min; MS (ES+) m/z 382 (M+H)

(iii) 3-(3-{[5-(3-Fluoro-phenyl)-furan-2-carbonyl]-amino}-phenyl)-propionic acid (163)

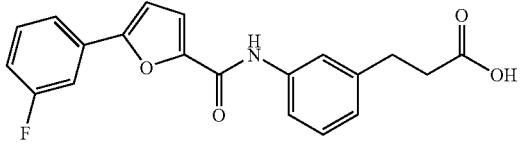

The ester (77 mg, 0.20 mmol) was hydrolysed using Method M to give the title compound.

Yield: 67 mg, 95%; LC/MS $t_r$ 1.41 min; MS (ES+) m/z 354 (M+H); HPLC Purity: 100%; $^1$H NMR (400 MHz, DMSO) δ 2.58 (t, 2H), 2.86 (t, 2H), 7.02 (d, 1H), 7.23-7.32 (m, 3H), 7.41 (d, 1H), 7.53-7.66 (m, 3H), 7.84 (d, 1H), 7.91-7.95 (m, 1H), 10.52 (s, 1H), 12.21 (s, 1H).

(kk) 3-{3-[(6-Phenyl-pyridine-2-carbonyl)-amino]-phenyl}-propionic acid (164)

(i) 3-{3-[(6-Phenyl-pyridine-2-carbonyl)-amino]-phenyl}-propionic acid ethyl ester

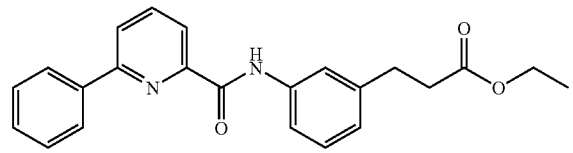

The pyridyl bromide (161) (100 mg, 0.27 mmol) was coupled to phenylboronic acid (30 mg, 0.25 mmol) using Method E. The residue was purified by column chromatography eluting with 15% EtOAc in heptane to give the title compound.

Yield: 55 mg, 59%; LC-MS $t_r$ 1.73 min; MS (ES+) m/z 375 (M+H)

(ii) 3-{3-[(6-Phenyl-pyridine-2-carbonyl)-amino]-phenyl}-propionic acid (164)

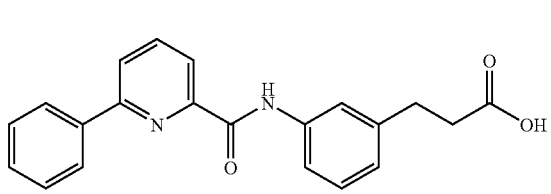

The ester (55 mg, 0.15 mmol) was hydrolysed using Method M to give the title compound.

Yield: 16 mg, 31%; LC/MS $t_r$ 1.46 min; MS (ES+) m/z 347 (M+H); HPLC Purity: 100%; $^1$H NMR (400 MHz, DMSO) δ 2.59 (t, 2H), 2.88 (t, 2H), 7.05 (d, 1H), 7.31-7.35 (m, 1H), 7.51-7.61 (m, 3H), 7.77-7.80 (m, 2H), 8.11-8.18 (m, 2H), 8.25-8.28 (m, 1H), 8.37-8.39 (m, 2H), 10.48 (s, 1H), 12.19 (s, 1H).

(ll) 3-[(4-Fluoro-biphenyl-3-carbonyl)-amino]-phenoxy}-acetic acid (165)

(i) 3-[(4-Fluoro-biphenyl-3-carbonyl)-amino]-phenoxy}-acetic acid ethyl ester

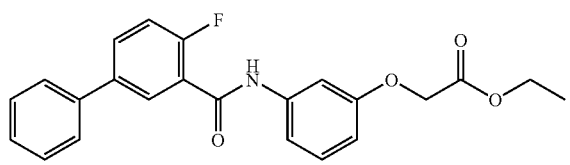

The phenyl bromide (139) (100 mg, 0.25 mmol) was coupled to phenylboronic acid (28 mg, 0.23 mmol) using Method E. During this reaction, partial hydrolysis occurred. The residue was extracted using Work-up E1 to give a mixture of acid and ester, which was used without further purification.

For the ester: LC/MS $t_r$ 1.61 min; MS (ES+) m/z 394 (M+H)

(ii) 3-[(4-Fluoro-biphenyl-3-carbonyl)-amino]-phenoxy}-acetic acid (165)

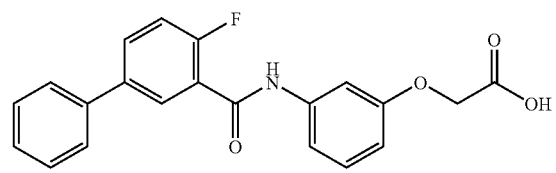

The mixture (90 mg, 0.23 mmol) was hydrolysed using Method M. The residue was triturated with TBME (2 ml) to give the title compound.

Yield: 41 mg, 49% over 2 steps; LC/MS $t_r$ 1.51 min; MS (ES+) m/z 366 (M+H); HPLC Purity: 92%; $^1$H NMR (250 MHz, DMSO) δ 4.66 (s, 2H), 6.66-6.71 (d, 1H), 7.23-7.53 (m, 7H), 7.73-7.76 (m, 2H), 7.85-7.93 (m, 2H), 10.52 (s, 1H).

(mm) 3-{3-[(6-Phenyl-pyridine-2-carbonyl)-amino]-phenyl}-propionic acid (167)

(i) {3-[(6-Bromo-pyridine-2-carbonyl)-amino]-phenoxy}-acetic acid ethyl ester (166)

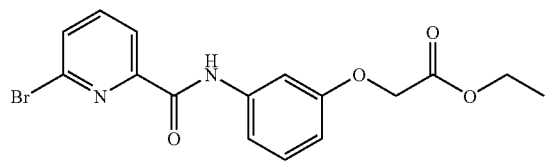

6-Bromo-pyridine-2-carboxylic acid (250 mg, 1.24 mmol) was coupled to aniline (64) (241 mg, 1.24 mmol) using Method C to give the title compound.

Yield: 387 mg, 82%; LC/MS $t_r$ 1.49 min; MS (ES+) m/z 379, 381 (M+H)

(ii) 3-{3-[(6-Phenyl-pyridine-2-carbonyl)-amino]-phenyl}-propionic acid (167)

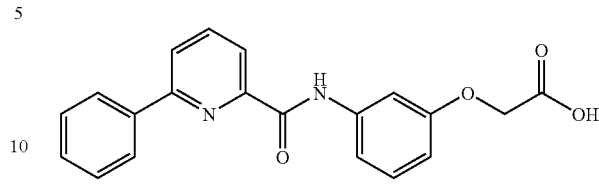

Bromo-derivative (166) (100 mg, 0.26 mmol) was coupled to phenylboronic (30 mg, 0.25 mmol) acid using Method E. During this reaction, hydrolysis occurred. The residue was extracted using Work-up E1 and triturated with TBME (2 ml) to give the title compound.

Yield: 48 mg, 55%; LC/MS $t_r$ 1.42 min; MS (ES+) m/z 349 (M+H); HPLC Purity: 100%; $^1$H NMR (400 MHz, DMSO) δ 4.71 (s, 2H), 6.72-6.75 (m, 1H), 7.29-7.34 (m, 1H), 7.52-7.63 (m, 5H), 8.10-8.18 (m, 2H), 8.25-8.28 (m, 1H), 8.36-8.38 (m, 2H), 10.51 (s, 1H), 13.07 (s, 1H).

(nn) (3-{[5-(3-Fluoro-phenyl)-furan-2-carbonyl]-amino}-phenoxy)-acetic acid (168)

(i) {3-[(5-Bromo-furan-2-carbonyl)-amino]-phenoxy}-acetic acid ethyl ester

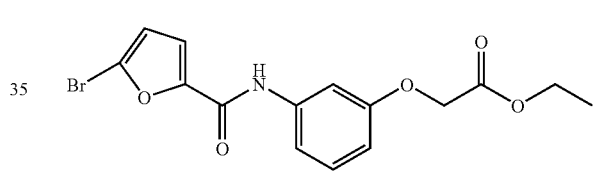

5-Bromo-furan-2-carboxylic acid (245 mg, 1.28 mmol) was coupled to aniline (64) (250 mg, 1.28 mmol) using Method C. The residue was purified by column chromatography eluting with 15% EtOAc in heptane to give the title compound.

Yield: 360 mg, 76%; LC/MS $t_r$ 1.41 min; MS (ES+) m/z 368, 370 (M+H)

(ii) (3-{[5-(3-Fluoro-phenyl)-furan-2-carbonyl]-amino}-phenoxy)-acetic acid ethyl ester

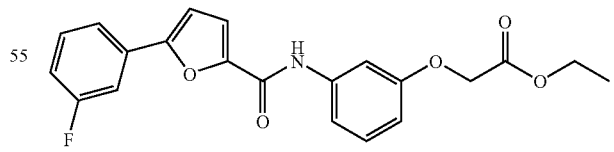

The furyl bromide (100 mg, 0.27 mmol) was coupled to 3-fluoro-phenylboronic acid (35 mg, 0.25 mmol) using Method E. During this reaction, partial hydrolysis occurred. The residue was extracted using Work-up E1 to give a mixture of acid and ester, which was used without further purification.

For the ester: LC/MS $t_r$ 1.57 min; MS (ES+) m/z 384 (M+H)

(iii) (3-{[5-(3-Fluoro-phenyl)-furan-2-carbonyl]-amino}-phenoxy)-acetic acid (168)

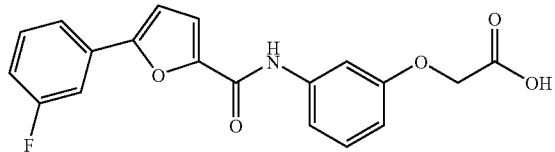

The mixture (95 mg, 0.25 mmol) was hydrolysed using Method M. The residue was triturated with TBME (2 ml) to give the title compound.

Yield: 71 mg, 80% over 2 steps; LC/MS $t_r$ 1.43 min; MS (ES+) m/z 356 (M+H); HPLC Purity: 100%; $^1$H NMR (250 MHz, DMSO): δ 4.69 (s, 2H), 6.70 (d, 1H), 7.19-7.33 (m, 3H), 7.36-7.47 (m, 3H), 7.51-7.61 (m, 1H), 7.81-7.96 (m, 2H), 10.20 (s, 1H).

(oo) {3-[(4,3'-Difluoro-biphenyl-3-carbonyl)-amino]-phenoxy}-acetic acid (169)

(i) {3-[(4,3'-Difluoro-biphenyl-3-carbonyl)-amino]-phenoxy}-acetic acid ethyl ester

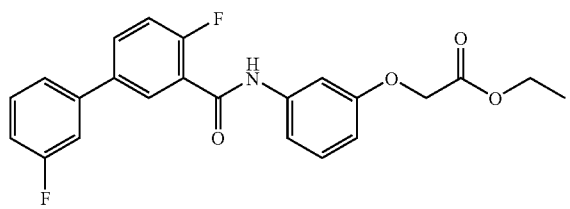

The phenyl bromide (139) (100 mg, 0.25 mmol) was coupled to 3-fluoro-phenylboronic acid (34 mg, 0.24 mmol) using Method E. During this reaction, partial hydrolysis occurred. The residue was extracted using Work-up E1 to give a mixture of acid and ester, which was used without further purification.

For the ester: LC/MS $t_r$ 1.62 min; MS (ES+) m/z 412 (M+H)

(ii) {3-[(4,3'-Difluoro-biphenyl-3-carbonyl)-amino]-phenoxy}-acetic acid (169)

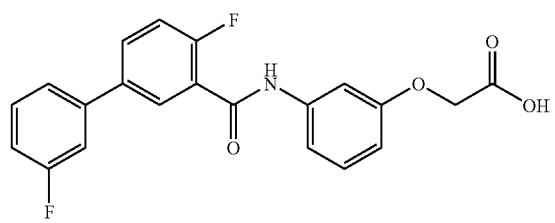

The mixture (99 mg, 0.24 mmol) was hydrolysed using Method M. The residue was triturated with TBME (2 ml) to give the title compound.

Yield: 30 mg, 33% over 2 steps; LC/MS $t_r$ 1.54 min; MS (ES+) m/z 384 (M+H);

HPLC Purity: 100%; $^1$H NMR (250 MHz, DMSO): δ 4.47 (s, 2H), 6.64 (d, 1H), 7.19-7.29 (m, 2H), 7.31-7.39 (m, 2H), 7.41-7.67 (m, 4H), 7.88-8.01 (m, 2H), 10.49 (s, 1H).

(pp) (3-{[6-(3-Fluoro-phenyl)-pyridine-2-carbonyl]-amino}-phenoxy)-acetic acid (170)

(i) (3-{[6-(3-Fluoro-phenyl)-pyridine-2-carbonyl]-amino}-phenoxy)-acetic acid ethyl ester

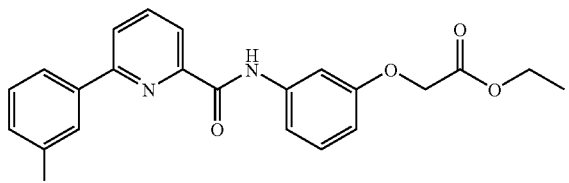

The pyridyl bromide (166) (100 mg, 0.26 mmol) was coupled to 3-fluoro-phenylboronic acid (34 mg, 0.24 mmol) using Method E. During this reaction, partial hydrolysis occurred. The residue was extracted using Work-up E1 to give a mixture of acid and ester, which was used without further purification.

For the ester: LC/MS $t_r$ 1.43 min; MS (ES+) m/z 395 (M+H)

(ii) (3-{[6-(3-Fluoro-phenyl)-pyridine-2-carbonyl]-amino}-phenoxy)-acetic acid (170)

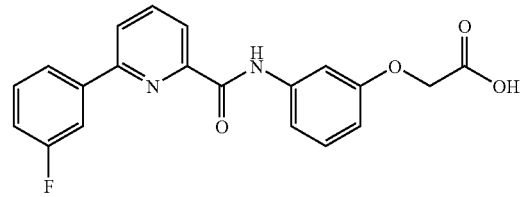

The mixture (94 mg, 0.24 mmol) was hydrolysed using Method M. The residue was triturated with TBME (2 ml) to give the title compound.

Yield: 88 mg, 100% over 2 steps; LC/MS $t_r$ 1.43 min; MS (ES+) m/z 367 (M+H); HPLC Purity: 97%; $^1$H NMR (250 MHz, DMSO): δ 4.49 (s, 2H), 6.51 (d, 1H), 7.06-7.18 (m, 2H), 7.27-7.46 (m, 3H), 7.89-7.99 (m, 3H), 8.04-8.12 (m, 2H), 10.32 (s, 1H).

(qq) {3-[(4,4'-Difluoro-biphenyl-3-carbonyl)-amino]-phenoxy}-acetic acid (171)

(i) {3-[(4,4'-Difluoro-biphenyl-3-carbonyl)-amino]-phenoxy}-acetic acid ethyl ester

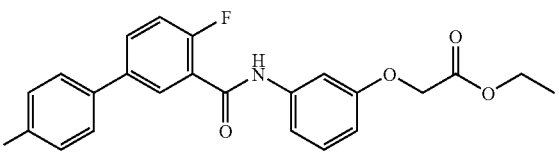

The phenyl bromide (139) (100 mg, 0.25 mmol) was coupled to 4-fluoro-phenylboronic acid (33 mg, 0.23 mmol) using Method E. During this reaction, partial hydrolysis occurred. The residue was extracted using Work-up E1 to give a mixture of acid and ester, which was used without further purification.

For the ester: LC/MS t$_r$ 1.62 min; MS (ES+) m/z 412 (M+H)

(ii) {3-[(4,4'-Difluoro-biphenyl-3-carbonyl)-amino]-phenoxy}-acetic acid (171)

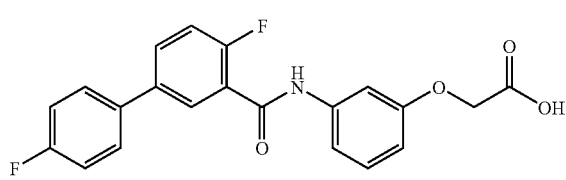

The mixture (95 mg, 0.23 mmol) was hydrolysed using Method M. The residue was triturated with TBME (2 ml) to give the title compound.

Yield: 32 mg, 36% over 2 steps; LC/MS t$_r$ 1.53 min; MS (ES+) m/z 384 (M+H);

HPLC Purity: 97%; $^1$H NMR (250 MHz, DMSO): δ 4.67 (s, 2H), 6.69 (d, 1H), 7.21-7.50 (m, 6H), 7.74-7.93 (m, 4H), 10.51 (s, 1H).

(rr) 3-{3-[(6-Phenyl-pyridine-2-carbonyl)-amino]-phenyl}-acrylic acid (178)

(i) 3-{3-[(6-Bromo-pyridine-2-carbonyl)-amino]-phenyl}-acrylic acid ethyl ester

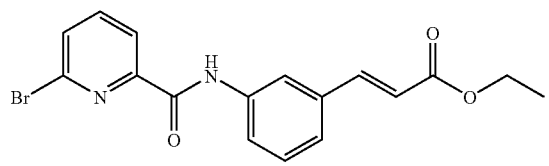

Aniline (60) (124 mg, 0.6 mmol) was coupled to 6-bromo-pyridine-2-carboxylic acid (131 mg, 0.6 mmol) using Method C. The residue was purified by column chromatography eluting in 10% EtOAc in heptane to give the title compound.

Yield: 25 mg, 11%; LC/MS t$_r$ 1.61 min; MS (ES+) m/z 375, 377 (M+)

(ii) 3-{3-[(6-Phenyl-pyridine-2-carbonyl)-amino]-phenyl}-acrylic acid ethyl ester

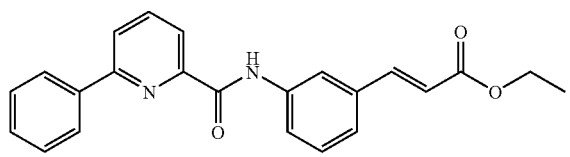

The pyridyl bromide (25 mg, 0.06 mmol) was coupled to benzeneboronic acid (7 mg, 0.05 mmol) using Method E. The residue was purified by column chromatography eluting in 10% EtOAc in heptane.

Yield: 5 mg, 22%; LC/MS t$_r$ 1.79 min; MS (ES+) m/z 373 (M+H)

(iii) 3-{3-[(6-Phenyl-pyridine-2-carbonyl)-amino]-phenyl}-acrylic acid (178)

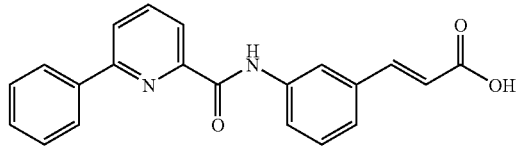

The ester (5 mg, 0.001 mmol) was hydrolysed using Method G to give the title compound.

Yield: 5 mg, 100%; LC/MS t$_r$ 1.50 min; MS (ES+) m/z 345 (M+H); HPLC Purity: 98%; $^1$H NMR (400 MHz; DMSO): δ 6.55 (d, 1H), 7.43-7.65 (m, 6H), 8.03 (m, 1H), 8.15 (m, 3H), 8.27 (d, 1H), 8.38 (d, 2H), 10.59 (s, 1H).

Example 11

(a) 5-Phenyl-furan-2-carboxylic acid [3-(1H-tetrazol-5-ylmethoxy)-phenyl]-amide (173)

(i) N-(3-Cyanomethoxy-phenyl)-acetamide

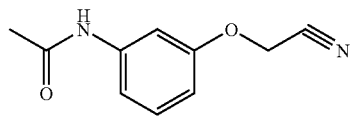

To a solution of N-(3-hydroxy-phenyl)-acetamide (5 g, 33.1 mmol) in acetone (50 ml) were added K$_2$CO$_3$ (5.49 g, 39.8 mmol) and bromo-acetonitrile (4.37 g, 36.4 mmol). The reaction mixture was heated to 100° C. for 3 h, filtered and the acetone layer evaporated in vacuo. This residue was dissolved in EtOAc (100 ml) and washed with 1M NaOH (10 ml×2). The organic layer was dried (Na$_2$SO$_4$), filtered and the solvent removed in vacuo. The crude residue was purified by column chromatography eluting with 80% EtOAc in heptane to give the title compound.

Yield: 6.25 g, 99%; LC/MS t$_r$ 0.92 min; MS (ES+) m/z 191 (M+H)

(ii) (3-Amino-phenoxy)-acetonitrile (172)

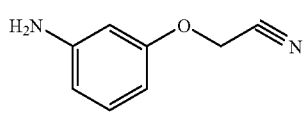

The acetamide (2 g, 10.5 mmol) was suspended in 1M HCl and heated to 100° C. for 4.5 h. The solution was allowed to cool to room temperature overnight, then the water was removed in vacuo to give the title compound as the hydrochloride salt.

Yield: 1.5 g, 97%; LC/MS t$_r$ 0.66 min; MS (ES+) m/z 149 (M+H)

(iii) 5-Bromo-furan-2-carboxylic acid (3-cyanomethoxy-phenyl)-amide

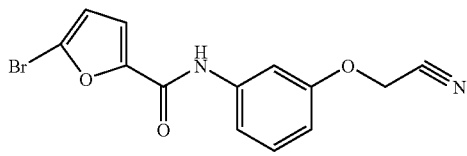

5-Bromo-furan-2-carboxylic acid (325 mg, 1.70 mmol) was coupled to (3-amino-phenoxy)-acetonitrile (172) (250 mg, 1.69 mmol) using Method C. The residue was purified by column chromatography eluting with a stepped gradient of 10-30% EtOAc in heptane to give the title compound.

Yield: 90 mg, 16%; LC/MS $t_r$ 1.34 min; MS (ES+) m/z 321, 323 (M+H)

(iv) 5-Bromo-furan-2-carboxylic acid [3-(1H-tetrazol-5-ylmethoxy)-phenyl]-amide

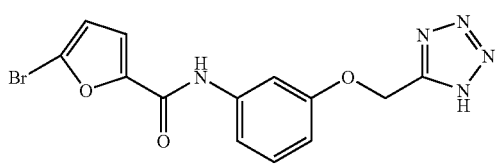

The nitrile (100 mg, 0.31 mmol) was treated with TMSN$_3$ and Bu$_2$SnO using Method L, except the reaction mixture was diluted with EtOAc (2 ml) and washed with H$_2$O (2×2 ml). The organic layer was dried (Na$_2$SO$_4$), filtered and the solvent removed in vacuo to give the title compound.

Yield: 110 mg, 97%; LC/MS $t_r$ 1.17 min; MS (ES+) m/z 364, 366 (M+H)

(v) 5-Phenyl-furan-2-carboxylic acid [3-(1H-tetrazol-5-ylmethoxy)-phenyl]-amide (173)

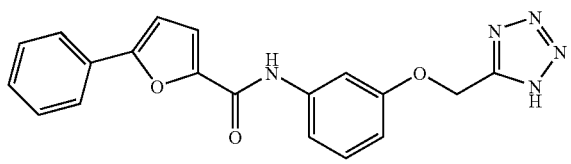

The bromo-derivative (110 mg, 0.30 mmol) was coupled to phenylboronic acid (37 mg, 0.30 mmol) acid using Method E, except for heating to 80° C. for 20 min. After reaction, 1M HCl (3 ml) was added, and the solvents were removed in vacuo. The residue was triturated with TBME (2 ml), DCM (2 ml), and recrystallised from hot 10% EtOH in H$_2$O mixture to give the title compound.

Yield: 62 mg, 57%; LC/MS $t_r$ 1.95 min; MS (ES+) m/z 362 (M+H); HPLC Purity: 95%; $^1$H NMR (400 MHz, DMSO): δ 5.34 (s, 2H), 6.69 (d, 1H), 7.03 (d, 1H), 7.17 (t, 1H), 7.22-7.29 (m, 3H), 7.36 (t, 2H), 7.42 (s, 1H), 7.82 (s, 2H), 10.03 (s, 1H).

(b) 6-Phenyl-pyridine-2-carboxylic acid [3-(1H-tetrazol-5-ylmethoxy)-phenyl]-amide (174)

(i) 6-Bromo-pyridine-2-carboxylic acid (3-cyanomethoxy-phenyl)-amide

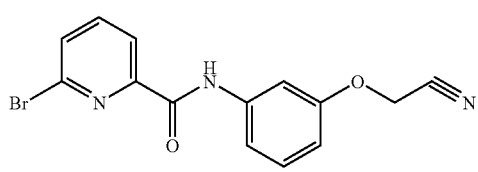

6-Bromo-pyridine-2-carboxylic acid (341 mg, 1.69 mmol) was coupled to aniline (172) (250 mg, 1.69 mmol) using Method C. The residue was purified by column chromatography eluting with 20% EtOAc in heptane to give the title compound.

Yield: 130 mg, 23%; LC/MS $t_r$ 1.43 min; MS (ES+) m/z 332, 334 (M+H)

(ii) 6-Bromo-pyridine-2-carboxylic acid [3-(1H-tetrazol-5-ylmethoxy)-phenyl]-amide

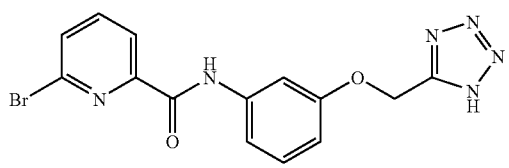

The nitrile (130 mg, 0.39 mmol) was treated with TMSN$_3$ and Bu$_2$SnO using Method L, except the reaction mixture was diluted with EtOAc (2 ml) and washed with H$_2$O (2×2 ml). The organic layer was dried (Na$_2$SO$_4$), filtered and the solvent removed in vacuo. The residue was purified by column chromatography eluting with 50% EtOAc in heptane followed by 5% AcOH in EtOAc to give the title compound.

Yield: 100 mg, 68%; LC/MS $t_r$ 1.20 min; MS (ES+) m/z 375, 377 (M+H)

(iii) 6-Phenyl-pyridine-2-carboxylic acid [3-(1H-tetrazol-5-ylmethoxy)-phenyl]-amide (174)

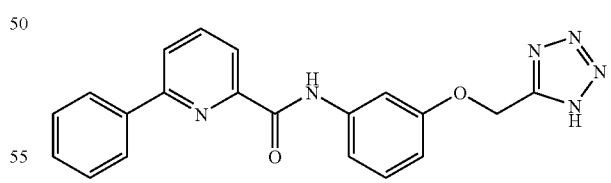

The bromo-derivative (100 mg, 0.27 mmol) was coupled to phenylboronic acid (27 mg, 0.22 mmol) acid using Method E, except for heating to 80° C. for 20 min. After reaction, 1M HCl (3 ml) was added, and the aqueous layer was extracted with EtOAc (2×2 ml). The organic layer was dried (Na$_2$SO$_4$), filtered and the solvent removed in vacuo. The residue was triturated with TBME (2 ml) and DCM (2 ml) to give the title compound.

Yield: 82 mg, 100%; LC/MS $t_r$ 2.03 min; MS (ES+) m/z 373 (M+H); HPLC Purity: 93%; $^1$H NMR (400 MHz, DMSO): δ 5.29 (s, 2H), 6.65 (d, 1H), 7.13 (t, 1H), 7.28-7.48 (m, 4H), 7.52 (s, 1H), 7.86-7.95 (m, 2H), 8.03 (d, 1H), 8.13 (d, 2H), 10.30 (s, 1H).

(c) 6-Phenyl-pyridine-2-carboxylic acid {3-[2-(1H-tetrazol-5-yl)-vinyl]phenyl}-amide (175)

(i) 6-Bromo-pyridine-2-carboxylic acid [3-(2-cyano-vinyl)-phenyl]-amide

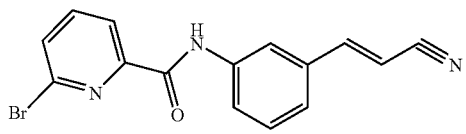

6-Bromo-pyridine-2-carboxylic acid (350 mg, 1.73 mmol) was coupled to aniline (88) (250 mg, 1.74 mmol) using Method C. The residue was purified by column chromatography eluting with 20% EtOAc in heptane to give the title compound.

Yield: 325 mg, 57%; LC/MS $t_r$ 1.52 min; MS (ES+) m/z 328, 330 (M+H)

(ii) 6-Bromo-pyridine-2-carboxylic acid {3-[2-(1H-tetrazol-5-yl)-vinyl]phenyl}-amide

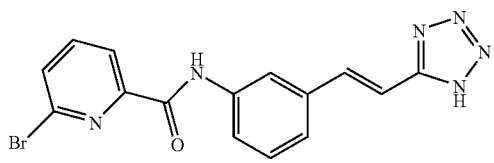

The nitrile (325 mg, 0.99 mmol) was reacted with TMSN$_3$ and Bu$_2$SnO using Method L, except the reaction mixture was diluted with EtOAc (4 ml) and washed with H$_2$O (3×4 ml). The organic layer was dried (Na$_2$SO$_4$), filtered and the solvent removed in vacuo. The residue was purified by column chromatography eluting with 50% EtOAc in heptane followed by 5% AcOH in EtOAc to give the title compound.

Yield: 334 mg, 25%; LC/MS $t_r$ 1.29 min; MS (ES+) m/z 371, 373 (M+H)

(iii) 6-Phenyl-pyridine-2-carboxylic acid {3-[2-(1H-tetrazol-5-yl)-vinyl]phenyl}-amide (175)

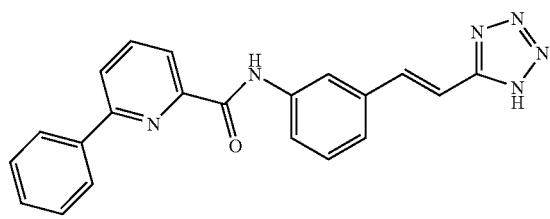

The bromo-derivative (100 mg, 0.27 mmol) was coupled to phenylboronic acid (27 mg, 0.22 mmol) using Method E, except that the reaction was heated to 80° C. After reaction, 1M HCl (3 ml) was added, and the aqueous layer was extracted with EtOAc (2×2 ml). The organic layer was dried (Na$_2$SO$_4$), filtered and the solvent removed in vacuo. The residue was triturated with TBME (2 ml) and DCM (2 ml) to give the title compound.

Yield: 54 mg, 67%; LC/MS $t_r$ 2.07 min; MS (ES+) m/z 369 (M+H); HPLC Purity: 92%; $^1$H NMR (400 MHz, DMSO): δ 7.29 (d, 1H), 7.39-7.55 (m, 5H), 7.67 (d, 1H), 7.92 (d, 1H), 8.02-8.12 (m, 2H), 8.03-8.23 (m, 2H), 8.26-8.34 (m, 2H), 10.59 (s, 1H).

(d) 4-Fluoro-biphenyl-3-carboxylic acid {3-[2-(1H-tetrazol-5-yl)-vinyl]phenyl}-amide (176)

(i) 5-Bromo-N-[3-(2-cyano-vinyl)-phenyl]-2-fluoro-benzamide

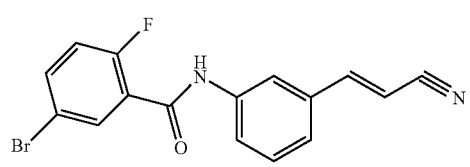

5-Bromo-2-fluoro-benzoic acid (380 mg, 1.74 mmol) was coupled to aniline (88) (250 mg, 1.74 mmol) using Method C. The residue was purified by column chromatography eluting with 20% EtOAc in heptane to give the title compound.

Yield: 353 mg, 59%; LC/MS $t_r$ 1.50 min; MS (ES+) m/z 345, 347 (M+H)

(ii) 5-Bromo-2-fluoro-N-{3-[2-(1H-tetrazol-5-yl)-vinyl]-phenyl}-benzamide

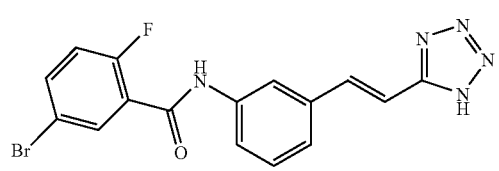

The nitrile (353 mg, 1.02 mmol) was treated with TMSN$_3$ and Bu$_2$SnO using Method L, except the reaction mixture was diluted with EtOAc (4 ml) and washed with H$_2$O (3×4 ml). The organic layer was dried (Na$_2$SO$_4$), filtered and the solvent removed in vacuo. The residue was triturated with DCM (5 ml) to give the title compound.

Yield: 280 mg, 71%; LC/MS $t_r$ 1.32 min; MS (ES+) m/z 388, 390 (M+H)

(iii) 4-Fluoro-biphenyl-3-carboxylic acid {3-[2-(1H-tetrazol-5-yl)-vinyl]phenyl}-amide (176)

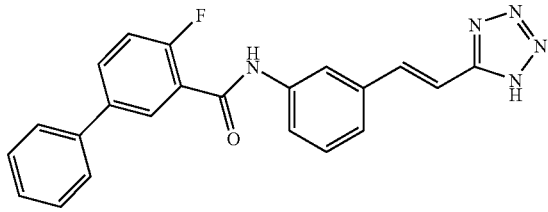

The phenyl bromide (100 mg, 0.27 mmol) was coupled to phenylboronic acid (27 mg, 0.22 mmol) using Method E, except that the reaction was heated at 80° C. After reaction, 1M HCl (3 ml) was added, and the aqueous layer was extracted with EtOAc (2×2 ml). The organic layer was dried (Na$_2$SO$_4$), filtered and the solvent removed in vacuo. The residue was triturated with TBME (2 ml) and DCM (2 ml) and further purified by preparative HPLC to give the title compound.

Yield: 15 mg, 18%; LC/MS t$_r$ 2.04 min; MS (ES+) m/z 386 (M+H); HPLC Purity: 97%; $^1$H NMR (400 MHz, DMSO): δ 7.39 (d, 1H), 7.49-7.69 (m, 6H), 7.76 (d, 1H), 7.83-7.90 (m, 3H), 7.98-8.03 (m, 1H), 8.08 (d, 1H), 8.22 (s, 1H), 10.72 (s, 1H).

Example 9

Biological Results

Binding Ability to Human EP Receptors

Membranes were prepared from cells stably transfected with human EP receptor cDNA. In brief, cells were cultured to confluency, scraped from culture flasks, and centrifuged (800 g, 8 minutes, 4° C.). Cells were twice washed in ice cold homogenisation buffer containing 10 mMTris-HCl, 1 mM EDTA.2Na, 250 mM sucrose, 1 mM PMSF, 0.3 mM indomethacin, pH 7.4, homogenised and re-centrifuged as before. The supernatant was stored on ice and pellets re-homogenised and re-spun. Supernatants were pooled and centrifuged at 40000 g, 10 minutes, 4° C. Resultant membrane pellets were stored at −80° C. until use.

For assay, membranes expressing human EP$_4$, EP$_3$, EP$_2$ or EP$_1$ receptors were incubated in Millipore (MHVBN45) plates containing assay buffer, radiolabelled [$^3$H]PGE$_2$ and 0.1 to 10 000 nM concentrations of compounds. Incubations were performed at suitable temperatures and for suitable times to allow equilibrium to be reached. Non-specific binding was determined in the presence of 10 uM PGE$_2$. Bound and free radiolabel was separated by vacuum manifold filtration using appropriate wash buffers, and bound radiolabel was determined by scintillation counting. Constituents of each of the buffers are included in table 1 below.

The affinity or pK$_i$ of each compound for each receptor was calculated from the concentration causing 50% radioligand displacement (IC$_{50}$) using the Cheng-Prusoff equation:

$$Ki = \frac{IC_{50}}{1 + \left(\frac{\text{radioligand concentration}}{\text{radioligand } KD}\right)}$$

This approach follows that set out in Kenakin, T. P., Pharmacologic analysis of drug receptor interaction. Raven Press, New York, 2$^{nd}$ edition.

TABLE 1

| Receptor | | EP$_1$ | EP$_2$ | EP$_3$ | EP$_4$ |
|---|---|---|---|---|---|
| Protein/well | | 6.5 µg | 8 µg | 5 µg | 5 µg |
| Final [$^3$H-PGE$_2$] | | 3.6 nM | 3 nM | 2.5 nM | 1 nM |
| Buffer | Assay | 10 mM MES pH 6.0; 10 mM MgCl$_2$; 1 mM EDTA, 3uM Indomethacin | 10 mM MES pH 6.0; 10 mM MgCl$_2$; 1 mM EDTA | 10 mM MES pH 6.0; 10 mM MgCl2; 1 mM EDTA, 100uM GTP-gamma-S | 10 mM MES pH 6.0; 10 mM MgCl$_2$; 1 mM EDTA, 3uM Indomethacin |
| | Wash | 10 mM MES pH 6.0; 10 mM MgCl$_2$ | 10 mM MES pH 6.0; 10 mM MgCl$_2$ | 10 mM MES pH 6.0; 10 mM MgCl$_2$ | 10 mM MES pH 6.0; 1 mM EDTA |

Determination of Agonist Activity at Recombinant Human EP$_2$ Prostanoid Receptors and Antagonist Activity at EP$_4$ Prostanoid Receptors HEK-293 cell clones stably transfected with human EP$_2$ or EP$_4$ prostanoid receptors were cultured at 37° C. in a 5% CO$_2$ incubator, in 96-well poly-L-lysine coated plates at a density of 50,000 cells/well. Culture media was Minimal essential media (MEM), supplemented with 10% foetal bovine serum, 100 U/ml penicillin, 100 ng/ml streptomycin, 2.5 µg/ml fungizone, 2 mM glutamine. Cells were cultured to confluency (3-4 days) prior to use.

Culture media was removed, and confluent cells washed three times in MEM. 175 µl assay buffer (MEM containing no supplements+1 mM IBMX) was incubated with the cells for 60 min. Cells were then stimulated by the addition of 25 µl of PGE$_2$ or agonists prepared in assay buffer. In antagonist studies, cells were pre-incubated with compounds for 30 minutes prior to PGE$_2$-mediated stimulation Plates were incubated for 15 min at 37° C., before termination of the reaction by the addition of 25 µl 1M HCl. The plate was then frozen at −20° C. overnight before determination of cAMP concentration.

Stimulated cAMP levels were determined by radioligand displacement binding. In brief, plates were thawed rapidly in a waterbath, and the samples neutralised by the addition of 25 µl 1M NaOH. 30 µl was transferred to Millipore plates pre-coated with 0.5% Polyethylenimine (PEI). Samples were diluted by addition of 90 µl cAMP determination buffer (50 mM Tris, 5 mM EDTA, pH 7.0). A cAMP standard curve ($10^{-11}$M to $10^{-5}$M) was constructed. 15 µl of 2 nM (final concentration) [$^3$H] cAMP, and 15 µl of 3'5'-cAMP protein kinase (8 μg/well final concentration) prepared in cAMP determination buffer containing 0.1% BSA, were added to each well.

Plates were incubated on ice for 2 hours, before bound and free radiolabel were separated by vacuum filtration harvesting using the Millipore vacuum manifold, using ice cold water as the termination buffer.

The sealing mat was removed from the Millipore plates, and the filters allowed to dry overnight. 50 μl Microscint 0 (Packard Bioscience) was added to each well, and the plate counted using the Micro-Beta Trilux topcount $^3$H program.

cAMP accumulation was determined from the standard curve, and values calculated in pmoles cAMP/well. Antagonists affinities ($pA_2$ values) were determined assuming a slope of unity and the Gaddam-Schild equation, where $pA_2$=log [concentration ratio−1]−log [antagonist]. Agonist potencies were determined from log $EC_{50}$ values, denoting the concentration of agonist required to produce 50% of the agonist response.

Binding and functional results are presented as $pK_i$ and $pEC_{50}/pA_2$ values in table 2 below.

TABLE 2

| Compound | pKi (M) $EP_2$ | $EP_4$ | $EP_3$ | $pEC_{50}$ $EP_2$ (M) | $pA_2$ $EP_4$ (M) | activity |
|---|---|---|---|---|---|---|
| 2 | >5 | >5 | — | >5 | >5 | $EP_2$ agonist/$EP_4$ antagonist |
| 4 | >5 | >5 | — | >5 | >5 | $EP_2$ agonist/$EP_4$ antagonist |
| 10 | >6 | — | — | >6 | | $EP_2$ agonist |
| 12 | >6 | — | — | >6 | | $EP_2$ agonist |
| 14 | >6 | — | — | >5 | | $EP_2$ agonist |
| 16 | >5 | — | — | >5 | | $EP_2$ agonist |
| 17 | >6 | — | — | >6 | | $EP_2$ agonist |
| 18 | >6 | — | — | >6 | | $EP_2$ agonist |
| 19 | >6 | — | — | >5 | | $EP_2$ agonist |
| 20 | >6 | — | — | >5 | | $EP_2$ agonist |
| 21 | >6 | — | — | >6 | | $EP_2$ agonist |
| 22 | >5 | — | — | | | |
| 23 | >5 | — | — | | | |
| 24 | >6 | — | — | | | |
| 25 | >5 | — | — | | | |
| 26 | >7 | >7 | — | >7 | >6 | $EP_2$ agonist/$EP_4$ antagonist |
| 27 | >7 | — | — | >7 | | $EP_2$ agonist |
| 28 | >6 | — | — | | | |
| 29 | >6 | — | — | | | |
| 30 | >5 | — | — | >6 | | $EP_2$ Agonist |
| 31 | >6 | >6 | — | >6 | | $EP_2$ agonist |
| 32 | >6 | >5 | — | | | |
| 33 | >5 | — | — | | | |
| 34 | >6 | >6 | — | >6 | | $EP_2$ agonist |
| 35 | >5 | — | — | | | |
| 36 | >6 | — | — | >7 | | $EP_2$ agonist |
| 37 | >6 | — | — | >6 | | $EP_2$ agonist |
| 38 | >5 | — | — | | | |
| 39 | >7 | — | — | >7 | | $EP_2$ agonist |
| 40 | >6 | — | — | >7 | | $EP_2$ agonist |
| 41 | >6 | — | — | >6 | | $EP_2$ agonist |
| 42 | >6 | — | — | >7 | | $EP_2$ agonist |
| 43 | >5 | — | — | | | |
| 44 | >6 | — | — | >7 | | $EP_2$ agonist |
| 45 | >6 | — | — | >7 | | $EP_2$ agonist |
| 46 | >5 | — | — | | | |
| 47 | >6 | — | — | | | |
| 48 | >5 | — | — | | | |
| 49 | >6 | — | — | >7 | | $EP_2$ agonist |
| 50 | >5 | — | — | | | |
| 51 | >6 | — | — | >7 | | $EP_2$ agonist |
| 52 | >6 | — | — | >7 | | $EP_2$ agonist |
| 53 | >5 | — | — | | | |
| 54 | >6 | — | — | >6 | | $EP_2$ agonist |
| 57 | >5 | — | — | >6 | | $EP_2$ Agonist |
| 59 | >5 | — | — | | | |
| 61 | >7 | >6 | — | >7 | >6 | $EP_2$ agonist/$EP_4$ agonist |
| 62 | >6 | — | — | >7 | | $EP_2$ agonist |
| 63 | >5 | — | — | | | |
| 66 | >7 | >6 | — | >7 | >6 | $EP_2$ agonist/$EP_4$ agonist |
| 68 | >7 | >6 | — | >7 | >6 | $EP_2$ agonist/$EP_4$ antagonist |
| 69 | >7 | >6 | — | | | $EP_2$ agonist/$EP_4$ antagonist |
| 70 | >7 | >6 | — | | | $EP_2$ agonist/$EP_4$ antagonist |
| 71 | >7 | — | — | | | $EP_2$ agonist |
| 72 | >6 | >5 | — | >6 | >6 | $EP_2$ agonist/$EP_4$ antagonist |
| 73 | >5 | — | — | | | |
| 74 | >5 | — | — | >5 | | $EP_2$ agonist |
| 75 | >7 | — | — | | | |
| 81 | >7 | — | — | >7 | | $EP_2$ Agonist |
| 82 | >7 | — | — | >7 | | $EP_2$ Agonist |

TABLE 2-continued

| Compound | pKi (M) | | | pEC$_{50}$ EP$_2$ (M) | pA$_2$ EP$_4$ (M) | activity |
|---|---|---|---|---|---|---|
| | EP$_2$ | EP$_4$ | EP$_3$ | | | |
| 85 | >7 | — | — | >7 | | EP$_2$ Agonist |
| 86 | >7 | — | — | >7 | | EP$_2$ Agonist |
| 87 | >7 | — | — | >7 | | EP$_2$ Agonist |
| 89 | >7 | — | — | >7 | | EP$_2$ Agonist |
| 90 | >7 | — | — | >7 | | EP$_2$ Agonist |
| 92 | >6 | — | — | >7 | | EP$_2$ Agonist |
| 93 | >7 | — | — | >7 | | EP$_2$ Agonist |
| 94 | >7 | — | — | >7 | | EP$_2$ Agonist |
| 95 | >7 | — | — | >7 | | EP$_2$ Agonist |
| 96 | >6 | — | — | | | |
| 97 | >6 | — | — | >6 | | EP$_2$ Agonist |
| 98 | >6 | — | — | >6 | | EP$_2$ Agonist |
| 100 | >7 | >5 | — | >7 | | EP$_2$ Agonist |
| 101 | >7 | — | — | >7 | | EP$_2$ Agonist |
| 102 | >7 | — | — | | | |
| 103 | >7 | >6 | — | | | |
| 104 | >6 | — | — | | | |
| 105 | >7 | — | — | | | |
| 107 | >7 | — | — | >7 | | EP$_2$ Agonist |
| 108 | >7 | — | — | >7 | | EP$_2$ Agonist |
| 110 | >7 | — | — | >7 | | EP$_2$ Agonist |
| 111 | >7 | — | — | >7 | | EP$_2$ Agonist |
| 112 | >7 | — | — | >7 | | EP$_2$ Agonist |
| 113 | >7 | — | — | >7 | | EP$_2$ Agonist |
| 115 | >7 | — | — | >7 | | EP$_2$ Agonist |
| 116 | >7 | — | — | >7 | | EP$_2$ Agonist |
| 117 | >6 | — | — | >5 | | EP$_2$ Agonist |
| 118 | >6 | — | — | >7 | | EP$_2$ Agonist |
| 120 | >5 | — | — | >6 | | EP$_2$ Agonist |
| 121 | >6 | — | — | >6 | | EP$_2$ Agonist |
| 122 | >7 | >6 | — | | | |
| 123 | >6 | — | — | | | |
| 125 | >7 | >5 | — | >7 | >5 | EP$_2$ Agonist/EP$_4$ Antagonist |
| 126 | >7 | >6 | — | >7 | >6 | EP$_2$ Agonist/EP$_4$ Antagonist |
| 127 | >7 | — | — | >7 | | EP$_2$ Agonist |
| 128 | >6 | — | — | >7 | | EP$_2$ Agonist |
| 129 | >7 | >6 | — | >7 | >6 | EP$_2$ Agonist/EP$_4$ Antagonist |
| 130 | >7 | >6 | — | >7 | >6 | EP$_2$ Agonist/EP$_4$ Antagonist |
| 132 | >7 | — | — | >7 | | EP$_2$ Agonist |
| 133 | >7 | >6 | — | >7 | >7 | EP$_2$ Agonist/EP$_4$ Agonist |
| 134 | >7 | — | — | >7 | | EP$_2$ Agonist |
| 135 | >6 | — | — | >6 | | EP$_2$ Agonist |
| 137 | >7 | >6 | — | >7 | | EP$_2$ Agonist |
| 138 | >7 | >7 | — | >7 | >6 | EP$_2$ Agonist/EP$_4$ Agonist |
| 140 | >7 | — | — | >7 | | EP$_2$ Agonist |
| 142 | >7 | — | — | >7 | | EP$_2$ Agonist |
| 143 | >7 | — | — | >7 | | EP$_2$ Agonist |
| 144 | >7 | >6 | — | >7 | >6 | EP$_2$ Agonist |
| 146 | >7 | — | — | >7 | | EP$_2$ Agonist |
| 147 | >7 | — | — | >7 | | EP$_2$ Agonist |
| 148 | >7 | — | — | >7 | | EP$_2$ Agonist |
| 150 | >6 | — | — | >6 | | EP$_2$ Agonist |
| 151 | >7 | — | — | >7 | | EP$_2$ Agonist |
| 153 | >7 | — | — | >7 | | EP$_2$ Agonist |
| 154 | >7 | — | — | >7 | | EP$_2$ Agonist |
| 155 | >7 | — | — | >7 | | EP$_2$ Agonist |
| 156 | >7 | — | — | >7 | | EP$_2$ Agonist |
| 157 | >7 | — | — | >7 | | EP$_2$ Agonist |
| 158 | >7 | >6 | — | >7 | | EP$_2$ Agonist |
| 159 | >7 | — | — | >7 | | EP$_2$ Agonist |
| 160 | >7 | — | — | >7 | | EP$_2$ Agonist |
| 162 | >7 | — | — | >7 | | EP$_2$ Agonist |
| 163 | >7 | — | — | >7 | | EP$_2$ Agonist |
| 164 | >6 | — | — | >7 | | EP$_2$ Agonist |
| 165 | >7 | — | — | >7 | | EP$_2$ Agonist |
| 167 | >7 | >6 | — | >7 | | EP$_2$ Agonist |
| 168 | >7 | — | — | >7 | | EP$_2$ Agonist |
| 169 | >7 | — | — | >7 | | EP$_2$ Agonist |
| 170 | >7 | >6 | — | >7 | | EP$_2$ Agonist |
| 171 | >7 | — | — | >7 | | EP$_2$ Agonist |
| 173 | >6 | — | — | >7 | | EP$_2$ Agonist |
| 174 | >7 | >6 | — | | | |
| 175 | >7 | >7 | — | | | |
| 176 | >7 | — | — | | | |

TABLE 2-continued

| Compound | pKi (M) | | | pEC$_{50}$ EP$_2$ (M) | pA$_2$ EP$_4$ (M) | activity |
| --- | --- | --- | --- | --- | --- | --- |
| | EP$_2$ | EP$_4$ | EP$_3$ | | | |
| 177 | >6 | — | — | >6 | | EP$_2$ Agonist |
| 178 | >7 | >7 | — | >7 | >6 | EP$_2$ Agonist/EP$_4$ Agonist |

— denotes no appreciable affinity up to 10 μM

The invention claimed is:

1. A compound of formula (I):

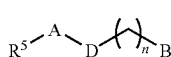
(I)

or a salt thereof, wherein:

R$^5$ is an optionally substituted phenyl group where the substituents are selected from the group consisting of: unsubstituted C$_{1-4}$ alkyl, C$_{1-4}$ alkoxy, —CF$_3$, halo, acyl, amino, and alkoxylene;

A is

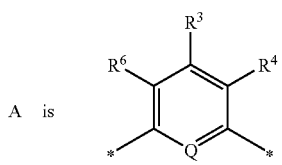

where Q is CH;

R$^3$ is selected from the group consisting of H, F, Cl, optionally substituted C$_{1-4}$ alkyl, C$_{1-4}$ alkoxy, C$_{5-7}$ aryl and C$_{5-7}$ aryl-C$_{1-4}$ alkyl groups;

R$^4$ is selected from the group consisting of H, F, Cl, optionally substituted C$_{1-4}$ alkyl, C$_{1-4}$ alkoxy, C$_{5-7}$ aryl, and C$_{5-7}$ aryl-C$_{1-4}$ alkyl groups;

R$^6$ is selected from the group consisting of H, F, Cl, optionally substituted C$_{1-4}$ alkyl, C$_{1-4}$ alkoxy, C$_{5-7}$ aryl, and C$_{5-7}$ aryl-C$_{1-4}$ alkyl groups;

D is selected from the group consisting of

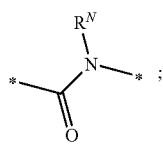
(i)

B is selected from the group consisting of

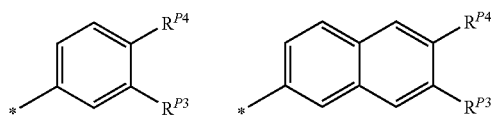

where one of R$^{P3}$ and R$^{P4}$ is —C$_m$ alkylene-R$^2$ and the other of R$^{P3}$ and R$^{P4}$ is H, m and n are independently 0 or 1, and m+n=1 or 2; and additionally when R$^{P3}$ is —C$_m$ alkylene-R$^2$, m is 2 or 3, and m+n=2, 3 or 4, and when R$^2$ is tetrazol-5-yl, m+n is 0; or where one of R$^{P3}$ and R$^{P4}$ is —O—CH$_2$—R$^2$, and the other of R$^{P3}$ and R$^{P4}$ is H, n is 0;

R$^N$ is H or optionally substituted C$_{1-4}$ alkyl;

R$^2$ is either:
(i) —CO$_2$H (carboxy);
(ii) —CONH$_2$;
(iii) —CH$_2$—OH (methoxy); or
(iv) tetrazol-5-yl.

2. A compound according to claim 1, wherein R$^5$ is unsubstituted phenyl.

3. A compound according to claim 1, wherein:
(i) R$^3$, R$^4$ and R$^6$ are H; or
(ii) one of R$^3$, R$^4$ and R$^6$ is Cl or F.

4. A compound according to claim 1, wherein R$^N$ is H.

5. A compound according to claim 1, wherein B is:

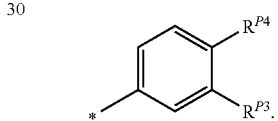

6. A compound according to claim 1, wherein R$^2$ is —CO$_2$H or tetrazoly-5-yl.

7. A compound according to claim 6, wherein R$^2$ is —CO$_2$H.

8. A compound according to claim 1, wherein R$^{P4}$ is H, and R$^{P3}$ is —CH=CH—R$^2$.

9. A compound according to claim 1, wherein R$^{P3}$ is —O—CH$_2$—R$^2$.

10. A compound which is:
{3-[(4-Chloro-biphenyl-3-carbonyl)-amino]-phenyl}-acetic acid;
{3-[(6-Fluoro-biphenyl-3-carbonyl)-amino]-phenyl}-acetic acid;
{3-[(Biphenyl-3-carbonyl)-amino]-phenyl}-acetic acid;
{3-[(4-Fluoro-biphenyl-3-carbonyl)-amino]-phenyl}-acetic acid;
{3-[(5-Fluoro-biphenyl-3-carbonyl)-amino]-phenyl}-acetic acid;
3-{3-[(4-Fluoro-biphenyl-3-carbonyl)-amino]-phenyl}-acrylic acid;
3-{3-[(4,3'-Difluoro-biphenyl-3-carbonyl)-amino]-phenyl}-acrylic acid;
{3-[(4,3'-Difluoro-biphenyl -3-carbonyl )-amino]-phenyl}-acetic acid;
3-{3- [(4,4'-Difluoro-biphenyl-3-carbonyl)-amino]-phenyl }acrylic acid;
[3-(Biphenyl-3-ylcarbamoyl)-phenyl]-acetic acid;
{3-[(3'-Chloro-4-fluoro-biphenyl-3-carbonyl)-amino]-phenoxy}-acetic acid;
3-{3-[(3'-Chloro-4-fluoro-biphenyl-3 -carbonyl)-amino]-phenyl}-acrylic acid;

{3-[(3',5'-Dichloro-4-fluoro-biphenyl-3-carbonyl)-amino]-phenoxy}-acetic acid;

3-{3-[(3',5'-Dichloro-4-fluoro-biphenyl-3-carbonyl)-amino]-phenyl}-acrylic acid;

{3-[(4-Fluoro-biphenyl-3-carbonyl)-amino]-phenoxy}-acetic acid;

{3-[(4,3'-Difluoro-biphenyl-3-carbonyl)-amino]-phenoxy}-acetic acid;

{3-[(4,4'-Difluoro-biphenyl-3-carbonyl)-amino]-phenoxy}-acetic acid; or

4-Fluoro-biphenyl-3-carboxylic acid {3-[2-(1H-tetrazol-5yl)-vinyl]phenyl}-amide.

11. The compound of claim 10 wherein the compound is:

3-{3-[(4-Fluoro-biphenyl-3-carbonyl)-amino]-phenyl}-acrylic acid;

3-{3-[(4,3'-Difluoro-biphenyl-3-carbonyl)-amino]-phenyl}-acrylic acid;

3-{3-[(4,4'-Difluoro-biphenyl-3-carbonyl)-amino]-phenyl}-acrylic acid;

{3-[(4,4'-Difluoro-biphenyl-3-carbonyl)-amino]-phenoxy}-acetic acid; or

{3-[(4,3'-Difluoro-biphenyl-3-carbonyl)-amino]-phenoxy}-acetic acid.

12. A pharmaceutical composition comprising a compound according to claim 1, or a pharmaceutically acceptable salt thereof together with a pharmaceutically acceptable carrier or diluent.

13. A method of treating a condition which can be alleviated by agonism of an $EP_2$ receptor, which method comprises administering to a patient, in need of treatment, an effective amount of a compound according to claim 1, or a pharmaceutically acceptable salt thereof, wherein the condition is glaucoma or ocular hypertension.

\* \* \* \* \*

UNITED STATES PATENT AND TRADEMARK OFFICE
CERTIFICATE OF CORRECTION

| | | |
|---|---|---|
| PATENT NO. | : 7,803,841 B2 | Page 1 of 1 |
| APPLICATION NO. | : 12/346516 | |
| DATED | : September 28, 2010 | |
| INVENTOR(S) | : Alexander William Oxford et al. | |

It is certified that error appears in the above-identified patent and that said Letters Patent is hereby corrected as shown below:

Claim 1, Column 171, line 23, "halo, acyl," should read "halo,".

Signed and Sealed this
Eighth Day of March, 2011

David J. Kappos
*Director of the United States Patent and Trademark Office*